US012583896B2

(12) United States Patent (10) Patent No.: US 12,583,896 B2
Baker et al. (45) Date of Patent: Mar. 24, 2026

(54) CAGED-DEGRON-BASED MOLECULAR FEEDBACK CIRCUITS AND METHODS OF USING THE SAME

(71) Applicants: The Regents of the University of California, Oakland, CA (US); University of Washington, Seattle, WA (US)

(72) Inventors: David Baker, Seattle, WA (US); Scott Boyken, Seattle, WA (US); Hana El-Samad, San Francisco, CA (US); Marc Lajoie, Seattle, WA (US); Robert Langan, Seattle, WA (US); Andrew Ng, San Francisco, CA (US)

(73) Assignees: THE REGENTS OF THE UNIVERSITY OF CALIFORNIA, Oakland, CA (US); UNIVERSITY OF WASHINGTON, Seattle, WA (US)

( * ) Notice: Subject to any disclaimer, the term of this patent is extended or adjusted under 35 U.S.C. 154(b) by 997 days.

(21) Appl. No.: 17/419,236

(22) PCT Filed: Jan. 6, 2020

(86) PCT No.: PCT/US2020/012355
§ 371 (c)(1),
(2) Date: Jun. 28, 2021

(87) PCT Pub. No.: WO2020/146254
PCT Pub. Date: Jul. 16, 2020

(65) Prior Publication Data
US 2022/0119467 A1 Apr. 21, 2022

Related U.S. Application Data

(60) Provisional application No. 62/789,418, filed on Jan. 7, 2019, provisional application No. 62/850,336, filed on May 20, 2019.

(51) Int. Cl.
| | |
|---|---|
| *C07K 14/47* | (2006.01) |
| *A61K 35/17* | (2025.01) |
| *C12N 1/16* | (2006.01) |
| *C12N 5/07* | (2010.01) |
| *C12N 5/10* | (2006.01) |
| *C12N 5/16* | (2006.01) |

(52) U.S. Cl.
CPC ............ *C07K 14/4705* (2013.01); *C12N 1/16* (2013.01); *C12N 5/06* (2013.01); *C12N 5/10* (2013.01); *C12N 5/16* (2013.01); *A61K 35/17* (2013.01); *C07K 2319/02* (2013.01); *C07K 2319/70* (2013.01); *C07K 2319/71* (2013.01); *C07K 2319/715* (2013.01); *C07K 2319/80* (2013.01); *C07K 2319/95* (2013.01); *C12N 2501/60* (2013.01)

(58) Field of Classification Search
CPC ............ C07K 14/4705; C07K 2319/02; C07K 14/7051; C07K 14/435; A61K 35/17; A61K 48/00; C12N 2740/16043; C12N 15/63; C12N 15/86; C12N 15/79; C12N 15/85; G01N 33/5047
USPC ........... 435/455, 366; 536/255.1, 23.1, 23.4; 530/324, 358
See application file for complete search history.

(56) References Cited

U.S. PATENT DOCUMENTS

| | | | |
|---|---|---|---|
| 7,574,306 | B1 | 8/2009 | Baker et al. |
| 2016/0202256 | A1 | 7/2016 | Church et al. |
| 2017/0198363 | A1 | 7/2017 | Medford et al. |
| 2017/0369892 | A1 | 12/2017 | Klavins et al. |
| 2019/0002578 | A1 | 1/2019 | Brayshaw et al. |

FOREIGN PATENT DOCUMENTS

| | | |
|---|---|---|
| CN | 106103475 A | 11/2016 |
| WO | WO 2009/114506 A2 | 9/2009 |
| WO | WO 2014/124301 A1 | 8/2014 |
| WO | WO 2017/173356 A1 | 10/2017 |
| WO | WO 2018/191032 A1 | 10/2018 |
| WO | WO 2018/206791 A1 | 11/2018 |
| WO | WO 2020/018935 A2 | 1/2020 |

OTHER PUBLICATIONS

Bretones et al. 2011, Journal of Biological Chemistry, vol. 286(11), 9815-9825. (Year: 2011).*
Ferrell & Sears 2014, Cold Spring Harbor Perspectives in Medicine, vol. 4, a014365, 1-16. (Year: 2014).*
Gur et al. 2004, European Molecular Biology Organization Journal, vol. 23(16), 3270-3281. (Year: 2004).*

(Continued)

*Primary Examiner* — Anne Marie S Wehbe
*Assistant Examiner* — Katie L Pennington
(74) *Attorney, Agent, or Firm* — James S. Keddie; Bozicevic, Field & Francis LLP

(57) ABSTRACT

Provided are molecular feedback circuits employing caged-degrons. Aspects of such circuits include the use of a caged-degron to modulate the output of a signaling pathway in a feedback-controlled manner. Also provided are nucleic acids encoding molecular circuits and cells containing such nucleic acids. Methods of using caged-degron-based molecular feedback circuits are also provided, including e.g., methods of modulating a signaling pathway of a cell that include genetically modifying the cell with a caged-degron-based molecular feedback circuit.

11 Claims, 38 Drawing Sheets
Specification includes a Sequence Listing.

(56) References Cited

OTHER PUBLICATIONS

Matsumura et al. 2003, Cell Cycle, vol. 2(4), 333-338. (Year: 2003).*

Yuan et al. 2009, Journal of Cell Biology, vol. 185(2), 203-11. (Year: 2009).*

Bonger et al. 2012, Nature Chemical Biology, vol. 7(8), 531-537. (Year: 2012).*

Jungbluth et al. 2010, BMC Systems Biology, vol. 4: 176, 1-12. (Year: 2010).*

Chakravarti & Wong 2015, Trends in Biotechnology, vol. 33(8), 449-461. (Year: 2015).*

Miller et al. 2016, CA: A Cancer Journal for Clinicians, vol. 66(4), 271-289. (Year: 2016).*

Arellano et al. 2016, Discovery Medicine, vol. 22(119), 73-80. (Year: 2016).*

Jensen et al. 2009, Cell Stem Cell, vol. 4(5), 427-439. (Year: 2009).*

Ordonez-Moran & Huelsken 2012, The European Molecular Biology Organization Journal, vol. 31, 2064-2066. (Year: 2012).*

Khatib et al. 2016, Stem Cells and Translational Medicine, vol. 5, 694-702 (Year: 2016).*

Boyken et al., "De novo design of protein homo-oligomers with modular hydrogen-bond network-mediated specificity", Science, 2016, 352(6286): 680-687.

Langan et al., "De Novo Design of Bioactive Protein Switches", Nature, Jul. 24, 2019, 572(7768): 205-210.

Ng et al., "Modular and tunable biological feedback control using a de novo protein switch", Nature, Jul. 24, 2019, 572 (7768): 265-269.

Drobnak et al., "Designed Protein Origami", Protein-based Engineered Nanostructures, Advances in Experimental Medicine and Biology, 2016, 940, DOI 10.1007/978-3-319-39196-0_2, pp. 7-27.

Heal et al., "Applying graph theory to protein structures: an Atlas of coiled coils", Bioinformatics, 2018, 34(19), 3316-3323.

Lapenta et al., "Coiled coil protein origami: from modular design principles towards biotechnological applications", Chem. Soc. Rev., 2018, 47: 3530-3542.

Rhys et al., "Navigating the structural landscape of de novo a-helical bundles", Journal of the American Chemical Society, 2019, 141(22): 8787-8797.

Rink et al., "De Novo Designed α-Helical Coiled-Coil Peptides asScaffolds for Chemical Reactions", Chemistry 2019, 25(7): 1665-1677, abstract only.

Roybal et al., "Precision Tumor Recognition by T Cells With Combinatorial Antigen-Sensing Circuits", Cell, 2016, 164: 770-779.

Slope et al., "De Novo Design of Xeno-Metallo Coiled Coils", Chemistry—An Asian Journal, 2016, 11(5): 660-666. https://doi.org/10.1002/asia.201501173.

Son et al., "Design patterns for engineering genetic stability", Curr Opin Biomed Eng., Sep. 2021, 19: doi:10.1016/j.cobme.2021.100297, 13 pages.

Stone et al., "Context-dependent redesign of robust synthetic gene circuits", Trends in Biotechnology, Jul. 2024, 42 (7): 895-909.

Thomas et al., "De Novo-Designed α-Helical Barrels as Receptors forSmall Molecules", ACS Synth Biol., Jul. 2018, 7 (7): 1808-1816, abstract only.

Truebestein et al., "Coiled-coils: The long and short of it", Bioessays, 2016, 38: 903-916,.

Varshavsky, "N-degron and C-degron pathways of protein degradation", PNAS, Jan. 2019, 116(2): 358-366.

Wood et al., "Tools for Protein Science, CCBuilder 2.0: Powerful and accessible coiled-coil modeling", Protein Science, 2017, vol. 00:00-00, pp. 1-9.

Cromm et al., "Targeted Protein Degradation: from Chemical Biology to Drug Discovery", Cell Chemical Biology, 2017, 24: 1181-1190.

Faden et al., "Phenotypes on demand via switchable target protein degradation in multicellular organisms", Nature Communications, 2016, 7:12202, 15 pages.

Furukawa et al., "Synthetic biology: lessons from engineering yeast MAPK signalling pathways", Molecular Microbiology, 2013, 88(1): 5-19.

Mcisaac et al., "Fast-acting and nearly gratuitous induction of gene expression and protein depletion in Saccharomyces cerevisiae", Molecular Biology of the Cell, 2011, 22: 4447-4459.

Taxis et al., "Efficient protein depletion by genetically controlled deprotection of a dormant N-degron", Molecular Systems Biology, 2009, 5:267, 7 pages.

Trost et al., "Regulated protein depletion by the auxin-inducible degradation system in Drosophila melanogaster", FLY, 2016, 10(1): 35-46.

Gao et al., "Programmable protein circuits in living cells", Science, Sep. 21, 2018, 361(6408): 1252-1258.

Chen et al., "A Barcoding Strategy Enabling Higher-Throughput Library Screening by Microscopy", ACS Synthetic Biology, 2015, 4: 1205-1216.

Elowitz et al., "A synthetic oscillatory network of transcriptional regulators", Nature, Jan. 2000, 403: 335-338.

Fivaz et al., "Specific Localization and Timing in Neuronal Signal Transduction Mediated by Protein-Lipid Interactions", Neuron, Oct. 2003, 40: 319-330.

Gardner et al., "Construction of a genetic toggle switch in Escherichia coli", Nature, Jan. 2000, 403: 339-342.

Landschulz et al., "The Leucine Zipper: A Hypothetical Structure Common to a New Class of DNA Binding Proteins", Science, 1988, 240: 1759-1764.

Teruel et al., "Translocation and Reversible Localization of Signaling Proteins: A Dynamic Future for Signal Transduction", Cell, Oct. 2000, 103: 181-184.

* cited by examiner

Native Input
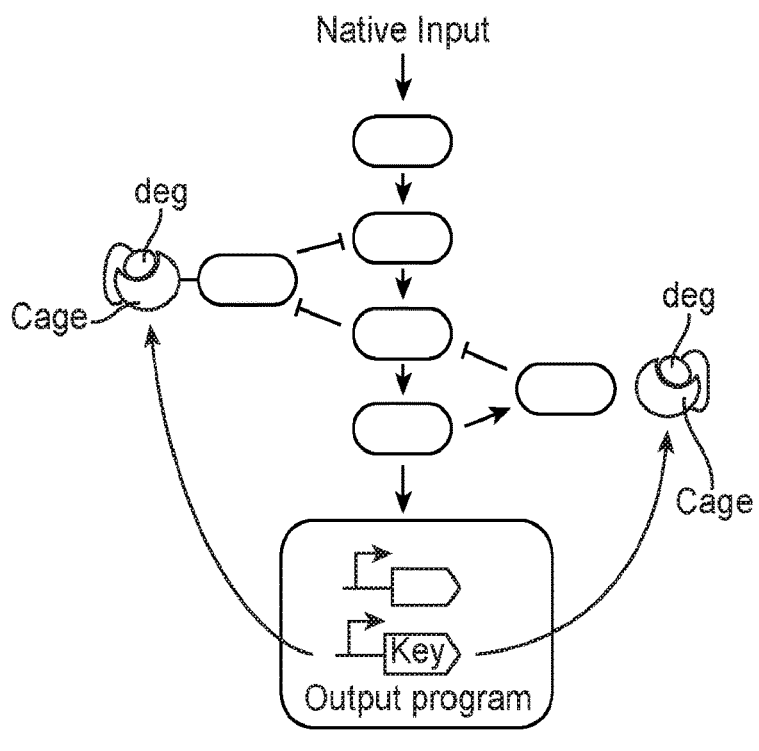
FIG. 5
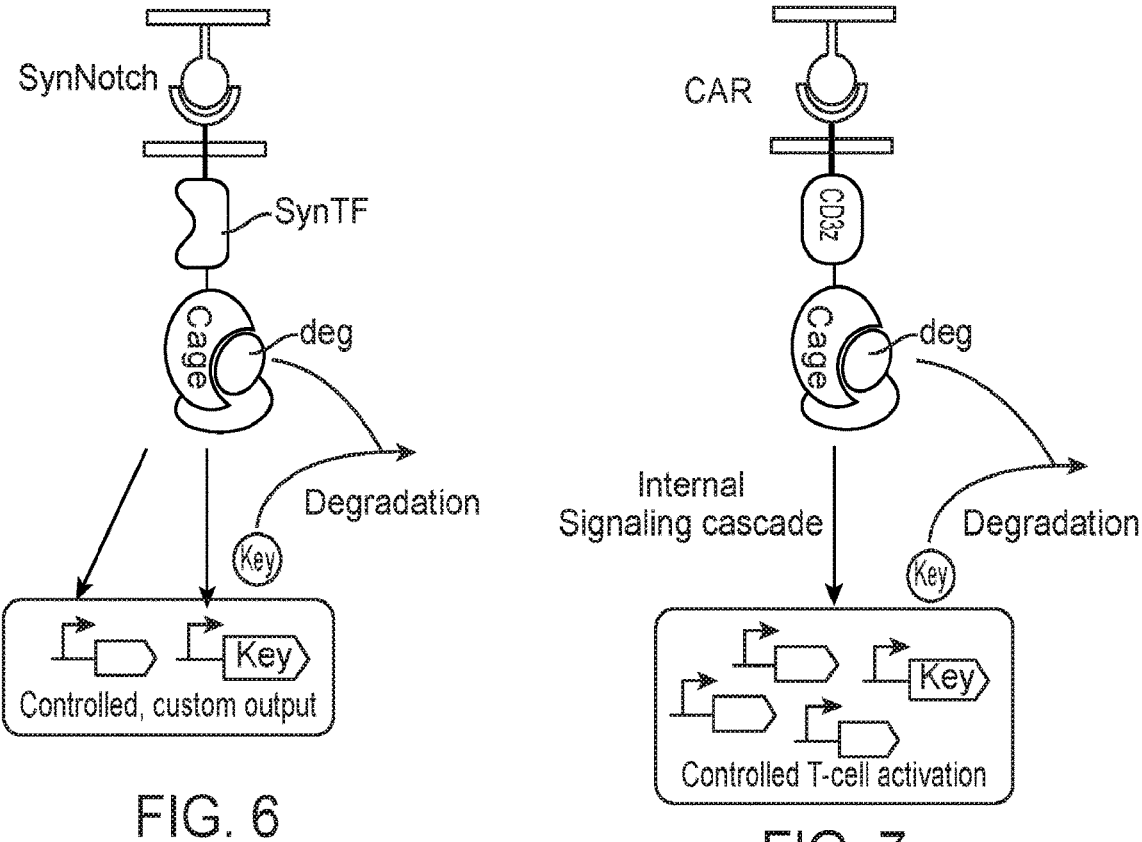
FIG. 6
FIG. 7

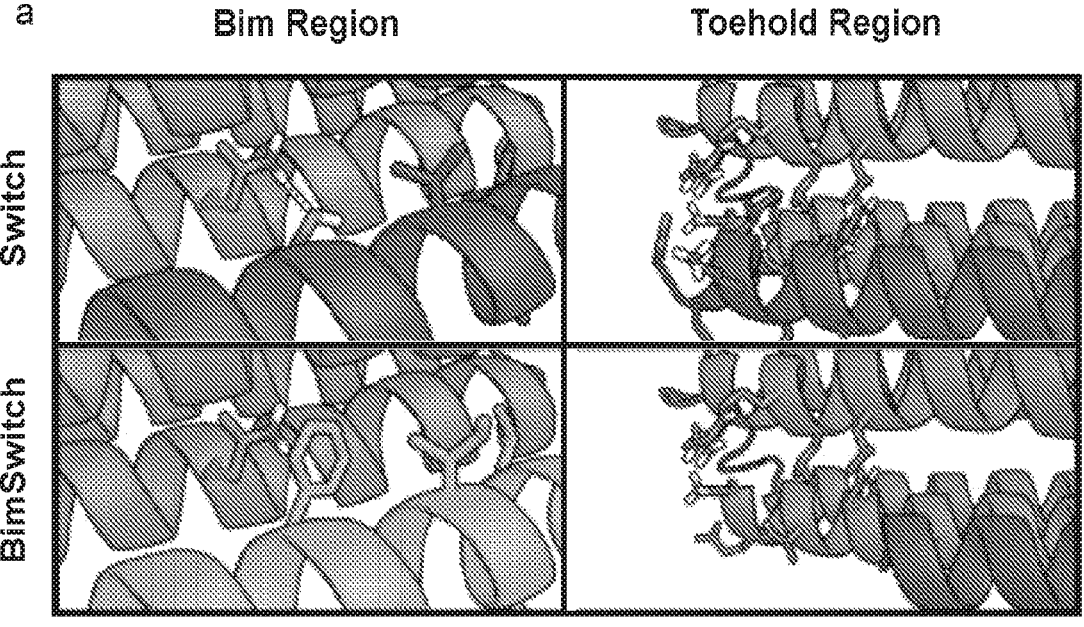
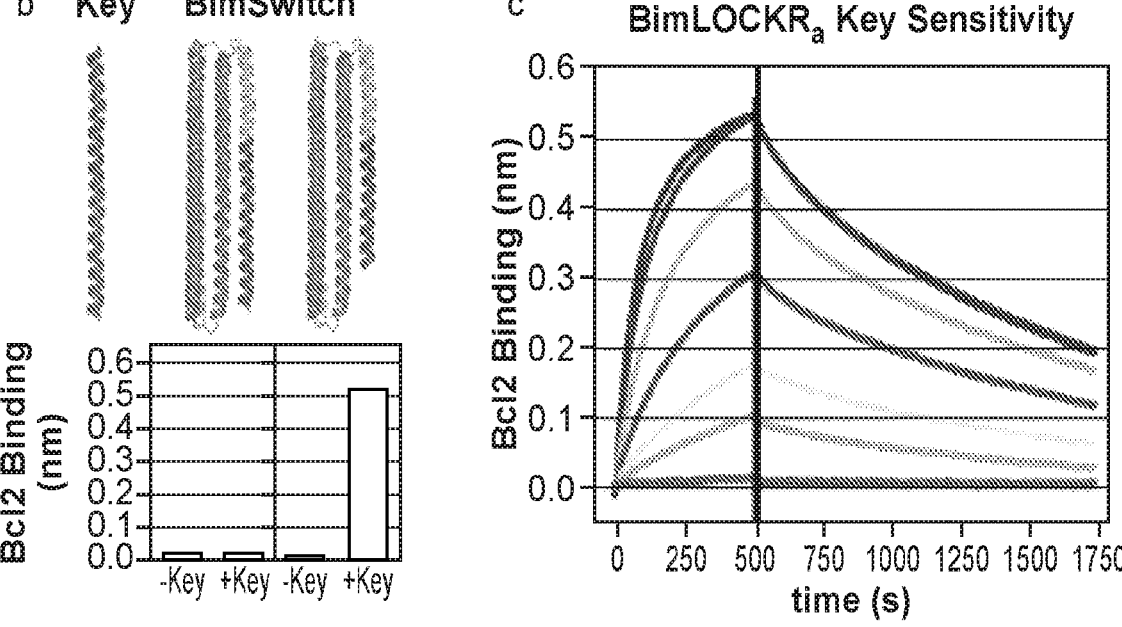
FIG. 11

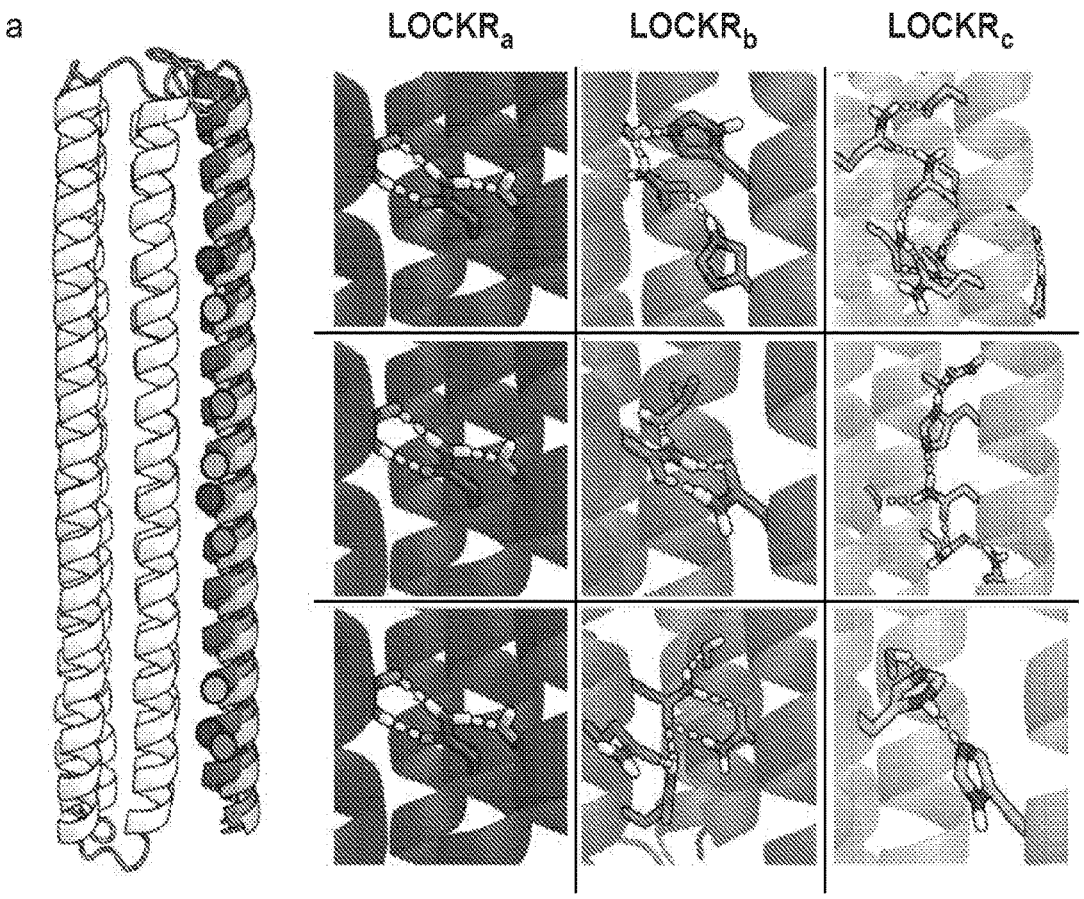
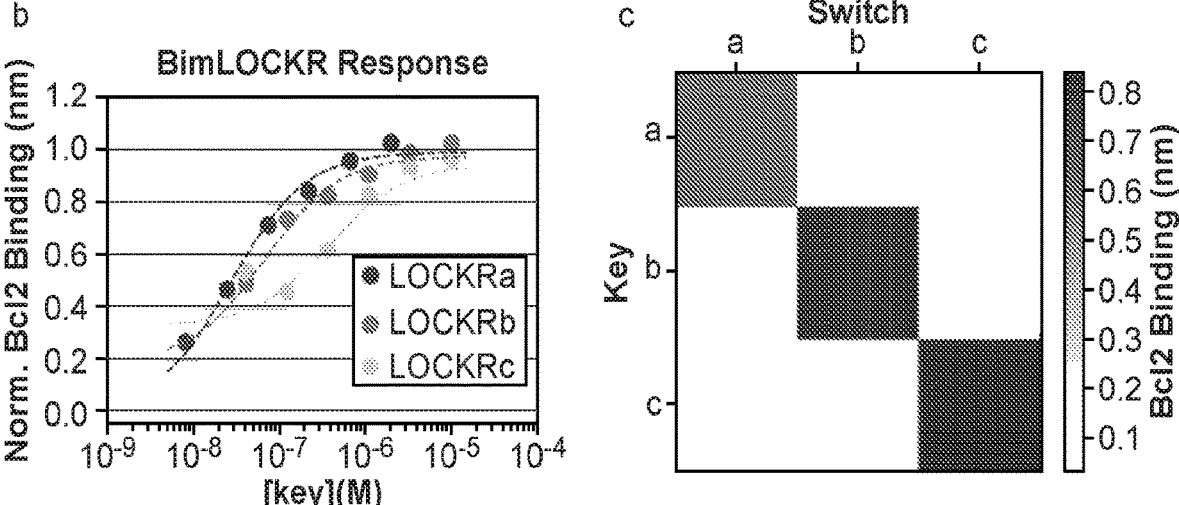
FIG. 12 a
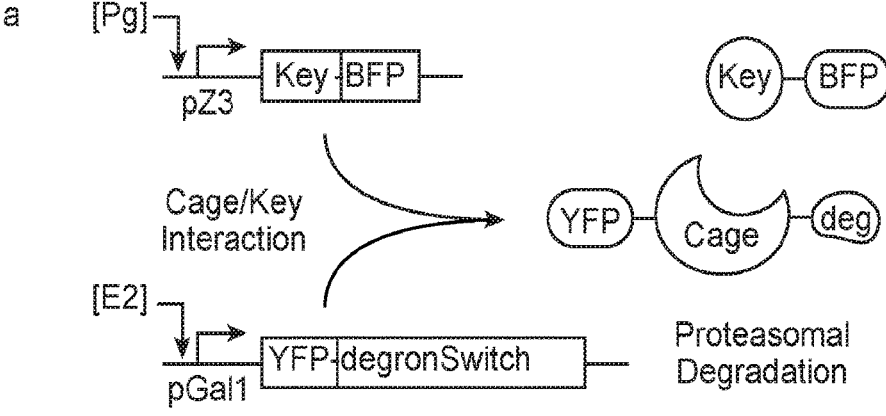
b
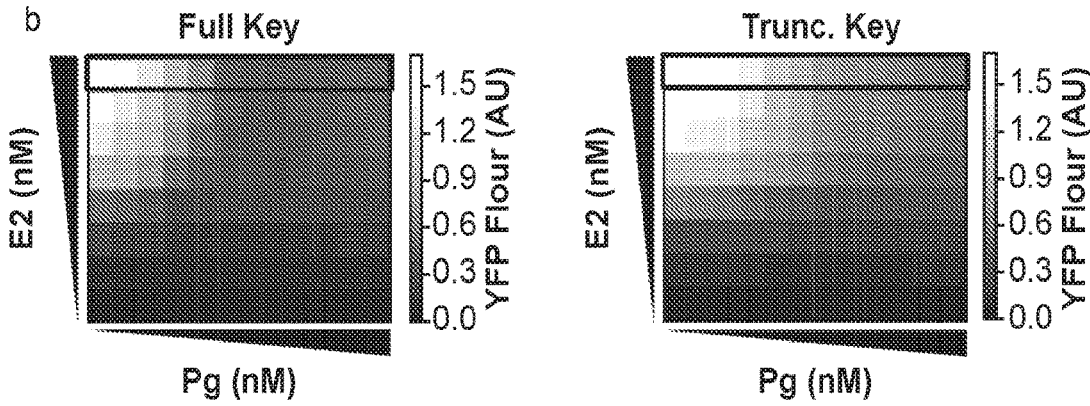
c
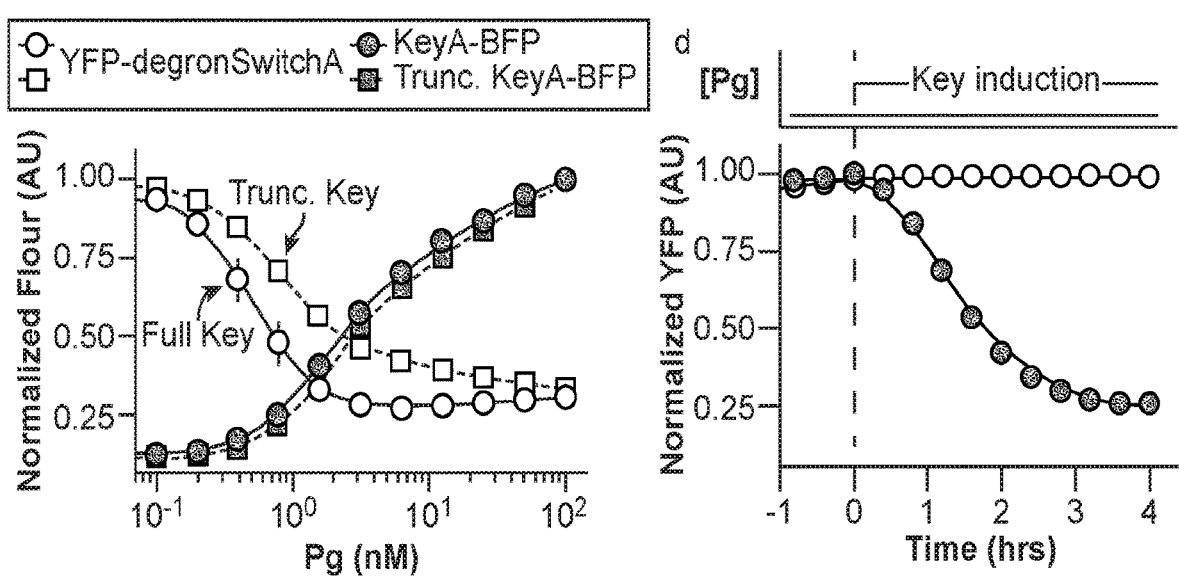
d
FIG. 13

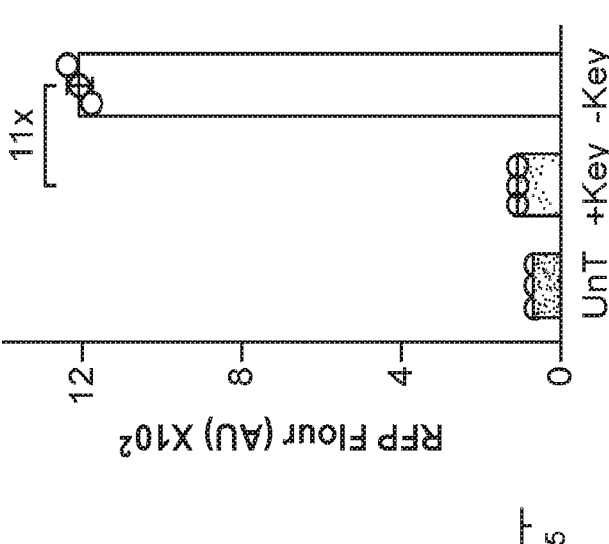
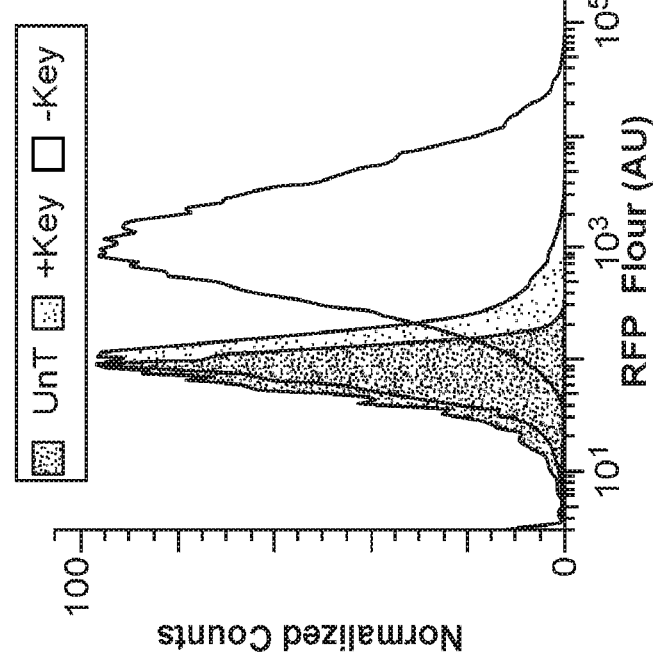
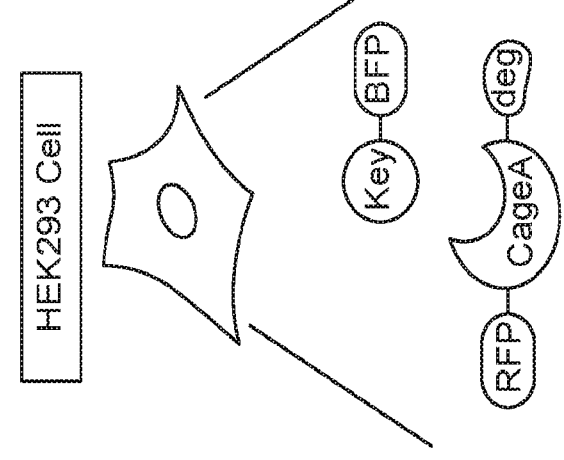
FIG. 13 (Cont. 1)

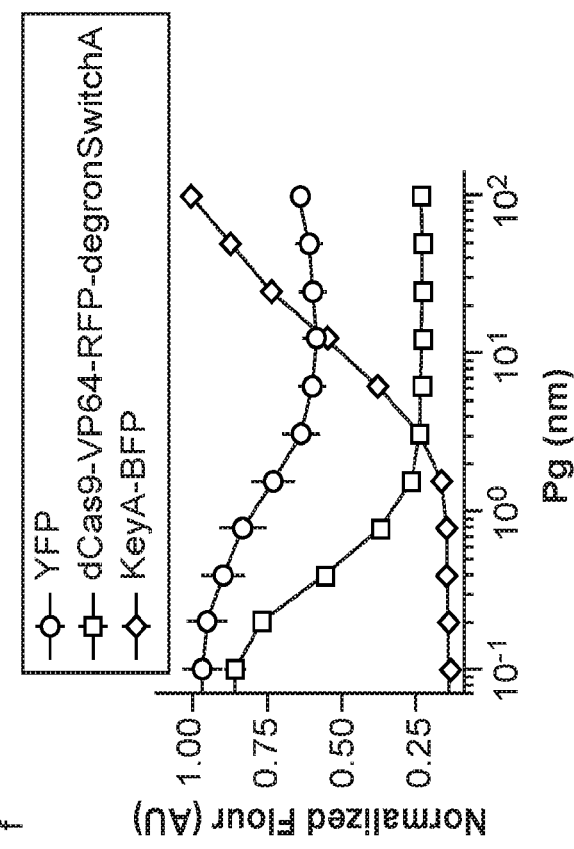
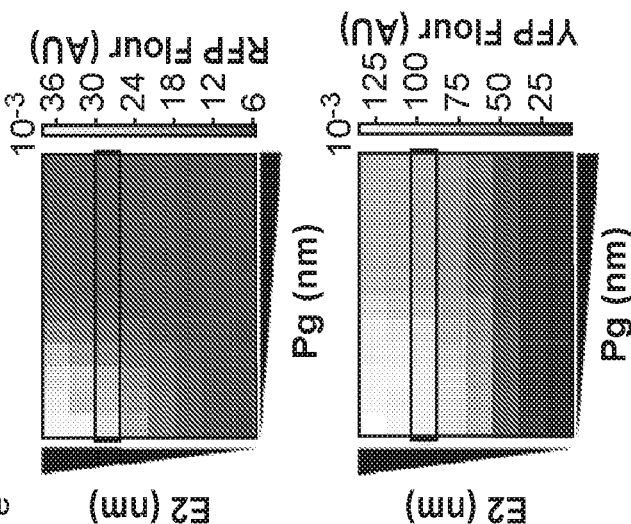
FIG. 14 (Cont.)

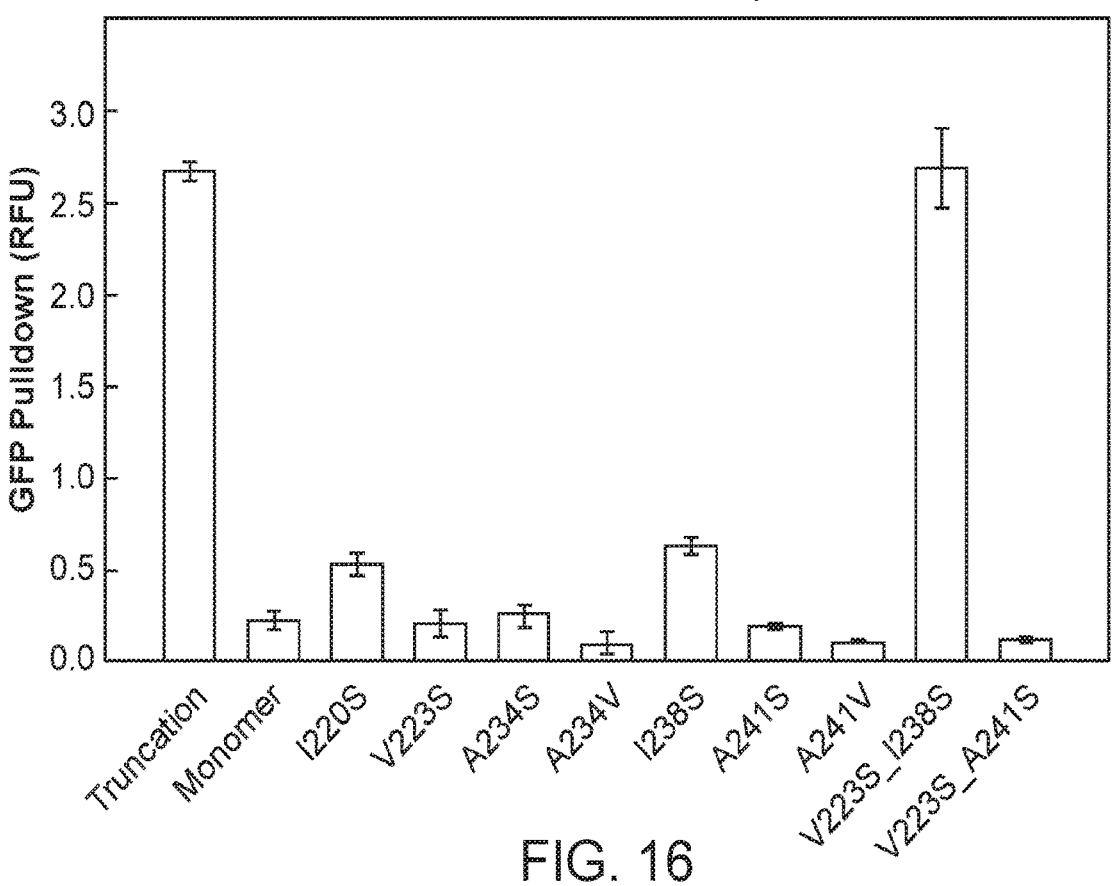
FIG. 16
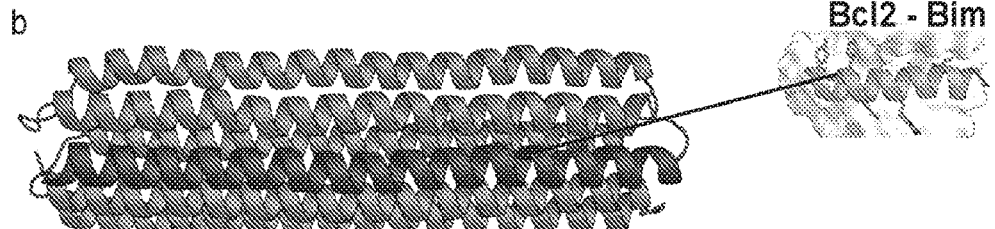
FIG. 17
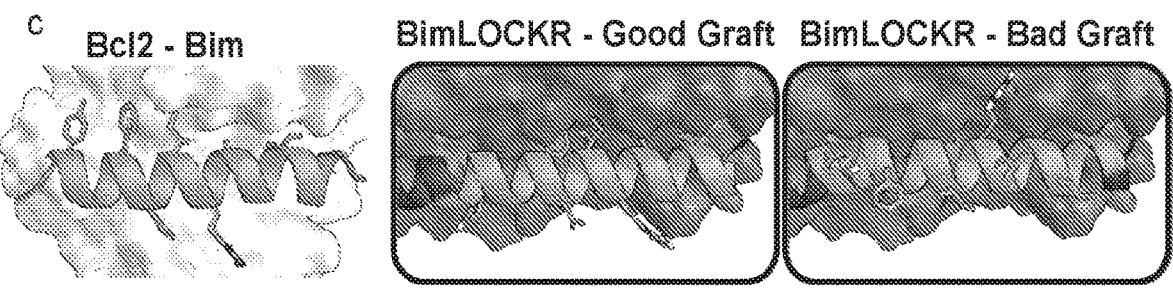

```
LOCKR_0002_0003  DSEELLKRLATESRKIAKKHAKTADDVERKIEKTLRDLRRKIDEAEKQAKKTEDDS
                 | | | | | | | | | | | | | | | | | | | | | | | | | | | | | | | | | | | | | | | | | | | | | | | | | | | | | | | | |
LOCKR_0002_0003  DSEELLKRLATESRKIAKKHAKTADDVERKIEKTLRDLRRKIDEAEKQAKKTEDDS
Score=272

LOCKR_0002_0003  DSEELLKRLATESRKIAKKHAKTADDVERKIEKTLRDLRRKIDEAEKQAKKTEDDS--------
                 | | | | | | | | | | | | | | | | | | | | | | | | | | | | | | | | | | | | | | | | | | | | | | | | | | | | | | | | | | | |
LOCKR_0007_0001  --------SSKELKDIATEAAKTLKKIQDDIEREAKKVEEEYEEKLKKSKKHADDVRKRLTDIS
Score=59

LOCKR_0002_0003  --DSEELLKRLATESRKIAKKHAKTADDVERKIEKTLRDLRRKIDEAEKQAKKTEDDS
                 | | | | | | | | | | | | | | | | | | | | | | | | | | | | | | | | | | | | | | | | | | | | | | | | | | | | | | |
LOCKR_0013_0005  DKKLLDDVKETLKEIAKTAKRIVEEAEKTARKIAKEAKDLARKSKRHAKEQQKTTS--
Score=63

LOCKR_0002_0003  DSEELLKRLATESRKIAKKHAKTADDVERKIEKTLRDLRRKIDEAEKQAKKTEDDS-
                 | | | | | | | | | | | | | | | | | | | | | | | | | | | | | | | | | | | | | | | | | | | | | | | | | | | | | | | | |
LOCKR_0013_0010  -DREALKKVKRTLTELAKTAEKIAQDANRTHKRLADEARKLLEKLKREAKKSQKDIS
Score=69

LOCKR_0002_0003  DSEELLKRLATESRKIAKKHAKTADDVERKIEKTLRDLRRKIDEAEKQAKKTEDDS-
                 | | | | | | | | | | | | | | | | | | | | | | | | | | | | | | | | | | | | | | | | | | | | | | | | | | | | | | | | | | |
LOCKR_0013_0014  -DKELLDTVKKILEDILRTAQKIADDTSRILERILREHEKLQRKLQEDAKKLEKDIS
Score=63
```

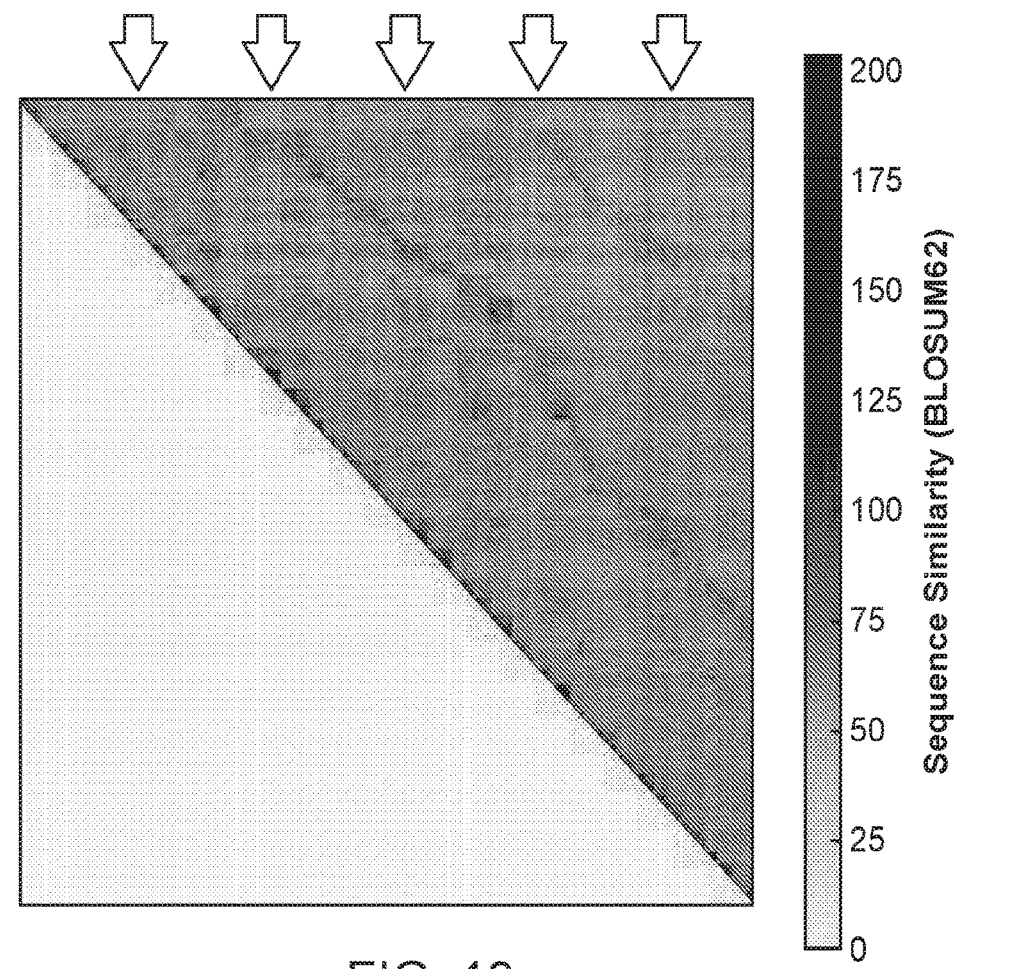

FIG. 19 a
```
cODC Full:     LPMSCAQES
cODC noPro:    L-MSCAQES
cODC CA_only:  ----CA---
``` b      Full                                no Pro a
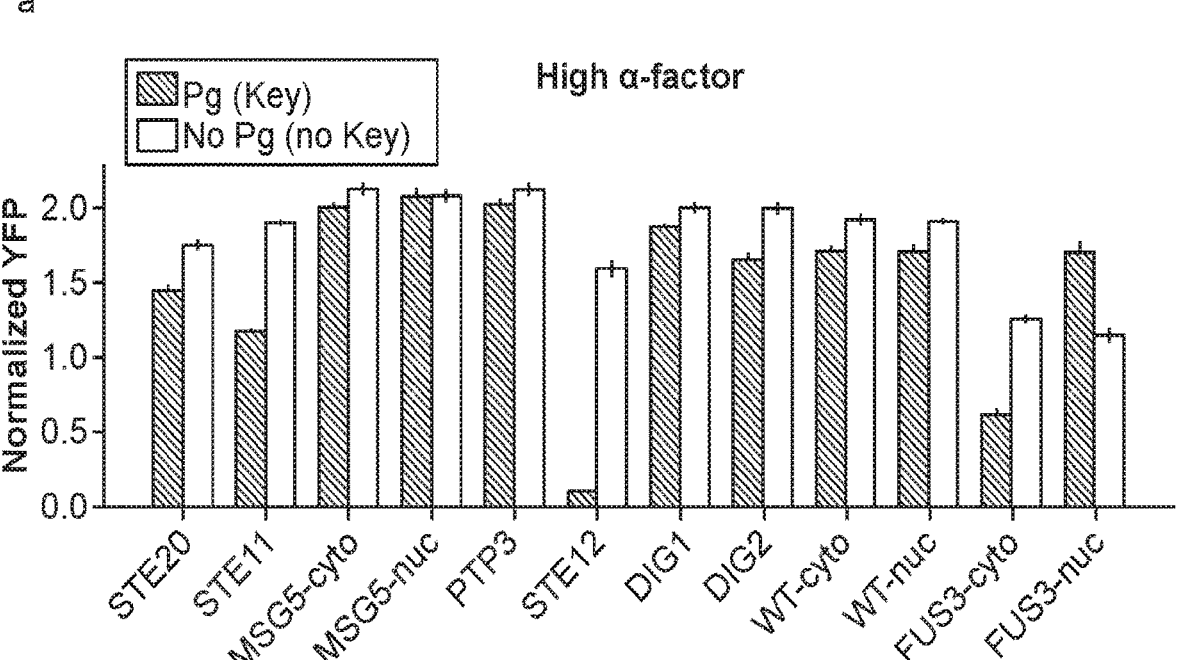
b
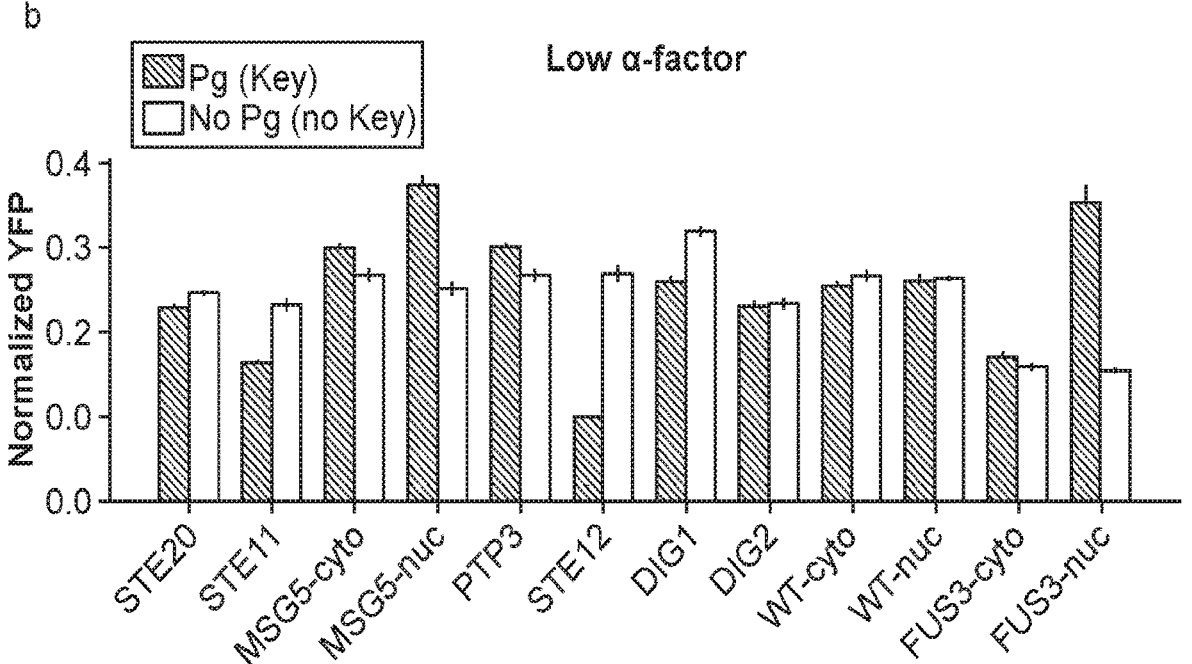
FIG. 29 a
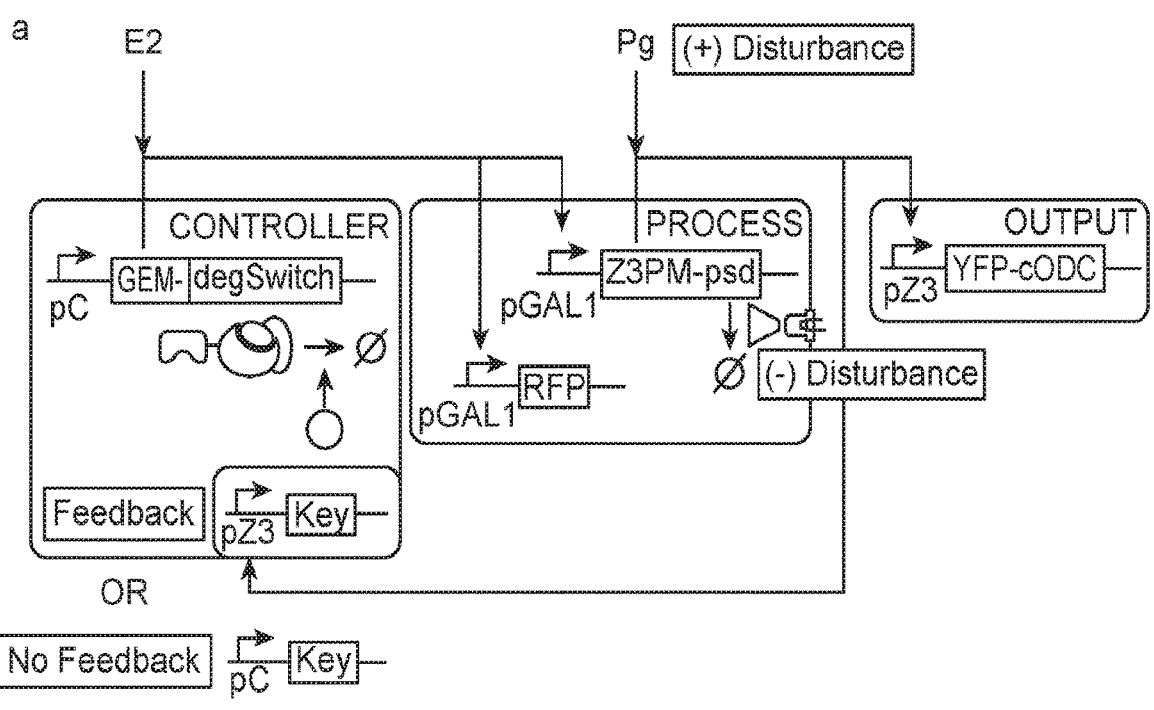
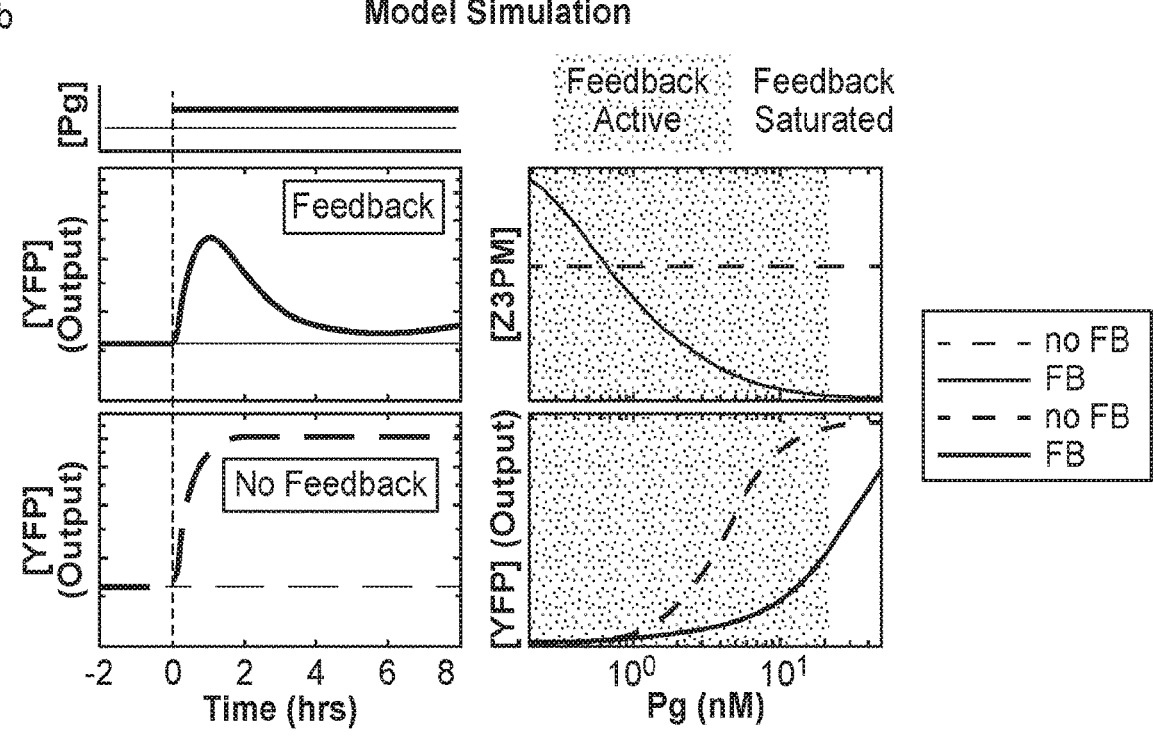
FIG. 31

FIG. 34

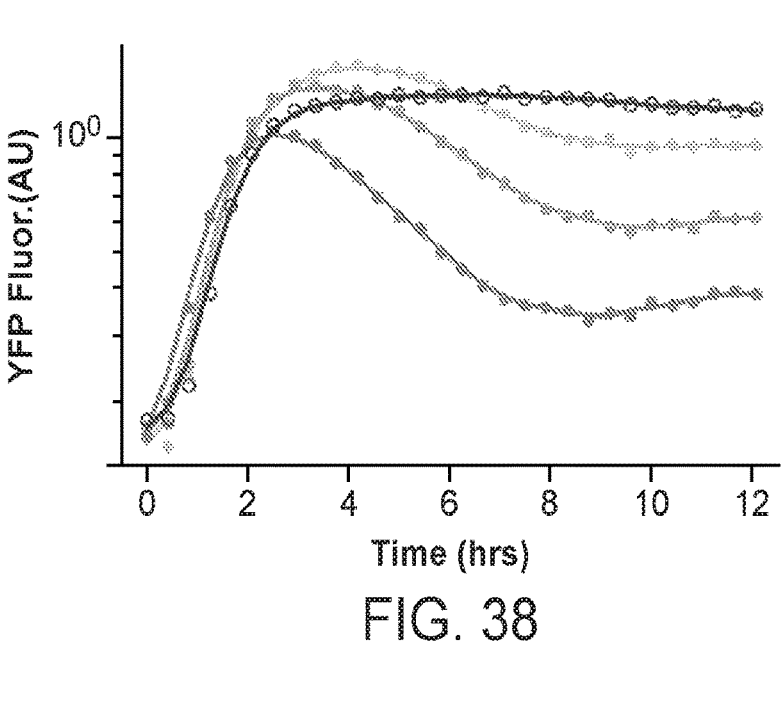
FIG. 38
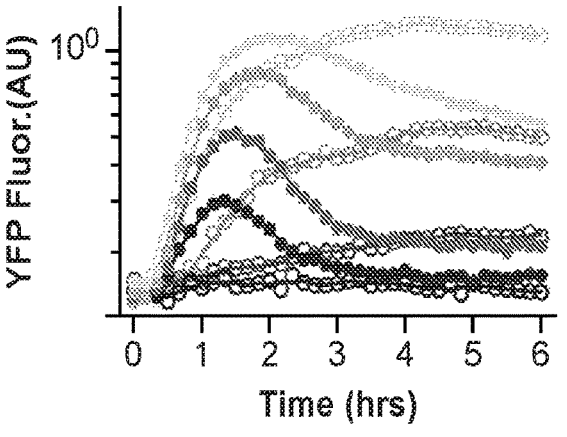
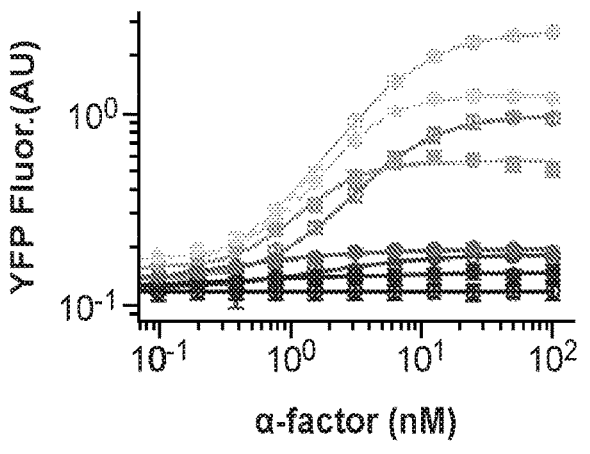
FIG. 39

CAGED-DEGRON-BASED MOLECULAR FEEDBACK CIRCUITS AND METHODS OF USING THE SAME

CROSS-REFERENCING

This application is a § 371 national phase of International Application No. PCT/US2020/012355, filed on Jan. 6, 2020, which claims the benefit of U.S. provisional applications 62/789,418, filed on Jan. 7, 2019, and 62/850,336, filed on May 20, 2019, which applications are incorporated by reference herein.

STATEMENT REGARDING FEDERALLY SPONSORED RESEARCH

This invention was made with government support under Grant No. HR0011-16-2-0045 awarded by the Defense Advanced Research Projects Agency. The government has certain rights in the invention.

INTRODUCTION

Conventionally, desired regulation of cellular activities has been controlled by repeated, user-provided inputs to cellular systems. For example, in the context of some medical treatments, a desired level of a cellular output in a subject over an extended period of time is achieved by repeated cycles of dosing an agent, assessing, re-dosing and re-assessing over the course of treatment. Similarly, in bioproduction applications and metabolic engineering, to coax production cells to output desired yields of product, growth media is repeatedly augmented, e.g., by supplementing growth factors and/or removing toxic byproducts.

Huge advances in the abilities of engineered cells to perform desired tasks, and methods for producing such engineered cells, have been made in recent decades. For example, recent progress in synthetic biology and systems metabolic engineering technologies provide the potential of microbial cell factories for the production of industrially relevant bulk and fine chemicals from renewable biomass resources in an eco-friendly manner. In addition, designer cell therapies, such as chimeric antigen receptor (CAR) T cell therapies, which may be directed to various user-defined targets, have shown great promise in the clinic and are gaining wide adoption and continued regulatory approval.

Without further user-input, the output of such engineered cells, e.g., as used for various purposes as described above, is constant once administered to a subject or set in motion in a bioreactor. Adjustments to modulate engineered cell output are made using an external input, e.g., in the form of small molecules, or other stimuli or user-performed actions.

SUMMARY

Provided are molecular feedback circuits employing caged-degrons. Aspects of such circuits include the use of a caged-degron to modulate the output of a signaling pathway in a feedback-controlled manner. Also provided are nucleic acids encoding molecular circuits and cells containing such nucleic acids. Methods of using caged-degron-based molecular feedback circuits are also provided, including e.g., methods of modulating a signaling pathway of a cell that include genetically modifying the cell with a caged-degron-based molecular feedback circuit.

BRIEF DESCRIPTION OF THE DRAWINGS

FIG. 5 schematically depicts strategies for negative and positive feedback using a molecular feedback circuit of the present disclosure.

FIG. 6 schematically depicts a molecular feedback circuit strategy employing a synthetic Notch receptor as described herein.

FIG. 7 schematically depicts a molecular feedback circuit strategy employing a chimeric antigen receptor (CAR) as described herein.

FIG. 12 depicts aspects related to design and validation of orthogonal BimLOCKR. a, Left: LOCKR in cartoon representation. Cage in white with three different latches superimposed and hydrogen bond networks marked by colored markers. Right: Design models of hydrogen-bond networks across the orthogonal LOCKR interfaces corresponding to the colored markers on the left. b, BimSwitches binding to Bcl2 in response to its cognate key, measured by biolayer interferometry (Octet). c, Binding response to Bcl2 from biolayer interferometry experiments for each switch at 250 nM against each key at 5 µM; average of two replicates.

FIG. 16 provides data related to a GFP Plate assay to find mutations for LOCKR.

FIG. 17 demonstrates the caging Bim-related sequences. a) Three Bcl2 binding sequences were grafted onto the latch. aBcl2 is a single helix from a designed Bcl2 binder (pdb: 5JSN) where non Bcl2-interacting residues were reverted back to the standard LOCKR latch sequence, shown as dashes. pBim is the partial Bim sequence where only Bcl2-interacting residues are grafted onto the latch. Bim is the full consensus sequence of the BH3 domain. b) LOCKR (left) with the latch in dark blue. The helical Bim sequence is taken from the Bim/Bcl2 interaction and grafted onto the latch c) Left: Bcl2 (tan) binding to Bim (purple) from pdb:2MV6 with pBim residues shown as sticks. Center: a well caged graft where important binding residues are caged. Right: a poor graft where Bcl2 binding residues are exposed and polar surface residues are against the cage interface.

FIG. 19 depicts sequence alignment of 1504 keys for filtering for orthogonality. From top to bottom SEQ ID NOS. 28214, 28214, 28214, 28215, 28214, 28216, 28214, 28217, 28214, and 28218.

FIG. 29 provides a panel of mating pathway regulators tested with degronLOCKR. degSwitch was fused to the C-terminus of the endogenous copy of each regulator. Key with or without SV40 NLS was expressed using a Pg inducible system. STE20, STE11, and PTP3 were degraded using cytoplasmic key (Key-CFP), and STE12, DIG1 and DIG2 were degraded using nuclear key (Key-CFP-NLS). MSG5 and FUS3 were degraded using either cytoplasmic (cyto) or nuclear (nuc) key. Cells were induced with (a) 100 nM (high) or (b) 1 nM (low) α-factor and 50 nM or 0 nM Pg and grown for four hours before YFP fluorescence was measured using a flow cytometer. Data represent mean±s.d. of three biological replicates.

FIG. 34 depicts circuit behavior as a function of E2 for a fixed dose of Pg.

FIG. 38 demonstrates that tuning feedback strength changes dynamic behavior of circuit output.

FIG. 39 depicts combinatorial tuning of synthetic feedback in mating pathway.

SEQUENCE LISTING

A Sequence Listing is provided herewith as a text file, "UCSF-578WO_SF2019-073-3_SeqList_ST25" created on Jan. 3, 2020, and having a size of 34,282 KB. The contents of the text file are incorporated by reference herein in their entirety.

SEQ ID NOS. 63-1169 are examples of degron-LOCKR cage polypeptide sequences.

SEQ ID NOS. 1170-13903 are examples of Key polypeptide sequences.

SEQ ID NOS. 13904-28210 are examples of Cage polypeptide sequences.

Figure 40:
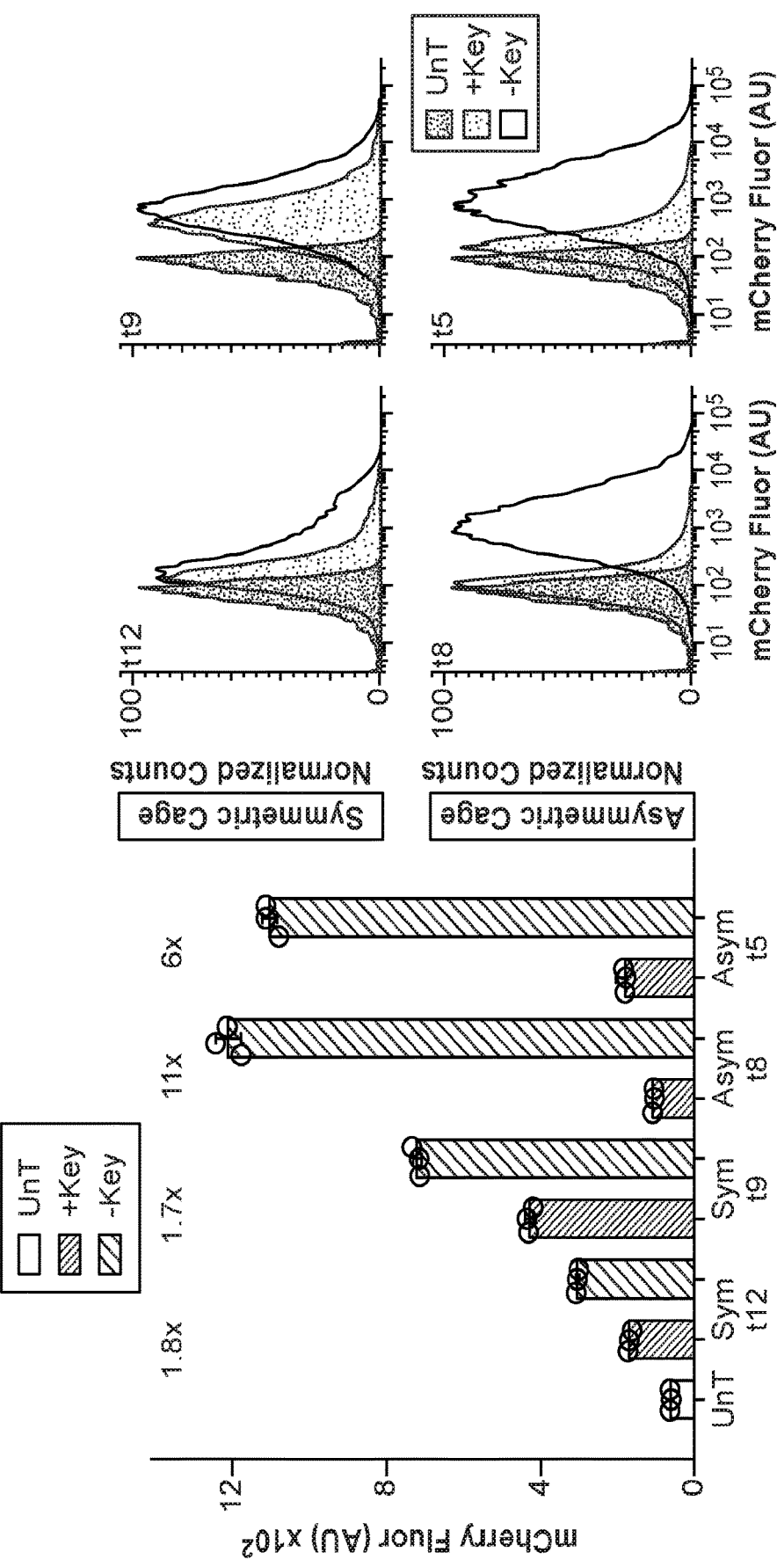
FIG. 40 provides a comparison of different degronSwitch variants in HEK293T cells.
Figure 41:
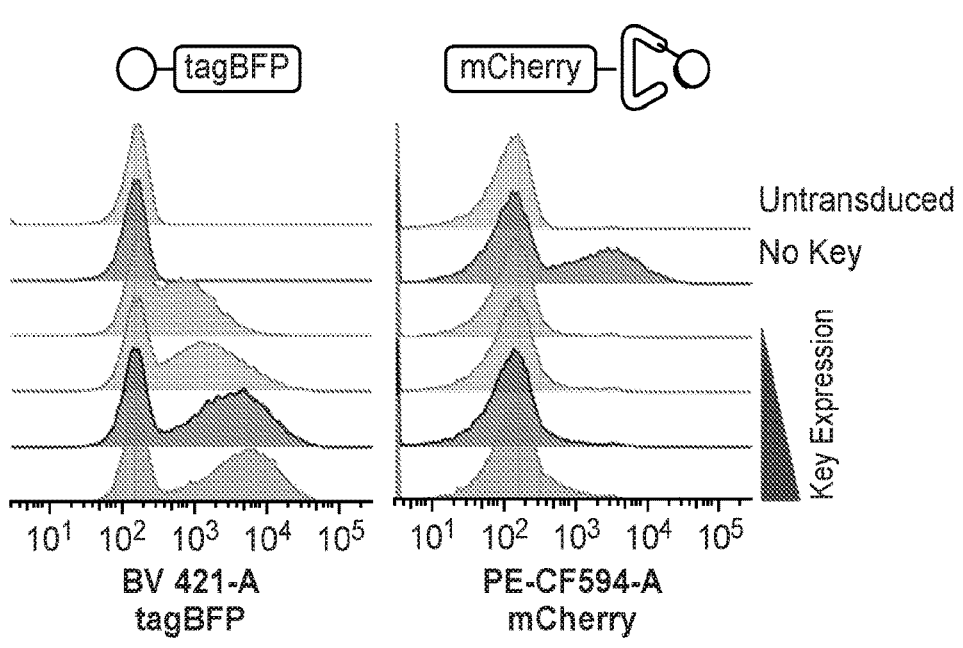
FIG. 41 shows fluorescence histograms of tagBFP (left panel) and fluorescence histograms of mCherry (right panel).
Figure 42:
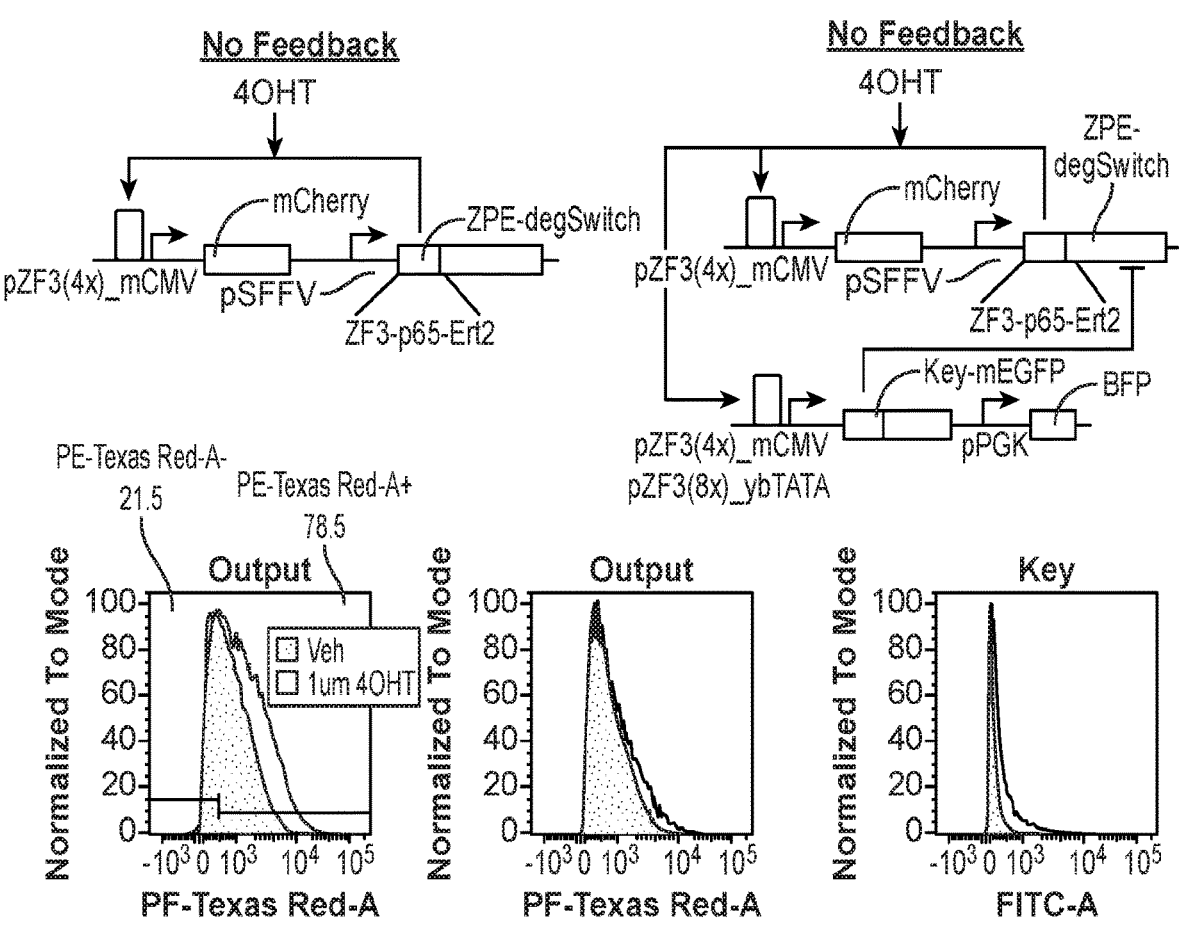
FIG. 42 shows no feedback and feedback circuit diagrams (top panels) and representative histograms comparing output and key fluorescence for both circuits in the presence and absence of drug (bottom panels).

FIGS. 40, 41 and 42 of provisional application Ser. No. 62/850,336, filed on May 20,2019, disclose SEQ ID NOS. 63-1169, 1170-13903 and 13904-28210, respectively, and are incorporated by reference herein for the disclosure of each sequence, including any annotation associated therewith.

Definitions

The terms "synthetic", "chimeric" and "engineered" as used herein generally refer to artificially derived polypeptides or polypeptide encoding nucleic acids that are not naturally occurring. Synthetic polypeptides and/or nucleic acids may be assembled de novo from basic subunits including, e.g., single amino acids, single nucleotides, etc., or may be derived from pre-existing polypeptides or polynucleotides, whether naturally or artificially derived, e.g., as through recombinant methods. Chimeric and engineered polypeptides or polypeptide encoding nucleic acids will generally be constructed by the combination, joining or fusing of two or more different polypeptides or polypeptide encoding nucleic acids or polypeptide domains or polypeptide domain encoding nucleic acids. Chimeric and engineered polypeptides or polypeptide encoding nucleic acids include where two or more polypeptide or nucleic acid "parts" that are joined are derived from different proteins (or nucleic acids that encode different proteins) as well as where the joined parts include different regions of the same protein (or nucleic acid encoding a protein) but the parts are joined in a way that does not occur naturally.

The term "recombinant", as used herein describes a nucleic acid molecule, e.g., a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a protein or polypeptide means a polypeptide produced by expression from a recombinant polynucleotide. The term recombinant as used with respect to a host cell or a virus means a host cell or virus into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "operably linked" refers to a juxtaposition wherein the components so described are in a relationship permitting them to function in their intended manner. For instance, a promoter is operably linked to a coding sequence if the promoter affects its transcription or expression. Operably linked nucleic acid sequences may but need not necessarily be adjacent. For example, in some instances a coding sequence operably linked to a promoter may be adjacent to the promoter. In some instances, a coding sequence operably linked to a promoter may be separated by one or more intervening sequences, including coding and non-coding sequences. Also, in some instances, more than two sequences may be operably linked including but not limited to e.g., where two or more coding sequences are operably linked to a single promoter.

A "biological sample" encompasses a variety of sample types obtained from an individual or a population of individuals and can be used in various ways, including e.g., the isolation of cells or biological molecules, diagnostic assays, etc. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by mixing or pooling of individual samples, treatment with reagents, solubilization, or enrichment for certain components, such as cells, polynucleotides, polypeptides, etc. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples, and cellular samples. Accordingly, biological samples may be cellular samples or acellular samples.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

Polypeptides may be "non-naturally occurring" in that the entire polypeptide is not found in any naturally occurring polypeptide. It will be understood that components of non-naturally occurring polypeptides may be naturally occurring, including but not limited to domains (such as functional domains) that may be included in some embodiments.

A "vector" or "expression vector" is a replicon, such as plasmid, phage, virus, or cosmid, to which another DNA segment, i.e. an "insert", may be attached so as to bring about the replication of the attached segment in a cell.

The terms "domain" and "motif", used interchangeably herein, refer to both structured domains having one or more particular functions and unstructured segments of a polypeptide that, although unstructured, retain one or more particular functions. For example, a structured domain may encompass but is not limited to a continuous or discontinuous plurality of amino acids, or portions thereof, in a folded polypeptide that comprise a three-dimensional structure which contributes to a particular function of the polypeptide. In other instances, a domain may include an unstructured segment of a polypeptide comprising a plurality of two or more amino acids, or portions thereof, that maintains a particular function of the polypeptide unfolded or disordered. Also encompassed within this definition are domains that may be disordered or unstructured but become structured or ordered upon association with a target or binding partner. Non-limiting examples of intrinsically unstructured domains and domains of intrinsically unstructured proteins are described, e.g., in Dyson & Wright. *Nature Reviews Molecular Cell Biology* 6:197-208.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more.

The term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (e.g., rats, mice), lagomorphs (e.g., rabbits), non-human primates, humans, canines, felines, ungulates (e.g., equines, bovines, ovines, porcines, caprines), etc.

A "therapeutically effective amount" or "efficacious amount" refers to the amount of an agent, or combined amounts of two agents, that, when administered to a mammal or other subject for treating a disease, is sufficient to effect such treatment for the disease. The "therapeutically effective amount" will vary depending on the agent(s), the disease and its severity and the age, weight, etc., of the subject to be treated.

The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. The term CAR is not limited specifically to CAR molecules but also includes CAR variants. CAR variants include split CARs wherein the extracellular portion (e.g., the ligand binding portion) and the intracellular portion (e.g., the intracellular signaling portion) of a CAR are present on two separate molecules. CAR variants also include ON-switch CARs which are conditionally activatable CARs, e.g., comprising a split CAR wherein conditional hetero-dimerization of the two portions of the split CAR is pharmacologically controlled (e.g., as described in PCT publication no. WO 2014/127261 A1 and US Patent Application No. 2015/0368342 A1, the disclosures of which are incorporated herein by reference in their entirety). CAR variants also include bispecific CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. CAR molecules and derivatives thereof (i.e., CAR variants) are described, e.g., in PCT Application No. US2014/016527; Fedorov et al. Sci Transl Med (2013); 5(215):215ra172; Glienke et al. Front Pharmacol (2015) 6:21; Kakarla & Gottschalk 52 Cancer J (2014) 20(2):151-5; Riddell et al. Cancer J (2014) 20(2):141-4; Pegram et al. Cancer J (2014) 20(2):127-33; Cheadle et al. Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety. Useful CARs also include the anti-CD19-4-1BB-CD3ζ CAR expressed by lentivirus loaded CTL019 (Tisagenlecleucel-T) CAR-T cells as commercialized by Novartis (Basel, Switzerland). The terms "chimeric antigen receptor" and "CAR" also include SUPRA CAR and PNE CAR (see, e.g., Cho et al Cell 2018 173: 1426-1438 and Rodgers et al, Proc. Acad. Sci. 2016 113: E459-468).

The terms "T cell receptor" and "TCR" are used interchangeably and will generally refer to a molecule found on the surface of T cells, or T lymphocytes, that is responsible for recognizing fragments of antigen as peptides bound to major histocompatibility complex (MHC) molecules. The TCR complex is a disulfide-linked membrane-anchored heterodimeric protein normally consisting of the highly variable alpha (α) and beta (β) chains expressed as part of a complex with CD3 chain molecules. Many native TCRs exist in heterodimeric αβ or γδ forms. The complete endogenous TCR complex in heterodimeric αβ form includes eight chains, namely an alpha chain (referred to herein as TCRα or TCR alpha), beta chain (referred to herein as TCRβ or TCR beta), delta chain, gamma chain, two epsilon chains and two zeta chains. In some instance, a TCR is generally referred to by reference to only the TCRα and TCRβ chains, however, as the assembled TCR complex may associate with endogenous delta, gamma, epsilon and/or zeta chains an ordinary skilled artisan will readily understand that reference to a TCR as present in a cell membrane may include reference to the fully or partially assembled TCR complex as appropriate.

Recombinant or engineered individual TCR chains and TCR complexes have been developed. References to the use of a TCR in a therapeutic context may refer to individual recombinant TCR chains. As such, engineered TCRs may include individual modified TCRα or modified TCRβ chains as well as single chain TCRs that include modified and/or unmodified TCRα and TCRβ chains that are joined into a single polypeptide by way of a linking polypeptide.

The terms "synthetic Notch receptor", "synNotch" and "synNotch receptor", used interchangeably herein, refer to recombinant chimeric binding-triggered transcriptional switches that include at least: an extracellular binding domain, a portion of a Notch receptor that includes at least one proteolytic cleavage site, and an intracellular domain that provides a signaling function. SynNotch polypeptides, the components thereof and methods of employing the same, are described in U.S. Pat. Nos. 9,834,608 and 9,670,281, as well as, Toda et al., Science (2018) 361(6398):156-16; Roybal & Lim, Annu Rev Immunol. (2017) 35:229-253; Lim & June Cell. (2017) 168(4):724-740; Roybal et al. Cell. (2016) 167(2):419-432.e16; Roybal et al. Cell. (2016) 164

(4):770-9; and Morsut et al. Cell. (2016) 164(4):780-91; the disclosures of which are incorporated herein by reference in their entirety.

As used herein, a "bioactive peptide" is any peptide of any length or amino acid composition that is capable of selectively binding to a defined target (i.e.: capable of binding to an "effector" polypeptide). Such bioactive peptides may comprise peptides of all three types of secondary structure in an inactive conformation: alpha helix, beta strand, and loop. The polypeptides of this aspect can be used to control the activity of a wide range of functional peptides. The ability to harness these biological functions with tight, inducible control is useful, for example, in engineering cells (inducible activation of function, engineering complex logic behavior and circuits, etc.), developing sensors, developing inducible protein-based therapeutics, and creating new biomaterials.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a circuit" includes a plurality of such circuits and reference to "the nucleic acid" includes reference to one or more nucleic acids and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

As summarized above, the present disclosure provides molecular feedback circuits employing caged-degrons. Aspects of such circuits include the use of a caged-degron to modulate the output of a signaling pathway in a feedback-controlled manner. Nucleic acids encoding such molecular circuits, cells containing the molecular circuits and/or nucleic acids, as well as methods of using the subject molecular circuits, are also provided.

Molecular Circuits

Molecular circuits of the present disclosure may, in some instances and in whole or in part, be encoded by nucleic acid sequences. Such circuits may, in some instances, be present and/or configured in expression vectors and/or expression cassettes. The subject nucleic acids of the present circuits may, in some instances, be contained within a vector, including e.g., viral and non-viral vectors. Such circuits may, in some instances, be present in cells, such as immune cells, stem cells, etc., or may be introduced into cells by various means, including e.g., through the use of a viral vector. Cells may, in some instances, be genetically modified to contain and/or encode a subject circuit, where such modification may be effectively permanent (e.g., integrated) or transient as desired.

Circuits of the present disclosure, the components of which are modular, may include a signaling protein that includes a caged degron. As used herein, the term "signaling protein" generally refers to a protein of a signaling pathway, including natural and synthetic signaling pathways, described in more detail below. Any convenient and appropriate signaling protein of any convenient signaling pathway may be employed. Generally, signaling proteins include proteins that may be activated by an input of the signaling pathway with which the signaling protein is associated. A signaling pathway may generate an output that is dependent upon, or at least influenced by, the function of the signaling protein. Such outputs may be a direct or indirect result of the response of the signaling protein to the input. Useful signaling proteins include members from any convenient and appropriate point a signaling pathway, including input-receiving members, intermediate members, and output-producing members.

By "input-receiving members", as used herein, is generally meant the initial component of a signaling pathway that receives an input to initiate signaling along the pathway. Examples of input-receiving members include but are not limited to e.g., extracellular receptors (e.g., G protein-coupled receptors, protein kinases, integrins, toll-like receptors, ligand-gated ion channels, and the like) and intracellular receptors (e.g., nuclear receptors, cytoplasmic receptors, etc.). In some instances, an input-receiving member may be a protein that directly binds an input of a signaling pathway, such as a ligand input of a signaling pathway. In some instances, a signaling protein that includes a caged degron in a circuit of the present disclosure may be an input-receiving member. In some instances, a signaling protein that includes a caged degron in a circuit of the present disclosure may not be an input-receiving member, e.g., it may be an intermediate member or an output-producing member.

By "intermediate member", as used herein, is generally meant a component of a signaling pathway that is required for, or at least involved in, signal transduction but does not directly receive the initial input or directly produce or cause the final output of the signaling pathway. Examples of intermediate members of a signaling pathway include but are not limited to e.g., enzymes, binding partners, protein complex subunits, scaffold proteins, transport proteins, co-activators, co-repressors, and the like. In some instances, a signaling protein that includes a caged degron in a circuit of the present disclosure may be an intermediate member. In some instances, a signaling protein that includes a caged degron in a circuit of the present disclosure may not be an intermediate member, e.g., it may be an input-receiving member or an output-producing member.

By "output-producing member", as used herein, is generally meant a component of a signaling pathway that directly produces an output of the signaling pathway or otherwise causes the output of the signaling pathway to occur. Examples of output-producing members of a signaling pathway include but are not limited to e.g., DNA binding proteins, such as e.g., transcription factors, enzymes, and the like. In some instances, a signaling protein that includes a caged degron in a circuit of the present disclosure may be an output-producing member. In some instances, a signaling protein that includes a caged degron in a circuit of the present disclosure may not be an output-producing member, e.g., it may be an input-receiving member or an intermediate member.

Figure 1:
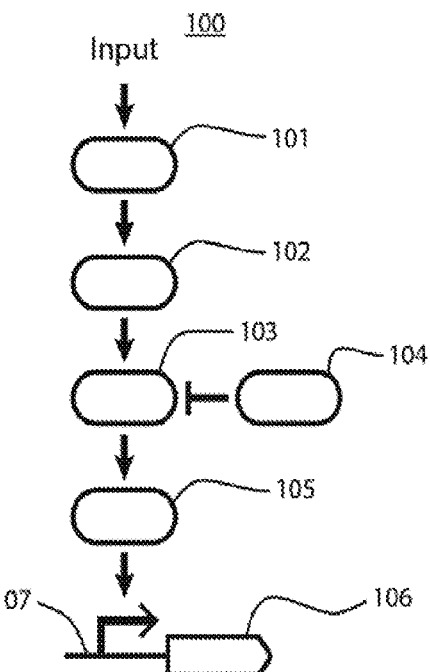
FIG. 1 schematically depicts a signaling pathway as described herein.

A schematized example of a signaling pathway is depicted in FIG. 1. As shown, the signaling pathway includes an input 100 that activates an input-receiving member 101 of the pathway. Activation of the input-receiving member 101 positively regulates a first intermediate member 102 of the pathway, which positively regulates a second intermediate member 103 of the pathway. In the pathway depicted, the second intermediate member 103 is negatively regulated by a third intermediate member 104. In the absence of inhibition by the third intermediate member 104, the second intermediate member 103 positively regulates an output-producing member 105 of the pathway. Thus, in the presence of activation by the second intermediate member 103, the output-producing member 105 is active and binds a regulatory region 107 operably linked to a sequence 106 encoding an output of the signaling pathway.

Useful signaling proteins may be a regulator of one or more signaling pathways with which the signaling protein is associated, including where the signaling protein may be a negative regulator of a signaling pathway or a positive regulator of a signaling pathway. Accordingly, molecular feedback circuits of the present disclosure include positive feedback circuits and negative feedback circuits.

For example, in some instances, a signaling protein employed in a circuit of the present disclosure may, when activated, drive an output of the signaling pathway. As such, uncaging of a caged degron, resulting in degradation of the signaling protein, may negatively regulate the output of the signaling pathway thus resulting in negative feedback. In some instances, a signaling protein employed in a circuit of the present disclosure may, when activated, inhibit an output of the signaling pathway. As such, uncaging of a caged degron, resulting in degradation of the signaling protein, may positively regulate the output of the signaling pathway thus resulting in positive feedback.

Figure 2:
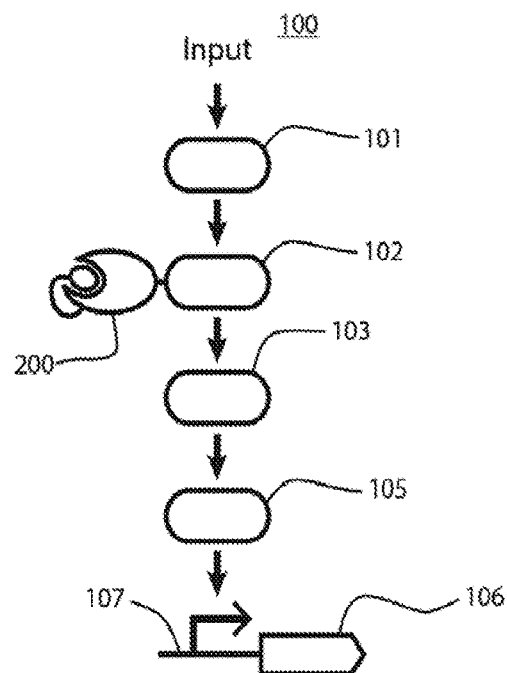
FIG. 2 schematically depicts a signaling pathway with a caged degron attached to a positive regulatory member of the signaling pathway of FIG. 1 as described herein.

FIG. 2 depicts the signaling pathway presented in FIG. 1 where a first intermediate signaling member 102, that positively regulates the pathway, has been modified to include a caged degron 200. Thus, when the caged degron 200 remains caged, signaling through the signaling pathway proceeds from the input 100, through the input-receiving member 101, to the first intermediate signaling member 102, which positively regulates downstream components of the pathway, such that, in the absence of inhibition by the third intermediate member (not pictured), the output-producing member 105 drives the output of the signaling pathway, depicted as expression of the product encoded by the sequence 106.

Figure 3:
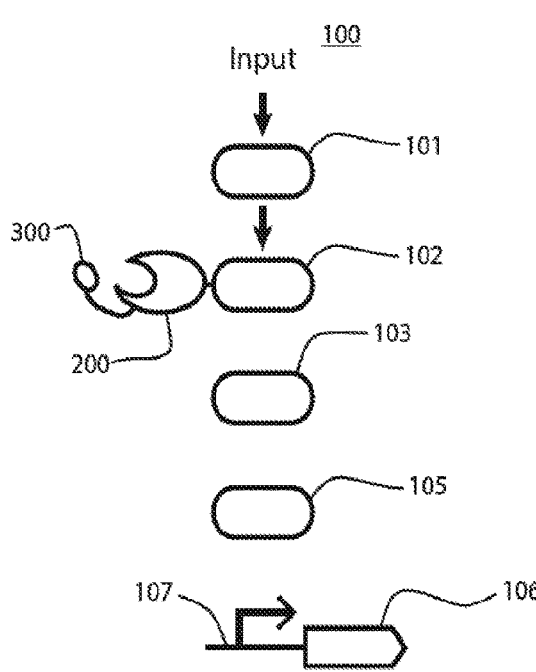
FIG. 3 depicts the uncaged degron in the schematically depicted signaling pathway of FIG. 2 as described herein.
Figure 4:
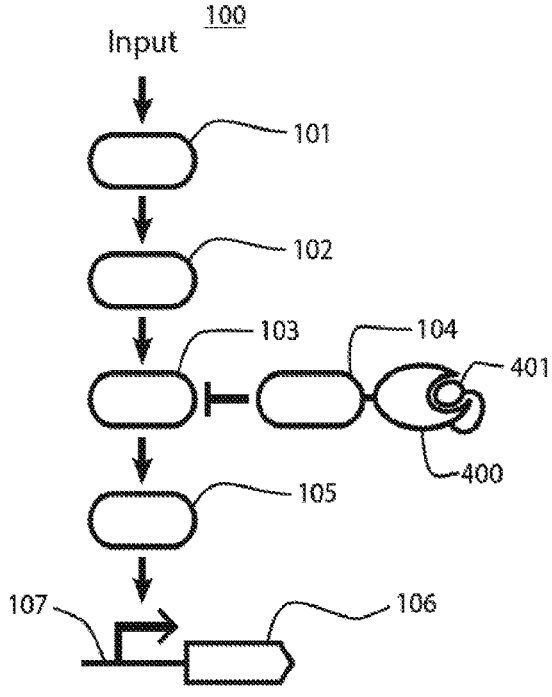
FIG. 4 schematically depicts a signaling pathway with a caged degron attached to a negative regulatory member of the signaling pathway of FIG. 1 as described herein.

As depicted in FIG. 3, uncaging of the degron 300 of the caged degron 200 results in degradation of the first intermediate member 102 and, thus a lack of positive signaling from the first intermediate member 102 to the second intermediate member 103 and subsequent points of the pathway. Accordingly, output from the sequence 106 is not generated or is reduced. In another example, depicted in FIG. 4, the inhibitory third intermediate member 104 includes a caged degron 400, such that, when the degron 401 remains caged, the presence of the third intermediate member 104 negatively regulates the second intermediate member thereby repressing expression and production of the product encoded by the output sequence 106. Correspondingly, upon uncaging (not pictured) the degron 401 induces degradation of the third intermediate member 104, thereby preventing negative regulation by the third intermediate member 104 and positively regulating the pathway 100 to promote generation of the output, i.e., at least an increase in expression of the product encoded by the sequence 106.

When integrated with a key polypeptide, the expression of which is driven by an output of the signaling pathway, coupling a caged degron to a signaling protein of the pathway may provide for positive or negative feedback as desired. For example, as depicted in FIG. 5, coupling the caged degron to positive signaling regulators creates negative feedback on the pathway, whereas coupling the caged degron to negative regulators creates positive feedback on the pathway. In some instances, negative pathway feedback can be used to dampen responses, whereas, in some instances, positive pathway feedback can be used to amplify responses or generate ultra-sensitivity. As will be readily evident, the feedback circuits of the present disclosure are highly modular and thus, circuits described herein may be readily modified as desired and/or applied to essentially any convenient and appropriate signaling pathway, including e.g., signaling pathways with measurable output via a promoter.

Feedback control enables robust, stable performance of a physical process through disturbance rejection. Implementation of feedback control may generally include: (1) the ability to measure or "sense" the output of the process, (2) a controller to generate a corrective signal based on a comparison of the output measurement against a desired output or "setpoint", and (3) a method to input or "actuate" the corrective signal to the process to be controlled. Provided herein are designed circuits that utilize degradation-based protein switches, such as the de novo protein switch degronLOCKR, to generate feedback control of biological systems. Specifically, three modules analogous to the ones described above: (1) a sensing promoter that is activated by the output of the process of interest, (2) a key peptide produced by the sensing promoter that activates degradation of (3) a signaling protein (i.e., transcription factor, kinase, etc.) that is fused to, e.g., the degronSwitch. Each of these modules can be independently tuned, as desired, via simple manipulations to achieve the desired feedback control of the process.

Signaling proteins that may be employed in the circuits of the present disclosure include signaling proteins that are endogenous components of the signaling pathway as well as heterologous or synthetic components of the signaling pathway. Such endogenous, heterologous and/or synthetic components of signaling pathways may be modified to include a caged degron, described in more detail below, for use in a circuit of the present disclosure. By "endogenous component of the signaling pathway" is generally meant a component of the signaling pathway as it occurs naturally in a cell.

By "heterologous component of the signaling pathway" is generally meant a component that functions in the signaling pathway but is derived from a cell or signaling pathway other than that in which it is employed in the subject circuit. Heterologous components may be derived from a signaling pathway separate from the signaling pathway of the subject circuit. Heterologous components may be derived from a different type of cell and/or a different organism from the cell and/or organism of the signaling pathway modulated in the subject circuit. For example, in some instances, a component of a signaling pathway from a first organism (e.g., mouse) may be employed in a corresponding signaling pathway of a second organism (e.g., human).

By "synthetic component of the signaling pathway" is generally meant a component that functions in the signaling pathway but is non-naturally derived. Non-naturally derived components may include recombinant components, including e.g., analogs, mimetics, fusions, mutants, truncated versions, fragments, and the like. Non-limiting examples of synthetic components of signaling pathways including synthetic receptors, synthetic enzymes, synthetic co-activators, synthetic co-repressors, synthetic binding partners, synthetic scaffold proteins, synthetic transcription factors, and the like.

Circuits of the present disclosure may employ one or more regulatory sequences, the control of which may be dependent upon a component of the signaling pathway with which the signaling protein is associated. For example, in some instances, a circuit of the present disclosure may include a regulatory sequence responsive to an output of the signaling pathway. Regulatory sequences may be operably linked to one or more nucleic acid sequences encoding one or more components of the subject circuit. For example, a regulatory sequence may be operably linked to a nucleic acid sequence encoding a key polypeptide.

In some instances, a circuit may include a regulatory sequence operably linked to a nucleic acid sequence encoding the signaling protein. Regulatory sequences operably linked to a sequence encoding the signaling protein of the subject circuits may vary and may include endogenous and heterologous regulatory sequences, including but not limited to e.g., native promoters, native enhancers, heterologous promoters, heterologous enhancers, synthetic regulatory sequences, and the like. Regulatory sequences operably linked to a sequence encoding the signaling protein may be constitutive or inducible as desired. In some instances, a regulatory sequence operably linked to the nucleic acid sequence encoding a signaling protein is a native promoter of the signaling protein.

In some instances, a regulatory sequence may include one or more binding sites (e.g., 1 or more, 2 or more, 2 to 10, 3 to 10, 4 to 10, 5 to 10, 2 to 6, 3 to 6, 4 to 6, 1, 2, 3, 4, 5, 6, 7, 8, 9, 10, etc.) for a transcription factor of the output, including e.g., where the transcription factor is an endogenous, heterologous, or synthetic transcription factor that functions in the signaling pathway.

Regulatory sequences of circuits of the present disclosure may be controlled by, or otherwise responsive to, an output of a signaling pathway. For example, in some instances, an output of a signaling pathway, which the subject circuit is configured to influence, may induce expression of a coding sequence through a regulatory sequence operably linked to the coding sequence. By connecting the regulation of a sequence encoding a component of a circuit of the present disclosure to an output of the signaling pathway, circuits of the present disclosure may provide feedback that is response to the output.

Useful signaling pathway outputs employing in circuits of the present disclosure may vary and may include essentially any output that may be configured to directly or indirectly influence expression through a regulatory sequence. Non-limiting examples of useful signaling pathway outputs include but are not limited to e.g., activity (e.g., activation, repression, etc.) of a transcription factor, expression of a transcription factor, translocation of a transcription factor, activity (e.g., activation, repression, etc.) of an enzyme, expression of an enzyme, production of a signaling molecule, secretion of a signaling molecule, cellular activation (including e.g., activation of native cellular programs, such as but not limited to e.g., immune activation, immune suppression, proliferation, etc.), and the like.

Signaling pathways may be modulated (e.g., activated, repressed, etc.) by one or more inputs. Inputs of signaling pathways may vary and may include endogenous (e.g., native) inputs of signaling pathways and heterologous (e.g., engineered or synthetic) signaling pathway inputs. As signaling pathways, and signaling pathway outputs, may be native or synthetic, signaling pathway inputs may similarly be native or synthetic.

Native signaling pathways may, in many instances, be controlled by a native or natural receptor of the pathway. Non-limiting examples of native signaling pathways include but are not limited to e.g., the AKT signaling pathway, the Akt/PKB signaling pathway, the AMPK signaling pathway, the apoptosis signaling pathway, the BMP signaling pathway, the cAMP-dependent pathway, the estrogen signaling pathway, the hedgehog signaling pathway, the hippo signaling pathway, an immune activation pathway, an immune suppression pathway, an immune cell differentiation pathway, an insulin signal transduction pathway, the JAK-STAT signaling pathway, the MAPK/ERK signaling pathway, the mTOR signaling pathway, the NF-κB signaling pathway, the nodal signaling pathway, the notch signaling pathway, the p53 signaling pathway, the PI3K signaling pathway, the TGF beta signaling pathway, the TLR signaling pathway, the TNF signaling pathway, the VEGF signaling pathway, the Wnt signaling pathway, and the like.

Non-limiting examples of synthetic signaling pathways include, but are not limited to, those pathways controlled by a synthetic or engineered receptor, such as but not limited to e.g., a CAR, an engineered TCR, a synNotch, etc. Signaling pathways are described in more detail below.

Schematized examples of modulating a synthetic syn-Notch signaling pathway and a synthetic CAR signaling pathway using circuits of the present disclosure are depicted in FIG. 6 and FIG. 7, respectively. As shown in FIG. 6, a synNotch receptor is triggered by an antigen input to release a synthetic transcription factor (synTF) that includes an attached caged degron. Release of the intracellular portion of the synNotch after antigen binding induces expression of a desired output which is controlled by the synTF. In the embodiment pictured, the synTF output also controls expression of a key polypeptide. Thus, when the released intracellular portion of the synNotch induces expression of the key polypeptide, the key polypeptide uncages the degron resulting in degradation of the key polypeptide and the synTF-containing intracellular portion of the synNotch receptor. Accordingly, by providing negative feedback through the synthetic synNotch signaling pathway a controlled custom output is generated.

As shown in FIG. 7, a CAR is triggered by an antigen input to induce an internal signaling cascade, e.g., leading immune cell activation through immune stimulatory signaling through the CD3z domain of the CAR. The CAR also includes an attached caged degron and the cell includes a regulatory sequence, operably linked to a sequence encoding a key polypeptide, that is responsive to a component of the internal signaling cascade. Thus, activation of the internal signaling cascade induces expression of a desired output, such as immune cell activation, which is controlled by the CAR. However, in the embodiment pictured, the CAR output also controls expression of the key polypeptide. Thus, when signaling cascade induces expression of the key polypeptide, the key polypeptide uncages the degron resulting in degradation of the key polypeptide and the CAR. Accordingly, by providing negative feedback through the synthetic CAR signaling pathway T-cell activation is controlled.

As will be readily apparent, these examples employing synthetic signaling pathways are not intended to be limiting.

Caged Degrons and Key Polypeptides

As summarized above, signaling proteins employed in the circuits of the present disclosure may include a caged degron. The caged degron included in a subject signaling protein of the present circuits may vary and may be attached or otherwise integrated into the signaling protein as desired. Any convenient method of attaching or integrating a caged degron into a subject signaling protein may be employed, including but not limited to e.g., where the caged degron is attached via a linker.

Caged degrons employed in the herein described circuits will generally include a single polypeptide that includes one or more degrons and multiple other domains that, when in a three dimensional configuration, prevent the degron(s) from triggering degradation of the polypeptide and any attached protein, such as e.g., an attached signaling protein. Caged degrons of the subject circuits may be uncaged by a key polypeptide that, when present, uncages the degron(s) thereby triggering degradation of the polypeptide and any attached proteins, such as e.g., an attached signaling protein.

The "cage" portion of a caged degron, also referred to herein in some instances as a "switch" or "switches", may be made up of multiple polypeptide domains having intramolecular affinity for one another such that the domains assemble into a three-dimensional structure sufficient for preventing the degron(s) from triggering degradation. For example, in some instances, a cage portion may include multiple units of secondary protein structure, such as alpha helices, that, in the absence of the key polypeptide, assemble into a three-dimensional structure, e.g., an alpha helix bundle, that cages a degron. A cage portion of a caged degron may include a "locker domain" or "cage domain" or "structural region" that provides the majority of the formed three-dimensional structure and a "latch domain" that is capable of being displaced by the key polypeptide to uncage the degron.

Cage polypeptides may comprise a helical bundle comprising between 2 and 7 alpha-helices. In various embodiments, the helical bundle comprises 3-7, 4-7, 5-7, 6-7, 2-6, 3-6, 4-6, 5-6, 2-5, 3-5, 4-5, 2-4, 3-4, 2-3, 2, 3, 4, 5, 6, or 7 alpha helices.

Each alpha helix may be of any suitable length and amino acid composition as appropriate for an intended use. In some embodiments, each helix is independently 38 to 58 amino acids in length. In some embodiments, each helix is independently between 18-60, 18-55, 18-50, 18-45, 22-60, 22-55, 22-50, 22-45, 25-60, 25-55, 25-50, 25-45, 28-60, 28-55, 28-50, 28-45, 32-60, 32-55, 32-50, 32-45, 35-60, 35-55, 35-50, 35-45, 38-60, 38-55, 38-50, 38-45, 40-60, 40-58, 40-55, 40-50, or 40-45 amino acids in length.

The amino acid linkers connecting each alpha helix can be of any suitable length or amino acid composition as appropriate for an intended use. In one embodiment, each amino acid linker is independently between 2 and 10 amino acids in length. In various embodiments, each amino acid linker is independently 3-10, 4-10, 5-10, 6-10, 7-10, 8-10, 9-10, 2-9, 3-9, 4-9, 5-9, 6-9, 7-9, 8-9, 2-8, 3-8, 4-8, 5-8, 6-8, 7-8, 2-7, 3-7, 4-7, 5-7, 6-7, 2-6, 3-6, 4-6, 5-6, 2-5, 3-5, 4-5, 2-4, 3-4, 2-3, 2, 3, 4, 5, 6, 7, 8, 9, or 10 amino acids in length. Linkers may be structured or flexible (e.g. poly-GS).

In some embodiments, a useful locker domain may include five alpha helices which may form a six helix bundle with a latch domain that includes an alpha helix. The alpha helices of the locker domain may interact with each other via hydrogen bond networks formed between helical interfaces. The alpha helix of the latch domain may interact with helices of the locker domain other via hydrogen bond networks formed between helical interfaces shared between the latch domain alpha helix and helices of the locker domain. Interactions between a latch domain helix and a locker domain helix may be weaker than a corresponding interaction between two locker domain helices.

A latch region may be present near either terminus of the cage polypeptide. In one embodiment, the latch region is placed at the C-terminal helix so as to position the bioactive peptide for maximum burial of the functional residues that need to be sequestered to maintain the bioactive peptide in an inactive state while simultaneously burying hydrophobic residues and promoting solvent exposure/compensatory hydrogen bonds of polar residues. In various embodiments, the latch region may comprise a part or all of a single alpha helix in the cage polypeptide at the N-terminal or C-terminal portions. In various other embodiments, the latch region may comprise a part or all of a first, second, third, fourth, fifth, sixth, or seventh alpha helix in the cage polypeptide. In other embodiments, the latch region may comprise all or part of two or more different alpha helices in the cage polypeptide; for example, a C-terminal part of one alpha helix and an N-terminal portion of the next alpha helix, or all of two consecutive alpha helices.

In some instances, one or more of a latch domain, a locker domain, a key polypeptide, or a portion thereof, may be modified to achieve a desired relative affinity. For example, in some instances, a latch domain may be modified to have an affinity for the locker domain that is lower relative to the affinity of the key polypeptide for the locker domain. In some instances, a key polypeptide may be modified to have an affinity for the locker domain that is higher relative to the affinity of the latch domain for the locker domain. In some instances, a locker domain may be modified to have an affinity for the latch domain that is lower relative to the affinity of the locker domain for the key polypeptide.

In some instances, all three of a latch domain, a locker domain, and a key polypeptide may be modified to "tune" the affinities of each element to facilitate caging and uncaging at desired amounts (e.g., expression levels, concentrations, etc.) of key polypeptide. Various modifications may be employed to modulate the affinities of latch domains, locker domains, and key polypeptides, including but not limited to e.g., modifications of the overall length of the domain/polypeptide or the length of a portion of the domain/polypeptide, e.g., an alpha helix of the domain/polypeptide. Other useful modifications include but are not limited to e.g., the presence and/or size of a toehold truncation, the presence and/or number of destabilizing mutations, and the like.

In some embodiments, the dynamic range of activation by key polypeptides can be tuned by truncating the latch region length to be shorter than the alpha-helices in the structural region, simultaneously weakening the cage polypeptide-latch region interaction and opening an exposed region on the cage polypeptide that the key polypeptide can bind to as a "toehold" (i.e., toehold truncations). Similarly, the dynamic range of activation by key polypeptides can also be tuned in a similar manner by designing mutations into the Latch that weaken the cage polypeptide-latch region interaction (i.e., destabilizing mutations). In some embodiments, the latch region can be one or more helices totaling in length 18-150 amino acids, 18-100 amino acids, or 18-58 amino acids. In some embodiments the latch region may include, in all or in part, helical secondary structure, beta strand secondary structure, loop secondary structure, or combinations thereof.

Accordingly, the overall length of a caged degron may vary and may range from about 200 amino acid residues or less to about 600 amino acid residues or more, including but not limited to e.g., 200 aa to 600 aa, 200 aa to 575 aa, 200 aa to 550 aa, 200 aa to 525 aa, 200 aa to 500 aa, 200 aa to 475 aa, 200 aa to 450 aa, 200 aa to 425 aa, 200 aa to 400 aa, 200 aa to 375 aa, 200 aa to 350 aa, 200 aa to 325 aa, 200 aa to 300 aa, 200 aa to 275 aa, 200 aa to 250 aa, 200 aa to 225 aa, 250 aa to 600 aa, 250 aa to 575 aa, 250 aa to 550 aa, 250 aa to 525 aa, 250 aa to 500 aa, 250 aa to 475 aa, 250 aa to 450 aa, 250 aa to 425 aa, 250 aa to 400 aa, 250 aa to 375 aa, 250 aa to 350 aa, 250 aa to 325 aa, 250 aa to 300 aa, 250 aa to 275 aa, 300 aa to 600 aa, 300 aa to 575 aa, 300 aa to 550 aa, 300 aa to 525 aa, 300 aa to 500 aa, 300 aa to 475 aa, 300 aa to 450 aa, 300 aa to 425 aa, 300 aa to 400 aa, 300 aa to 375 aa, 300 aa to 350 aa, 300 aa to 325 aa, 325 aa to 600 aa, 325 aa to 575 aa, 325 aa to 550 aa, 325 aa to 525 aa, 325 aa to 500 aa, 325 aa to 475 aa, 325 aa to 450 aa, 325 aa to 425 aa, 325 aa to 400 aa, 325 aa to 375 aa, 325 aa to 350 aa, 350 aa to 600 aa, 350 aa to 575 aa, 350 aa to 550 aa, 350 aa to 525 aa, 350 aa to 500 aa, 350 aa to 475 aa, 350 aa to 450 aa, 350 aa to 425 aa, 350 aa to 400 aa, 350 aa to 375 aa, etc.

In some instances, the length of a domain, e.g., an alpha helix domain, of a polypeptide or domain thereof may range from 2 amino acid residues to 300 amino acid residues or more, including but not limited to e.g., 2 aa to 300 aa, 2 aa to 250 aa, 2 aa to 200 aa, 2 aa to 150 aa, 2 aa to 100 aa, 2 aa to 50 aa, 5 aa to 300 aa, 5 aa to 250 aa, 5 aa to 200 aa, 5 aa to 150 aa, 5 aa to 100 aa, 5 aa to 50 aa, 10 aa to 300 aa, 10 aa to 250 aa, 10 aa to 200 aa, 10 aa to 150 aa, 10 aa to 100 aa, 10 aa to 50 aa, 20 aa to 300 aa, 20 aa to 250 aa, 20 aa to 200 aa, 20 aa to 150 aa, 20 aa to 100 aa, 20 aa to 90 aa, 20 aa to 80 aa, 20 aa to 70 aa, 20 aa to 60 aa, 20 aa to 50 aa, 20 aa to 40 aa, 20 aa to 30 aa, 30 aa to 300 aa, 30 aa to 250 aa, 30 aa to 200 aa, 30 aa to 150 aa, 30 aa to 100 aa, 30 aa to 90 aa, 30 aa to 80 aa, 30 aa to 70 aa, 30 aa to 60 aa, 30 aa to 50 aa, 30 aa to 40 aa, 40 aa to 300 aa, 40 aa to 250 aa, 40 aa to 200 aa, 40 aa to 150 aa, 40 aa to 100 aa, 40 aa to 90 aa, 40 aa to 80 aa, 40 aa to 70 aa, 40 aa to 60 aa, 40 aa to 50 aa, 50 aa to 300 aa, 50 aa to 250 aa, 50 aa to 200 aa, 50 aa to 150 aa, 50 aa to 100 aa, 50 aa to 90 aa, 50 aa to 80 aa, 50 aa to 70 aa, 50 aa to 60 aa, etc.

In some instances, the length of one or more, including each of the, helices of a locker domain and/or a helix of a latch domain may range from 20 amino acid residues or less to 60 amino acids or more, including but not limited to e.g., 20 aa to 60 aa, 25 aa to 60 aa, 25 aa to 55 aa, 30 aa to 60 aa, 30 aa to 55 aa, 30 aa to 50 aa, 30 aa to 45 aa, 35 aa to 60 aa, 35 aa to 55 aa, 35 aa to 50 aa, 35 aa to 45 aa, etc.

In some instances, a latch domain may include a toehold truncation and/or a key polypeptide may include toehold amino acids. The term "toehold", as used herein, generally refers to a number of amino acid residues present in a key polypeptide, e.g., that are absent in a corresponding latch polypeptide, that provide the key polypeptide with a toehold to outcompete the latch domain for binding of the locker domain. The term "toehold truncation", as used herein, generally refer to amino acid residues removed from a latch domain, e.g., an alpha helix of a latch domain and/or the c-terminus of a latch domain, to reduce the affinity of the latch domain for the locker domain, e.g., to reduce the affinity of the latch domain for the locker domain relative to the affinity of the key polypeptide for the locker domain. Accordingly, a latch polypeptide without a toehold truncation will have a higher affinity for the locker domain as compared to a latch domain with a toehold truncation. Correspondingly, the difference in affinity to a locker domain of a corresponding latch and key pair will be greater when the pair includes a toehold than when the pair does not include a toehold. The length of toeholds and toehold truncations will vary and may range from 2 amino acid residues to 20 amino acid residues or more, including but not limited to e.g., 2 aa to 20 aa, 2 aa to 18 aa, 2 aa to 16 aa, 2 aa to 14 aa, 2 aa to 12 aa, 2 aa to 10 aa, 2 aa to 8 aa, 4 aa to 20 aa, 4 aa to 18 aa, 4 aa to 16 aa, 4 aa to 14 aa, 4 aa to 14 aa, 4 aa to 10 aa, 4 aa to 9 aa, 4 aa to 8 aa, 2 aa, 3 aa, 4 aa, 5 aa, 6 aa, 7 aa, 8 aa, 9 aa, 10 aa, 11 aa, 12 aa, 13 aa, 14 aa, 15 aa, 16 aa, 17 aa, 18 aa, etc.

In some instances, the length of a toehold may be indicated in the naming of a particular construct, e.g., as included as a suffix to the design name: For example "–t0" may indicate no toehold, and "–t9" means a toehold of 9 residues (i.e. Latch truncated by 9 residues).

In some instances, one or more portions of a caged degron and/or key polypeptide may be mutated or otherwise made to contain a mutation, including were such mutations may be made relative to various starting amino acid sequences, such as e.g., an initial locker domain sequence, an initial latch domain sequence, an initial alpha helix sequence, an initial key polypeptide. In some instances, mutations in a domain of a polypeptide may be made relative to a corresponding structure in another domain of the polypeptide or a corresponding domain in another polypeptide. For example, in some instances, a latch domain may be mutated relative to locker domain, a locker domain may be mutated relative to a latch domain, a latch domain may be mutated relative to a key polypeptide, a key polypeptide may be mutated relative to a latch domain, a locker domain may be mutated relative to a key polypeptide, a key polypeptide may be mutated relative to a locker domain, and the like.

Useful mutations include amino acid substitutions, amino acid insertions, truncations, deletions, and the like. In some instances, an introduced mutation may increase or decrease the relative affinity of an intra- or intermolecular interaction between two domains of a polypeptide or two domains of two polypeptides. In some instances, mutation may be employed to modify and/or tune the affinity of components of a caged degron and key polypeptide system for one another. Essentially any mutation may find use in modifying one or more polypeptides of, or encoded by, a circuit of the present disclosure. The number of mutations in a subject polypeptide or domain thereof may vary and may range from one to 20 or more, including but not limited to e.g., at least 1, at least 2, at least 3, at least 4, at least 5, no more than 20, no more than 15, no more than 10, no more than 5, 5 to 20, 10 to 20, 15 to 20, 1 to 15, 1 to 10, 1 to 5, 2 to 20, 2 to 15, 2 to 20, 2 to 5, 1, 2, 3, 4, 5, 6, 7, 8, 9, 10, 11, 12, 13, 14, 15, 16, 17, 18, 19, 20, etc.

Useful mutations include destabilizing mutations. The term "destabilizing mutation", as used herein, generally refers to a mutation that destabilizes the formation of a structure or interaction. A polypeptide having one or more destabilizing mutations may form a subject structure less readily than the corresponding polypeptide without the destabilizing mutation(s). Structures that may be destabilized by the presence of a destabilizing mutation include secondary and tertiary protein structures, including e.g., alpha helices, helix bundles, and the like. A polypeptide having one or more destabilizing mutations may form an interaction, including intermolecular and intramolecular interactions, less readily than the corresponding polypeptide without the destabilizing mutation(s). For example, in some instances, a latch domain may include one or more destabilizing mutations that destabilize the formation of a helix bundle structure, that includes the latch domain and a corresponding locker domain, relative to the formation of the structure, or an interaction necessary to form the structure, in the absence of the destabilizing mutations.

Mutation useful as destabilizing mutations will vary an may include, but are not limited to, e.g., substitution mutations. Non-limiting examples of useful substitution mutations include substitution of a hydrophobic amino acid (e.g., alanine, valine, isoleucine, leucine, methionine, phenylalanine, proline, tyrosine or tryptophan) for a less hydrophobic, non-hydrophobic or polar amino acid (e.g., serine, threonine, asparagine, glutamine, arginine, histidine, lysine, aspartic acid, glutamic acid, cystine, etc.); substitution of a large hydrophobic amino acid (e.g., phenylalanine, tyrosine or tryptophan) for a smaller amino acid (e.g., an alanine, a serine, etc.); substitution of a small hydrophobic amino acid (e.g., an alanine, valine, etc.) for a large hydrophobic amino acid (e.g., phenylalanine, tyrosine or tryptophan), and the like. In some instances, a useful destabilizing mutation may be a serine substitution or an alanine substitution. In some instances, useful serine substitutions may include e.g., a valine to serine substitution, an isoleucine to serine substitution, or the like.

In some instances, components of a helical bundle may be asymmetrized, e.g., an employed LOCKR may be an asymmetrized LOCKR switch. For example, initial LOCKR switch design were built starting from a de novo designed symmetric homotrimer, 5L6HC3_1, which contains 6 helices. In some instance, the symmetric designs may be redesigned to be asymmetric (such examples provided herein include those with the prefix "asym"). For example, a symmetric LOCKR may be redesigned using computational software; where residues known to be important for LOCKR function are kept fixed, and remaining residues are optimized to preserve hydrophobic packing while introducing sequence diversity that minimizes the number of repeating amino acid sequences and motifs. Synthetic DNA coding for the designs may then be obtained and designs may be expressed, purified, and biophysically characterized. Asymmetrized LOCKR switches are described in more detail in U.S. Provisional Patent Application Nos. 62/700,681; 62/785,537; and 62/788,398, the disclosures of which are incorporated herein by reference in their entirety.

In some instances, a cage of a caged degron employed in a circuit of the present disclosure may include a polypeptide having at least 40%, 45%, 50%, 55%, 60%, 65%, 70%, 75%, 80%, 85%, 90%, 91%, 92%, 93%, 94%, 95%, 96%, 97%, 98%, 99%, or 100% sequence identity along its length to the amino acid sequence of a cage polypeptide disclosed in U.S. Provisional Patent Application Nos. 62/700,681, 62/785, 537, 62/788,398 (the disclosures of which are incorporated herein by reference in their entirety), and/or disclosed herein, not including optional amino acid residues, and optionally not including amino acid residues in the latch region, such as a cage polypeptide provided by SEQ ID NOS. 63-1169 and/or Table 3 (inclusive of any appendices therein). As noted in the disclosure, cage polypeptides may include residues that are optional; in some instances these residues are indicated in parentheses, and in some embodiments such residues are not included in determining percent sequence identity. In some embodiments, optional residues may be included in determining percent sequence identity.

In some instances, nomenclature for the cage may be identified by 1fix-short and 1fix-latch, indicating similar, yet distinct, embodiments of cage polypeptides as described above. A cage polypeptide (e.g., Cage$_a$) may be activated by a corresponding key polypeptide (e.g., Key$_a$) as outlined in the following "Cage/Key Correspondence" table. The functional groups encoded in the latch may be identified by the third portion of the name while the suffix may indicate the presence of a toehold. For example, 1fix-short-Bim-t0 encodes Bim on the 1fix-short scaffold with no toehold. In another example, 1fix-latch_Mad1SID_T0_2 indicates that the 1fix-latch scaffold was used to encode Mad1SID with no residues. The suffix 2 indicates that there are two versions where the functional sequence is encoded in different locations on the latch region.

Cage/Key Correspondence Table:

| Row number | Cage (column 1) | Key (column 2) |
|---|---|---|
| 1 | SB76L SB76L_17, SB76L_18, LOCKR_extend5, LOCKR_extend9, LOCKR_extend18, miniLOCKRa_1, miniLOCKRa_2, aBc12LOCKR, pBimLOCKR, BimLOCKR_extend5, BimLOCKR_extend9, BimLOCKR_extend18, strepLOCKRa (all variants), SB13_LOCKR (and extend18), ZCX12_LOCKR (and extend18), fretLOCKRa, 1fix_302_L3455_t9_Mad1SID, 1fix_302_t5_Mad1SID, 1fix_302_t0_latch_Mad1SID, 1fix_302_I329S_Mad1SID_t9, 1fix_302_I328S_L3455_Mad1SID_t9, 1fix_309_Mad1SID_t9, 1fix_302_Mad1SID_t9, 1fix-long-Bim-t0, 1fix-long-GFP-t0, 1fix-short-BIM-t0, 1fix-short-GFP-t0, 1fix-short-noBim-t0, 1fix-short-noBim(AYYA)-t0, 1fix-short-Bim-t0-relooped, 1fix-short-spytag-t0_2, 1fix-short-spytag-t0_8, 1fix-short-TEV-t0_1 , 1fix-short-TEV-t0_6, 1fix-short-nanoBit-t0_1, 1fix-short-nanoBit-t0_3, 1fix-short-RHIM-t0_8, 1fix-short-RHIM-t0_19, 1fix-short-RHIM-t0_22, 1fix-short-gcn4-t0_4, 1fix-short-ccDi-t0_6, 1fix-short-cc-a-t0_6, 1fix-short-cc-b-t0_6 | SB76_C-helix, SB76_C-helix-biotin, p5_MBP, p9_MBP, p18_MBP, p76-long, p76-short, k76-long, k76-short, p76_GLISE, p76_GSSEKIS, p76_R26G, p76-short_E19G, p76-short_GLISE_E01_EGFR, p76-short_AE_EGFR, p76-short_AAE_EGFR, p76-short_EE_EGFR |
| 2 | LOCKRb, BimLOCKRb, fretLOCKRb | key_b |
| 3 | LOCKRc, miniLOCKRc_1, miniLOCKRc_2, BimLOCKRc, fretLOCKRc | key_c |
| 4 | LOCKRd, BimLOCKRd, fretLOCKRd | key_d |
| 5 | LOCKRe | key_e |
| 6 | LOCKRf | key_f |
| 7 | Histag_TEV_1fix_VMAc_C_BIMlatcht9 | HIStag_sfGFP_VMAn_p18 |
| 8 | HIStag_sfGFP_VMAn_1fix_BIM_t0_latch | Histag_p18_VMAc_mCherry |
| 9 | Spycatcher-1fix-long-GFP-t0, Spycatcher-1fix-short-GFP-t0 | p76-spytag, p76-short-spytag |
| 10 | STREPII-2plus1_LOCK_1 | 2plus1_Key_1 |
| 11 | STREPII-2plus1_LOCK_2 | 2plus1_Key_2 |
| 12 | STREPII-2plus1_LOCK_3, STREPII-2plus1_LOCK_3-relooped | 2plus1_Key_3 |
| 13 | STREPII-2plus1_LOCK_4C | 2plus1_Key_4C |
| 14 | STREPII-2plus1_LOCK_4N | 2plus1_Key_4N |
| 15 | STREPII-3plus1_LOCK_1 | 3plus1_Key_1 |
| 16 | STREPII-3plus1_LOCK_2 | 3plus1_Key_2 |
| 17 | STREPII-3plus1_LOCK 3, STREPII-3plus1_LOCK_3-relooped | 3plus1_Key_3 |
| 18 | STREPII-3plus1_LOCK_4 | 3plus1_Key_4 |

-continued

| Cage/Key Correspondence Table: | | |
|---|---|---|
| Row number | Cage (column 1) | Key (column 2) |
| 19 | 1fix-short_cODC_t11, 1fix-short_cODC_t8, 1fix-short_cODC_t5, 1 fix-short_cODC, 1fix-short_cODC_mut_t6, 1fix-short_cODC_mut, degron-miniLOCKRa_t12, degron-miniLOCKRa_2_t9, degron-miniLOCKRa_l_t12, degron-miniLOCKRa_l_t9, degronLOCKRa_320_t16, degronLOCKRa_324_t12, degronLOCKRa_CAonly, degronLOCKRa_327_noPro, degronLOCKRa_327 | key_a, key_a_m4, key_a_m9, key_a_m12, key_a_m15 |
| 20 | degronLOCKRb, degronLOCKRb_t13 | key_b |
| 21 | degronLOCKRc, degronLOCKRc_t13, degron-miniLOCKRc_l_t9, miniLOCKRc_l_t13, miniLOCKRc_2_t9, miniLOCKRc_t13, | key_c degron- degron- degron- degronLOCKRc_1fix_t13 |
| 22 | degronLOCKRd | key_d, key_d_m4, key_d_m7 |

As noted above, orthogonal LOCKR designs are denoted by lowercase letter subscripts: LOCKR$_a$ includes Cage$_a$ and Key$_a$, and LOCKR$_b$ includes Cage$_b$ and Key$_b$, etc. such that Cage$_a$ is only activated by Key$_a$, and Cage$_b$ is only activated by Key$_b$, etc. Prefixes in the polypeptide and LOCKR names denote the functional group that is encoded and controlled by the LOCKR switch. In one embodiment, all 3plus1 (3+1) and 2plus1 (2+1) cage and key polypeptides disclosed herein and in the attached appendices are matched by identification numbers. In some examples additional features of cage and key polypeptide sequences are enumerated. For example in the provided tables, the prefix 2plus1 or 3plus1 defines the helix architecture with the first number defining the number of helices in the structural region, with the second number defining the number of helices in the latch region. The N-term or C-term suffix defines if the latch on the cage component of the kit encompasses the N or C terminus respectively, as is denoted by brackets [ ] in certain sequences. The N-term versus C-term and numerical suffix in some examples corresponds to the same suffix on the key with which it is activated. For example, cage 2plus1_Cage_Cterm_26 in is activated by 2plus2_Key_Cterm_26.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of degronLOCKR_a_327:

(SEQ ID NO: 1)
SKEAVTKLQALNIKLAEKLLEAVTKLQALNIKLAEKLLEALARLQELNIA

LVYLAVELTDPKRIADEIKKVKDKSKEIVERAEEEIARAAAESKKILDEA

EEEIARAAAESKKILDEGSGSGSDAVAELQALNLKLAELLLEAVAELQAL

NLKLAELLLEAIAKLQELNIKLVELLTKLTDPATIREAIRKVKEDSERIV

AEAERLIAAAKAESERIIREAERLIAAAKAESERIIREGSGSGDPDVARL

QELNIELARELLRDVARLQELNIELARELLRAAAELQELNIKLVELASEL

TDPDEARKAIARVKRESKRIVEDAERLPMSCAQESEKISREAERLIREA

A.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of degronLOCKR_a_327_noPro:

(SEQ ID NO: 2)
SKEAVTKLQALNIKLAEKLLEAVTKLQALNIKLAEKLLEALARLQELNIA

LVYLAVELTDPKRIADEIKKVKDKSKEIVERAEEEIARAAAESKKILDEA

EEEIARAAAESKKILDEGSGSGSDAVAELQALNLKLAELLLEAVAELQAL

NLKLAELLLEAIAKLQELNIKLVELLTKLTDPATIREAIRKVKEDSERIV

AEAERLIAAAKAESERIIREAERLIAAAKAESERIIREGSGSGDPDVARL

QELNIELARELLRDVARLQELNIELARELLRAAAELQELNIKLVELASEL

TDPDEARKAIARVKRESKRIVEDAERLAMSCAQESEKISREAERLIR

EAA.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of degronLOCKR_a_CAonly:

(SEQ ID NO: 3)
SKEAVTKLQALNIKLAEKLLEAVTKLQALNIKLAEKLLEALARLQELNIA

LVYLAVELTDPKRIADEIKKVKDKSKEIVERAEEEIARAAAESKKILDEA

EEEIARAAAESKKILDEGSGSGSDAVAELQALNLKLAELLLEAVAELQAL

NLKLAELLLEAIAKLQELNIKLVELLTKLTDPATIREAIRKVKEDSERIV

AEAERLIAAAKAESERIIREAERLIAAAKAESERIIREGSGSGDPDVARL

QELNIELARELLRDVARLQELNIELARELLRAAAELQELNIKLVELASEL

TDPDEARKAIARVKRESKRIVEDAERLIRECAAASEKISREAERLIR

EAA.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of degronLOCKR_a_324_t12:

```
                                           (SEQ ID NO: 4)
SKEAVTKLQALNIKLAEKLLEAVTKLQALNIKLAEKLLEALARLQELNIA

LVYLAVELTDPKRIADEIKKVKDKSKEIVERAEEEIARAAAESKKILDEA

EEEIARAAAESKKILDEGSGSGSDAVAELQALNLKLAELLLEAVAELQAL

NLKLAELLLEAIAKLQELNIKLVELLTKLTDPATIREAIRKVKEDSERIV

AEAERLIAAAKAESERIIREAERLIAAAKAESERIIREGSGSGDPDVARL

QELNIELARELLRDVARLQELNIELARELLRAAAELQELNIKLVELASEL

TDPDEARKAIARVKRESKRIVEDLIMSCAQESAASEKISREAERLIR.
```

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of degronLOCKR_a_320_t16:

```
                                           (SEQ ID NO: 5)
SKEAVTKLQALNIKLAEKLLEAVTKLQALNIKLAEKLLEALARLQELNIA

LVYLAVELTDPKRIADEIKKVKDKSKEIVERAEEEIARAAAESKKILDEA

EEEIARAAAESKKILDEGSGSGSDAVAELQALNLKLAELLLEAVAELQAL

NLKLAELLLEAIAKLQELNIKLVELLTKLTDPATIREAIRKVKEDSERIV

AEAERLIAAAKAESERIIREAERLIAAAKAESERIIREGSGSGDPDVARL

QELNIELARELLRDVARLQELNIELARELLRAAAELQELNIKLVELASEL

TDPDEARKAIARVKRESKRLVMSCAQESREAAAASEKISREAE.
```

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of mini-degronLOCKRa_1_t9:

```
                                           (SEQ ID NO: 6)
NKEDATEAOKKAIRAAEELLKDVTRIOERAIREAEKALERLARVQEEAIR

RVYEAVESKNKEELKKVKEEIEELLRRLKRELDELEREIRELLKEIKEKA

DRLEKEIRDLIERIRRDRNASDEVVTRLARLNEELIRELREDVRRLAELN

KELLRELERAARELARLNEKLLELADRVETEEEARKAIARVKRESKRIVE

DAERLAMSCAQESEKISREAERLIREAA.
```

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of mini-degronLOCKRa_1_t12:

```
                                           (SEQ ID NO: 7)
NKEDATEAQKKAIRAAEELLKDVTRIQERAIREAEKALERLARVQEEAIR

RVYEAVESKNKEELKKVKEEIEELLRRLKRELDELEREIRELLKEIKEKA
```

```
DRLEKEIRDLIERIRRDRNASDEVVTRLARLNEELIRELREDVRRLAELN

KELLRELERAARELARLNEKLLELADRVETEEEARKAIARVKRESKRIVE

DLIMSCAQESAASEKISREAERLIR.
```

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of mini-degronLOCKRa_2_t9:

```
                                           (SEQ ID NO: 8)
DERLKRLNERLADELDKDLERLLRLNEELARELTRAAEELRELNEKLVEL

AKKLQGGRSREVAERAEKEREKIRRKLEEIKKEIKEDADRIKKRADELRR

RLEKTLEDAARELEKLKREPRTEELKRKATELQKEAIRRAEELLKEVTDV

QRRAIERAEELLEKLARLQEEAIRTVYLLVELNKVDRARKAIARVKRESK

RIVEDAERLAMSCAQESEKISREAERLIREAA.
```

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of mini-degronLOCKRa_t12:

```
                                           (SEQ ID NO: 9)
DERLKRLNERLADELDKDLERLLRLNEELARELTRAAEELRELNEKLVEL

AKKLQGGRSREVAERAEKEREKIRRKLEEIKKEIKEDADRIKKRADELRR

RLEKTLEDAARELEKLKREPRTEELKRKATELQKENIRRAEELLKEVTDV

QRRNIERAEELLEKLARLQEENIRTVYLLVELNKVDRARKAIARVKRESK

RIVEDLIMSCAQESAASEKISREAERLIR.
```

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of asym-degronLOCKR_a_mut:

```
                                           (SEQ ID NO: 10)
SKEAAKKLQDLNIELARKLLEASTKLQRLNIRLAEALLEAIARLQELNLE

LVYLAVELTDPKR1RDEIKEVKDKSKEIIRRAEKEIDDAAKESKKILEEA

RKAIRDAAEESRKILEEGSGSGSDALDELQKLNLELAKLLLKAIAETQDL

NLRAAKAFLEAAAKLQELNIRAVELLVKLTDPATIRRALEHAKRRSKEII

DEAERAIRAAKRESERIIEEARRLIEKAKEESERIIREGSGSGDPDIKKL

QDLNIELARELLRAHAQLQRLNLELLRELLRALAQLQELNLDLLRLASEL

TDPDEARKAIARVKRESKRIVEDAERLSREAAALSMSCAQESERSIREAA

AASEKISRE.
```

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of asym-degronLOCKR_a_mut_t6:

(SEQ ID NO: 11)
SKEAAKKLQDLNIELARKLLEASTKLQRLNIRLAEALLEAIARLQELNLE

LVYLAVELTDPKR1RDEIKEVKDKSKEIIRRAEKEIDDAAKESKKILEEA

RKAIRDAAEESRKILEEGSGSGSDALDELQKLNLELAKLLLKAIAETQDL

NLRAAKAFLEAAAKLQELNIRAVELLVKLTDPATIRRALEHAKRRSKEII

DEAERAIRAAKRESERIIEEARRLIEKAKEESERIIREGSGSGDPDIKKL

QDLNIELARELLRAHAQLQRLNLELLRELLRALAQLQELNLDLLRLASEL

TDPDEARKAIARVKRESKRIVEDAERLSMSCAQESEKISREAERSIREAA

AAS.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of asym-degronLOCKR_a_short:

(SEQ ID NO: 12)
SELARKLLEASTKLQRLNIRLAEALLEAIARLQELNLELVYLAVELTDPK

RIRDEIKEVKDKSKEIIRRAEKEIDDAAKESEKILEEAREAISGSGSELA

KLLLKAIAETQDLNLRAAKAFLEAAAKLQELNIRAVELLVKLTDPATIRE

ALEHAKRRSKEIIDEAERAIRAAKRESERIIEEARRLIEKGSGSGSELAR

ELLRAHAQLQRLNLELLRELLRALAQLQELNLDLLRLASELTDPDEARKA

IARVKRESKRIVEDLEMSCAQESAASEKISREAERLIR.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of asym_degronLOCKR_a_short_t5:

(SEQ ID NO: 13)
SELARKLLEASTKLQRLNIRLAEALLEAIARLQELNLELVYLAVELTDPK

RIRDEIKEVKDKSKEIIRRAEKEIDDAAKESEKILEEAREAISGSGSELA

KLLLKAIAETQDLNLRAAKAFLEAAAKLQELNIRAVELLVKLTDPATIRE

ALEHAKRRSKEIIDEAERAIRAAKRESERIIEEARRLIEKGSGSGSELAR

ELLRAHAQLQRLNLELLRELLRALAQLQELNLDLLRLASELTDPDEARKA

IARVKRESKRLVMSCAQESREAAAASEKISREA.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of asym-degronLOCKR_a_short_t8:

(SEQ ID NO: 14)
SELARKLLEASTKLQRLNIRLAEALLEAIARLQELNLELVYLAVELTDPK

RIRDEIKEVKDKSKEIIRRAEKEIDDAAKESEKILEEAREAISGSGSELA

KLLLKAIAETQDLNLRAAKAFLEAAAKLQELNIRAVELLVKLTDPATIRE

ALEHAKRRSKEIIDEAERAIRAAKRESERIIEEARRLIEKGSGSGSELAR

ELLRAHAQLQRLNLELLRELLRALAQLQELNLDLLRLASELTDPDEARKA

IARVKRLSMSCAQESERLIREAAAASEKIK.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of asym-degronLOCKR_a_short_t11:

(SEQ ID NO: 15)
SELARKLLEASTKLQRLNIRLAEALLEAIARLQELNLELVYLAVELTDPK

RIRDEIKEVKDKSKEIIRRAEKEIDDAAKESEKILEEAREAISGSGSELA

KLLLKAIAETQDLNLRAAKAFLEAAAKLQELNIRAVELLVKLTDPATIRE

ALEHAKRRSKEIIDEAERAIRAAKRESERIIEEARRLIEKGSGSGSELAR

ELLRAHAQLQRLNLELLRELLRALAQLQELNLDLLRLASELTDPDEARKA

IARLKMSCAQESEDAERLIREAAAASE.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of degronLOCKR_b:

(SEQ ID NO: 16)
SHAAVIKLSDLNIRLLDKLLQAVIKLTELNAELNRKLIEALQRLFDLNVA

LVHLAAELTDPKRIADEIKKVKDKSKEIVERAEEEIARAAAESKKILDEA

EEEIARAAAESKKILDEGSGSGSDAVAELQALNLKLAELLLEAVAELQAL

NLKLAELLLEAIAKLQELNIKLVELLTKLTDPATIREAIRKVKEDSERIV

AEAERLIAAAKAESERIIREAERLIAAAKAESERIIREGSGSNDPQVAQN

QETFIELARDALRLVAENQEAFIEVARLTLRAAALAQEVAIKAVEAASEG

GSGSGPNKEEIEKLAKEAREKLKKAEKEHKMSCAQERKKNKKAREDLKKK

ADK.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of degronLOCKR_b_t13:

(SEQ ID NO: 17)
SHAAVIKLSDLNIRLLDKLLQAVIKLTELNAELNRKLIEALQRLFDLNVA

LVHLAAELTDPKRIADEIKKVKDKSKEIVERAEEEIARAAAESKKILDEA

EEEIARAAAESKKILDEGSGSGSDAVAELQALNLKLAELLLEAVAELQAL

NLKLAELLLEAIAKLQELNIKLVELLTKLTDPATIREAIRKVKEDSERIV

AEAERLIAAAKAESERIIREAERLIAAAKAESERIIREGSGSNDPQVAQN

QETFIELARDALRLVAENQEAFIEVARLTLRAAALAQEVAIKAVEAASEG

GSGSGPNKEEIEKLAKEAREKLKKAEMSCAQEHDKLRKKNKKAREDLKK.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of degronLOCKR_c:

(SEQ ID NO: 18)
SLEAVLKLAELNLKLSDKLAEAVQKLAALLNKLLEKLSEALQRLFELNVA

LVTLAIELTDPKRIADEIKKVKDKSKEIVERAEEEIARAAAESKKILDEA

EEEIARAAAESKKILDEGSGSGSDAVAELQALNLKLAELLLEAVAELQAL

NLKLAELLLEAIAKLQELNIKLVELLTKLTDPATIREAIRKVKEDSERIV

AEAERLIAAAKAESERIIREAERLIAAAKAESERIIREGSGSNDPLVARL

QELLIEHARELLRLVATSQEIFIELARAFLANAAQLQEAAIKAVEAASEN

GSGSGPSSEKVRRELKESLKENHKQNQKLLMSCAQEQEKLNRELEELKKK

HKK.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of degronLOCKR_c_t13:

(SEQ ID NO: 19)
SLEAVLKLAELNLKLSDKLAEAVQKLAALLNKLLEKLSEALQRLFELNVA

LVTLAIELTDPKRIADEIKKVKDKSKEIVERAEEEIARAAAESKKILDEA

EEEIARAAAESKKILDEGSGSGSDAVAELQALNLKLAELLLEAVAELQAL

NLKLAELLLEAIAKLQELNIKLVELLTKLTDPATIREAIRKVKEDSERIV

AEAERLIAAAKAESERIIREAERLIAAAKAESERIIREGSGSNDPLVARL

QELLIEHARELLRLVATSQEIFIELARAFLANAAQLQEAAIKAVEAASEN

GSGSGPSSEKVRRELKESLKENHKQNMSCAQEHKRAQEKLNRELEELKK.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of mini-degronLOCKR_c_1_t9:

(SEQ ID NO: 20)
LIERLTRLEKEHVRELKRLLDTSLEILRRLVEAFETNLRQLKEALKRALE

AANLHNEEVEEVLRKLEEDLRRLEEELRKTLDDVRKEVKRLKEELDKRIK

EVEDELRKIKEKLKKGDKNEKRVLEEILRLAEDVLKKSDKLAKDVQERAR

ELNEILEELSRKLQELFERVVEEVTRNVPTTERIEKVRRELKESLKENHK

QNQKLLMSCAQEQEKLNRELEELKKKHKK.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of miniLOCKR_c_1_t13:

(SEQ ID NO: 21)
LIERLTRLEKEHVRELKRLLDTSLEILRRLVEAFETNLRQLKEALKRALE

AANLHNEEVEEVLRKLEEDLRRLEEELRKTLDDVRKEVKRLKEELDKRIK

EVEDELRKIKEKLKKGDKNEKRVLEEILRLAEDVLKKSDKLAKDVQERAR

ELNEILEELSRKLQELFERVVEEVTRNVPTTERIEKVRRELKESLKENHK

LNMSCAQEHKRAQEKLNRELEELKK.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of mini-degronLOCKR_c_2_t9:

(SEQ ID NO: 22)
SEERVLELAEEALRLSDEAAKEIQELARRLNEELEKLSKELQDLFERIVE

TVTRLIDADEETLKRAAEEIKKRLEDARKKAKEAADKAREELDRARKKLK

ELVDEIRKKAKDALEKAGADEELVARLLRLLEEHARELERLLRTSARIIE

RLLDAFRRNLEQLKEAADKAVEAAEEAVRRVEDVRVWSEKVRRELKESLK

ENHKQNQKLLMSCAQEQEKLNRELEELKKKHKK.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of miniLOCKR_c_t13:

(SEQ ID NO: 23)
SEERVLELAEEALRLSDEAAKEIQELARRLNEELEKLSKELQDLFERIV

ETVTRLIDADEETLKRAAEEIKKRLEDARKKAKEAADKAREELDRARKK

LKELVDEIRKKAKDALEKAGADEELVARLLRLLEEHARELERLLRTSAR

IIERLLDAFRRNLEQLKEAADKAVEAAEEAVRRVEDVRVWSEKVRRELK

ESLKENHKLNMSCAQEHKRAQEKLNRELEELKK.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of asym-degronLOCKR_c_t13:

(SEQ ID NO: 24)
SLEAALKLAELNLKLSDKLAEASQKLAALLNKLLEKLSEAIQRLFELNLA

LVTLAIELTDPKRIADEIKKVKDKSKEIIERAEEEIARAAAESKKILDEA

EEEIARAAAESKKILDEGSGSGSDALAELQALNLKLAELLLEAIAETQAL

NLKAAEAFLEAAAKLQELNIKAVELLVKLTDPATIREALRKAKEDSERII

AEAERAIAAAKAESERIIREAERLIAAAKAESERIIREGSGSNDPLIARL

QELLIEHARELLRLHATSQEIFVELLRAFLANLAQLQEAALKALEAASEN

GSGSGPSSEKVRRELKESLKENHKQNQKLLMSCAQEQEKLNRELEELKKK

HKK.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with the following amino acid sequence of degronLOCKR_d:

(SEQ ID NO: 25)
SLEAVLKLFELNHKLSEKLLEAVLKLHALNQKLSQKLLEALARLLELNVA

LVELAIELTDPKRIADEIKKVKDKSKEIVERAEEEIARAAAESKKILDEA

EEEIARAAAESKKILDEGSGSGSDAVAELQALNLKLAELLLEAVAELQAL

NLKLAELLLEAIAKLQELNIKLVELLTKLTDPATIREAIRKVKEDSERIV

AEAERLIAAAKAESERIIREAERLIAAAKAESERIIREGSGSGDPEVARL

QEAFIEQAREILRNVAAAQEALIEQARRLLALAALAQEAAIKAVELASEH

GSGSGPDTVKRILEELRRRFEKLAKDLDDIAMSCAQEHKKHNKELKDKQR

KIK.

In some instances, a caged degron of the present disclosure may share at least 70% sequence identity, including e.g., at least 75%, at least 80%, at least 85%, at least 90%, at least 95%, at least 96%, at least 97%, at least 98%, at least 99%, or 100% sequence identity with any of the degron-LOCKR cage polypeptide amino acid sequences of SEQ ID NOS. 63-1169.

As summarized above, caged degrons of the circuits of the present disclosure include a degron. The location of the degron within a caged degron polypeptide may vary and, in some instances, the degron may be located within a latch region. Degrons include portions of proteins that signal and/or target for degradation (or otherwise increase the degradation rate of) the protein to which the degron is attached or otherwise associated (e.g., grafted onto). Non-limiting examples of degrons include short amino acid sequences, structural motifs, exposed amino acids, and the like. Degrons may be prokaryote or eukaryote derived and may be employed in naturally occurring or non-naturally occurring (i.e., recombinant) forms. Degrons may be post-translationally modified to target a protein for degradation where such post-translational modifications include but are not limited to e.g., ubiquitination, proteolytic cleavage, phosphorylation, methylation, ADP-ribosylation, ampy-lation, lipidation, alkylation, nitrosylation, succinylation, sumoylation, neddylation, isgylation, etc.

In some instances, the degron may be added to the latch region without removing any residues of the latch region, or may replace one or more (1, 2, 3, 4, 5, 6, 7, 8, 9, 10, or more) amino acid residues in the cage scaffold latch region to produce the final polypeptide. Thus, the latch region may be significantly modified upon inclusion of the degron. In some embodiments, the optional residues are not included in determining percent sequence identity. In some embodiments, the latch region residues may be included in deter-mining percent sequence identity. In some embodiments, each of the optional residues and the latch residues may or may not be included in determining percent sequence identity.

In some instances, the degron may be present within about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 amino acids from either the N-terminus or the C-terminus of the latch region, and/or within about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 amino acids from either the N-terminus or the C-terminus of the cage polypeptide. In some embodiments, where the latch region is at the terminus of the cage polypeptide, the recited distance in amino acids of the degron from that terminus and from the terminus of the latch region may both be met. In other embodiments, such as where one or more polypeptide functional domains are added to the N-terminus or C-terminus of the cage polypeptide (as described below), the degron may be within the recited distance in amino acids from the terminus of the latch region but not from the terminus of the cage polypeptide.

In some embodiments, the latch region is N-terminal to the structural region, and the degron may be located within about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 amino acid residues of the N-terminus of the latch region. In some embodiments, the degron may be located within about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 amino acid residues of the N-terminus of the cage polypeptide.

In some embodiments, the latch region is C-terminal to the structural region, and the degron may be located within about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 amino acid residues or less of the C-terminus of the latch region. In some embodiments, the degron may be located within about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 amino acid residues of the C-terminus of the cage polypeptide. In some embodiments, the degron may comprise a ubiquitin-inde-pendent degradation signal. In some embodiments, the degron comprises a CA dipeptide located between 10-30 residues from the C-terminus of the cage polypeptide; in this embodiment, the "C" residue in the CA dipeptide is between 10-30 residues from the C-terminus of the cage polypeptide. The CA dipeptide is the minimal domain for degradation activity of the murine ornithine decarboxylase (cODC) degron, as described below. In other embodiments employ-ing a cODC degron, the degron may comprise the peptide sequence MSCAQES (SEQ ID NO: 26) or L(X)MSCAQES (SEQ ID NO: 27), wherein X can be any amino acid residue, wherein X is optionally not proline.

In some embodiments, the degron may comprise an amino acid sequence or peptide selected from the group consisting of -GG; -RG; -KG; -QG; -WG; -PG; -AG; -RxxG; -EE; -R; -Rxx; -Vx; -Ax; -A, wherein "x" can be any amino acid residue. In some embodiments, the degron may be located within about 10-30 amino acid residues, or within about 20 amino acid residues, of the C-terminus of the cage polypeptide.

In some embodiments, the degron may comprise or consist of a peptide sequence selected from the group consisting of the following (residues within brackets are optional):

```
                                         (SEQ ID NO: 28)
[[KTRGVEEVAEGVVLL]]RRRG [[NK(FAM)KKK]], (SEQ ID NO: 29)
[[KPFLNGGPY]] HSREQSTDSG [[LGLGSYK(FAM)KKK]], (SEQ ID NO: 30)
ASADLDLEALAPYIPADDDFQLRK(FAM)KKK, (SEQ ID NO: 31)
[[K-(PEG)-KEEK]] DINNN [[VKKTK(FAM)KKK]], (SEQ ID NO: 32)
[[K-(PEG)]] DVQKADVSST [[GQGIDSK(FAM)KKK]], (SEQ ID NO: 33)
KAAEEEEVSLASTPTDVRDVDIK(FAM)KKK, (SEQ ID NO: 34)
[[KKYSSQTSQ]] DSGNYS [[NK(FAM)KKK]], (SEQ ID NO: 35)
KPLSSSVPSQKTYQGSYGFRLGK(FAM)KKK,
and (SEQ ID NO: 36)
[[KAWQQQSYL]] DSGIHSG [[ATTTAPK(FAM)KKK]].
```

In some embodiments, useful degrons may include a polypeptide sequence that recruits an ubiquitin ligase. Such degrons (e.g., proteolysis-targeting chimeric molecules, PROTACs) have been previously described by Sakamoto et al. (2001) PNAS (15) 8554-8559 and Schneekloth et al. (2004) JACS 126(12):3748-54; the disclosures of which are incorporated herein by reference in their entirety. Ubiquibodies and peptide PROTACs are described in, e.g., Ludwicki et al, ACS Central Science 2019 5: 852-866; Portnoff et al, J. Biol. Chem. 2014 289: 7844-7855; Fan et al Nature Neuroscience 2014 17: 471 480; and Hines et al Proc. Natl. Acad. Sci. 2013 110: 8942-8947.

Useful degrons include ubiquitin-dependent degrons and ubiquitin-independent degrons. For example, in some instances, a protein may be targeted for ubiquitin-independent proteasomal degradation by attachment of an ornithine decarboxylase (ODC) degron, including but not limited to e.g., a mammalian ODC such as e.g., a rodent ODC, including but not limited to e.g., the c-terminal mouse ODC (cODC). In some instances, useful degrons include those described in Takeuchi et al., Biochem. J (2008) 410:401-407 and/or Matsuzawa et al., PNAS (2005) 102(42):14982-7; the disclosures of which are incorporated herein by reference in their entirety. In some instances, a protein may be targeted for ubiquitin-independent proteasomal degradation by post-translational modification (including but not limited to e.g., proteolytic cleavage, phosphorylation, methylation, ADP-ribosylation, ampylation, lipidation, alkylation, nitrosylation, succinylation, sumoylation, neddylation, isgylation, etc.) of a degron, where such modification leads, directly or indirectly, to partial or complete unfolding of the protein or other mechanisms that lead to degradation of the protein.

In some instances, a degron employed in the herein described circuits may include a ubiquitin-independent degradation signal, where such signals may vary. For example, in some instances, a ubiquitin-independent degradation signal may include a dipeptide motif, such as e.g., a cysteine-alanine (i.e., CA) dipeptide motif. In some instances, a ubiquitin-independent degradation signal may include only a dipeptide motif. In some instances, a ubiquitin-independent degradation signal may include amino acid residues in addition to a dipeptide motif, such as but not limited to e.g., a LXMSCAQE (SEQ ID NO: 37) motif, where X may be any amino acid or a LXMSCAQES (SEQ ID NO: 27) motif, where X may be any amino acid. In some instances, a LXMSCAQE motif or a LXMSCAQES motif may include where X is any amino acid except proline.

Accordingly, in some instances, a degradation signal of a degron may include a sequence selected from: LPMSCAQES (SEQ ID NO: 38) where the final S is present or absent, LAMSCAQES (SEQ ID NO: 39) where the final S is present or absent, LVMSCAQES (SEQ ID NO: 40) where the final S is present or absent, LSMSCAQES (SEQ ID NO: 41) where the final S is present or absent, LEMSCAQES (SEQ ID NO: 42) where the final S is present or absent, and LKMSCAQES (SEQ ID NO: 43) where the final S is present or absent. In some instances, a degradation signal of a degron may include a MSCAQE (SEQ ID NO: 44) sequence or a MSCAQES (SEQ ID NO: 26) sequence.

Ubiquitin-dependent degrons include, but are not limited to, e.g., PEST (SEQ ID NO: 45) (proline (P), glutamic acid (E), serine (S), and threonine (T)) sequence-containing degrons, as well as those degrons described in Melvin et al. (PLoS One. (2013) 29; 8: e78082; the disclosure of which is incorporated herein by reference in its entirety, including degrons identified as Bonger and those described as derived from TAZ, HIF-1α, iNOS, SRC3, Cyclin D1, IFNAR1, p53, and β-Catenin.

Useful degrons may also include E3 ubiquitin ligase domains. Such degrons are often defined as the substrate site that is recognized by E3 ubiquitin ligases and a variety of such degrons, including short peptide motifs and specific structural elements, have been characterized. Non-limiting examples of E3 ligase/degrons and the corresponding motif patterns include: APC/C (DBOX), primary motif .R . . . L . . . [LIVM].; APC/C (KEN), primary motif .KEN.; APC/C (ABBA), primary motif [FIVL].[ILMVP][FHY].[DE].{0,3}[DEST]; APCC_TPR_1, primary motif .[ILM]R$; CBL (PTK), primary motif [DN].Y[ST] . . . P; CBL (MET), primary motif DYR; COP1, primary motif [DE][DE].{2,3}VP[DE]; CRL4_CDT2_1, primary motif [NQ]{0,1} . . . [ILMV][ST][DEN][FY][FY].{2,3}[KR]{2,3}[ˆDE]; CRL4_CDT2_2, primary motif [NQ]{0,1} . . . [ILMV]T[DEN][HMFY][FMY].{2,3}[KR]{2,3}[ˆDE]; Kelch_KEAP1_1, primary motif [DNS].[DES][TNS]GE; Kelch_KEAP1_2, primary motif QD.DLGV; Kelch_actinfilin, primary motif [AP]P[MV][IM]V; Kelch_KLHL3, primary motif E.EE.E[AV]DQH; MDM2_SWIB, primary motif F[ˆP]{3}W[ˆP]{2,3}[VIL]; Nend_Nbox_1, primary motif ˆM{0,1}[FYLIW][ˆP]; Nend_UBRbox_1, primary motif ˆM{0,1}[RK][ˆP].; Nend_UBRbox_2, primary motif ˆM{0,1}([ED]).; Nend_UBRbox_3, primary motif ˆM{0,1}([NQ]).; Nend_UBRbox_4, primary motif ˆM{0,1}(C).; ODPH_VHL_1, primary motif [IL]A(P).{6,8}[FLIVM].[FLIVM]; SCF_COI1_1, primary motif . . . [RK][RK].SL . . . F[FLM].[RK]R[HRK].[RK].; SCF_FBW7_1, primary motif [LIVMP].{0,2}(T)P . . . ([ST]); SCF_FBW7_2, primary motif [LIVMP].{0,2}(T)P . . . E; SCF_SKP2-CKS1_1, primary motif . . . [DE].(T)P.K; SCF_TIR1_1, primary motif .[VLIA][VLI]GWPP[VLI] . . . R.; SCF-TRCP1, primary motif D(S)G.{2,3}([ST]); SIAH, primary motif .P.A.V.P[^P]; SPOP, primary motif [AVP].[ST][ST][ST]; where '.' specifies any amino acid type, '[X]' specifies the allowed amino acid type(s) at that position, '^X' at the beginning of the pattern specifies that the sequence starts with amino acid type X, '[^X]' means that the position can have any amino acid other than type X, numbers specified as the following 'X{x,y}', where x and y specify the minimum and maximum number of 'X' amino acid type required at that position. '$' sign implies the C-terminal of the protein chain. Degrons that include E3 ubiquitin ligase domains are described in Guharoy et al., Nature Communications (2016) 7:10239; the disclosure of which is incorporated herein by reference in its entirety. In some instances, useful degrons may include those degrons that contain signals for ER-associated degradation (ERAD), including but not limited to e.g., those described in Maurer et al., Genes Genomes & Genetics (2016) 6:1854-1866; the disclosure of which is incorporated herein by reference in its entirety. In some instances, useful degrons may also include drug-inducible degrons, such as but not limited to e.g., the auxin inducible degron (AID) which utilizes a specific E3 ubiquitin ligase (e.g., as described in Nishimura et al., Nature Methods (2009) 6(12):917-922; the disclosure of which is incorporated herein by reference in its entirety).

As will be readily understood, degrons that include E3 ubiquitin ligase domains will vary and circuit of the present disclosure may not be limited to use of those E3 ubiquitin degrons specifically described herein.

Other useful examples of degrons that may be employed in inducible degradation strategies adapted for use in the circuits of the present disclosure include but are not limited to e.g., N-end degrons (such as but not limited to e.g., those described in Tasaki & Kwon, Trends in Biochemical Sciences (2007) 32(11):520-528, the disclosure of which is incorporated herein by reference in its entirety); unstructured regions (such as but not limited to e.g., those described in Chung et al., Nat Chem Biol. 2015; 11(9): 713-720, the disclosure of which is incorporated herein by reference in its entirety); ligand induced degradation (LID) and destabilization domain (DD) domains (such as but not limited to e.g., those described in Bonger et al., Nat Chem Biol. 2012; 7(8): 531-537; Grimley et al., Bioorg. Med. Chem. Lett. (2008) 18: 759-761; and Chu et al. Bioorg. Med. Chem. Lett. (2008) 18: 5941-5944; Iwamoto et al., Chemistry & Biology (2010) 17: 981-988; the disclosures of which are incorporated herein by reference in their entirety); prokaryotic proteasome recognition sequences such as, e.g., ssrA and mf-Lon (such as those described in Cameron et al., (2014) Nature biotechnology 32(12): 1276-1281, the disclosure of which is incorporated herein by reference in its entirety); and the like.

As summarized above, circuits of the present disclosure may include a key polypeptide, the expression of which may be controlled by a regulatory sequence to which a sequence encoding the key polypeptide is operably linked. The term "key polypeptide", as used herein, generally refers to a polypeptide that, when expressed in the presence of a corresponding caged degron, uncages the degron. The key polypeptide can be used in conjunction with a cage polypeptides to displace the latch through competitive intermolecular binding that induces conformational change, exposing the degron and thus activating the system. Uncaging of the degron thereby triggers degradation of the polypeptide to which it is linked or otherwise incorporated and any other attached proteins, such as e.g., an attached signaling protein. The configuration of key polypeptides will vary, e.g., depending on the "cage" or "switch" component which the key is designed to uncage or actuate.

Key polypeptides configured to function with a particular caged degron may, in some instances, be configured as an orthogonal system. By "orthogonal system" is generally meant that a particular key polypeptide functions together with a particular caged degron, but the key polypeptide does not necessarily function with other caged degrons and/or the caged degron does not necessarily function with other key polypeptides. Accordingly, two or more different orthogonal systems of key polypeptide and caged degron may function together, e.g., simultaneously, in the same organism or cell without interfering. Put another way, a first key polypeptide of a first orthogonal system may function to uncage a first caged degron of the first system, while the key polypeptide does not substantially interfere with the function of any component of a second orthogonal system (e.g., second key polypeptide, second caged degron, etc.). Orthogonal systems may be employed, in some instances, to allow for the parallel operation of two or more molecular feedback circuits, including e.g., two or more molecular feedback circuits that each modulate a different signaling pathway, two or more molecular feedback circuits that each modulate a different component of the same signaling pathway, and the like.

Each key polypeptide and caged degron need not necessarily be configured into orthogonal pairs. For example, in some instances, two or more different key polypeptides may function to uncage the same caged degron. Correspondingly, in some instances, two or more different caged degrons may be configured to be uncaged by the same key polypeptide.

In some instances, a key polypeptide may be configured to bind a locker domain of a caged degron. In some instances, the intermolecular binding of a key polypeptide to a locker domain may be of higher affinity than the intramolecular binding of a latch domain to the locker protein. A key polypeptide may include an alpha helix. In some instances, a key polypeptide, or an alpha helix thereof, may be longer than the latch domain, or an alpha helix thereof, which the key polypeptide displaces to bind a locker domain of a caged degron. In some instances, a key polypeptide, or an alpha helix thereof, may be shorter than the latch domain, or an alpha helix thereof, which the key polypeptide displaces to bind a locker domain of a caged degron. In some instances, a key polypeptide, or an alpha helix thereof, may be the same length as the latch domain, or an alpha helix thereof, which the key polypeptide displaces to bind a locker domain of a caged degron.

The length of the key polypeptide, or an alpha helix thereof, may vary and may range from 25 amino acid residues or less to 80 amino acid residues or more, including but not limited to e.g., 25 aa to 80 aa, 25 aa to 75 aa, 25 aa to 70 aa, 25 aa to 65 aa, 25 aa to 60 aa, 25 aa to 55 aa, 25 aa to 50 aa, 25 aa to 45 aa, 25 aa to 40 aa, 25 aa to 35 aa, 30 aa to 80 aa, 30 aa to 75 aa, 30 aa to 70 aa, 30 aa to 65 aa, 30 aa to 60 aa, 30 aa to 55 aa, 30 aa to 50 aa, 30 aa to 45 aa, 30 aa to 40 aa, 35 aa to 80 aa, 35 aa to 75 aa, 35 aa to 70 aa, 35 aa to 65 aa, 35 aa to 60 aa, 35 aa to 55 aa, 35 aa to 50 aa, 35 aa to 45 aa, 40 aa to 80 aa, 40 aa to 75 aa, 40 aa to 70 aa, 40 aa to 65 aa, 40 aa to 60 aa, 40 aa to 55 aa, 40 aa to 50 aa, etc., amino acid residues in length.

In some instances, a key polypeptide may be truncated. Truncation of a subject key polypeptide may be relative to e.g., an untruncated version of the key polypeptide, the length of a corresponding latch domain, etc. The size of a truncation of a key polypeptide, where present, may vary and may range from e.g., 2 to 20 or more amino acid residues, including but not limited to e.g., 2 aa to 20 aa, 2 aa to 18 aa, 2 aa to 16 aa, 2 aa to 14 aa, 2 aa to 12 aa, 2 aa to 10 aa, 2 aa to 8 aa, 2 aa to 6 aa, 2 aa to 4 aa, etc., amino acid residues. In some instances, a key polypeptide may be untruncated, i.e., full-length.

In some instances, a key polypeptide of the present disclosure may share at least 70% sequence identity, including e.g., at least 75%, at least 80%, at least 85%, at least 90%, at least 95%, at least 96%, at least 97%, at least 98%, at least 99%, or 100% sequence identity with Key$_a$, having the following amino acid sequence:

```
                                    (SEQ ID NO: 46)
EARKAIARVKRESKRIVEDAERLIREAAAASEKISREAERLIREAAAASE

KISRE.
```

In some instances, a key polypeptide of the present disclosure may share at least 70% sequence identity, including e.g., at least 75%, at least 80%, at least 85%, at least 90%, at least 95%, at least 96%, at least 97%, at least 98%, at least 99%, or 100% sequence identity with Key$_b$, having the following amino acid sequence:

```
                                    (SEQ ID NO: 47)
NKEEIEKLAKEAREKLKKAEKEHKEIHDKLRKKNKKAREDLKKKADELRE

TNKRVN.
```

In some instances, a key polypeptide of the present disclosure may share at least 70% sequence identity, including e.g., at least 75%, at least 80%, at least 85%, at least 90%, at least 95%, at least 96%, at least 97%, at least 98%, at least 99%, or 100% sequence identity with Key$_c$, having the following amino acid sequence:

```
                                    (SEQ ID NO: 48)
SSEKVRRELKESLKENHKQNQKLLKDHKRAQEKLNRELEELKKKHKKTLD

DIRRES.
```

In some instances, a key polypeptide of the present disclosure may share at least 70% sequence identity, including e.g., at least 75%, at least 80%, at least 85%, at least 90%, at least 95%, at least 96%, at least 97%, at least 98%, at least 99%, or 100% sequence identity with Key$_d$, having the following amino acid sequence:

```
                                    (SEQ ID NO: 49)
DTVKRILEELRRRFEKLAKDLDDIARKLLEDHKKHNKELKDKQRKIKKEA

DDAARS.
```

In some instances, a key polypeptide of the present disclosure may share at least 70% sequence identity, including e.g., at least 75%, at least 80%, at least 85%, at least 90%, at least 95%, at least 96%, at least 97%, at least 98%, at least 99%, or 100% sequence identity with a key polypeptide having an amino acid sequence set forth in Table 3 (inclusive of any appendices included therein).

Polypeptides employed in the circuits of the present disclosure may or may not include additional residues at the N-terminus, C-terminus, internal to the polypeptide, or a combination thereof; these additional residues may or may not be included in determining the percent identity of the polypeptides of the invention relative to the reference polypeptide. Such residues may be any residues suitable for an intended use, including but not limited to tags. As used herein, "tags" may include general detectable moieties (i.e.: fluorescent proteins, antibody epitope tags, etc.), therapeutic agents, purification tags (His tags, etc.), linkers, ligands suitable for purposes of purification, ligands to drive localization of the polypeptide, peptide domains that add functionality to the polypeptides, etc.

Linkers

Polypeptides employed in the circuits of the present disclosure may or may not include peptide linkers. For example, in some instances, two domains of a subject polypeptide may be joined by a peptide linker. Correspondingly, nucleic acid sequences encoding components of the circuits of the present disclosure may be joined by sequence encoding a peptide linker.

A peptide linker can vary in length of from about 3 amino acids (aa) or less to about 200 aa or more, including but not limited to e.g., from 3 aa to 10 aa, from 5 aa to 15 aa, from 10 aa to 25 aa, from 25 aa to 50 aa, from 50 aa to 75 aa, from 75 aa to 100 aa, from 100 aa to 125 aa, from 125 aa to 150 aa, from 150 aa to 175 aa, or from 175 aa to 200 aa. A peptide linker can have a length of from 3 aa to 30 aa, e.g., 3, 4, 5, 6, 7, 8, 9, 10, 11, 12, 13, 14, 15, 16, 17, 18, 19, 20, 21, 22, 23, 24, 25, 26, 27, 28, 29, or 30 aa. A peptide linker can have a length of from 5 aa to 50 aa, e.g., from 5 aa to 40 aa, from 5 aa to 35 aa, from 5 aa to 30 aa, from 5 aa to 25 aa, from 5 aa to 20 aa, from 5 aa to 15 aa or from 5 aa to 10 aa.

Suitable linkers can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

Exemplary linkers include glycine polymers (G)n, glycine-serine polymers (including, for example, (GS)n, (GSGGS)n (SEQ ID NO: 50) and (GGGS)n (SEQ ID NO: 51), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, Rev. Computational Chem. 11173-142 (1992)). Exemplary linkers can comprise amino acid sequences including, but not limited to, GGSG (SEQ ID NO: 52), GGSGG (SEQ ID NO: 53), GSGSG (SEQ ID NO: 54), GSGGG (SEQ ID NO: 55), GGGSG (SEQ ID NO: 56), GSSSG (SEQ ID NO: 57), and the like.

Amino acid linkers connecting alpha helices, include each alpha helix, can be of any suitable length or amino acid composition as appropriate for an intended use. In some embodiments, each amino acid linker is independently between 2 and 10 amino acids in length in embodiments in which no functional polypeptide domain is inserted within a linker. In various embodiments, each amino acid linker is independently 3-10, 4-10, 5-10, 6-10, 7-10, 8-10, 9-10, 2-9, 3-9, 4-9, 5-9, 6-9, 7-9, 8-9, 2-8, 3-8, 4-8, 5-8, 6-8, 7-8, 2-7, 3-7, 4-7, 5-7, 6-7, 2-6, 3-6, 4-6, 5-6, 2-5, 3-5, 4-5, 2-4, 3-4, 2-3, 2, 3, 4, 5, 6, 7, 8, 9, or 10 amino acids in length. As described below linkers may further comprise one or more functional polypeptide domains-in this embodiment, the linkers may be of any size suitable to include the one or more functional polypeptide domains, while maintaining the ability of the structural region and the latch region to interact.

Signaling Pathways

As summarized above, various signaling pathways, including native and synthetic signaling pathways may be modulated using the herein described molecular circuits. Suitable signaling pathways include those that are modulated (e.g., activated, repressed, etc.) by one or more inputs to produce one or more outputs. Inputs and outputs of signaling pathways may vary and may include endogenous (e.g., native) inputs or outputs of signaling pathways and heterologous (e.g., engineered or synthetic) signaling pathway inputs and outputs.

In some instances, an input of a signaling pathway relevant to a circuit of the present disclosure may include an intracellular signal, including e.g., where the output of the pathway may be intracellular or intercellular. In some instances, an output of a signaling pathway relevant to a circuit of the present disclosure may include an intracellular signal, including e.g., where the input of the pathway may be intracellular or intercellular. In some instances, an input of a signaling pathway relevant to a circuit of the present disclosure may include an intercellular signal, including e.g., where the output of the pathway may be intracellular or intercellular. In some instances, an output of a signaling pathway relevant to a circuit of the present disclosure may include an intercellular signal, including e.g., where the input of the pathway may be intracellular or intercellular.

In some instances, both the input and the output of a signaling pathway relevant to a circuit of the present disclosure may include intracellular signals. In some instances, both the input and the output of a signaling pathway relevant to a circuit of the present disclosure may include intercellular signals.

Suitable non-limiting examples of native signaling pathways that may be modulated using a circuit of the present disclosure include but are not limited to e.g., the AKT signaling pathway, the Akt/PKB signaling pathway, the AMPK signaling pathway, the apoptosis signaling pathway, the BMP signaling pathway, the cAMP-dependent pathway, the estrogen signaling pathway, the hedgehog signaling pathway, the hippo signaling pathway, an immune activation pathway, an immune suppression pathway, an immune cell differentiation pathway, an insulin signal transduction pathway, the JAK-STAT signaling pathway, the MAPK/ERK signaling pathway, the mTOR signaling pathway, the NF-κB signaling pathway, the nodal signaling pathway, the notch signaling pathway, the p53 signaling pathway, the PI3K signaling pathway, the TGF beta signaling pathway, the TLR signaling pathway, the TNF signaling pathway, the VEGF signaling pathway, the Wnt signaling pathway, and the like.

Suitable non-limiting examples of pathways, the components of which may be modified to include a caged degron as described herein, also include those PANTHER (Protein ANalysis THrough Evolutionary Relationships) pathways described as part of the Gene Ontology Phylogenetic Annotation Project, descriptions of which (including descriptions of the components of such pathways) are available online at www(dot)pantherdb(dot)org. Non-limiting examples include 2-arachidonoylglycerol biosynthesis, the 5HT1 type receptor mediated signaling pathway, the 5HT2 type receptor mediated signaling pathway, the 5HT3 type receptor mediated signaling pathway, the 5HT4 type receptor mediated signaling pathway, 5-Hydroxytryptamine biosynthesis, 5-Hydroxytryptamine degredation, Acetate utilization, the Activin beta signaling pathway, the Adenine and hypoxanthine salvage pathway, Adrenaline and noradrenaline biosynthesis, Alanine biosynthesis, Allantoin degradation, the ALP23B signaling pathway, the Alpha adrenergic receptor signaling pathway, the Alzheimer disease-amyloid secretase pathway, the Alzheimer disease-presenilin pathway, Aminobutyrate degradation, Anandamide biosynthesis, Anandamide degradation, Androgen/estrogene/progesterone biosynthesis, the Angiogenesis pathway, Angiotensin II-stimulated signaling through G proteins and beta-arrestin, the Apoptosis signaling pathway, Arginine biosynthesis, Ascorbate degradation, Asparagine and aspartate biosynthesis, ATP synthesis, Axon guidance mediated by netrin, Axon guidance mediated by semaphorins, Axon guidance mediated by Slit/Robo, the B cell activation pathway, the Beta1 adrenergic receptor signaling pathway, the Beta2 adrenergic receptor signaling pathway, the Beta3 adrenergic receptor signaling pathway, Biotin biosynthesis, Blood coagulation, the BMP/activin signaling pathway, Bupropion degradation, the Cadherin signaling pathway, Coenzyme A linked carnitine metabolism, Carnitine metabolism, CCKR signaling, the Cell cycle, Cholesterol biosynthesis, Chorismate biosynthesis, Circadian clock system, Cobalamin biosynthesis, Coenzyme A biosynthesis, the Cortocotropin releasing factor receptor signaling pathway, Cysteine biosynthesis, Cytoskeletal regulation by Rho GTPase, De novo purine biosynthesis, De novo pyrimidine deoxyribonucleotide biosynthesis, De novo pyrimidine ribonucleotides biosythesis, DNA replication, the Dopamine receptor mediated signaling pathway, the DPP-SCW signaling pathway, the DPP signaling pathway, the EGF receptor signaling pathway, the Endogenous cannabinoid signaling, the Endothelin signaling pathway, Enkephalin release, the FAS signaling pathway, the FGF signaling pathway, Flavin biosynthesis, Tetrahydrofolate biosynthesis, Formyltetrahydroformate biosynthesis, Fructose galactose metabolism, GABA-B receptor II signaling, Gamma-aminobutyric acid synthesis, the GBB signaling pathway, General transcription by RNA polymerase I, General transcription regulation, Glutamine glutamate conversion, Glycolysis, the Gonadotropin-releasing hormone receptor pathway, the Hedgehog signaling pathway, Heme biosynthesis, the Heterotrimeric G-protein signaling pathway-Gi alpha and Gs alpha mediated pathway, the Heterotrimeric G-protein signaling pathway-Gq alpha and Go alpha mediated pathway, Heterotrimeric G-protein signaling pathway-rod outer segment phototransduction, the Histamine H1 receptor mediated signaling pathway, the Histamine H2 receptor mediated signaling pathway, Histamine synthesis, Histidine biosynthesis, the Huntington disease pathway, Hypoxia response via HIF activation, the Inflammation mediated by chemokine and cytokine signaling pathway, Insulin/IGF pathway-mitogen activated protein kinase kinase/MAP kinase cascade, Insulin/IGF pathway-protein kinase B signaling cascade, the Integrin signalling pathway, the Interferon-gamma signaling pathway, the Interleukin signaling pathway, the Ionotropic glutamate receptor pathway, Isoleucine biosynthesis, the JAK/STAT signaling pathway, Leucine biosynthesis, Lipoate_biosynthesis, Lysine biosynthesis, Mannose metabolism, the Metabotropic glutamate receptor group III pathway, the Metabotropic glutamate receptor group II pathway, the Metabotropic glutamate receptor group I pathway, Methionine biosynthesis, Methylcitrate cycle, the Methylmalonyl pathway, mRNA splicing, the Muscarinic acetylcholine receptor 1 and 3 signaling pathway, the Muscarinic acetylcholine receptor 2 and 4 signaling pathway, the MYO signaling pathway, N-acetylglucosamine metabolism, Nicotine degradation, the Nicotine pharmacodynamics pathway, the Nicotinic acetylcholine receptor signaling pathway, the Notch signaling pathway, O-antigen biosynthesis, the Opioid pro-dynorphin pathway, the Opioid proenkephalin pathway, the Opioid proopiomelanocortin pathway, Ornithine degradation, Oxidative stress response, the Oxytocin receptor mediated signaling pathway, the p38 MAPK pathway, the p53 pathway, p53 pathway by glucose deprivation, P53 pathway feedback loops 1, p53 pathway feedback loops 2, Pantothenate biosynthesis, Parkinson disease, the PDGF signaling pathway, the Pentose phosphate pathway, Peptidoglycan biosynthesis, Phenylacetate degradation, Phenylalanine biosynthesis, Phenylethylamine degradation, Phenylpropionate degradation, the PI3 kinase pathway, Plasminogen activating cascade, Pyridoxal-5-phosphate biosynthesis, Proline biosynthesis, PRPP biosynthesis, Purine metabolism, the Pyridoxal phosphate salvage pathway, Pyrimidine Metabolism, Pyruvate metabolism, the Ras Pathway, S-adenosyl-methionine biosynthesis, Salvage pyrimidine deoxyribonucleotides, Salvage pyrimidine ribonucleotides, the SCW signaling pathway, Serine glycine biosynthesis, Succinate to proprionate conversion, Sulfate assimilation, Synaptic vesicle trafficking, TCA cycle, the T cell activation pathway, the TGF-beta signaling pathway, Thiamin biosynthesis, Thiamin metabolism, Threonine biosynthesis, the Thyrotropin-releasing hormone receptor signaling pathway, the Toll pathway, the Toll receptor signaling pathway, Transcription regulation by bZIP transcription factor, Triacylglycerol metabolism, Tryptophan biosynthesis, Tyrosine biosynthesis, the Ubiquitin proteasome pathway, Valine biosynthesis, Vasopressin synthesis, the VEGF signaling pathway, Vitamin B6 biosynthesis, Vitamin B6 metabolism, the Vitamin D metabolism and pathway, the Wnt signaling pathway, the Xanthine and guanine salvage pathway, and the like.

Further non-limiting examples of signaling pathways, and description thereof, include the following: AKT Signaling Pathway (AKT is a serine/threonine kinase that is involved in mediating various biological responses, such as inhibition of apoptosis), Angiopoietin-TIE2 Signaling (The angiopoietins are a new family of growth factor ligands that bind to TIE2/TEK RTK (Receptor Tyrosine Kinase)), Antigen Processing and Presentation by MHCs (Antigen processing and presentation are the processes that result in association of proteins with major histocompatibility complex (MHC) molecules for recognition by a T-cell), Apoptosis Through Death Receptors (Certain cells have unique sensors, termed death receptors (DRs), which detect the presence of extracellular death signals and rapidly ignite the cell's intrinsic apoptosis machinery), APRIL Pathway (In immune responses, APRIL acts as a co-stimulator for B-cell and T-cell proliferation and supports class switch), B-Cell Development Pathway (The B-cell receptor (BCR) complex usually consists of an antigen-binding subunit that is composed of two Ig heavy chains, two Ig light chains, and a signaling subunit), BMP Pathway (Bone morphogenetic proteins (BMPs) are a large subclass of the transforming growth factor-beta (TGF-beta) superfamily), Cancer Immunoediting (The immune system attempts to constrain tumor growth, but sometimes tumor cells might escape or attenuate this immune pressure), CCR5 Pathway in Macrophages (C-C motif chemokine receptor type 5 (CCR5) is a member of the chemokine receptor subclass of the G protein-coupled receptor (GPCR) superfamily), CD4 and CD8 T-Cell Lineage (Each mature T-cell generally retains expression of the co-receptor molecule (CD4 or CD8) that has a major histocompatibility complex (MHC)-binding property that matches that of its T-cell receptor (TCR)), Cellular Apoptosis Pathway (Apoptosis is a naturally occurring process by which a cell is directed to programmed cell death), CTL- Mediated Apoptosis (The cytotoxic T lymphocytes (CTLs), also known as killer T-cells, are produced during cell-mediated immunity designed to remove body cells displaying a foreign epitope), CTLA4 Signaling Pathway (The co-stimulatory CTLA4 pathway attenuates or down-regulates T-cell activation CTLA4 is designed to remove body cells displaying a foreign epitope), Cytokine Network (Cytokines have been classified on the basis of their biological responses into pro- or anti-inflammatory cytokines, depending on their effects on immunocytes), ErbB Family Pathway (The ErbB family of transmembrane receptor tyrosine kinases (RTKs) plays an important role during the growth and development of organs), Fas Signaling (FAS (also called APO1 or CD95) is a death domain—containing member of the tumor necrosis factor (TNF) receptor superfamily), FGF Pathway (One of the most well characterized modulators of angiogenesis is the heparin-binding fibroblast growth factor (FGF)), Granulocyte Adhesion and Diapedesis (Adhesion and diapedesis of granulocytes have mostly been analyzed in context to non-lymphoid endothelium), Granzyme Pathway (Granzyme A (GzmA) activates a caspase-independent cell death pathway with morphological features of apoptosis), GSK3 Signaling (GSK3 is a ubiquitously expressed, highly conserved serine/threonine protein kinase found in all eukaryotes), Hematopoiesis from Multipotent Stem Cells (Hematopoietic stem cells are classified into long-term, short-term and multipotent progenitors, based on the extent of their self-renewal abilities), Hematopoiesis from Pluripotent Stem Cells (Pluripotent stem cells are capable of forming virtually all of the possible tissue types found in human beings), IL-2 Gene Expression in Activated and Quiescent T-Cells (IL-2 is a cytokine that stimulates the growth, proliferation, and differentiation of T-cells, B-cells, NK cells, and other immune cells), IL-6 Pathway (IL-6 is a pleiotropic cytokine that affects the immune system and many physiological events in various organs), IL-10 Pathway (IL-10 is a pleiotropic cytokine with important immunoregulatory functions and whose activities influence many immune cell types), IL-22 Pathway (IL-22 is a member of the IL-10 family of cytokines and exerts multiple effects on the immune system), Interferon Pathway (Interferons are pleiotropic cytokines best known for their ability to induce cellular resistance to viral infection), JAK/STAT Pathway (The JAK/STAT pathway is a signaling cascade whose evolutionarily conserved roles include cell proliferation and hematopoiesis), MAPK Family Pathway (Mitogen-activated protein kinases (MAPKs) belong to a large family of serine/threonine protein kinases that are conserved in organisms as diverse as yeast and humans), Nanog in Mammalian ESC Pluripotency (NANOG is a transcription factor transcribed in pluripotent stem cells and is down-regulated upon cell differentiation), p53-Mediated Apoptosis Pathway (Tumor protein p53 is a nuclear transcription factor that regulates the expression of a wide variety of genes involved in apoptosis, growth arrest, or senescence in response to genotoxic or cellular stress), Pathogenesis of Rheumatoid Arthritis (Rheumatoid arthritis (RA) is a chronic symmetric polyarticular joint disease that primarily affects the small joints of the hands and feet), PI3K Signaling in B Lymphocytes (The phosphoinositide 3-kinases (PI3Ks) regulate numerous biological processes, including cell growth, differentiation, survival, proliferation, migration, and metabolism), RANK Pathway (RANKL and its receptor RANK are key regulators of bone remodeling, and are essential for the development and activation of osteoclasts), RANK Signaling in Osteoclasts (RANKL induces the differentiation of osteoclast precursor cells and stimulates the resorption function and survival of mature osteoclasts), TGF-Beta Pathway (Members of the transforming growth factor (TGF)-beta family play an important role in the development, homeostasis, and repair of most tissues), THC Differentiation Pathway (T-helper cells of type 1 (TH1) and type 2 (TH2) are derived from T-helper cells and provide help to cells of both the innate and adaptive immune systems), TNF Signaling Pathway (Tumor necrosis factor (TNF) is a multifunctional pro-inflammatory cytokine with effects on lipid metabolism, coagulation, insulin resistance, and endothelial function), TNF Superfamily Pathway (The tumor necrosis factor (TNF) superfamily consists of 19 members that signal through 29 receptors that are members of the TNF receptor (TNFR) superfamily), Transendothelial Migration of Leukocytes (Transport of plasma proteins and solutes across the endothelium involves two different routes: transcellular and paracellular junctions), Tumoricidal Effects of Hepatic NK Cells (The liver is a major site for the formation and metastasis of tumors), TWEAK Pathway (TWEAK is a cell surface-associated protein belonging to the tumor necrosis factor (TNF) superfamily and has multiple biological activities), VEGF Family of Ligands and Receptor Interactions (Vascular endothelial growth factor (VEGF) is a highly-conserved genetic pathway that has evolved from simple to complex systems), and the like.

As summarized above, a component of a signaling pathway, including but not limited to a pathway described herein, may be modified to include a caged degron such that degradation of the signaling pathway member may be controlled by expression of a key polypeptide. Suitable pathway components that may be employed include e.g., input-receiving members, intermediate members, and output-producing members, including but not limited to e.g., the corresponding member of the pathways listed above.

Similarly, essentially any synthetic pathway may modulated using a molecular circuit as described herein. Suitable non-limiting examples of synthetic signaling pathways that may be modulated using a circuit of the present disclosure include, but are not limited to, those pathways controlled by a synthetic or engineered receptor, such as but not limited to e.g., a CAR, an engineered TCR, a synNotch, etc.

In some instances, a pathway modulated using a circuit of the present disclosure may include an immune modulation pathway, such as e.g., an immune activation pathway or an immune suppression pathway. Such immune modulation pathways may be natural or synthetic and may be endogenous to the cell in which the circuit is employed or heterologous to the cell in which the circuit is employed.

Suitable non-limiting examples of synthetic signaling pathways that may be modulated using a circuit of the present disclosure also include biosynthesis and/or bioproduction pathways. Biosynthesis and/or bioproduction pathways may be natural or synthetic and may be employed in cells and/or organisms where the pathway is endogenous or heterologous.

Non-limiting examples of biosynthesis pathways that may be modulated using a circuit of the present disclosure include, but are not limited to, hormone production pathways (e.g., an insulin production pathway, an estrogen/progesterone production pathway, an androgen production pathway, a growth hormone production pathway, and the like), opioid production pathways, isobutanol production pathways, non-ribosomal polyketide synthetase (NRPS) production pathways, antibiotic production pathways, chemotherapeutic production pathways, artemisinic acid production pathways, terpenoid production pathways, polyketide production pathways, and the like.

Non-limiting examples of synthetic biosynthesis pathways include but are not limited to e.g., synthetic hormone production pathways, synthetic opioid production pathways, synthetic antibiotic production pathways, synthetic chemotherapeutic production pathways, synthetic artemisinic acid production pathways, synthetic terpenoid production pathways, synthetic polyketide production pathways, and the like Nucleic Acids As summarized above, the present disclosure also provides nucleic acids encoding molecular feedback circuits. The subject nucleic acids may include, e.g., a sequence encoding a key polypeptide, sequence encoding a signaling protein that includes a caged degron, and the like. Such nucleic acids may be configured such that one or more of the sequences are operably linked to a regulatory sequence. For example, a nucleic acid may be configured such that the sequence encoding the key polypeptide is operably linked to a regulatory sequence responsive to an output of the signaling pathway. Provided are nucleic acids encoding essentially any circuit employing a caged degron, including but not limited to those circuits specifically described herein. Encompassed are isolated nucleic acids encoding the subject circuits as well as various configurations containing such nucleic acids, such as vectors, e.g., expression cassettes, recombinant expression vectors, viral vectors, and the like.

Recombinant expression vectors of the present disclosure include those comprising one or more of the described nucleic acids. A nucleic acid comprising a nucleotide sequence encoding all or a portion of the components of a circuit of the present disclosure will in some embodiments be DNA, including, e.g., a recombinant expression vector. A nucleic acid comprising a nucleotide sequence encoding all or a portion of the components of a circuit of the present disclosure will in some embodiments be RNA, e.g., in vitro synthesized RNA.

As summarized above, in some instances, the subject circuits may make use of an encoding nucleic acid (e.g., a nucleic acid encoding a key polypeptide or a caged degron-linked signaling protein) that is operably linked to a regulatory sequence such as a transcriptional control element (e.g., a promoter; an enhancer; etc.). In some cases, the transcriptional control element is inducible. In some cases, the transcriptional control element is constitutive. In some cases, the promoters are functional in eukaryotic cells. In some cases, the promoters are functional in prokaryotic cells. In some cases, the promoters are cell type-specific promoters. In some cases, the promoters are tissue-specific promoters.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., the cell cycle, the hair follicle cycle in mammals, circadian cycles in mammals, etc.).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, yeast promoters (e.g., promoters of yeast mating pathway genes, yeast galactose-inducible promoters, etc.), light and/or heavy chain immunoglobulin gene promoter and enhancer elements; cytomegalovirus immediate early promoter; herpes simplex virus thymidine kinase promoter; early and late SV40 promoters; promoters present in long terminal repeats from a retrovirus; mouse metallothionein-I promoter; and various art-known tissue specific promoters.

In some instances, transcriptional control elements of varied strength may be employed. For example, promoters, e.g., constitutive or inducible promoters, of varied strength, such as e.g., weak, intermediate, and strong promoters, such as but not limited to e.g., constitutive promoters pREV1, pRNR2, pRET2, etc. may be employed. In some instances, the strength of a promoter may be modulated, e.g., made weaker or made stronger, by decreasing or increasing, respectively, the number of binding sites (e.g., DBD binding sites) within the promoter. Accordingly, the number of binding sites present in a subject promoter may vary and may range from 1 to 6 or more, including but not limited to e.g., 1, 2, 3, 4, 5, 6, etc.

In some instances, a transcriptional control element of a herein described nucleic acid may include a cis-acting regulatory sequence. Any suitable cis-acting regulatory sequence may find use in the herein described nucleic acids. For example, in some instances a cis-acting regulatory sequence may be or include an upstream activating sequence or upstream activation sequence (UAS). In some instances, a UAS of a herein described nucleic acid may be a Gal4 responsive UAS.

In some instances, transcriptional control of a circuit of the present disclosure may include the use of one or more regulatory elements responsive to a synthetic transcription factor. Synthetic transcription factors, and regulatory elements responsive thereto, will vary and may include but are not limited to e.g., estradiol ligand binding domain (LBD) based synthetic transcription factors, progesterone LBD based synthetic transcription factors, zinc-finger based synthetic transcription factors, and the like. Synthetic transcription factors may by chimeric and may include various domains, e.g., a DNA binding domain (DBD), activation domain, zinc-finger domain(s), and the like. Useful domains, e.g., LBDs, DBDs, activation domains, etc., will vary and may include but are not limited to e.g., the Gal4p DBD, the Zif268 transcription factor DBD, viral activation domains (e.g., VP16, VP64, etc.), Msn2p activation domains, and the like. Non-limiting examples of useful synthetic transcription factors include but are not limited to e.g., GEM (Gal4 DNA binding domain-Estradiol hormone binding domain-Msn2 activation domain), Z3PM (Z3 zinc finger-Progesterone hormone binding domain-Msn2 activation domain), and the like. Correspondingly, useful regulatory elements will vary and may include promoters responsive to synthetic transcription factors, including but not limited to e.g., pZ promoters, pZ3 promoters, pGAL1 promoters, and the like. Examples of suitable promoters and synthetic transcription factors include, but are not limited to e.g., those described herein, those described in Aranda-Diaz et al. ACS Synth Biol. (2017) 6(3): 545-554; the disclosure of which is incorporated herein by reference in its entirety, and the like.

Suitable promoters may, in some instances, include suitable reversible promoters. Reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some instances, a useful promoter may be an immune cell promoter. For example, in embodiments were components of a circuit are expressed in an immune cell, an immune cell promoter may be employed. Suitable immune cell promoters include but are not limited to e.g., CD8 cell-specific promoters, CD4 cell-specific promoters, neutrophil-specific promoters, and NK-specific promoters. For example, a CD4 gene promoter can be used; see, e.g., Salmon et al. (1993) *Proc. Natl. Acad. Sci. USA* 90: 7739; and Marodon et al. (2003) *Blood* 101:3416. As another example, a CD8 gene promoter can be used. NK cell-specific expression can be achieved by use of an Ncr1 (p46) promoter; see, e.g., Eckelhart et al. (2011) *Blood* 117:1565.

In some instances, an immune cell specific promoter of a nucleic acid of the present disclosure may be a promoter of a B29 gene promoter, a CD14 gene promoter, a CD43 gene promoter, a CD45 gene promoter, a CD68 gene promoter, a IFN-β gene promoter, a WASP gene promoter, a T-cell receptor β-chain gene promoter, a V9 γ (TRGV9) gene promoter, a V2 δ (TRDV2) gene promoter, and the like.

In some cases, a nucleic acid comprising a nucleotide sequence encoding a circuit of the present disclosure, or one or more components thereof, is a recombinant expression vector or is included in a recombinant expression vector. In some embodiments, the recombinant expression vector is a viral construct, e.g., a recombinant adeno-associated virus (AAV) construct, a recombinant adenoviral construct, a recombinant lentiviral construct, a recombinant retroviral construct, etc. In some cases, a nucleic acid comprising a nucleotide sequence encoding a circuit of the present disclosure, or one or more components thereof, is a recombinant lentivirus vector. In some cases, a nucleic acid comprising a nucleotide sequence encoding a circuit of the present disclosure, or one or more components thereof, is a recombinant AAV vector.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., Hum Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, the vector is a lentivirus vector. Also suitable are transposon-mediated vectors, such as piggyback and sleeping beauty vectors.

In some instances, nucleic acids of the present disclosure may have a single sequence encoding two or more polypeptides where expression of the two or more polypeptides is made possible by the presence of a sequence element between the individual coding regions that facilitates separate expression of the individual polypeptides. Such sequence elements, may be referred to herein as bicistronic-facilitating sequences, where the presence of a bicistronic-facilitating sequence between two coding regions makes possible the expression of a separate polypeptide from each coding region present in a single nucleic acid sequence. In some instances, a nucleic acid may contain two coding regions encoding two polypeptides present in a single nucleic acid with a bicistronic-facilitating sequence between the coding regions. Any suitable method for separate expression of multiple individual polypeptides from a single nucleic acid sequence may be employed and, similarly, any suitable method of bicistronic expression may be employed.

In some instances, a bicistronic-facilitating sequence may allow for the expression of two polypeptides from a single nucleic acid sequence that are temporarily joined by a cleavable linking polypeptide. In such instances, a bicistronic-facilitating sequence may include one or more encoded peptide cleavage sites. Suitable peptide cleavage sites include those of self-cleaving peptides as well as those cleaved by a separate enzyme. In some instances, a peptide cleavage site of a bicistronic-facilitating sequence may include a furin cleavage site (i.e., the bicistronic-facilitating sequence may encode a furin cleavage site).

In some instances, the bicistronic-facilitating sequence may encode a self-cleaving peptide sequence. Useful self-cleaving peptide sequences include but are not limited to e.g., peptide 2A sequences, including but not limited to e.g., the T2A sequence.

In some instances, a bicistronic-facilitating sequence may include one or more spacer encoding sequences. Spacer encoding sequences generally encode an amino acid spacer, also referred to in some instances as a peptide tag. Useful spacer encoding sequences include but are not limited to e.g., V5 peptide encoding sequences, including those sequences encoding a V5 peptide tag.

Multi- or bicistronic expression of multiple coding sequences from a single nucleic acid sequence may make use of but is not limited to those methods employing furin cleavage, T2A, and V5 peptide tag sequences. For example, in some instances, an internal ribosome entry site (IRES) based system may be employed. Any suitable method of bicistronic expression may be employed including but not limited to e.g., those described in Yang et al. (2008) Gene Therapy. 15(21):1411-1423; Martin et al. (2006) BMC Biotechnology. 6:4; the disclosures of which are incorporated herein by reference in their entirety.

Cells

As summarized above, the present disclosure also provides cells containing nucleic acids encoding molecular feedback circuits. Cells modified to include one or more nucleic acids encoding one or more molecular feedback circuits and/or one or more components thereof may be referred to herein as having been genetically modified, where such modification may be stable or transient as desired. Useful cells may include prokaryotic and eukaryotic cells, including but not limited to e.g., bacterial cells, plant cells, animal cells, yeast cells, mammalian cells, rodent cells, non-human primate cells, human cells, and the like.

Suitable cells include stem cells, progenitor cells, as well as partially and fully differentiated cells. Suitable cells include, neurons, liver cells; kidney cells; immune cells; cardiac cells; skeletal muscle cells; smooth muscle cells; lung cells; and the like.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is a stem cell. In some cases, the cell is an induced pluripotent stem cell. In some cases, the cell is a mesenchymal stem cell. In some cases, the cell is a hematopoietic stem cell. In some cases, the cell is an adult stem cell.

Suitable cells include bronchioalveolar stem cells (BASCs), bulge epithelial stem cells (bESCs), corneal epithelial stem cells (CESCs), cardiac stem cells (CSCs), epidermal neural crest stem cells (eNCSCs), embryonic stem cells (ESCs), endothelial progenitor cells (EPCs), hepatic oval cells (HOCs), hematopoetic stem cells (HSCs), keratinocyte stem cells (KSCs), mesenchymal stem cells (MSCs), neuronal stem cells (NSCs), pancreatic stem cells (PSCs), retinal stem cells (RSCs), and skin-derived precursors (SKPs).

In some instances, a cell is an immune cell. Suitable mammalian immune cells include primary cells and immortalized cell lines. Suitable mammalian cell lines include human cell lines, non-human primate cell lines, rodent (e.g., mouse, rat) cell lines, and the like. In some instances, the cell is not an immortalized cell line, but is instead a cell (e.g., a primary cell) obtained from an individual. For example, in some cases, the cell is an immune cell, immune cell progenitor or immune stem cell obtained from an individual. As an example, the cell is a lymphoid cell, e.g., a lymphocyte, or progenitor thereof, obtained from an individual. As another example, the cell is a cytotoxic cell, or progenitor thereof, obtained from an individual. As another example, the cell is a stem cell or progenitor cell obtained from an individual.

As used herein, the term "immune cells" generally includes white blood cells (leukocytes) which are derived from hematopoietic stem cells (HSC) produced in the bone marrow. "Immune cells" includes, e.g., lymphoid cells, i.e., lymphocytes (T cells, B cells, natural killer (NK) cells), and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), T-regulatory cells (Treg) and gamma-delta T cells. A "cytotoxic cell" includes CD8+ T cells, natural-killer (NK) cells, and neutrophils, which cells are capable of mediating cytotoxicity responses. "B cell" includes mature and immature cells of the B cell lineage including e.g., cells that express CD19 such as Pre B cells, Immature B cells, Mature B cells, Memory B cells and plasmablasts. Immune cells also include B cell progenitors such as Pro B cells and B cell lineage derivatives such as plasma cells.

Cells encoding a circuit of the present disclosure may be generated by any convenient method. Nucleic acids encoding one or more components of a subject circuit may be stably or transiently introduced into the subject immune cell, including where the subject nucleic acids are present only temporarily, maintained extrachromosomally, or integrated into the host genome. Introduction of the subject nucleic acids and/or genetic modification of the subject immune cell can be carried out in vivo, in vitro, or ex vivo.

In some cases, the introduction of the subject nucleic acids and/or genetic modification is carried out ex vivo. For example, an immune cell, a stem cell, etc., is obtained from an individual; and the cell obtained from the individual is modified to express components of a circuit of the present disclosure. The modified cell can thus be modified with control feedback to one or more signaling pathways of choice, as defined by the one or more molecular feedback circuits present on the introduced nucleic acids. In some cases, the modified cell is modulated ex vivo. In other cases, the cell is introduced into (e.g., the individual from whom the cell was obtained) and/or already present in an individual; and the cell is modulated in vivo, e.g., by administering a nucleic acid or vector to the individual in vivo.

In some instances, cells employing a feedback circuit of the present disclosure may be therapeutic cells useful in cellular therapy of a subject. For example, in an application such as cellular therapy employing immune cells, the immune cells are engineered to deliver a therapeutic payload of interest in the human body. If the output of these engineered cells is too high, toxic effects may occur (such as e.g., cytokine release syndrome (CRS) as observed in CAR T cell therapies), but on the other hand an output that is too low then the therapy may be ineffective. Therapeutic cells can be fine-tuned to achieve a desired level of output (i.e., a setpoint) under well-controlled laboratory conditions. However, the dynamic environments in which engineered therapeutic cells function make guaranteeing that the output will remain constant over time difficult. Using the molecular circuits described herein for implementing feedback control, engineered cells have the ability to automatically correct against disturbances encountered the environment, including e.g., disturbances that cause the output to drift. In one aspect, self-regulating engineered cells are more robust in in vivo scenarios, thus improving existing cell therapy applications of synthetic biology.

In some instances, cellular therapeutics such as CAR T cells or synthetic receptor (e.g., SynNotch) enabled T cells greatly benefit from feedback control as a safety mechanism. A feedback controller in a CAR T cell may regulate the level of T cell activation and prevents toxic effects such as CRS which result from overstimulation of immune cells. Similarly, in SynNotch T cells, e.g., feedback control may enable delivery of a precise concentration of a payload of interest regardless of any disturbances to the engineered cell that are present or introduced. As will be readily understood, use of feedback control in therapeutic cells is not limited to these approaches and include other approaches as well.

Figures 8, 9:
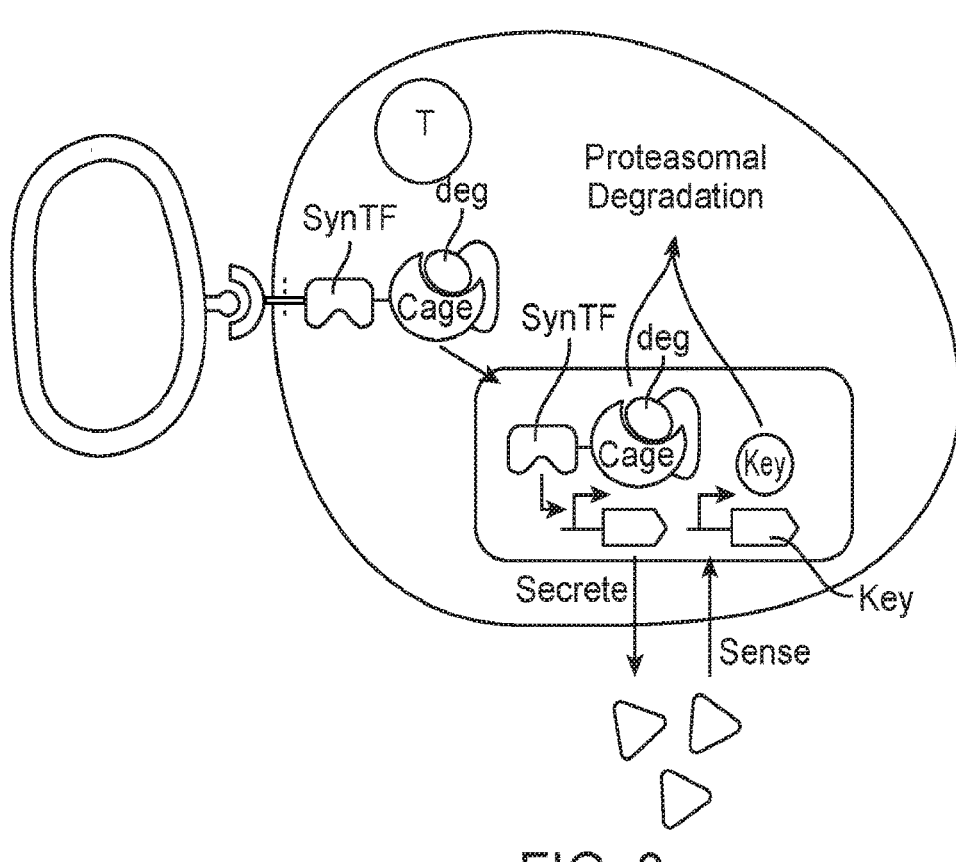
FIG. 8 schematically depict a T lymphocyte employing a molecular feedback circuit of the present disclosure for intercellular control of cytokine signaling.
FIG. 9 schematically depict a T lymphocyte employing a molecular feedback circuit of the present disclosure for environmental control of T cell activation.

For example, the use of feedback control to provide for intercellular control of cytokine signaling in a T lymphocyte is depicted in FIG. 8. As shown, the T cell is modified to express a synNotch receptor responsive to an antigen present on a target cell. The synNotch receptor includes an intracellular portion including a synthetic transcription factor (SynTF) and a caged degron that includes a cage (Cage) and a degron (deg). The cell has been further modified to include a nucleic acid that includes a sequence encoding a cytokine (triangle) operably linked to a transcriptional regulator element responsive to the SynTF and a nucleic acid that that includes a sequence encoding a key polypeptide operably linked to a transcriptional regulator element responsive to the cytokine (or a signaling member downstream of the cytokine). Upon antigen binding, the synNotch is proteolytically cleaved, releasing the intracellular portion such that the SynTF induces production and secretion of the cytokine. When cytokine levels reach a predetermined threshold, e.g., determined by tuning components of the circuit, the cytokine, or a downstream component of a signaling pathway activated by the cytokine, induces expression of the key polypeptide (Key). Once expressed, the key polypeptide uncages the caged degron, resulting in proteasomal degradation of SynNotch receptor and the key polypeptide, thereby downregulating production of the cytokine.

As another example, FIG. 9 schematically depicts the environmental control of T cell activation in a T lymphocyte expressing a CAR. As shown, the T cell is modified to express a CAR responsive to an antigen present on a target cell. The CAR includes an intracellular portion that includes an immune activating portion (CD3z) and a caged degron that includes a cage (Cage) and a degron (deg). The cell has been further modified to include a nucleic acid that that includes a sequence encoding a key polypeptide operably linked to a transcriptional regulator element responsive to a cytokine (or a signaling member downstream of the cytokine) produced in response to activation of the native T-cell program by the CAR binding its antigen. Thus, upon antigen binding, the CAR activates the native T-cell program and the cytokine (IL-6), to which the transcriptional regulator is response, is produced and secreted. The level of IL-6 is sensed by the cell and when IL-6 levels reach a predetermined threshold, e.g., determined by tuning components of the circuit, IL-6, or a downstream component of a signaling pathway activated by IL-6, induces expression of the key polypeptide (Key). Once expressed, the key polypeptide uncages the caged degron, resulting in proteasomal degradation of the CAR and the key polypeptide, thereby downregulating production of the cytokine.

Useful cells, within which circuits of the present disclosure may be employed, are not limited to therapeutic cells. For example, in some instances cells used in bioproduction may be employed. By "bioproduction", as used herein, is generally meant processes by which a desired component is produced by cell for various applications, e.g., for industrial, commercial, biomedical, research, etc., applications. Biological products produced in bioproduction processes may vary and such products may be endogenous or heterologous to the cell and/or organism used in its production. In some instances, biological products of interest include, but are not limited to, recombinant therapeutic proteins, viruses (e.g. recombinant viruses for gene therapy), vaccines, antibodies, proteins and peptides (e.g., enzymes, growth factors, etc.), polysaccharides, nucleic acids (including DNA and RNA), cells, and nutritional products. Circuits and/or methods of the present disclosure may be used in conjunction with several different production techniques known in the art, such as the production of biological products using cells in a bioreactor (e.g., mammalian, yeast, bacteria, and/or insect cells), methods involving the use of transgenic animals (e.g. goats or chickens), methods involving the use of transgenic plants (e.g., tobacco, seeds or moss), and other methods known to those of skill in the art.

Where employed, suitable cells for bioproduction may include but are not limited to e.g., COS cells, NS0 cells, SP2/0 cells, YB2/0 cells, and the like. Useful cells may be of prokaryotic (e.g., bacterial) or eukaryotic origin (including e.g., mammalian, yeast, plant, etc.) and may, in some instances, be established cell culture lines. Suitable cells may, in some instances, also include HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some instances, useful bioproduction cells may include yeast cells. Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp.,

54

*Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii,* and the like.

In some instances, useful bioproduction cells may include prokaryotic cells. Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) Science 270:299-302. Examples of *Salmonella* strains which can be employed include, but are not limited to, *Salmonella typhi* and *S. typhimurium.* Suitable *Shigella* strains include, but are not limited to, *Shigella flexneri, Shigella sonnei,* and *Shigella disenteriae.* Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the cell is *Escherichia coli.*

In some instances, feedback control useful is cells employed for metabolic engineering, where the balance of enzymes in a metabolic pathway is essential to obtain an optimal titer of product. It is common for intermediates or even final products of metabolic pathways to have at least some level of toxicity to the host cell. Therefore, optimization of the ratios of enzymes is beneficial to maximizing the amount of product produced while maintaining effective cell growth. As an additional, due to the large size of reactors employed industrial fermentations, cells across a fermentation may experience highly variable environments and may be subjected to various different stressors at differing levels. These disturbances may cause the activity of enzymes to shift, necessitating "re-balancing" of pathway activity. A feedback controller employing a molecular circuit of the present disclosure mitigates the effects of disturbances, maximizing titers by dynamically rebalancing enzyme ratios.

Methods

As summarized above, the present disclosure also provides methods of using caged-degron-based molecular feedback circuits. Such methods include but are not limited to e.g., methods of modulating a signaling pathway of a cell where the cell is or has been genetically modified with a caged-degron-based molecular feedback circuit.

Methods employed for modulating signaling of a signaling pathway of a cell may serve various purposes. For example, in some instances, a circuit of the present disclosure may be employed in a method to provide feedback control of a signaling pathway of interest. In some instances, feedback control may include negative feedback control, which may, among other aspects, e.g., prevent the pathway from remaining active when a particular pathway output is produced and/or produced at or above a threshold level. In some instances, feedback control may include positive feedback control, which may, among other aspects, e.g., provide for amplification of a particular pathway output. In some instances, feedback control may provide for more stable output of a signaling pathway, including e.g., where the signaling output of the pathway is insulated from variables such as but not limited to e.g., environmental factors and inputs.

As described above, cells of the methods of the present disclosure may vary and may include in vitro and/or ex vivo cells genetically modified with one or more nucleic acids encoding one or more components of one or more circuits as described herein. In some instances, cells are primary cells obtained from a subject. In some instances, cells are obtained from a cell culture.

Accordingly, methods of the present disclosure may include obtaining cells used in the method, including where such cells are unmodified or have already been genetically modified to include a circuit of the present disclosure. In some instances, methods of the present disclosure may involves performing the genetic modification. In some instances, methods of the present disclosure may include collecting cells, including where cells are collected before and/or after genetic modification. Methods of collecting cells may vary and may include e.g., collecting cells from a cell culture, collecting a cellular sample from a subject that includes the cells of interest, and the like.

In some instances, methods of the present disclosure may include modulating (e.g., increasing and/or decreasing) signaling of a signaling pathway, where such modulating involves uncaging of a caged degron, such as e.g., a degron-LOCKR protein, to cause degradation of a signaling protein of the pathway. As described herein, the circuits of the present disclosure may include feedback, including positive and negative feedback. Feedback of the present methods may be dependent upon, at least in part, an output of the signaling pathway. Thus, once the circuit is initiated and/or a cell containing the circuit is delivered, modulation of the signaling pathway in accordance with the circuit may not necessitate further manipulation, i.e., feedback regulation of the signaling pathway by the circuit may be essentially automatic.

Accordingly, in methods employing cells that contain a molecular feedback circuit of the present disclosure, in some instances, the cells may be administered to the subject and no further manipulation of the circuit need be performed. For example, where a subject is treated with cells that contain a molecular feedback circuit of the present disclosure, the treatment may include administering the cells to the subject, including where such administration is the sole intervention to treat the subject.

In such methods, cells that may be administered may include, but are not limited to e.g., immune cells. In such methods, the circuit may be configured, in some instances, to modulate signaling of a native or synthetic signaling pathway of the immune cell, such as but not limited to e.g., an immune activation pathway or an immune suppression pathway. Non-limiting examples of suitable immune activation pathways, whether regulated by native or synthetic means, include cytokine signaling pathways, B cell receptor signaling pathways, T cell receptor signaling pathways, and the like. Non-limiting examples of suitable immune suppression pathways, whether regulated by native or synthetic means, include inhibitory immune checkpoint pathways, and the like.

Methods of the present disclosure may include administering to a subject cells that express a therapeutic agent. Such cells may include a molecular feedback circuit of the present disclosure and may or may not be immune cells. For example, in some instances, a method may include administering to a subject a non-immune cell that produces a therapeutic agent, either endogenously or heterologously, where production of the therapeutic is controlled, in whole or in part, by the molecular feedback circuit. In some instances, a method may include administering to a subject an immune cell that produces a therapeutic agent, either endogenously or heterologously, where production of the therapeutic is controlled, in whole or in part, by the molecular feedback circuit. Non-limiting examples of suitable encoded therapeutic agents, include but are not limited to e.g., hormones or components of hormone production pathways, such as e.g., insulins or a component of an insulin production pathway, estrogen/progesterone or a component of an estrogen/progesterone production pathway, testosterone or a component of an androgen production pathway, growth hormone or a component of a growth hormone production pathway, or the like.

Such methods may be employed, in some instances, to treat a subject for a condition, including e.g., where the condition is a deficiency in a metabolic or a hormone. In such instances, the molecular feedback circuit may be configured such that the output of the molecular feedback circuit controls, in whole or in part, production and/or secretion of a metabolic or a hormone.

In some instances, the instant methods may include contacting a cell with one or more nucleic acids encoding a circuit wherein such contacting is sufficient to introduce the nucleic acid(s) into the cell. Any convenient method of introducing nucleic acids into a cell may find use herein including but not limited viral transfection, electroporation, lipofection, bombardment, chemical transformation, use of a transducible carrier (e.g., a transducible carrier protein), and the like. Nucleic acids may be introduced into cells maintained or cultured in vitro or ex vivo. Nucleic acids may also be introduced into a cell in a living subject in vivo, e.g., through the use of one or more vectors (e.g., viral vectors) that deliver the nucleic acids into the cell without the need to isolate, culture or maintain the cells outside of the subject.

Any convenient method of delivering the circuit encoding components may find use in the subject methods. In some instances, the subject circuit may be delivered by administering to the subject a cell expressing the circuit. In some instances, the subject circuit may be delivered by administering to the subject a nucleic acid comprising one or more nucleotide sequences encoding the circuit. Administering to a subject a nucleic acid encoding the circuit may include administering to the subject a cell containing the nucleic acid where the nucleic acid may or may not yet be expressed. In some instances, administering to a subject a nucleic acid encoding the circuit may include administering to the subject a vector designed to deliver the nucleic acid to a cell.

The subject methods may include introducing into a subject in need thereof, cells that contain nucleic acid sequences encoding a therapeutic, the expression of which is controlled, at least in part by a molecular feedback circuit. The therapeutic may be a therapeutic for the treatment of cancer. The introduced cells may be immune cells, including e.g., myeloid cells or lymphoid cells.

Non-limiting examples of cancers that may be treated include, e.g., Acute Lymphoblastic Leukemia (ALL), Acute Myeloid Leukemia (AML), Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.), Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, ect.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia, Head and Neck Cancer, Heart Cancer, Hepatocellular (Liver) Cancer, Histiocytosis (e.g., Langerhans Cell, etc.), Hodgkin Lymphoma, Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic (ALL), Acute Myeloid (AML), Chronic Lymphocytic (CLL), Chronic Myelogenous (CML), Hairy Cell, etc.), Lip and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin, Primary Central Nervous System (CNS), etc.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloproliferative Neoplasms (e.g., Chronic, etc.), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (e.g., Ewing, Kaposi, Osteosarcoma, Rhabdomyosarcoma, Soft Tissue, Uterine, etc.), Sézary Syndrome, Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric)

Cancer, T-Cell Lymphoma, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer, Vulvar Cancer, Waldenström Macroglobulinemia, Wilms Tumor, and the like.

In some instances, methods of the present disclosure may be employed to treat a subject for an immune dysfunction, including but not limited to e.g., where the condition is an autoimmune disease. For example, in some instances, a molecular feedback circuit of the present disclosure may be configured to regulate the immune activation level of a subject having an autoimmune disease, thus controlling the subject's autoimmune response to treat the subject for the autoimmune disease. In some instances, a subject having an autoimmune disease may be administered cells configured to contain a molecular feedback circuit of the present disclosure where the output of the molecular feedback circuit is immune suppression.

The present disclosure further includes methods of making the nucleic acids, circuits, and cells employed in the herein described methods. In making the subject nucleic acids and circuits, and components thereof, any convenient methods of nucleic acid manipulation, modification and amplification (e.g., collectively referred to as "cloning") may be employed. In making the subject cells, containing the nucleic acids encoding the described circuits, convenient methods of transfection, transduction, culture, etc., may be employed.

A nucleotide sequence encoding all or a portion of the components of a circuit of the present disclosure can be present in an expression vector and/or a cloning vector. Where a subject circuit or component thereof is split between two or more separate polypeptides, nucleotide sequences encoding the two or more polypeptides can be cloned in the same or separate vectors. An expression vector can include a selectable marker, an origin of replication, and other features that provide for replication and/or maintenance of the vector. Suitable expression vectors include, e.g., plasmids, viral vectors, and the like.

Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, in some embodiments, a nucleic acid comprising a nucleotide sequence encoding a circuit or component thereof of the present disclosure will in some embodiments be DNA or RNA, e.g., in vitro synthesized DNA, recombinant DNA, in vitro synthesized RNA, recombinant RNA, etc. Methods for in vitro synthesis of DNA/ RNA are known in the art; any known method can be used to synthesize DNA/RNA comprising a desired sequence. Methods for introducing DNA/RNA into a host cell are known in the art. Introducing DNA/RNA into a host cell can be carried out in vitro or ex vivo or in vivo. For example, a host cell (e.g., an NK cell, a cytotoxic T lymphocyte, etc.) can be transduced, transfected or electroporated in vitro or ex vivo with DNA/RNA comprising a nucleotide sequence encoding all or a portion of a circuit of the present disclosure.

Methods of the instant disclosure may further include culturing a cell genetically modified to encode a circuit of the instant disclosure including but not limited to e.g., culturing the cell prior to administration, culturing the cell in vitro or ex vivo (e.g., the presence or absence of one or more antigens), etc. Any convenient method of cell culture may be employed whereas such methods will vary based on various factors including but not limited to e.g., the type of cell being cultured, the intended use of the cell (e.g., whether the cell is cultured for research or therapeutic purposes), etc. In some instances, methods of the instant disclosure may further include common processes of cell culture including but not limited to e.g., seeding cell cultures, feeding cell cultures, passaging cell cultures, splitting cell cultures, analyzing cell cultures, treating cell cultures with a drug, harvesting cell cultures, etc.

Methods of the instant disclosure may, in some instances, further include receiving and/or collecting cells that are used in the subject methods. In some instances, cells are collected from a subject. Collecting cells from a subject may include obtaining a tissue sample from the subject and enriching, isolating and/or propagating the cells from the tissue sample. Isolation and/or enrichment of cells may be performed using any convenient method including e.g., isolation/enrichment by culture (e.g., adherent culture, suspension culture, etc.), cell sorting (e.g., FACS, microfluidics, etc.), and the like. Cells may be collected from any convenient cellular tissue sample including but not limited to e.g., blood (including e.g., peripheral blood, cord blood, etc.), bone marrow, a biopsy, a skin sample, a cheek swab, etc. In some instances, cells are received from a source including e.g., a blood bank, tissue bank, etc. Received cells may have been previously isolated or may be received as part of a tissue sample thus isolation/enrichment may be performed after receiving the cells and prior to use. In certain instances, received cells may be non-primary cells including e.g., cells of a cultured cell line. Suitable cells for use in the herein described methods are further detailed herein.

Kits

Aspects of the present disclosure also include kits. The kits may include, e.g., one or more of any of the reaction mixture components described above with respect to the subject methods. For example, the kits may include a caged degron polypeptide (or nucleic acid encoding the same), a key polypeptide (or nucleic acid encoding the same), components for delivery, cloning and/or expression, and the like, in various combinations.

Components of the kits may be present in separate containers, or multiple components may be present in a single container. In some instances, components of the subject kits may be presented as a "cocktail" where, as used herein, a cocktail refers to a collection or combination of two or more different but similar components in a single vessel.

In addition to the above-mentioned components, a subject kit may further include instructions for using the components of the kit, e.g., to practice the subject methods as described above. The instructions are generally recorded on a suitable recording medium. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A molecular feedback circuit, the circuit comprising:
   a signaling protein that, when activated by an input of a signaling pathway, drives an output of the signaling pathway, wherein the signaling protein comprises a caged degron; and
   a regulatory sequence responsive to the output and operably linked to a nucleic acid sequence encoding a key polypeptide that, when expressed, uncages the degron thereby degrading the signaling protein.

2. The circuit according to aspect 1, wherein the caged degron comprises:
   a degron;
   a locker domain comprising five alpha helices; and
   a latch domain comprising an alpha helix that, in the absence of the key polypeptide, forms a six helix bundle with the locker domain to cage the degron.

3. The circuit according to aspect 2, wherein the key comprises an alpha helix that binds the locker domain with higher affinity than the latch domain.

4. The circuit according to aspects 2 or 3, wherein the degron is grafted within the latch domain.

5. The circuit according to any of aspects 2 to 4, wherein the helices of locker domain and the latch domain are 30 to 50 residues in length.

6. The circuit according to any of aspects 3 to 5, wherein the helix of the key polypeptide is 40 to 60 residues in length.

7. The circuit according to any of aspects 2 to 6, wherein the latch domain comprises a toehold truncation.

8. The circuit according to any of the preceding aspects, wherein the degron comprises a ubiquitin-independent degradation signal.

9. The circuit according to aspect 8, wherein the ubiquitin-independent degradation signal comprises a CA dipeptide motif.

10. The circuit according to aspect 9, wherein the ubiquitin-independent degradation signal comprises a LXMSCAQE motif, wherein X is any amino acid.

11. The circuit according to aspect 10, wherein X is any amino acid except proline.

12. The circuit according to any of the preceding aspects, wherein the caged degron comprises an asymmetrized locker domain.

13. The circuit according to any of the preceding aspects, wherein the caged degron shares at least 70% sequence identity with the amino acid sequence of one or more of: degronLOCKR_a_327, degronLOCKR_a_327_noPro, degronLOCKR_a_CAonly, degronLOCKR_a_324_t12, degronLOCKR_a_320_t16, degronLOCKR_b, degronLOCKR_b_t13, degronLOCKR_c, degronLOCKR_c_t13, and degronLOCKR_d.

14. The circuit according to any of the preceding aspects, wherein the caged degron shares at least 90% sequence identity with one or more of: degronLOCKR_a_327, degronLOCKR_a_327_noPro, degronLOCKR_a_CAonly, degronLOCKR_a_324_t12, and degronLOCKR_a_320_t16.

15. The circuit according to any of the preceding aspects, wherein the caged degron shares at least 90% sequence identity with one or more of: degronLOCKR_b, and degronLOCKR_b_t13.

16. The circuit according to any of the preceding aspects, wherein the caged degron shares at least 90% sequence identity with one or more of: degronLOCKR_c, and degronLOCKR_c_t13.

17. The circuit according to any of the preceding aspects, wherein the caged degron shares at least 90% sequence identity with degronLOCKR_d.

18. The circuit according to any of the preceding aspects, wherein the caged degron comprises an amino acid sequence selected from those set forth in SEQ ID NOS. 63-1169.

19. The circuit according to any of the preceding aspects, wherein the input, the output, or both comprise an intracellular signal.

20. The circuit according to any of aspects 1 to 18, wherein the input, the output, or both comprise an intercellular signal.

21. The circuit according to any of the preceding aspects, wherein the signaling protein is a positive regulator of the signaling pathway.

22. The circuit according to any of aspects 1 to 20, wherein the signaling protein is a negative regulator of the signaling pathway.

23. The circuit according to any of the preceding aspects, wherein the signaling protein is an intermediate member of the signaling pathway or a transcription factor.

24. The circuit according to aspect 23, wherein the transcription factor is a synthetic transcription factor.

25. The circuit according to aspects 23 or 24, wherein the regulatory sequence comprises a binding site for a transcription factor of the output.

26. The circuit according to aspect 25, wherein the regulatory sequence comprises a plurality of binding sites for the transcription factor.

27. The circuit according to aspect 26, wherein the plurality of binding sites is 2 to 10 binding sites.

28. The circuit according to any of aspects 23 to 27, wherein the output is expression of the transcription factor.

29. The circuit according to any of aspects 1 to 22, wherein the signaling protein is a receptor and the input is a ligand for the receptor.

30. The circuit according to any of the preceding aspects, wherein the signaling pathway is selected from the group consisting of: a AKT signaling pathway, an Akt/PKB signaling pathway, an AMPK signaling pathway, an apoptosis signaling pathway, a BMP signaling pathway, a cAMP-dependent pathway, an estrogen signaling pathway, a hedgehog signaling pathway, a hippo signaling pathway, an immune activation pathway, an immune suppression pathway, an immune cell differentiation pathway, an insulin signal transduction pathway, a JAK-STAT signaling pathway, a MAPK/ERK signaling pathway, a mTOR signaling pathway, an NF-κB signaling pathway, a nodal signaling pathway, a notch signaling pathway, a p53 signaling pathway, a PI3K signaling pathway, a TGF beta signaling pathway, a TLR signaling pathway, a TNF signaling pathway, a VEGF signaling pathway, and a Wnt signaling pathway.

31. The circuit according to any of the preceding aspects, wherein the circuit further comprises a regulatory sequence operably linked to a nucleic acid sequence encoding the signaling protein.

32. The circuit according to aspect 31, wherein the regulatory sequence operably linked to the nucleic acid sequence encoding the signaling protein is a native promoter of the signaling protein.

33. The circuit according to any of aspects 1 to 31, wherein the signaling pathway is a synthetic signaling pathway.

34. The circuit according to aspect 33, wherein the receptor is a synthetic receptor.

35. The circuit according to aspect 34, wherein the synthetic receptor is a synNotch receptor.

36. The circuit according to aspect 34, wherein the synthetic receptor is a chimeric antigen receptor (CAR) or an engineered T cell receptor (TCR).

37. The circuit according to aspect 36, wherein the output is immune activation or immune suppression.

38. The circuit according to any of the preceding aspects, wherein the key polypeptide is full-length.

39. The circuit according to any of the preceding aspects, wherein the key polypeptide is truncated.

40. The circuit according to any of the preceding aspects, wherein the key polypeptide is truncated by 2 to 20 amino acids.

41. The circuit according to any of the preceding aspects, wherein the key polypeptide shares at least 90% sequence identity with a key polypeptide sequence selected from those set forth in SEQ ID NOS. 1170-13903.

63

42. The circuit according to any of the preceding aspects, wherein the key polypeptide comprises a key polypeptide sequence selected from those set forth in SEQ ID NOS. 1170-13903.

43. One or more nucleic acid molecules encoding the molecular feedback circuit according to any of the preceding aspects.

44. A cell genetically modified to comprise the one or more nucleic acid molecules according to aspect 43.

45. The cell according to aspect 44, wherein the cell is a eukaryotic cell.

46. A method of treating a subject for a condition, the method comprising administering to the subject an effective amount of the eukaryotic cell according to aspect 41.

47. The method according to aspect 46, wherein the condition is a cancer and the output of the molecular feedback circuit is immune activation.

48. The method according to aspect 46, wherein the condition is an autoimmune disease and the output of the molecular feedback circuit is immune suppression.

49. The method according to aspect 46, wherein the condition is a deficiency in a metabolic or a hormone and the output of the molecular feedback circuit is production and/or secretion of the metabolic or the hormone.

50. A method of modulating signaling of a signaling pathway of a cell, the method comprising:

genetically modifying the cell with a molecular feedback circuit comprising:

a nucleic acid sequence encoding a signaling protein of the signaling pathway, the signaling protein comprising a caged degronLOCKR domain; and a regulatory sequence, responsive to an output of the signaling pathway, that is operably linked to a nucleic acid sequence encoding a key polypeptide that uncages the degronLOCKR domain, wherein the uncaged degronLOCKR domain causes degradation of the signaling protein thereby modulating signaling of the signaling pathway.

51. The method according to aspect 50, wherein the modulating comprises negative feedback.

52. The method according to aspect 50, wherein the modulating comprises positive feedback.

53. The method according to any of aspects 50 to 52, wherein the cell is an in vitro or ex vivo cell.

54. The method according to any of aspects 50 to 53, wherein the signaling pathway is a native signaling pathway of the cell.

55. The method according to aspect 54, wherein the native signaling pathway is a native biosynthesis pathway.

56. The method according to aspect 47, wherein the native biosynthesis pathway is a hormone production pathway.

57. The method according to aspect 48, wherein the hormone production pathway is selected from the group consisting of: an insulin production pathway, an estrogen/progesterone production pathway, an androgen production pathway, and a growth hormone production pathway.

58. The method according to aspect 54, wherein the cell is an immune cell and the native signaling pathway is an immune activation pathway or an immune suppression pathway.

59. The method according to aspect 58, wherein the immune activation pathway is selected from the group consisting of: a cytokine signaling pathway, a B cell receptor signaling pathway, and a T cell receptor signaling pathway.

60. The method according to aspect 58, wherein the immune suppression pathway is an inhibitory immune checkpoint pathway.

64

61. The method according to any of aspects 50 to 53, wherein the signaling pathway is a synthetic signaling pathway.

62. The method according to aspect 61, wherein the signaling protein is a synNotch receptor and the output is release of an intracellular domain of the synNotch receptor.

63. The method according to aspect 61, wherein the cell is an immune cell and the signaling pathway is a synthetic immune activation pathway or a synthetic immune suppression pathway.

64. The method according to aspect 63, wherein the immune cell is a myeloid cell or a lymphoid cell.

65. The method according to aspect 64, wherein the immune cell is a lymphoid cell selected from the group consisting of: a T lymphocyte, a B lymphocyte and a Natural Killer cell.

66. The method according to any of aspects 63 to 65, wherein the signaling protein is a synthetic immune receptor.

67. The method according to aspect 66, wherein the synthetic immune receptor is a chimeric antigen receptor (CAR) or an engineered T cell receptor (TCR).

68. The method according to any of aspects 58 to 67, wherein the output is immune activation or immune suppression.

69. The method according to aspect 50, wherein the synthetic signaling pathway is a synthetic biosynthesis pathway.

70. The method according to aspect 69, wherein the synthetic biosynthesis pathway is selected from the group consisting of: a hormone production pathway, an opioid production pathway, an antibiotic production pathway, a chemotherapeutic production pathway, an artemisinic acid production pathway, a terpenoid production pathway, and a polyketide production pathway.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: De Novo Design of Bioactive Protein Switches

Switchable protein systems were design de novo guided by the following general considerations. First, accounting for the free energy differences between a starting state and an induced conformational change is more straightforward in a system governed by inter- and intra-molecular competition at the same site rather than allosteric activation at distant sites. Second, a stable protein framework with an extended binding surface available for the competing interactions is more programmable and less likely to engage in off-target interactions than a framework that only becomes ordered upon binding. These features are described by the abstract system depicted in FIG. 10, panel a, which undergoes thermodynamically-driven switching between a binding incompetent and a binding competent state. A latch (blue) contains a peptide sequence (orange) that can bind a target (yellow) unless blocked by intramolecular interactions to a cage (cyan); a key (green) that binds more tightly to the cage outcompetes the latch, allowing the peptide to bind the target. The behavior of such a system is governed by the binding equilibrium constants for the individual subreactions (FIG. 10, panel a): $K_{open}$, the dissociation of latch from cage; $K_{LT}$, the binding of latch to target; and $K_{CK}$, the binding of key to cage. Solving this set of equations (FIG. 10, panel b) shows that when the latch-cage interaction is too weak (red and orange curves), the system binds target with little to no key and the fold induction by key is low, while when the latch-cage interaction is too strong (purple curve), the system only partially binds target, even at high key concentrations. The latch-cage interaction affinity that gives optimal switching (FIG. 10, panel b, blue curve left, green curve right) is a function of the latch-target binding affinity. This model was used to guide design of switchable protein systems, as described in the following sections.

LOCKR Design

Figure 10:
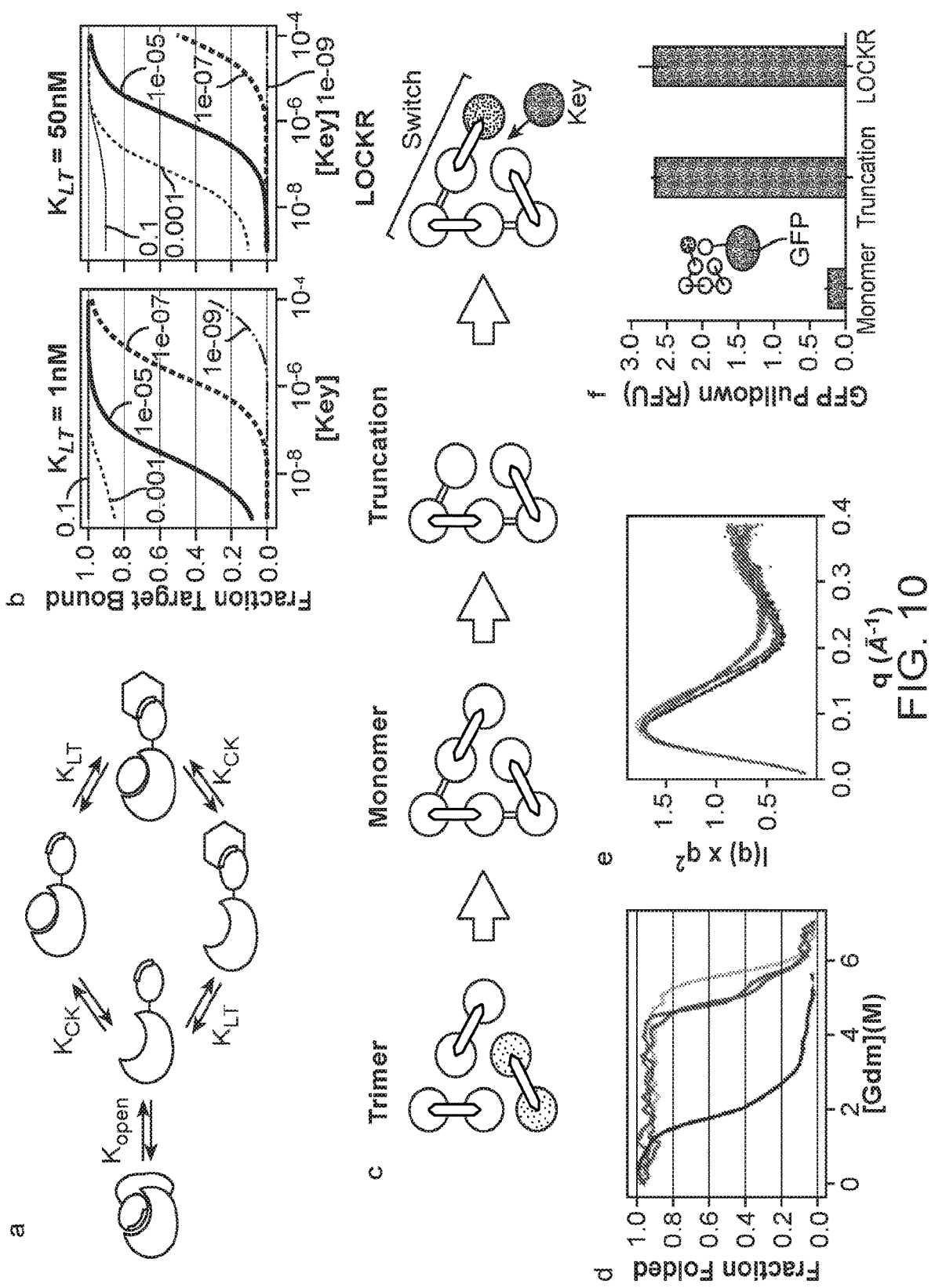
FIG. 10 depicts aspects related to design of the LOCKR switch system according to an embodiment of the disclosure. a, Thermodynamic model describing the design goal. The cage (cyan) and latch (blue) form the switch with some equilibrium in the open and closed states. The key (green) can bind the cage to promote the open state to allow target (yellow) binding to the latch. b, Plots from the model in (a) for two values of $K_{LT}$ showing how fraction target bound is affected by addition of key ($K_{CK}=1$ nM); the different colored curves show the effect of log-decreasing values of $K_{open}=$[open]/[closed]. c, Loops were added to homotrimer 5L6HC3 to form monomeric five- and six-helix frameworks; double mutant V217S/I232S weakens the Latch allowing it to be displaced by key, resulting in a LOCKR system able to bind an exogenous key. d, Chemical denaturation with guanidinium chloride (Gdm) of the trimer (dark blue), monomer (cyan), truncated five-helix framework (red), and LOCKR (green) monitoring mean residue ellipticity (MRE) at 222 nm. e, Small-angle x-ray scattering (SAXS) Kratky plots for the monomeric frameworks are similar to that of the input trimer, with the greatest deviation for the 5 helix framework. Colors continued from (d). f, Pulldown assay showing that Key binds to the truncation and LOCKR (V217S/I232S), but not the six-helix monomer; free GFP-Key was added to monomeric frameworks immobilized onto a plate via a hexahistidine tag; after a series of wash steps, binding was measured by GFP fluorescence (n=2, error bars indicate standard deviation).

To physically implement the switchable system of FIG. 10, panel a, structural features amenable to tuning the affinities of the cage-latch and cage-key interactions over a wide dynamic range were chosen. Alpha helices have advantages over beta strands in that inter-helical interfaces are dominated by sidechain-sidechain interactions, which can be more readily tuned than the backbone hydrogen bonding interactions between beta strands. To allow fine control over the specificity and relative affinities of the cage-latch and cage-key interactions, it was chosen to design interfaces containing buried hydrogen bond networks. As illustrated by Watson-Crick base pairing, considerable alterations of specificity can be obtained with relatively minor changes in the positions of hydrogen bond donors and acceptors. A designed homo-trimer of α-helical hairpins with hydrogen bond network-mediated subunit-subunit interaction specificity (5L6HC3_1 (Boyken, et al. Science 352, 680-687 (2016), the disclosure of which is incorporated herein by reference in its entirety); PDB ID: 5IZS) was chosen as a starting point. By designing short unstructured loops connecting the subunits, monomeric protein frameworks with five or six helices and 40 residues per helix were generated (FIG. 10, panel c). In the five-helix framework, there is an open binding site for a sixth helix added in trans, whereas this site is filled by a sixth helix in cis in the six-helix framework.

Figure 15:
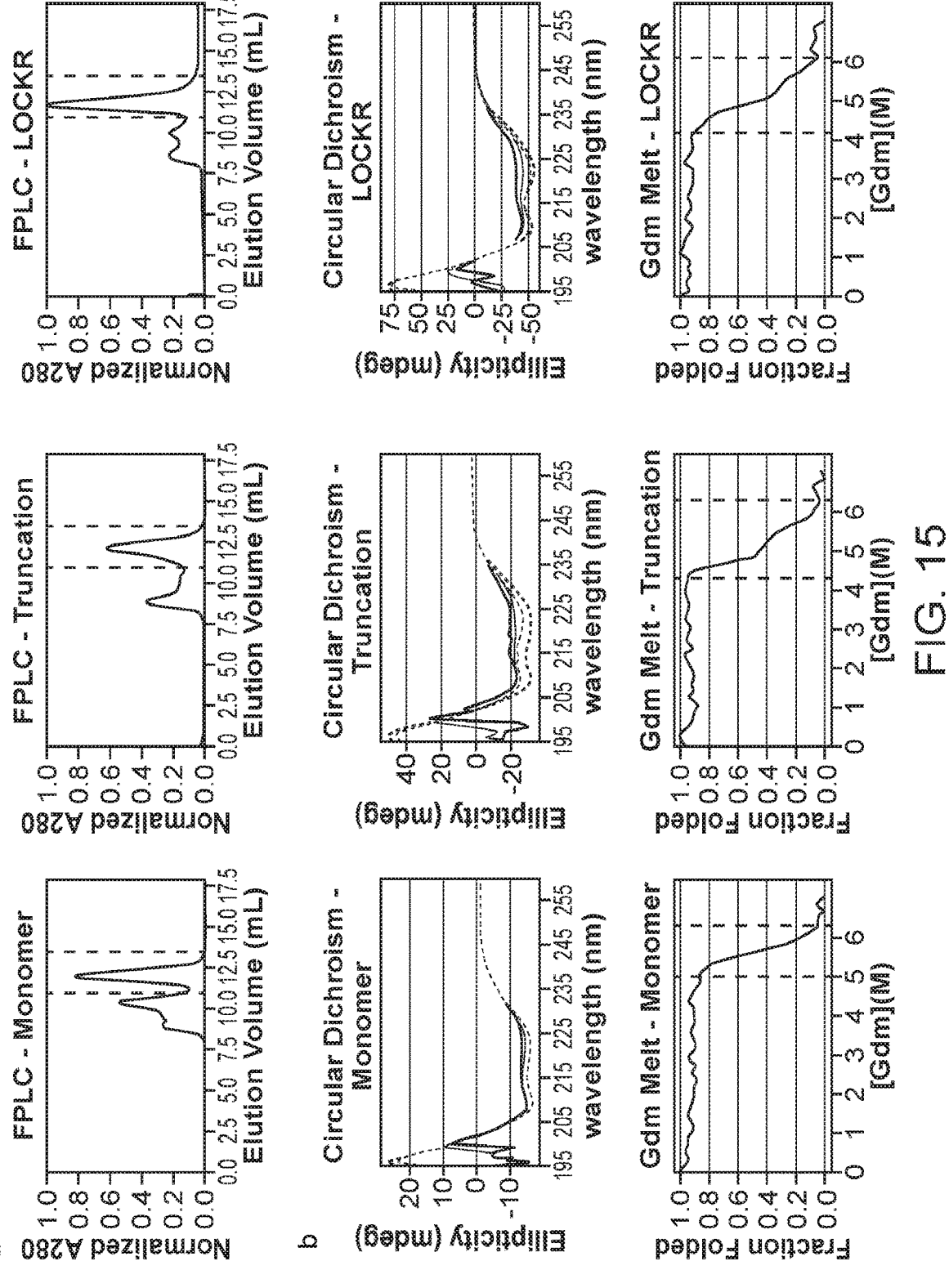
FIG. 15 provides biophysical data related to LOCKR design. a) Size Exclusion Chromatography for the Monomer, Truncation, and LOCKR designs on Superdex 75. Peaks indicated by vertical dashed lines represent monomeric protein used in downstream characterization and functional assays. b) Circular dichroism spectroscopy to determine protein stability upon heating and chemical denaturant, Guanidinium Chloride-HCl. Top row: full wavescan at 25° C. (blue), 75° C. (orange), 95° C. (red), then cooled to 25° C. (cyan). Middle row: guanidine melts also shown overlapped in FIG. 1d. Bottom row: fraction folded was converted to equilibrium constant, then to $\Delta G_{unfolding}$ value. The linear unfolding region, marked by vertical lines in middle row, was fit to determine the $\Delta G_{folding}$ for each design. c) SAXS spectra (black) referenced in FIG. 1e fit to Rosetta design models (red) using FoXS with chi-values referenced in the upper right.
Figure 15:
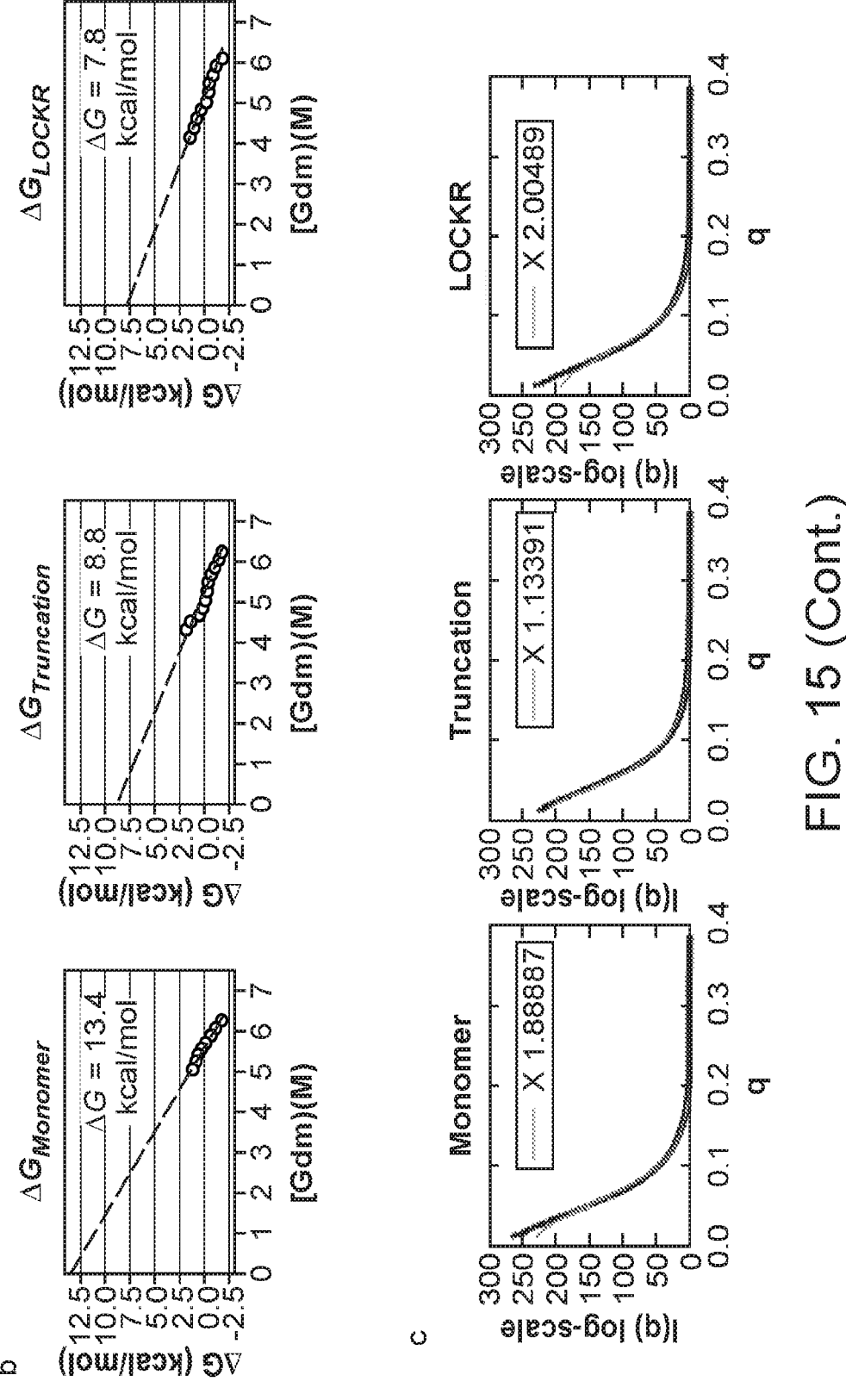

The five helix (cage) and six helix (cage plus latch) designs were soluble when recombinantly expressed in *E. coli*; the purified proteins were largely monomeric by size-exclusion chromatography (FIG. 15), and very stable, remaining folded up to 5 M guanidine hydrochloride (FIG. 10, panel d). Small-angle x-ray scattering (SAXS) spectra of the connected designs are similar to that of the starting trimer and indicative of a well folded protein (FIG. 10, panel e), suggesting that the structure is not altered by the loops. The five-helix framework, but not the six-helix framework, binds to the sixth helix fused to GFP in a pull-down assay (FIG. 10, panel f); the latter result is expected since if the interfaces are otherwise identical and the connecting linker unstrained, the intramolecular interaction should outcompete its intermolecular counterpart because of the reduced entropic cost of formation of intramolecular interactions. To enable the key to outcompete the latch, $K_{open}$ was tuned by incorporating mutations in the latch that weaken its interaction with the cage: large hydrophobics to alanine or serine, and alanine residues to larger hydrophobics or serine. A double mutant, V223S/I238S, bound key as strongly as the five-helix cage without the latch (FIG. 10, panel f; FIG. 16); the two serines likely weaken the cage-latch interaction by decreasing the helical propensity of the latch and increasing the cost of desolvating the latch when it binds the cage. In the absence of the key, the latch is bound to the cage as in the original monomer (their SAXS spectra are nearly identical and data closely matches the design models; FIG. 10, panel e; FIG. 15), but the guanidine hydrochloride denaturation midpoint and $\Delta G_{folding}$ are more similar to the truncated 5 helix design indicating the mutations are in fact destabilizing (FIG. 10, panels d and e; FIG. 15). Such cage-latch frameworks are referred to in some instances as switches, and the switch-key pair is, in some instances, referred to as LOCKR for Latching Orthogonal Cage-Key pRoteins.

LOCKR Inducible Bim-Bcl2 Binding

Figure 18:
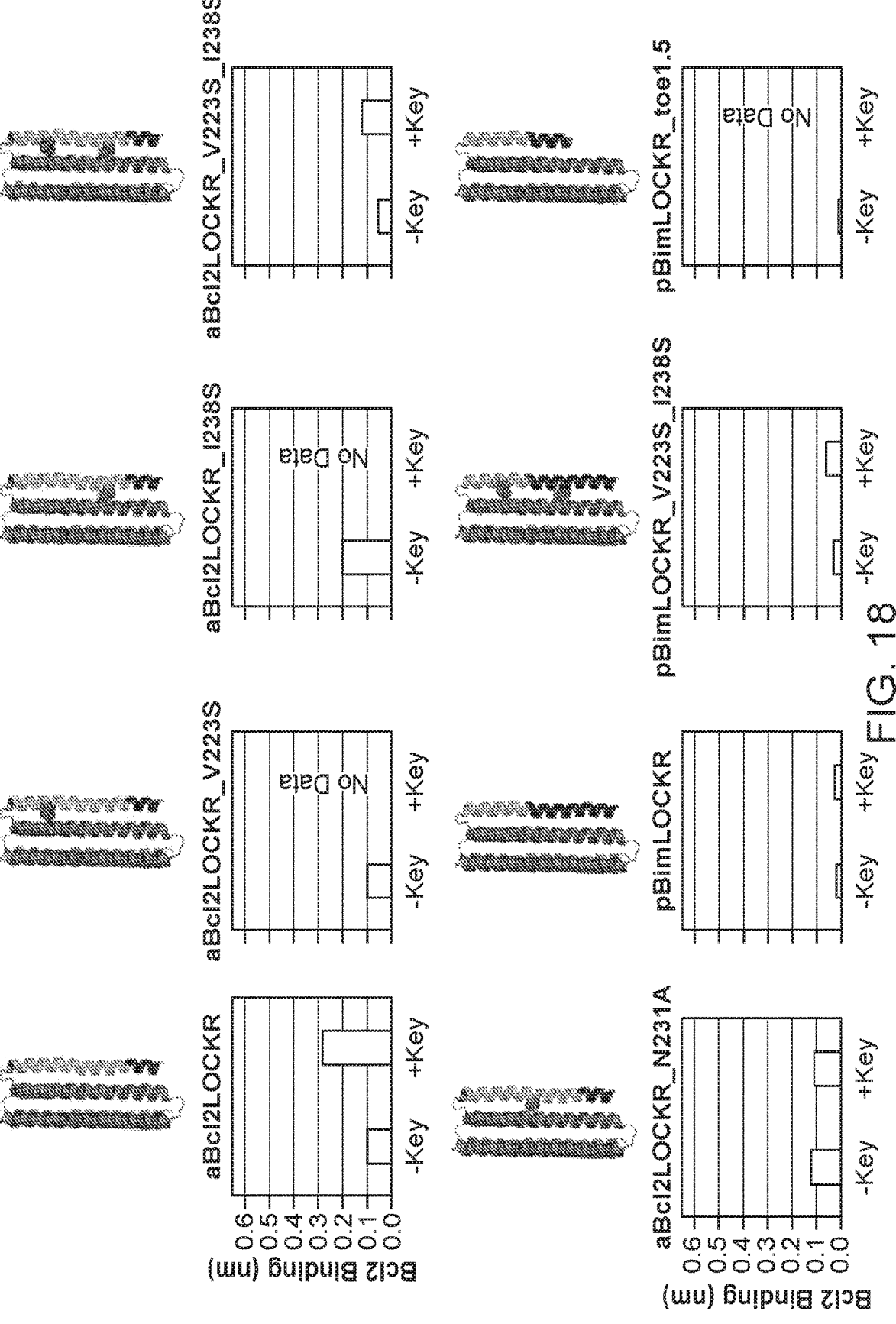
FIG. 18 demonstrate an example of tuning BimLOCKR.
Figure 18:
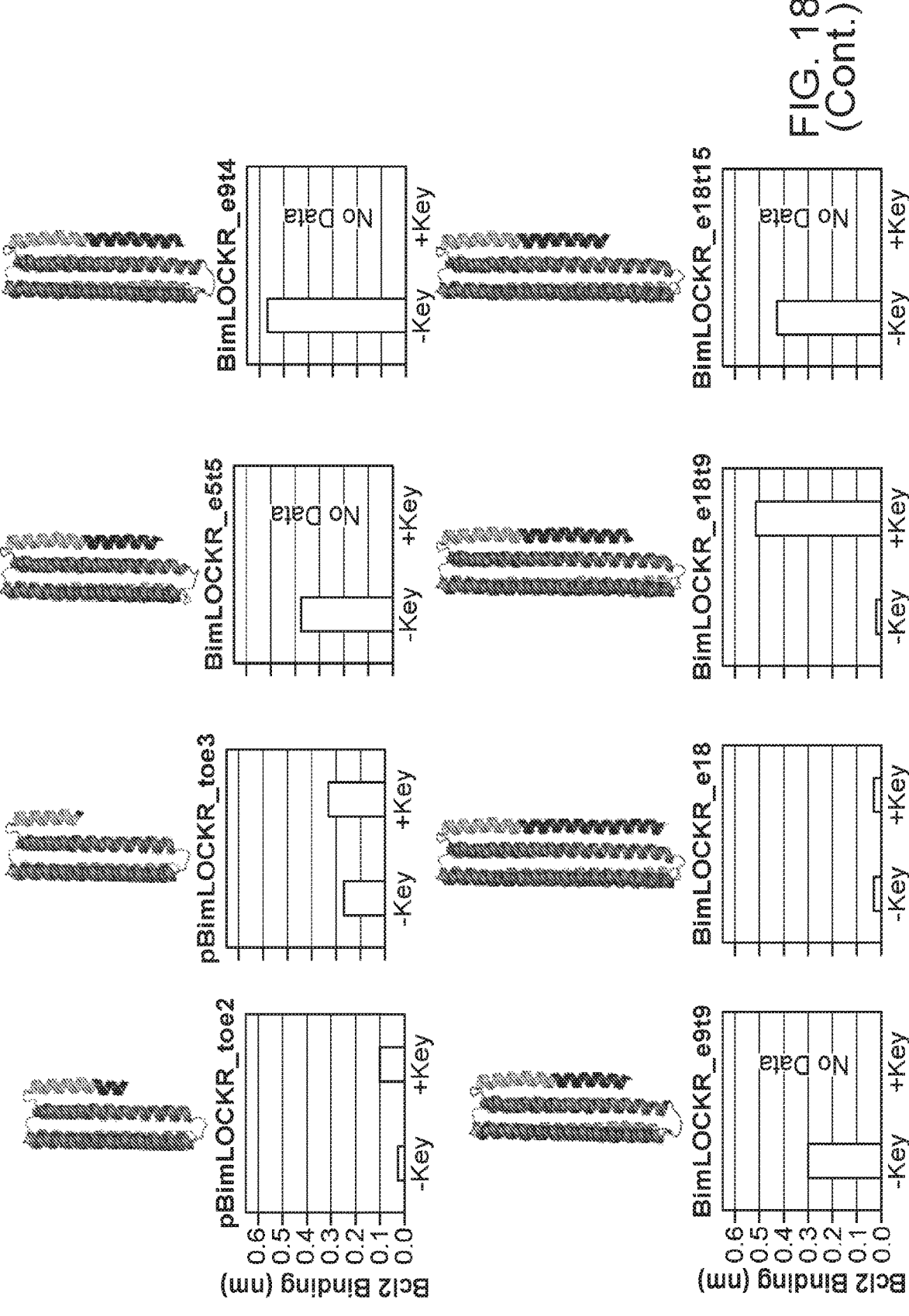

The latch, while folded, can cage a functional peptide sequence in an 'off' state such that the switch is active only once the key binds and the latch is released as per the model in FIG. 10, panel a. The system can then be tuned to the desired dynamic range based on the outlined thermodynamic parameters (FIG. 10, panel a). To install function into the initial LOCKR design, the Bim-Bcl2 interaction central to apoptosis was selected as a model system. Thus, the system was used to cage Bim such that binding to Bcl2 only occurred in the presence of key. Two Bim-related sequences were incorporated into the switch: the eight Bim residues which interact with Bcl2 (Delgado-Soler, et al. J. Chem. Inf. Model. 52, 2107-2118 (2012)) and a larger designed Bcl2 binding protein (Berger, et al. Elife 5, (2016)), to explore the effect of changes in $K_{open}$: the two sequences will have different interactions with the cage, destabilizing the latch in different ways. These sequences also bind Bcl2 differently providing sampling of $K_{LT}$. The two sequences were grafted onto the latch by sampling different helical registers such that residues involved in binding to Bcl2 are sequestered in the cage-latch interface (FIG. 17), optimizing for the burial of hydrophobic residues and surface exposure of polar residues. These initial designs either bound Bcl2 in the absence of key, or were not inducible (FIG. 18). The range of accessible $K_{open}$ and $K_{CK}$ values were evidently not matched to $K_{LT}$ as the key induced response was far from the ideal curves in FIG. 10, panel b.

Figure 11:
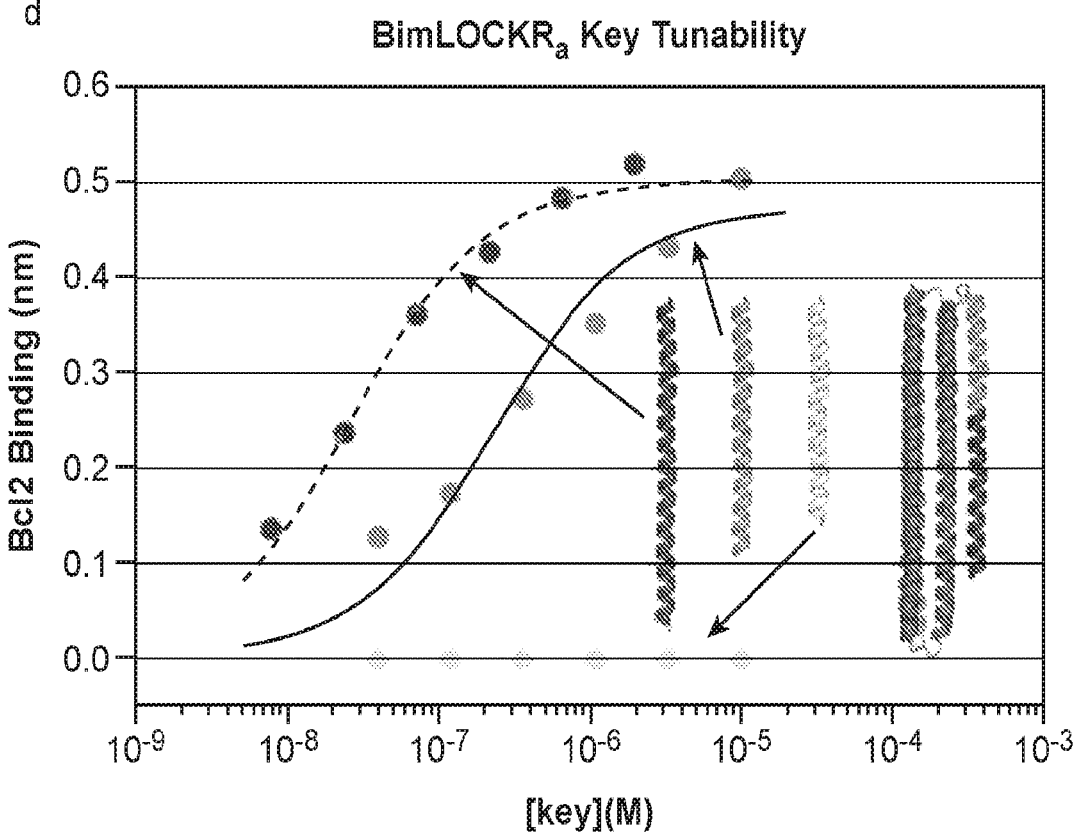
FIG. 11 depicts aspects related to BimLOCKR design and activation. a, Following incorporation of the BIM peptide into the LOCKR latch, the free energy of the latch-cage interface was reduced by introducing sub-optimal interactions (left, removal of a buried hydrogen bond) and by truncating the latch, leaving exposed hydrophobic residues in the cage available for key binding (right). b, The lengthened BimLOCKR constructs show tight caging of Bim in the absence of key while introduction of the toehold (right) allows activation of 250 nM BimLOCKR with addition of 5 µM key via Bio-layer interferometry. c, Bio-layer interferometry shows key-dependent binding to Bcl2 with 250 nM BimLOCKR. Association from 0-500 s, then dissociation from 500-1700 s. Purple is at 3 µM key, then a three fold dilution of the key through blue, cyan, green, yellow, and orange. Red line is 250 nM LOCKR without key added. d, Each point in dark green is a result of fitting data in (c) and extracting the response at equilibrium; the lighter green curves show binding response at equilibrium for shorter keys that alter $K_{CK}$ of LOCKR to tune its range of activation. Dashed lines are the data fit to a logistic curve.

A wider range of $K_{open}$ and $K_{CK}$ values could be accessed by lengthening the helices in the cage to provide more accessible interaction surface area: extending the latch:cage interface could then increase the interaction affinity (decrease $K_{open}$) to make the system more "off" in absence of key. At the same time, extending the key to increase its affinity to the cage could allow it to better outcompete the latch once $K_{open}$ is appropriately tuned (decrease $K_{CK}$ relative to $K_{open}$), making the system more inducible. Taking advantage of the modular nature of de novo parametric helical bundles, the cage, latch and key were each extended by 5, 9 or 18 residues. To enable the key to outcompete the latch, the latter was truncated by four to nine residues to generate a range of $K_{open}$ values (FIG. 18; this creates a "toehold" on the cage for the key to bind). Both the full length Bim containing latch and the truncated versions were fully off in the absence of key (no binding to Bcl2 was observed, left bars in FIG. 11, panel b). The most strongly inducible binding (FIG. 11, panel b, right bar in right panel)

was observed with the system with 18-residue extensions of the cage and the key, and a 9-residue shorter latch that leaves an exposed 9-residue toehold on the cage (the key does not interact directly with Bcl2 (FIG. 18)). This extended design with toehold exhibits an approximately 40-fold activation on addition of key in biolayer interferometry experiments (FIG. 11, panel c), comparable to or better than many naturally occurring protein interaction induced switches.

According to the model in FIG. 10, panel a, the range of key concentrations over which BimLOCKR is activated should be controllable by tuning $K_{CK}$ by altering the length of the key. A lower affinity of key for cage (higher $K_{CK}$) requires that more key must be added for activation to occur. Biolayer interferometry experiments in which different length keys were titrated against fixed concentrations of Bcl2 and BimSwitch demonstrate that the LOCKR system can be tuned in this manner to achieve a wide dynamic range of key-induced activation (FIG. 11, panel d). With Bcl2 present on the sensor tip, and BimSwitch at 250 nM, no binding to the sensor was observed in the absence of key. As keys of different length were titrated into the solution (key concentration on x axis), BimSwitch activated and bound to Bcl2 on the sensor (binding signal on y axis). The concentration at which activation occurred differs dramatically for the different length keys: a 40 residue key provided no activation (pale green), a 45 residue key activated with an $EC_{50}$ of 230+/−58 nM (green), and the full length 58 residue key activated with an $EC_{50}$ of 27.0+/−2.8 nM (dark green, FIG. 11, panels c and d). As expected from the model in FIG. 10, panel a, the equilibria involved in activation are indeed sensitive to small changes in binding free energy (FIG. 11, panel d).

To examine the function of BimLOCKR over a range of $K_{LT}$, key induced binding to the Bcl2 homologs BclB and Bak, which bind Bim with Kds of 0.17 nM (Bcl2), 20 nM (BclB), and 500 nM was studied. Bio-layer interferometry experiments were performed with different Bcl2 homologs immobilized on the tip, and BimLOCKR with and without key in solution. Consistent with the FIG. 10, panel a, model, activation of BclB binding requires higher key concentrations than activation of Bcl2 binding while Bak does not activate in this range of key concentrations. The formal symmetry of the FIG. 10, panel a, model with regard to key and target is observed experimentally: when the key is immobilized on the tip, binding of the switch to the tip is activated by addition of target just as binding of the switch to target is activated by addition of key (FIG. 19).

To enable independent caging and specific unlocking of different protein functions in the same compartment, orthogonal switch-key pairs were created by incorporating different hydrogen bond networks at the cage-latch/key interface. Alternative backbone conformations for the latch/key helix were generated by parametrically sampling the distance from the center of the bundle, helical phase, and z-offset relative to the 5 helix cage. New hydrogen bond networks were designed using HBNet (Boyken, et al. Science 352, 680-687 (2016)) to span the interface between the new sixth helix and the 5 helix cage with all buried polar atoms participating in hydrogen bonds; the remaining interface around the networks was subjected to full sequence and sidechain rotamer optimization using Rosetta design (Leaver-Fay et al. Chapter nineteen—Rosetta3: An Object-Oriented Software Suite for the Simulation and Design of Macromolecules. in Methods in Enzymology (eds. Johnson, M. L. & Brand, L.) 487, 545-574 (Academic Press, 2011)). Five well-packed and sequence-dissimilar designs with all buried polar atoms participating in hydrogen bonds (FIG.

Figure 21:
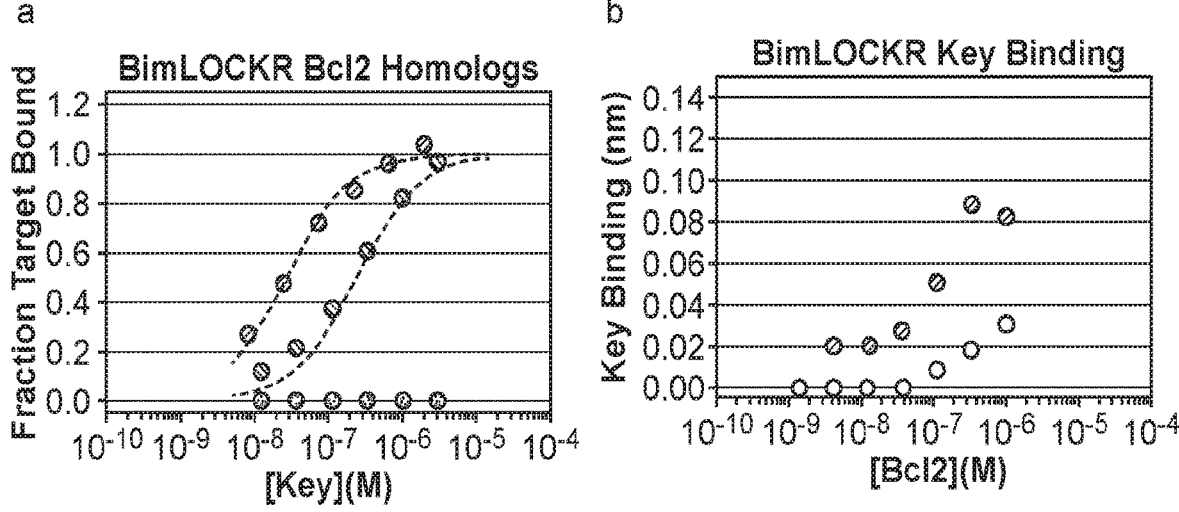
FIG. 21 provides validation of the model in depicted in FIG. 10. a) BLI measurement of BimLOCKR$_a$ (400 nM) binding to Bcl2 (gold), BclB (yellow), and Bak (lighter yellow-BimLOCKR at 1 µM) as key is added to solution. Normalized due to differences in $R_{max}$ for Bcl2 and BclB on the tip. b) BLI measurement of BimLOCKR$_a$ binding to key$_a$ immobilized on the tip. Open circles are with no Bcl2 present, gold points are with Bcl2 present at 500 nM.

20, FIG. 21) were selected for Bim switch assays. Bim-LOCKR$_b$ and BimLOCKR$_c$ show 22-fold and 8-fold activation with their cognate keys and a nine residue toehold on the latch (FIG. 12, panels a and b). The three LOCKR systems are orthogonal: each switch is activated only by its cognate key at concentrations up to 5 μM (FIG. 12, panel c), illustrating the power and consistency of the buried hydrogen bond network approach to achieving specificity.

LOCKR Inducible Protein Degradation

Figure 13:
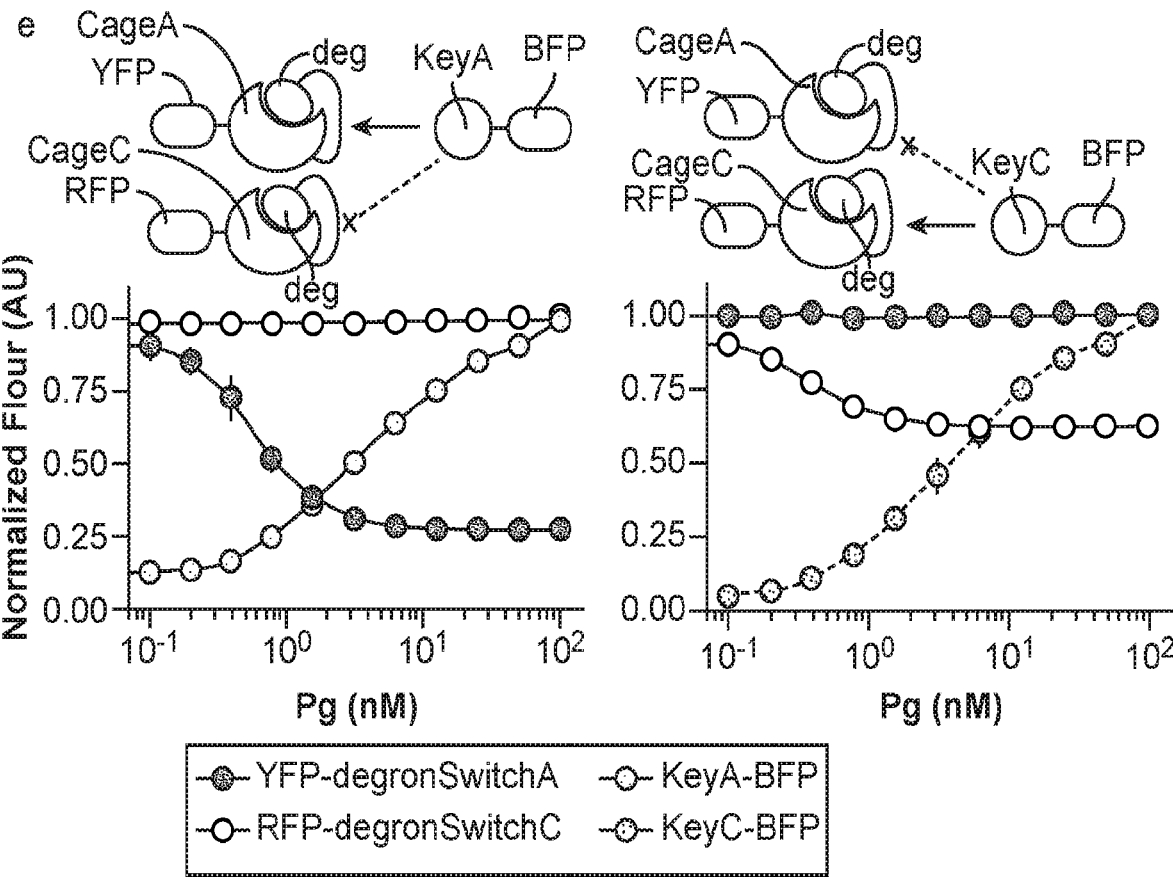
FIG. 13 depicts aspects related to design and in vivo testing of degronLOCKR. a, Schematic of dual inducible system used in *S. cerevisiae* to test functionality of degron-LOCKR. Progesterone (Pg) induces production of Key-BFP, and estradiol (E2) induces production of YFP-degron-Switch. b, Heatmaps of YFP fluorescence as a function of E2 (0-50 nM) and Pg (0-100 nM) for full length key (left) and a key that was truncated by 12 residues (right) as measured by flow cytometry. c, Line plot comparing the fluorescence of the YFP-degronSwitch$_a$ and Key$_a$-BFP at a max dose of E2 (black rectangle in (b) as a function of Pg induction. Fluorescence values were normalized to the maximum YFP or BFP fluorescence. Error bars represent s.d. of three biological replicates. d, Dynamic measurements of active degLOCKR using an automated flow cytometry platform. E2 was induced to activate expression of YFP-degronSwitch$_a$, and Pg was induced at $t_{4\ hrs}$ to activate expression of Key$_a$-BFP. Measurements were taken every 24 minutes. e, Coexpression of orthogonal LOCKRs in the same cell. YFP-degronSwitch$_a$ and RFP-degronSwitch$_c$ were expressed using constitutive promoters and either Key$_a$-BFP (left) or Key$_c$-BFP (right) were expressed using the pZ3 inducible promoter. Normalized fluorescence of YFP-degronSwitch$_a$, RFP-degronSwitch$_c$ and either Key$_a$-BFP or Key$_c$-BFP are plotted as a function of Pg induction. Error bars represent s.d. of biological replicates. f, Asymmetric RFP-degronSwitch$_a$ was expressed in HEK293T cells with and without Key. Flow cytometry distribution of RFP fluorescence for a representative sample indicates decreased RFP expression in the presence of Key. Geometric mean of RFP expression is quantified in the bar plot. Data in all panels represent mean±s.d. of three biological replicates.
Figure 22:
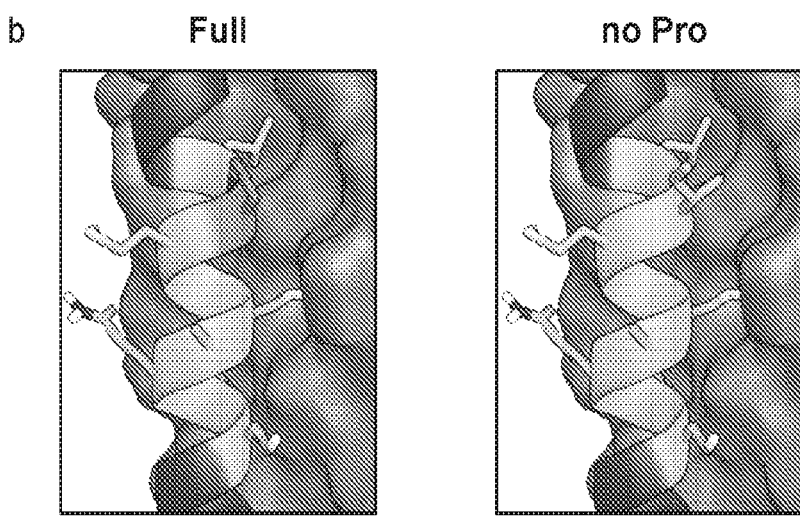
FIG. 22 demonstrates examples of caging cODC sequences. From top to bottom SEQ ID NOS. 28219-28220. a) Three variations of the cODC degron to cage. Variations meant to tune $K_{open}$ by removing the destabilizing proline (noPro) and minimizing mutations to the latch (CA only). b) Predicted models of the full and noPro cODC sequences (orange) threaded onto the latch (dark blue). Thread position chosen such that the cysteine residue needed for degradation is sequestered against the cage (light blue). Proline highlighted in red in the full cODC mutated to an isoleucine in the noPro variant.
Figure 23:
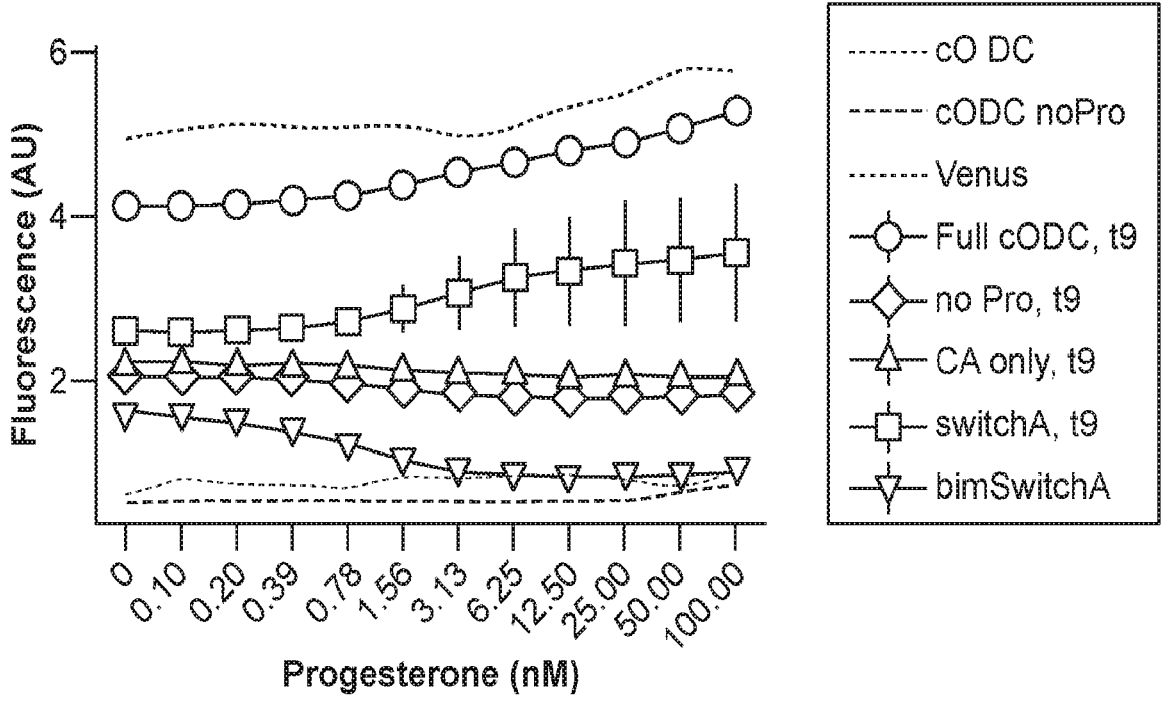
FIG. 23 compares the stability of YFP fused to cODC variants caged in $Switch_a$ to an empty $Switch_a$ and to $bimSwitch_a$.
Figures 24, 25:
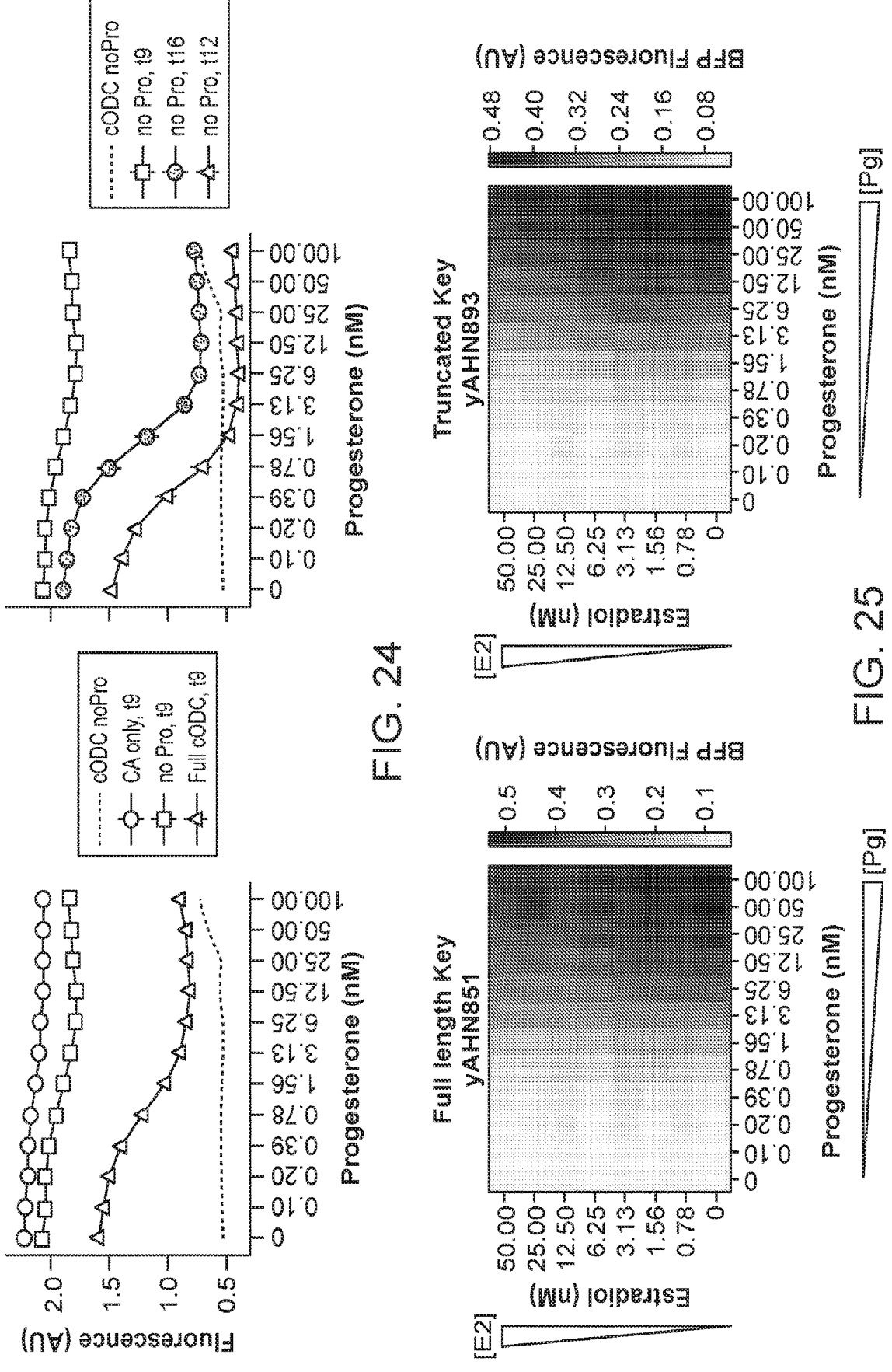
FIG. 24 provides an example of tuning toehold lengths of $degronLOCKR_a$.
FIG. 25 provides BFP expression corresponding to FIG. 13, panel b.

The functionality of LOCKR in vivo was assessed by caging the cODC degron, a ubiquitin-independent degradation signal from the C-terminus of murine ornithine decarboxylase (Takeuchi et al. Biochem. J 410, 401-407 (2008)). The system was configured such that degradation of the switch, and any protein fused to it, would be inducible by key. The caging strategy employed for Bim was used to embed three variants of cODC into Switch$_a$: the wild-type sequence, wild-type with a proline removed (since proline destabilizes alpha helices), and the dipeptide sequence CA, believed to be the minimal functional residues of the degron (FIG. 22). Each switch variant was tested in budding yeast *S. cerevisiae*, using a dual inducible system (Aranda-Diaz et al. ACS Synth. Biol. 6, 545-554 (2017)) to independently titrate the concentration the switch with a yellow fluorescent protein (YFP) N-terminal fusion and the key with a blue fluorescent protein (BFP) C-terminal fusion (FIG. 13, panel a). To assess the dynamic range of switch activation different amounts of key were titrated in using a range of progesterone (Pg) concentrations at a fixed amount of YFP-degron-Switch$_a$ (at a single concentration of estradiol (E2)) and steady-state fluorescence was measured using flow cytometry. Key induced degradation observed for these initial constructs was dependent on the presence of the cODC degron in the switch, and was not observed when YFP was fused to either BimSwitch$_a$ or Switch$_a$ (FIG. 23). The amount of inducible degradation was optimized by varying the switch toehold length to tune $K_{open}$. The switch with the largest dynamic range was the proline-removed cODC and a 12-residue toehold (herein referred to as degronSwitch$_a$). Using this variant, YFP fluorescence fused to degronSwitch$_a$ was reduced up to 73% upon full induction of key$_a$ (FIG. 24).

The dynamic range of degronLOCKR$_a$ was explored at different concentrations of YFP-degronSwitch$_a$ and key$_a$-BFP for two different key lengths (FIG. 13, panel b) by testing the full range of E2 and Pg combinations. The extent of key$_a$-induced degradation of degronSwitch$_a$ varied as a function of the concentration of both proteins. Key$_a$ fluorescence was stable as a function of degronSwitch$_a$ concentration (FIG. 25), suggesting the key is not co-degraded with the degronSwitch. With a truncated key$_a$ (43 residues versus 55 residues), the same dynamic range of switch activation was observed, but a higher key concentration was required for the same amount of switch activation (FIG. 13, panel c). This is similar to the behavior observed with BimLOCKR (FIG. 11, panel d), and shows our model of cage/key interaction holds true within living cells. To assess the dynamics of degronLOCKR$_a$ activation, an automated flow cytometry platform was used to measure YFP fluorescence as a function of time. Cells were grown at a constant concentration of E2 until YFP-degronSwitch$_a$ reached steady-state and then induced with Pg to activate production of key$_a$-BFP. It was found that the in vivo half-life for active degronLOCKR$_a$ is 24 minutes, which is very similar to the reported half life of 11-30 minutes for the constitutive cODC degron.

To enhance the functionality of degronLOCKR to trigger orthogonal degradation of different proteins in the same cell was enhanced by installing the proline removed cODC degron in $LOCKR_b$, $LOCKR_c$, and $LOCKR_d$. Each orthogonal switch variant was constitutively expressed fused to YFP (FIG. 26) and the degradation of YFP was measured with constitutive expression of each key variant fused to cyan fluorescent protein (CFP). DegronLOCKR$_a$ and degron-LOCKR$_c$ were strongly activated by their cognate keys, but not by each other's key (other constructs did not activate in vivo; FIG. 27). The orthogonality of the degronLOCKRs was tested by constitutively co-expressing degronLOCKR$_a$ and degronLOCKR$_c$ in the same cell fused to YFP and red fluorescent protein (RFP), respectively, and the Pg inducible system was used to titrate expression of each key variant in separate strains. Expression of key$_a$ led to selective degradation of YFP but not RFP, and expression of key$_c$ led to selective degradation of RFP but not YFP (FIG. 13, panel d). This demonstrates that the dual degronLOCKR system can function orthogonally and simultaneously in living cells.

To evaluate degronLOCKR function in mammalian cells, degronSwitch$_a$ fused to mCherry RFP was expressed in human HEK293T cells, and RFP fluorescence was measured in the presence and absence of Key. A redesigned asymmetric degronSwitch$_a$ with an 8-residue toehold (see FIG. 43) triggered a 11-fold reduction in mean RFP fluorescence in the presence of Key (FIG. 13, panel f). These data demonstrate the functionality of the degronLOCKR system in mammalian cells.

degronLOCKR Control of Gene Expression In Vivo

Figure 14:
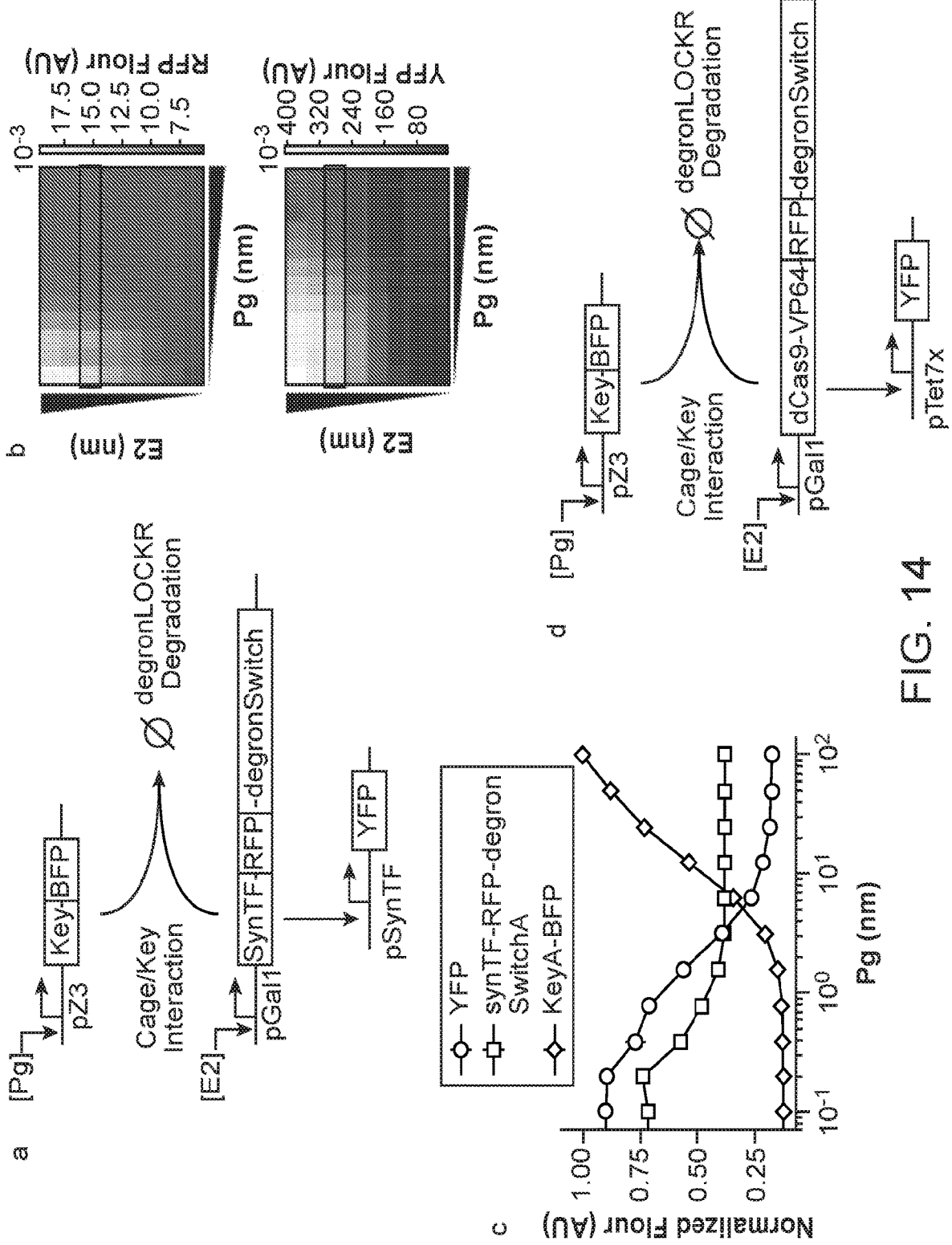
FIG. 14 demonstrates control of gene expression using degronLOCKR. a, Schematic of dual induction assay to determine the effect of degronLOCKR$_a$ on a synthetic transcription factor (SynTF). Pg induces expression of Key$_a$-BFP, and E2 induces expression of SynTF-RFP-degronSwitch$_a$ fusion. The pSynTF promoter is activated by SynTF and expresses YFP. b, Heatmaps of YFP and RFP fluorescence as a function of E2 (0-125 nM) and Pg (0-100 nM) measured by flow cytometry. c, Line plot comparing the fluorescence of YFP, SynTF-RFP-degronSwitch$_a$ and Key$_a$-BFP at 31.25 nM E2 (black rectangle in 5b) as a function of Pg induction. Fluorescence values were normalized to the maximum YFP, RFP, or BFP fluorescence. Error bars represent s.d. Of three biological replicates. d, Schematic of dual induction assay to determine the effect of degronLOCKR$_a$ on a dCas9-VP64 targeted to the pTet7x promoter via a constitutively expressed sgRNA (not shown). Pg induces expression of Key$_a$-BFP, and E2 induces expression of dCas9-VP64-RFP-degronSwitch$_a$ fusion. The pTet7x promoter is activated by dCas9-VP64 and expresses YFP. e, Heatmaps of YFP and RFP fluorescence as a function of E2 (0-125 nM) and Pg (0-100 nM) measured by flow cytometry. f. Line plot comparing the fluorescence of YFP, dCas9-VP64-RFP-degron-Switch$_a$ and Key$_a$-BFP at 31.25 nM E2 (black rectangle in 5d) as a function of Pg induction. Fluorescence values were normalized to the maximum YFP, RFP, or BFP fluorescence. Error bars represent s.d. of three biological replicates.

To demonstrate the utility of degronLOCKR, it was used as a tool to modulate the intracellular concentration of a synthetic transcription factor and dCas9. A zinc-finger based synthetic transcription factor (SynTF) (Khalil, et al. Cell 150, 647-658 (2012)) was fused to both RFP and degron-Switch$_a$ under the control of the E2 inducible promoter, and key$_a$-BFP-NLS under the control of the Pg inducible promoter. To monitor SynTF activity, measured pSynTF-YFP fluorescence was measured in the same cell (FIG. 14, panel a). An increase in expression of SynTF-RFP-degronSwitch$_a$ increased both RFP and YFP fluorescence, while an increase in key expression decreased both outputs (FIG. 14, panel b). For example, at 31.25 nM E2 (FIG. 14, panel b), maximal key induction caused a 61% reduction of RFP and 82% reduction of YFP (FIG. 14, panel c). Notably, degron-LOCKR caused a graded change in YFP fluorescence as a function of key concentration, which contrasts with the more digital behavior of transcription factors typically used in synthetic biology applications. To further establish degron-LOCKR as a general method of transcriptional control, degradation of an activating dCas9-VP64 fusion (Perez-Pinera, et al. Nat. Methods 10, 973-976 (2013)) was next tested. dCas9 was targeted to the tet operator site of the pTet7x with a constitutively expressed sgRNA to induce expression of YFP (FIG. 14, panel d), and key expression was titrated at different concentrations of dCas9 (FIG. 14, panel e). A 78% reduction of RFP and 41% reduction of YFP were observed upon induction of key at 31.25 nM E2 (FIG. 14, panel f). Together, these results demonstrate the modularity and functionality of degronLOCKR as a tool to control the stability of proteins in vivo.

The LOCKR system has several advantages. First, LOCKR is a universal platform to cage and then activate at will functionalities ranging from inducible activation of high-affinity protein-protein interactions to controlled degradation to localization of an attached cargo. Second, for any functional modality, many cargos can be regulated: For example, here it is shown how a transcription factor and hence gene expression can be efficiently modulated by LOCKR gated degradation, but other cargoes including kinases and other enzymes can also be controlled in the same way. In addition, altering the affinities of LOCKR components is tunable based on simple design principles that are general irrespective of the functional modality or application.

Supplementary Methods

PCR Mutagenesis and Isothermal Assembly

All primers for mutagenesis were ordered from Integrated DNA Technologies (IDT). Mutagenic primers were designed to anneal >18 bp on either side of the site for mutagenesis with the desired mutation encoded in the primer. PCR was used to create fragments upstream and downstream of the mutation site with >20 bp overlap with the desired pET vector. The resulting amplicons were isothermally assembled into either pET21b, pET28b, or pET29b restriction digested with XhoI and NdeI and transformed into chemically competent E. coli XL1-Blue cells. Monoclonal colonies were sequenced with Sanger sequencing. Sequence verified plasmid was purified using Qiagen miniprep kit and transformed into chemically competent E. coli BL21(DE3)Star, BL21(DE3)Star-pLysS cells (Invitrogen), or Lemo21 (DE3) cells (NEB) for protein expression.

Synthetic Gene Construction

Synthetic genes were ordered from Genscript Inc. (Piscataway, NJ, USA) and delivered in pET 28b+, pET21b+, or pET29b+E. coli expression vectors, inserted at the NdeI and XhoI sites of each vector. For pET28b+ constructs, synthesized DNA was cloned in frame with the N-terminal hexahistidine tag and thrombin cleavage site and a stop codon was added at the C-terminus. For pET21b+ constructs, a stop codon was added at the C-terminus such that the protein was expressed with no hexahistidine tag. For pET29b+ constructs, the synthesized DNA was cloned in frame with the C-terminal hexahistidine tag. Plasmids were transformed into chemically competent E. coli BL21(DE3)Star, BL21 (DE3)Star-pLysS cells (Invitrogen), or Lemo21(DE3) cells (NEB) for protein expression.

Bacterial Protein Expression and Purification

Starter cultures were grown in Lysogeny Broth (LB) or Terrific Broth II (TBII) overnight in the presence of 50 μg/mL carbenicillin (pET21b+) or 30 μg/mL (for LB) to 60 μg/mL (for TBII) kanamycin (pET28b+ and pET29b+). Starter cultures were used to inoculate 500 mL of Studier TBM-5052 autoinduction media containing antibiotic and grown at 37° C. for 24 hours. Cells were harvested by centrifugation at 4000 rcf for 20 minutes at 4° C. and resuspended in lysis buffer (20 mM Tris, 300 mM NaCl, 20 mM Imidazole, pH 8.0 at room temperature), then lysed by microfluidization in the presence of 1 mM PMSF. Lysates were cleared by centrifugation at 24,000 rcf for at least 30 minutes at 4° C. Supernatant was applied to Ni-NTA (Qiagen) columns pre-equilibrated in lysis buffer. The column was washed twice with 15 column volumes (CV) of wash buffer (20 mM Tris, 300 mM NaCl, 40 mM Imidazole, pH 8.0 at room temperature), followed by 15 CV of high-salt wash buffer (20 mM Tris, 1 M NaCl, 40 mM Imidazole, pH 8.0 at room temperature) then 15 CV of wash buffer. Protein was eluted with 20 mM Tris, 300 mM NaCl, 250 mM Imidazole, pH 8.0 at room temperature. Proteins were further purified by gel filtration using FPLC and a Superdex™ 75 Increase 10/300 GL (GE) size exclusion column, pooling fractions containing monomeric protein.

Size-Exclusion Chromatography, Multi-Angle Light Scattering (SEC-MALS)

SEC-MALS experiments used a Superdex™ 75 Increase 10/300 GL (GE) size exclusion column connected to a miniDAWN TREOS multi-angle static light scattering and an Optilab T-rEX (refractometer with EXtended range) detector (Wyatt Technology Corporation, Santa Barbara CA, USA). Protein samples were injected at concentrations of 3-5 mg/mL in TBS (pH 8.0). Data was analyzed using ASTRA™ (Wyatt Technologies) software to estimate the weight average molar mass (Mw) of eluted species, as well as the number average molar mass (Mn) to assess monodispersity by polydispersity index (PDI)=Mw/Mn.

Circular Dichroism (CD) Measurements

CD wavelength scans (260 to 195 nm) and temperature melts (25 to 95° C.) were measured using an AVIV model 420 CD spectrometer. Temperature melts monitored absorption signal at 222 nm and were carried out at a heating rate of 4° C./min. Protein samples were at 0.3 mg/mL in PBS pH 7.4 in a 0.1 cm cuvette. Guanidinium chloride (GdmCl) titrations were performed on the same spectrometer with an automated titration apparatus in PBS pH 7.4 at 25° C., monitored at 222 nm with protein sample at 0.03 mg/mL in a 1 cm cuvette with stir bar. Each titration consisted of at least 40 evenly distributed concentration points with one minute mixing time for each step. Titrant solution consisted of the same concentration of protein in PBS+GdmCl. GdmCl concentration was determined by refractive index.

Small Angle X-Ray Scattering (SAXS)

Samples were exchanged into SAXS buffer (20 mM Tris, 150 mM NaCl, 2% glycerol, pH 8.0 at room temperature) via gel filtration. Scattering measurements were performed at the SIBYLS 12.3.1 beamline at the Advanced Light Source. The X-ray wavelength ($\lambda$) was 1.27 Å and the sample-to-detector distance of the Mar165 detector was 1.5 m, corresponding to a scattering vector q ($q=4\pi*sin(\theta/\lambda)$ where $2\theta$ is the scattering angle) range of 0.01 to 0.59 $Å^{-1}$. Data sets were collected using 34 0.2 second exposures over a period of 7 seconds at 11 keV with protein at a concentration of 6 mg/mL. Data were also collected at a concentration of 3 mg/mL to determine concentration-dependence; all presented data was collected at the higher concentration as no concentration-dependent aggregation was observed. Data from 32 exposures was averaged separately over the Gunier, Parod, and Wide-q regions depending on signal quality over each region and frame. The averages were analyzed using the ScAtter software package to analyze data and report statistics. FoXS was used to compare design models to experimental scattering profiles and calculate quality of fit (X) values. The hexahistidine tags and thrombin cleavage sites on the N-termini of LOCKR proteins were modeled using Rosetta Remodel so that the design sequence matched that of the experimentally tested protein. To capture conformational flexibility of these residues, 100 independent models were generated, clustered, and the cluster center of the largest cluster was selected as a representative model for FoXS fitting without bias.

GFP Pulldown Assay

His-tagged LOCKR was expressed per the above protocol from pET28b+ while the key was expressed fused to super-folder GFP (sfGFP) without a his-tag in pET21b+. The his-tagged LOCKR was purified to completion and dialyized into TBS (20 mM Tris, 150 mM NaCl, pH 8.0 at room temperature); the key-GFP remained as lysate for this assay. 100 μL LOCKR at >1 μM was applied to a 96-well black Pierce® Nickel Coated Plate (ThermoFisher) and incubated at room temperature for 1 hour. Sample was discarded from the plate and washed 3× with 200 μL TBST (TBS+0.05% Tween-20). 100 μL of lysate containing key-GFP was added to each well and incubated at room temperature for 1 hour. Sample was discarded from the plate and washed 3× with 200 μL TBST (TBS+0.05% Tween-20). The plate was washed 1× with TBS, and 100 μL of TBS was added to each well. sfGFP fluorescence was measured on a Molecular Devices SpectraMax M5 plate reader or BioTek Synergy Neo2 plate reader; fluorescence was measured at 485 nm excitation and 530 nm emission, with a bandwidth of 20 nm for excitation and emission.

Bio-Layer Interferometry (BLI)

BLI measurements were made on an Octet® RED96 System (ForteBio) with streptavidin (SA) coated biosensors and all analysis was performed within ForteBio Data Analysis Software version 9.0.0.10. Assays were performed with protein diluted into HBS-EP+ Buffer from GE (10 mM HEPES, 150 mM NaCl, 3 mM EDTA, 0.05% v/v Surfactant P20, 0.5% non-fat dry milk, pH 7.4 at room temperature). Biotinylated Bcl2 was loaded onto the SA tips to a threshold of 0.5 nm programmed into the machine's protocol. Baseline was obtained by dipping the loaded biosensors into HBS-EP+ buffer; association kinetics were observed by dipping into wells containing defined concentrations of LOCKR and key, then dissociation kinetics were observed by dipping into the buffer used to obtain the baseline. Kinetic constants and response at equilibrium were computed by fitting a 1:1 binding model.

Construction of DNA Circuits

Hierarchical golden gate assembly was used to assemble plasmids for yeast strain construction using the method in Lee et al. (ACS Synth. Biol. 4, 975-986 (2015)). Individual parts had their BsaI, BsmBI, and NotI cut sites removed to facilitate downstream assembly and linearization. Parts were either generated via PCR or purchased as gBlocks from IDT. These parts were assembled into transcriptional units (promoter-gene-terminator) on cassette plasmids. These cassettes were then assembled together to form multi-gene plasmids for insertion into the yeast genome.

Yeast Strains and Growth Media

The base S. cerevisiae strain used in all experiments was BY4741 (MATa his3Δ1 leu2Δ0 met15Δ0 ura3Δ0). All yeast cultures were grown in YPD media (10 g/L Bacto Yeast Extract, 20 g/L Bacto peptone, 20 g/L dextrose) or synthetic complete medium (SDC) (6.7 g/L Bacto-yeast nitrogen base without amino acids, 2 g/L complete supplement amino acid mix, 20 g/L dextrose). Selection of auxotrophic markers (URA3, LEU2, and/or HIS3) was performed on synthetic complete medium with the appropriate dropout amino acid mix.

Estradiol and Progesterone Induction

Yeast strains were grown overnight by picking a single colony from a plate into YPD media. Saturated culture was diluted 1:500 in fresh SDC and aliquoted into individual wells of a 2 mL 96 well storage block (Corning) for a three hour outgrowth at 30° C. and 900 RPM in a Multitron shaker (Infors HT). Estradiol (Sigma-Aldrich) and progesterone (Fisher Scientific) were prepared at a 10× concentration by making the appropriate dilutions into SDC from a 3.6 mM estradiol and 3.2 mM progesterone stock solution. After the three hour outgrowth, 50 μL of estradiol and progesterone inducer were added to the 96 well block in the appropriate combinations and the block was returned to the shaker.

Mammalian Cell Culture and Lentiviral Transduction

HEK293T cells (from ATCC® CRL-3216™) were maintained in DMEM (Dulbecco's Modified Eagle Medium, Gibco) supplemented with 10% Fetal Calf Serum (SAFC)

and passaged every ~3 days. Pantropic VSV-G pseudotyped lentivirus was produced via transfection of Lenti-X 293T cells (Clontech) with a custom pHR'SIN:CSW transgene expression vector and the viral packaging plasmids pCMVdR8.91 and pMD2.G using Fugene HD (Promega). At 48 hr, viral supernatant was harvested and the HEK293T cells were exposed to the virus for 24 hr. Transductions were performed in triplicate.

HEK293T Experiments

Analysis of fluorescent protein expression was performed using a BD Fortessa flow cytometer (BD Biosciences) equipped with a high-throughput sampler. Cells were harvested and washed twice in PBS before running through the instrument in PBS+5% FBS. RFP (mCherry) fluorescence was measured using the PE-CF594 channel and BFP (tagBFP) was measured using the BV 421 channel. 50,000 events were collected per sample. Live cells were gated according to FSC-A and SSC-A, and singlets were gated according to SSC-A and SSC-H. Analysis of HEK293T flow cytometry data was performed using FlowJo v10.

Description of Automated Flow Cytometry and Continuous Culture System

Hardware

We adapted an existing automated experimental platform (Harrigan et al. bioRxiv 244020 (2018). doi:10.1101/244020) to perform variable concentration small molecule induction and long-term culturing. Yeast cultures were grown in 50 mL optically clear conical tubes (Falcon) that were held in eight custom temperature-controlled, magnetically stirred chambers. Liquid handling was accomplished using a 14 position stream selector (VICI Cheminert) and two syringe pumps (Cavro XCalibur Pump, TECAN) of a BD High-Throughput Sampler. Commands to the HTS were controlled using LABVIEW 2013. This setup allowed for periodic sampling and dilution of individual cultures. Each sampling period consisted of three main steps: 1) send sample to flow cytometer for measurement, 2) extract culture and send to waste, and 3) replenish culture with fresh media at desired hormone concentration. Each sampling period can be designated to either induce cultures to a new higher hormone concentration or to maintain desired hormone concentration. A sampling frequency of 24 minutes and a dilution volume of 3 mL were used.

Yeast Culture

Yeast strains were grown overnight by picking a single colony from a plate into YPD media. Saturated culture was diluted 1:200 into fresh SDC. Cultures were grown for 2 hours in glass tubes at 30 C and 250 RPM in a Innova 44 shaker (New Brunswick). Cultures were then diluted to 0.01 OD600 in fresh SDC and aliquoted into individual 50 mL optically clear conical tubes (Falcon) at a total volume of 30 mL YPD. Another one hour outgrowth was performed in bioreactors with magnetically-controlled stir bars at 30 C. All SDC media was supplemented with 5,000 U/mL Penicillin Streptomycin (Thermo-Fisher).

Estradiol and Progesterone Induction to Test degronLOCKR Dynamics

A 1× concentration was determined by the highest desired hormone concentration at which to test strains (30 nM E2 and 50 nM Pg, respectively). A solution of E2 and SDC media was created at a 10× concentration to bring pre-induced cultures to a desired concentration in one sampling period. A second solution of Pg and SDC media was created at a 10× concentration to induce key expression after degSwitch-YFP expression reached steady-state. SDC media was prepared at three different concentrations of hormone: (1) 10× E2/no Pg, (2) 1× E2/no Pg, (3) 1× E2/10× Pg, and (4) 1× E2/1× Pg. After a one hour outgrowth in bioreactors (t=−6 hr), the first induction was performed to achieve E2 concentration by extracting 3 mL from all cultures and replenishing with (1). After E2 induction, sampling proceeded as described above (see Hardware). All sampling periods following the first induction time point included sending a sample to the cytometer for measurement, extracting 3 mL from all cultures, and replenishing cultures with (2). During the second induction time point (t=0 hr), cultures were induced with (3) to activate key expression. This induction was followed by the same procedure as the first induction, except that hormone concentrations were maintained by (4). Controls (no activated key expression) did not undergo a second induction and, instead, continued to be replenished by (2).

Flow Cytometry

Analysis of fluorescent protein expression was performed using a BD LSRII flow cytometer (BD Biosciences) equipped with a high-throughput sampler. Cultures were diluted in TE before running through the instrument to obtain an acceptable density of cells. YFP (Venus) fluorescence was measured using the FITC channel, RFP (mScarlet) was measured using the PE-Texas Red channel, and BFP (mTagBFP2) was measured using the DAPI channel. For steady-state measurements, 5,000-10,000 events were collected per sample. For dynamic measurements, 2,000-10,000 events were collected per sample. Fluorescence values were calculated as the height (H) measurement for the appropriate channel and normalized to cell size by dividing by side scatter (SSC-H). All analysis of flow cytometry data was performed in Python 2.7 using the package FlowCytometryTools and custom scripts.

Fluorescence Microscopy

Saturated culture was diluted 1:100 in fresh SC media followed by a 3 hour outgrowth at 30° C. with shaking at 700 RPM in a Multitron shaker (Infors HT). Estradiol (Sigma-Aldrich) and progesterone (Fisher Scientific) were prepared at a 20× concentration by making the appropriate dilutions into SC media from a 3.6 mM estradiol and 3.2 mM progesterone stock solution. Cells were induced with estradiol and/or progesterone at a final concentration of [200 µM] and [250 µM] respectively. After 8 hours of growth, cells were resuspended in 1×PBS and imaged on a Zeiss Axio Observer Z1 microscope with X-Cite Series 120 fluorescent lamp and Hamamatsu Orca-Flash 4.0 Digital Camera.

Structural Visualization and Figures

All structural images for figures were generated using PyMOL.

Code Availability

Python scripts, bash scripts, and Rosetta XMLs are available for download at https(colon)//github(dot)com/Bobby-Langan/DeNovoDesignofBioactiveProteinS witches.

Functional Peptides Designed into LOCKR

```
aBcl2-Designed Bcl2 Binder:
                              (SEQ ID NO: 58)
M-QEL-DK-RAASLQ-NGD-FYA-LR-L pBim:
                              (SEQ ID NO: 59)
I---LR-IGD-F---Y Bim:
                              (SEQ ID NO: 60)
EIWIAOELRRIGDEFNAYYA cODC:
                              (SEQ ID NO: 61)
LPMSCAQES cODC_noPro:
                              (SEQ ID NO: 62)
L-MSCAQES cODC_CA_only:
CA
```

Amino Acid Sequences of Designed Key and LOCKR
Proteins:

Key_a:

(SEQ ID NO: 46)

EARKAIARVKRESKRIVEDAERLIREAAAASEKISREAERLIREAAAASEKISRE

Key_b:

(SEQ ID NO: 47)

NKEEIEKLAKEAREKLKKAEKEHKEIHDKLRKKNKKAREDLKKKADELRETNKR

VN

Key_c:

(SEQ ID NO: 48)

SSEKVRRELKESLKENHKQNQKLLKDHKRAQEKLNRELEELKKKHKKTLDDIRR

ES

Key_d:

(SEQ ID NO: 49)

DTVKRILEELRRRFEKLAKDLDDIARKLLEDHKKHNKELKDKQRKIKKEADDAA

RS

>degronLOCKR_a_327

(SEQ ID NO: 1)

SKEAVTKLQALNIKLAEKLLEAVTKLQALNIKLAEKLLEALARLQELNIALVYLAVELT

DPKRIADEIKKVKDKSKEIVERAEEEIARAAAESKKILDEAEEEIARAAAESKKILDEGSG

SGSDAVAELQALNLKLAELLLEAVAELQALNLKLAELLLEAIAKLQELNIKLVELLTKL

TDPATIREAIRKVKEDSERIVAEAERLIAAAKAESERIIREAERLIAAAKAESERIIREGSG

SGDPDVARLQELNIELARELLRDVARLQELNIELARELLRAAAELQELNIKLVELASELT

DPDEARKAIARVKRESKRIVEDAERLPMSCAQESEKISREAERLIREAA

>degronLOCKR_a_327_noPro (SEQ ID NO: 2)

SKEAVTKLQALNIKLAEKLLEAVTKLQALNIKLAEKLLEALARLQELNIALVYLAVELT

DPKRIADEIKKVKDKSKEIVERAEEEIARAAAESKKILDEAEEEIARAAAESKKILDEGSG

SGSDAVAELQALNLKLAELLLEAVAELQALNLKLAELLLEAIAKLQELNIKLVELLTKL

TDPATIREAIRKVKEDSERIVAEAERLIAAAKAESERIIREAERLIAAAKAESERIIREGSG

SGDPDVARLQELNIELARELLRDVARLQELNIELARELLRAAAELQELNIKLVELASELT

DPDEARKAIARVKRESKRIVEDAERLAMSCAQESEKISREAERLIREAA

>degronLOCKR_a_CAonly (SEQ ID NO: 3)

SKEAVTKLQALNIKLAEKLLEAVTKLQALNIKLAEKLLEALARLQELNIALVYLAVELT

DPKRIADEIKKVKDKSKEIVERAEEEIARAAAESKKILDEAEEEIARAAAESKKILDEGSG

SGSDAVAELQALNLKLAELLLEAVAELQALNLKLAELLLEAIAKLQELNIKLVELLTKL

TDPATIREAIRKVKEDSERIVAEAERLIAAAKAESERIIREAERLIAAAKAESERIIREGSG

SGDPDVARLQELNIELARELLRDVARLQELNIELARELLRAAAELQELNIKLVELASELT

DPDEARKAIARVKRESKRIVEDAERURECAAASEKISREAERLIREAA

>degronLOCKR_a_324_t12

(SEQ 1D NO: 4)

SKEAVTKLQALNIKLAEKLLEAVTKLQALNIKLAEKLLEALARLQELNIALVYLAVELT

DPKRIADEIKKVKDKSKEIVERAEEEIARAAAESKKILDEAEEEIARAAAESKKILDEGSG

SGSDAVAELQALNLKLAELLLEAVAELQALNLKLAELLLEAIAKLQELNIKLVELLTKL

TDPATIREAIRKVKEDSERIVAEAERLIAAAKAESERIIREAERLIAAAKAESERIIREGSG

SGDPDVARLQELNIELARELLRDVARLQELNIELARELLRAAAELQELNIKLVELASELT

DPDEARKAIARVKRESKRIVEDLIMSCAQESAASEKISREAERLIR

-continued

>degronLOCKR_a_320_t16
                                                    (SEQ ID NO: 5)
SKEAVTKLQALNIKLAEKLLEAVTKLQALNIKLAEKLLEALARLQELNIALVYLAVELT

DPKRIADEIKKVKDKSKEIVERAEEEIARAAAESKKILDEAEEEIARAAAESKKILDEGSG

SGSDAVAELQALNLKLAELLLEAVAELQALNLKLAELLLEAIAKLQELNIKLVELLTKL

TDPATIREAIRKVKEDSERIVAEAERLIAAAKAESERIIREAERLIAAAKAESERIIREGSG

SGDPDVARLQELNIELARELLRDVARLQELNIELARELLRAAAELQELNIKLVELASELT

DPDEARKAIARVKRESKRLVMSCAQESREAAAASEKISREAE

>mini-degronLOCKRa_1_t9 (wherein "mini" refers to a
re-designed scaffold that contains fewer helices but
maintains functionality)
                                                    (SEQ ID NO: 6)
NKEDATEAQKKA1RAAEELLKDVTRIQERAIREAEKALERLARVQEEAIRRVYEAVESK

NKEELKKVKEEIEELLRRLKRELDELEREIRELLKEIKEKADRLEKEIRDLIERIRRDRNA

SDEVVTRLARLNEELIRELREDVRRLAELNKELLRELERAARELARLNEKLLELADRVE

TEEEARKAIARVKRESKRIVEDAERLAMSCAQESEKISREAERLIREAA

>mini-degronLOCKRa_1_t12
                                                    (SEQ ID NO: 7)
NKEDATEAQKKA1RAAEELLKDVTRIQERAIREAEKALERLARVQEEAIRRVYEAVESK

NKEELKKVKEEIEELLRRLKRELDELEREIRELLKEIKEKADRLEKEIRDLIERIRRDRNA

SDEVVTRLARLNEELIRELREDVRRLAELNKELLRELERAARELARLNEKLLELADRVE

TEEEARKAIARVKRESKRIVEDLIMSCAQESAASEKISREAERLIR

>mini-degronLOCKRa_2_t9
                                                    (SEQ ID NO: 8)
DERLKRLNERLADELDKDLERLLRLNEELARELTRAAEELRELNEKLVELAKKLQGGR

SREVAERAEKEREKIRRKLEEIKKEIKEDADRIKKRADELRRRLEKTLEDAARELEKLKR

EPRTEELKRKATELQKEAIRRAEELLKEVTDVQRRAIERAEELLEKLARLQEEAIRTVYL

LVELNKVDRARKAIARVKRESKRIVEDAERLAMSCAQESEKISREAERLIREAA

>mini-degronLOCKRa_t12
                                                    (SEQ ID NO: 9)
DERLKRLNERLADELDKDLERLLRLNEELARELTRAAEELRELNEKLVELAKKLQGGR

SREVAERAEKEREKIRRKLEEIKKEIKEDADRIKKRADELRRRLEKTLEDAARELEKLKR

EPRTEELKRKATELQKENIRRAEELLKEVTDVQRRNIERAEELLEKLARLQEENIRTVYL

LVELNKVDRARKAIARVKRESKRIVEDLIMSCAQESAASEKISREAERLIR

>asym-degronLOCKR_a_mut (wherein "asym" refers to an
asymmetrized scaffold design)
                                                    (SEQ ID NO: 10)
SKEAAKKLQDLNIELARKLLEASTKLQRLNIRLAEALLEAIARLQELNLELVYLAVELT

DPKRIRDEIKEVKDKSKEIIRRAEKEIDDAAKESKKILEEARKAIRDAAEESRKILEEGSG

SGSDALDELQKLNLELAKLLLKAIAETQDLNLRAAKAFLEAAAKLQELNIRAVELLVKL

TDPATIRRALEHAKRRSKEIIDEAERAIRAAKRESERIIEEARRLIEKAKEESERIIREGSGS

GDPDIKKLQDLNIELARELLRAHAQLQRLNLELLRELLRALAQLQELNLDLLRLASELT

DPDEARKAIARVKRESKRIVEDAERLSREAAALSMSCAQESERSIREAAAASEKISRE

>asym-degronLOCKR_a_mut_t6
                                                    (SEQ ID NO: 11)
SKEAAKKLQDLNIELARKLLEASTKLQRLNIRLAEALLEAIARLQELNLELVYLAVELT

DPKRIRDEIKEVKDKSKEIIRRAEKEIDDAAKESKKILEEARKAIRDAAEESRKILEEGSG

SGSDALDELQKLNLELAKLLLKAIAETQDLNLRAAKAFLEAAAKLQELNIRAVELLVKL

TDPATIRRALEHAKRRSKEIIDEAERAIRAAKRESERIIEEARRLIEKAKEESERIIREGSGS

-continued

GDPDIKKLQDLNIELARELLRAHAQLQRLNLELLRELLRALAQLQELNLDLLRLASELT

DPDEARKAIARVKRESKRIVEDAERLSMSCAQESEKISREAERSIREAAAAS

>asym-degronLOCKR_a_short (wherein "short" refers to a
shortened version of the asym scaffold, where all the
helices have been truncated)

(SEQ ID NO: 12)

SELARKLLEASTKLQRLNIRLAEALLEAIARLQELNLELVYLAVELTDPKRIRDEIKEVK

DKSKEIIRRAEKEIDDAAKESEKILEEAREAISGSGSELAKLLLKAIAETQDLNLRAAKAF

LEAAAKLQELNIRAVELLVKLTDPATIREALEHAKRRSKEIIDEAERAIRAAKRESERIIE

EARRLIEKGSGSGSELARELLRAHAQLQRLNLELLRELLRALAQLQELNLDLLRLASEL

TDPDEARKAIARVKRESKRIVEDLEMSCAQESAASEKISREAERLIR

>asym_degronLOCKR_a_short_t5

(SEQ ID NO: 13)

SELARKLLEASTKLQRLNIRLAEALLEAIARLQELNLELVYLAVELTDPKRIRDEIKEVK

DKSKEIIRRAEKEIDDAAKESEKILEEAREAISGSGSELAKLLLKAIAETQDLNLRAAKAF

LEAAAKLQELNIRAVELLVKLTDPATIREALEHAKRRSKEIIDEAERAIRAAKRESERIIE

EARRLIEKGSGSGSELARELLRAHAQLQRLNLELLRELLRALAQLQELNLDLLRLASEL

TDPDEARKAIARVKRESKRLVMSCAQESREAAAASEKISREA

>asym-degronLOCKR_a_short_t8

(SEQ ID NO: 14)

SELARKLLEASTKLQRLNIRLAEALLEAIARLQELNLELVYLAVELTDPKRIRDEIKEVK

DKSKEIIRRAEKEIDDAAKESEKILEEAREAISGSGSELAKLLLKAIAETQDLNLRAAKAF

LEAAAKLQELNIRAVELLVKLTDPATIREALEHAKRRSKEIIDEAERAIRAAKRESERIIE

EARRLIEKGSGSGSELARELLRAHAQLQRLNLELLRELLRALAQLQELNLDLLRLASEL

TDPDEARKAIARVKRLSMSCAQESERLIREAAAASEKIK

>asym-degronLOCKR_a_short_t11

(SEQ ID NO: 15)

SELARKLLEASTKLQRLNIRLAEALLEAIARLQELNLELVYLAVELTDPKRIRDEIKEVK

DKSKEIIRRAEKEIDDAAKESEKILEEAREAISGSGSELAKLLLKAIAETQDLNLRAAKAF

LEAAAKLQELNIRAVELLVKLTDPATIREALEHAKRRSKEIIDEAERAIRAAKRESERIIE

EARRLIEKGSGSGSELARELLRAHAQLQRLNLELLRELLRALAQLQELNLDLLRLASEL

TDPDEARKAIARLKMSCAQESEDAERLIREAAAASE

>degronLOCKR_b (SEQ ID NO: 16)

SHAAVIKLSDLNIRLLDKLLQAVIKLTELNAELNRKLIEALQRLFDLNVALVHLAAELTD

PKRIADEIKKVKDKSKEIVERAEEEIARAAAESKKILDEAEEEIARAAAESKKILDEGSGS

GSDAVAELQALNLKLAELLLEAVAELQALNLKLAELLLEAIAKLQELNIKLVELLTKLT

DPATIREAIRKVKEDSERIVAEAERLIAAAKAESERIIREAERLIAAAKAESERIIREGSGS

NDPQVAQNQETFIELARDALRLVAENQEAFIEVARLTLRAAALAQEVAIKAVEAASEG

GSGSGPNKEEIEKLAKEAREKLKKAEKEHKMSCAQERKKNKKAREDLKKKADK

>degronLOCKR_b_t13

(SEQ ID NO: 17)

SHAAVIKLSDLNIRLLDKLLQAVIKLTELNAELNRKLIEALQRLFDLNVALVHLAAELTD

PKRIADEIKKVKDKSKEIVERAEEEIARAAAESKKILDEAEEEIARAAAESKKILDEGSGS

GSDAVAELQALNLKLAELLLEAVAELQALNLKLAELLLEAIAKLQELNIKLVELLTKLT

DPATIREAIRKVKEDSERIVAEAERLIAAAKAESERIIREAERLIAAAKAESERIIREGSGS

NDPQVAQNQETFIELARDALRLVAENQEAFIEVARLTLRAAALAQEVAIKAVEAASEG

GSGSGPNKEEIEKLAKEAREKLKKAEMSCAQEHDKLRKKNKKAREDLKK

-continued

>degronLOCKR_c
                                                                    (SEQ ID NO: 18)
SLEAVLKLAELNLKLSDKLAEAVQKLAALLNKLLEKLSEALQRLFELNVALVTLAIELT

DPKRIADEIKKVKDKSKEIVERAEEEIARAAAESKKILDEAEEEIARAAAESKKILDEGSG

SGSDAVAELQALNLKLAELLLEAVAELQALNLKLAELLLEAIAKLQELNIKLVELLTKL

TDPATIREAIRKVKEDSERIVAEAERLIAAAKAESERIIREAERLIAAAKAESERIIREGSG

SNDPLVARLQELLIEHARELLRLVATSQEIFIELARAFLANAAQLQEAAIKAVEAASENG

SGSGPSSEKVRRELKESLKENHKQNQKLLMSCAQEQEKLNRELEELKKKHKK

>degronLOCKR_c_t13
                                                                    (SEQ ID NO: 19)
SLEAVLKLAELNLKLSDKLAEAVQKLAALLNKLLEKLSEALQRLFELNVALVTLAIELT

DPKRIADEIKKVKDKSKEIVERAEEEIARAAAESKKILDEAEEEIARAAAESKKILDEGSG

SGSDAVAELQALNLKLAELLLEAVAELQALNLKLAELLLEAIAKLQELNIKLVELLTKL

TDPATIREAIRKVKEDSERIVAEAERLIAAAKAESERIIREAERLIAAAKAESERIIREGSG

SNDPLVARLQELLIEHARELLRLVATSQEIFIELARAFLANAAQLQEAAIKAVEAASENG

SGSGPSSEKVRRELKESLKENHKQNMSCAQEHKRAQEKLNRELEELKK

>mini-degronLOCKR_c_1_t9
                                                                    (SEQ ID NO: 20)
LIERLTRLEKEHVRELKRLLDTSLEILRRLVEAFETNLRQLKEALKRALEAANLHNEEVE

EVLRKLEEDLRRLEEELRKTLDDVRKEVKRLKEELDKRIKEVEDELRKIKEKLKKGDK

NEKRVLEEILRLAEDVLKKSDKLAKDVQERARELNEILEELSRKLQELFERVVEEVTRN

VPTTERIEKVRRELKESLKENHKQNQKLLMSCAQEQEKLNRELEELKKKHKK

>miniLOCKR_c_1_t13
                                                                    (SEQ ID NO: 21)
LIERLTRLEKEHVRELKRLLDTSLEILRRLVEAFETNLRQLKEALKRALEAANLHNEEVE

EVLRKLEEDLRRLEEELRKTLDDVRKEVKRLKEELDKRIKEVEDELRKIKEKLKKGDK

NEKRVLEEILRLAEDVLKKSDKLAKDVQERARELNEILEELSRKLQELFERVVEEVTRN

VPTTERIEKVRRELKESLKENHKLNMSCAQEHKRAQEKLNRELEELKK

>mini-degronLOCKR_c_2_t9
                                                                    (SEQ ID NO: 22)
SEERVLELAEEALRLSDEAAKEIQELARRLNEELEKLSKELQDLFERIVETVTRLIDADEE

TLKRAAEEIKKRLEDARKKAKEAADKAREELDRARKKLKELVDEIRKKAKDALEKAG

ADEELVARLLRLLEEHARELERLLRTSARIIERLLDAFRRNLEQLKEAADKAVEAAEEA

VRRVEDVRVWSEKVRRELKESLKENHKQNQKLLMSCAQEQEKLNRELEELKKKHKK

>miniLOCKR_c_t13
                                                                    (SEQ ID NO: 23)
SEERVLELAEEALRLSDEAAKEIQELARRLNEELEKLSKELQDLFERIVETVTRLIDADEE

TLKRAAEEIKKRLEDARKKAKEAADKAREELDRARKKLKELVDEIRKKAKDALEKAG

ADEELVARLLRLLEEHARELERLLRTSARIIERLLDAFRRNLEQLKEAADKAVEAAEEA

VRRVEDVRVWSEKVRRELKESLKENHKLNMSCAQEHKRAQEKLNRELEELKK

>asym-degronLOCKR_c_t13
                                                                    (SEQ ID NO: 24)
SLEAALKLAELNLKLSDKLAEASQKLAALLNKLLEKLSEAIQRLFELNLALVTLAIELTD

PKRIADEIKKVKDKSKEIIERAEEEIARAAAESKKILDEAEEEIARAAAESKKILDEGSGS

GSDALAELQALNLKLAELLLEAIAETQALNLKAAEAFLEAAAKLQELNIKAVELLVKLT

DPATIREALRKAKEDSERIIAEAERAIAAAKAESERIIREAERLIAAAKAESERIIREGSGS

-continued

NDPLIARLQELLIEHARELLRLHATSQEIFVELLRAFLANLAQLQEAALKALEAASENGS

GSGPSSEKVRRELKESLKENHKQNQKLLMSCAQEQEKLNRELEELKKKHKK

>degronLOCKR_d (SEQ ID NO: 25)

SLEAVLKLFELNHKLSEKLLEAVLKLHALNQKLSQKLLEALARLLELNVALVELAIELT

DPKRIADEIKKVKDKSKEIVERAEEEIARAAAESKKILDEAEEEIARAAAESKKILDEGSG

SGSDAVAELQALNLKLAELLLEAVAELQALNLKLAELLLEAIAKLQELNIKLVELLTKL

TDPATIREAIRKVKEDSERIVAEAERLIAAAKAESERIIREAERLIAAAKAESERIIREGSG

SGDPEVARLQEAFIEQAREILRNVAAAQEALIEQARRLLALAALAQEAAIKAVELASEH

GSGSGPDTVKRILEELRRRFEKLAKDLDDIAMSCAQEHKKHNKELKDKQRKIK

FIG. 10. Design of the LOCKR switch system. a, Thermodynamic model describing the design goal. The cage (cyan) and latch (blue) form the switch with some equilibrium in the open and closed states. The key (green) can bind the cage to promote the open state to allow target (yellow) binding to the latch. b, Plots from the model in (a) for two values of $K_{LT}$ showing how fraction target bound is affected by addition of key ($K_{CK}$=1 nM); the different colored curves show the effect of log-decreasing values of $K_{open}$=[open]/[closed]. c, Loops were added to homotrimer 5L6HC3 to form monomeric five- and six-helix frameworks; double mutant V217S/I232S weakens the Latch allowing it to be displaced by key, resulting in a LOCKR system able to bind an exogenous key. d, Chemical denaturation with guanidinium chloride (Gdm) of the trimer (dark blue), monomer (cyan), truncated five-helix framework (red), and LOCKR (green) monitoring mean residue ellipticity (MRE) at 222 nm. e, Small-angle x-ray scattering (SAXS) Kratky plots for the monomeric frameworks are similar to that of the input trimer, with the greatest deviation for the 5 helix framework. Colors continued from (d). f, Pulldown assay showing that Key binds to the truncation and LOCKR (V217S/I232S), but not the six-helix monomer; free GFP-Key was added to monomeric frameworks immobilized onto a plate via a hexahistidine tag; after a series of wash steps, binding was measured by GFP fluorescence (n=2, error bars indicate standard deviation).

FIG. 11. BimLOCKR design and activation. a, Following incorporation of the BIM peptide into the LOCKR latch, the free energy of the latch-cage interface was reduced by introducing sub-optimal interactions (left, removal of a buried hydrogen bond) and by truncating the latch, leaving exposed hydrophobic residues in the cage available for key binding (right). b, The lengthened BimLOCKR constructs show tight caging of Bim in the absence of key while introduction of the toehold (right) allows activation of 250 nM BimLOCKR with addition of 5 μM key via Bio-layer interferometry. c, Bio-layer interferometry shows key-dependent binding to Bcl2 with 250 nM BimLOCKR. Association from 0-500 s, then dissociation from 500-1700 s. Purple is at 3 μM key, then a three fold dilution of the key through blue, cyan, green, yellow, and orange. Red line is 250 nM LOCKR without key added. d, Each point in dark green is a result of fitting data in (c) and extracting the response at equilibrium; the lighter green curves show binding response at equilibrium for shorter keys that alter $K_{CK}$ of LOCKR to tune its range of activation. Dashed lines are the data fit to a logistic curve.

FIG. 12. Design and validation of orthogonal Bim-LOCKR. a, Left: LOCKR in cartoon representation. Cage in white with three different latches superimposed and hydrogen bond networks marked by colored markers. Right: Design models of hydrogen-bond networks across the orthogonal LOCKR interfaces corresponding to the colored markers on the left. b, BimSwitches binding to Bcl2 in response to its cognate key, measured by biolayer interferometry (Octet). c, Binding response to Bcl2 from biolayer interferometry experiments for each switch at 250 nM against each key at 5 μM; average of two replicates.

FIG. 13. Design and in vivo testing of degronLOCKR. a, Schematic of dual inducible system used in *S. cerevisiae* to test functionality of degronLOCKR. Progesterone (Pg) induces production of Key-BFP, and estradiol (E2) induces production of YFP-degronSwitch. b, Heatmaps of YFP fluorescence as a function of E2 (0-50 nM) and Pg (0-100 nM) for full length key (left) and a key that was truncated by 12 residues (right) as measured by flow cytometry. c, Line plot comparing the fluorescence of the YFP-degronSwitch$_a$ and Key$_a$-BFP at a max dose of E2 (black rectangle in (b) as a function of Pg induction. Fluorescence values were normalized to the maximum YFP or BFP fluorescence. Error bars represent s.d. of three biological replicates. d, Dynamic measurements of active degLOCKR using an automated flow cytometry platform. E2 was induced to activate expression of YFP-degronSwitch$_a$, and Pg was induced at t4 hrs to activate expression of Key$_a$-BFP. Measurements were taken every 24 minutes. e, Coexpression of orthogonal LOCKRs in the same cell. YFP-degronSwitch$_a$ and RFP-degron-Switch$_c$ were expressed using constitutive promoters and either Key$_a$-BFP (left) or Key$_c$-BFP (right) were expressed using the pZ3 inducible promoter. Normalized fluorescence of YFP-degronSwitch$_a$, RFP-degronSwitch$_c$ and either Key$_a$-BFP or Key$_c$-BFP are plotted as a function of Pg induction. Error bars represent s.d. of biological replicates. f, Asymmetric RFP-degronSwitch$_a$ was expressed in HEK293T cells with and without Key. Flow cytometry distribution of RFP fluorescence for a representative sample indicates decreased RFP expression in the presence of Key. Geometric mean of RFP expression is quantified in the bar plot. Data in all panels represent mean±s.d. of three biological replicates.

FIG. 14. Controlling gene expression using degron-LOCKR. a, Schematic of dual induction assay to determine the effect of degronLOCKR$_a$ on a synthetic transcription factor (SynTF). Pg induces expression of Key$_a$-BFP, and E2 induces expression of SynTF-RFP-degronSwitch$_a$ fusion. The pSynTF promoter is activated by SynTF and expresses YFP. b, Heatmaps of YFP and RFP fluorescence as a function of E2 (0-125 nM) and Pg (0-100 nM) measured by flow cytometry. c, Line plot comparing the fluorescence of YFP, SynTF-RFP-degronSwitch$_a$ and Key$_a$-BFP at 31.25 nM E2 (black rectangle in 5b) as a function of Pg induction. Fluorescence values were normalized to the maximum YFP, RFP, or BFP fluorescence. Error bars represent s.d. Of three biological replicates. d, Schematic of dual induction assay to determine the effect of degronLOCKR$_a$ on a dCas9-VP64 targeted to the pTet7× promoter via a constitutively expressed sgRNA (not shown). Pg induces expression of Key$_a$-BFP, and E2 induces expression of dCas9-VP64-RFP-degronSwitch$_a$ fusion. The pTet7× promoter is activated by dCas9-VP64 and expresses YFP. e, Heatmaps of YFP and RFP fluorescence as a function of E2 (0-125 nM) and Pg (0-100 nM) measured by flow cytometry. f, Line plot comparing the fluorescence of YFP, dCas9-VP64-RFP-degron-Switch$_a$ and Key$_a$-BFP at 31.25 nM E2 (black rectangle in 5d) as a function of Pg induction. Fluorescence values were normalized to the maximum YFP, RFP, or BFP fluorescence. Error bars represent s.d. of three biological replicates.

FIG. 15: Biophysical data from LOCKR design. a) Size Exclusion Chromatography for the Monomer, Truncation, and LOCKR designs on Superdex 75. Peaks indicated by vertical dashed lines represent monomeric protein used in downstream characterization and functional assays. b) Circular dichroism spectroscopy to determine protein stability upon heating and chemical denaturant, Guanidinium Chloride-HCl. Top row: full wavescan at 25° C. (blue), 75° C. (orange), 95° C. (red), then cooled to 25° C. (cyan). Middle row: guanidine melts also shown overlapped in FIG. 1d. Bottom row: fraction folded was converted to equilibrium constant, then to $\Delta G_{unfolding}$ value. The linear unfolding region, marked by vertical lines in middle row, was fit to determine the $\Delta G_{folding}$ for each design. c) SAXS spectra (black) referenced in FIG. 1e fit to Rosetta design models (red) using FoXS with chi-values referenced in the upper right.

FIG. 16: GFP Plate assay to find mutations for LOCKR. Different putative LOCKR constructs were adhered via 6×-His tag to a Ni coated 96-well plate, Key-GFP was applied, and excess washed. Resulting fluorescence represents Key-GFP bound to LOCKR constructs. The truncation was used as a positive control, since the key binds to the open interface. The monomer as a negative control since it does not bind the key. Error bars represent the standard deviation of three replicates.

FIG. 17: Caging Bim-related sequences. a) Three Bcl2 binding sequences were grafted onto the latch. aBcl2 is a single helix from a designed Bcl2 binder (pdb: SJSN) where non Bcl2-interacting residues were reverted back to the standard LOCKR latch sequence, shown as dashes. pBim is the partial Bim sequence where only Bcl2-interacting residues are grafted onto the latch. Bim is the full consensus sequence of the BH3 domain. b) LOCKR (left) with the latch in dark blue. The helical Bim sequence is taken from the Bim/Bcl2 interaction and grafted onto the latch c) Left: Bcl2 (tan) binding to Bim (purple) from pdb:2MV6 with pBim residues shown as sticks. Center: a well caged graft where important binding residues are caged. Right: a poor graft where Bcl2 binding residues are exposed and polar surface residues are against the cage interface.

FIG. 18: Tuning BimLOCKR. aBcl2, pBim, and Bim were caged to varying degrees of success. Early versions of the switch, with aBcl2 and pBim did not efficiently cage Bcl2 binding in the off state. They also only weakly bound the key leading to small dynamic range. The cage and key was extended by 5, 9, and 18 residues in an attempt to provide a larger interface to tightly hold the latch in the off state and provide a larger interface for key binding to increase the dynamic range of activation. Mutations on the latch, identified in FIG. 16, and providing toeholds for key binding were the two strategies employed to tune the switch. In graphs, "off" refers to 250-310 nM switch an absence of key while "on" refers to excess key added. The height of the bar graph shows the $R_{eq}$ as measured by Bio-layer interferometry.

FIG. 19: Sequence alignment of 1504 keys for filtering for orthogonality. Every pairwise alignment was scored using BLOSUM62 scoring, disallowing gaps while not penalizing end-gaps. This algorithm finds the BLOSUM62 score of the most similar superposition of each pair of keys taking into account amino acid identity.

Figure 20:
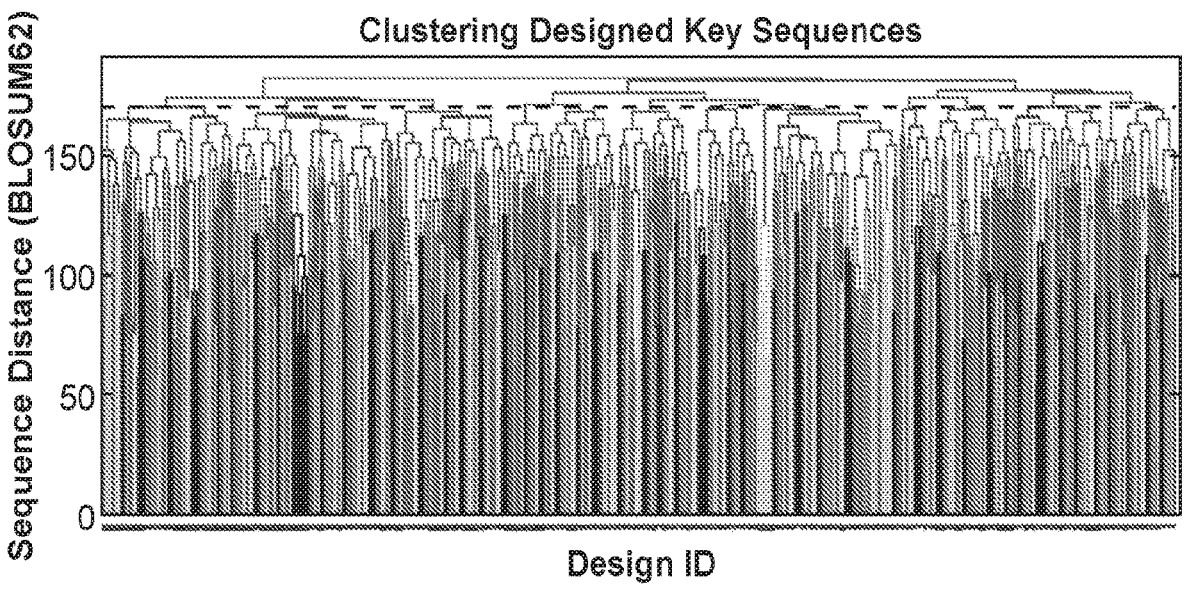
FIG. 20 provides clustering of the sequences aligned in FIG. 19.

FIG. 20: Clustering sequences aligned in FIG. 19. Each sequence along the y-axis was clustered using a hierarchical clustering algorithm. The cutoff at 170 (horizontal, black dotted line) selects 13 clusters from which the centers were chosen as designs to order.

FIG. 21: Validation of model in FIG. 10, panel a. a) BLI measurement of BimLOCKR$_a$ (400 nM) binding to Bcl2 (gold), BclB (yellow), and Bak (lighter yellow—Bim-LOCKR at 1 μM) as key is added to solution. Normalized due to differences in $R_{max}$ for Bcl2 and BclB on the tip. b) BLI measurement of BimLOCKR$_a$ binding to key$_a$ immobilized on the tip. Open circles are with no Bcl2 present, gold points are with Bcl2 present at 500 nM.

FIG. 22: Caging cODC sequences. a) Three variations of the cODC degron to cage. Variations meant to tune $K_{open}$ by removing the destabilizing proline (noPro) and minimizing mutations to the latch (CA only). b) Predicted models of the full and noPro cODC sequences (orange) threaded onto the latch (dark blue). Thread position chosen such that the cysteine residue needed for degradation is sequestered against the cage (light blue). Proline highlighted in red in the full cODC mutated to an isoleucine in the noPro variant.

FIG. 23: Comparing the stability of YFP fused to cODC variants caged in Switch$_a$ to an empty Switch$_a$ and to bimSwitch$_a$. The dual inducible system from FIG. 13, panel a, was used to express the various YFP-Switch$_a$ fusions (solid lines and dots) via pGal1 and E2, and Key$_a$-BFP via pZ3 and Pg. YFP (Venus) alone, YFP fused to the WT cODC (cODC) or YFP fused to the proline removed cODC (cODC noPro), were also expressed using pGal1 and E2 (dashed lines). Cells were induced with a saturating dose of E2 (50 nM) and Pg was titrated in from 0-100 nM. Fluorescence was measured at steady-state using a flow cytometer and error bars represent s.d. of biological replicates. A moderate decrease in YFP fluorescence was observed as a function of Pg for the full cODC variant, whereas only a small decrease was observed for the proline removed and CA only. No decrease in fluorescence was observed as a function of key induction for YFP alone, empty Switch$_a$, or bimSwitch$_a$.

FIG. 24: Tuning toehold lengths of degronLOCKR$_a$. The dual inducible system from FIG. 13, panel a, was used to express the various YFP-Switch$_a$ fusions via pGal1 and E2, and Key$_a$-BFP via pZ3 and Pg. YFP fused to the proline removed cODC (cODC no Pro) was also expressed using pGal1 and E2 (dashed line). Cells were induced with a saturating dose of E2 (50 nM) and Pg was titrated in from 0-100 nM. Fluorescence was measured at steady-state using a flow cytometer and error bars represent s.d. of biological replicates. (Left) cODC variants from FIG. 22 alone to show dynamic range of Full cODC. (Right) Extending toehold on proline removed version from 9 to 12 and 16aa. Proline removed with 12aa toehold shows the greatest dynamic range of all the switches tested.

FIG. 25: BFP expression corresponding to FIG. 13, panel b. E2 and Pg were used to induce expression of YFP-degronSwitch$_a$ and Key$_a$ (Full length or truncated)-BFP, respectively. Fluorescence was measured at steady-state using a flow cytometer. BFP expression was not dependent on expression of the Switch, suggesting the Key does not co-degrade with the Switch.

Figure 26:
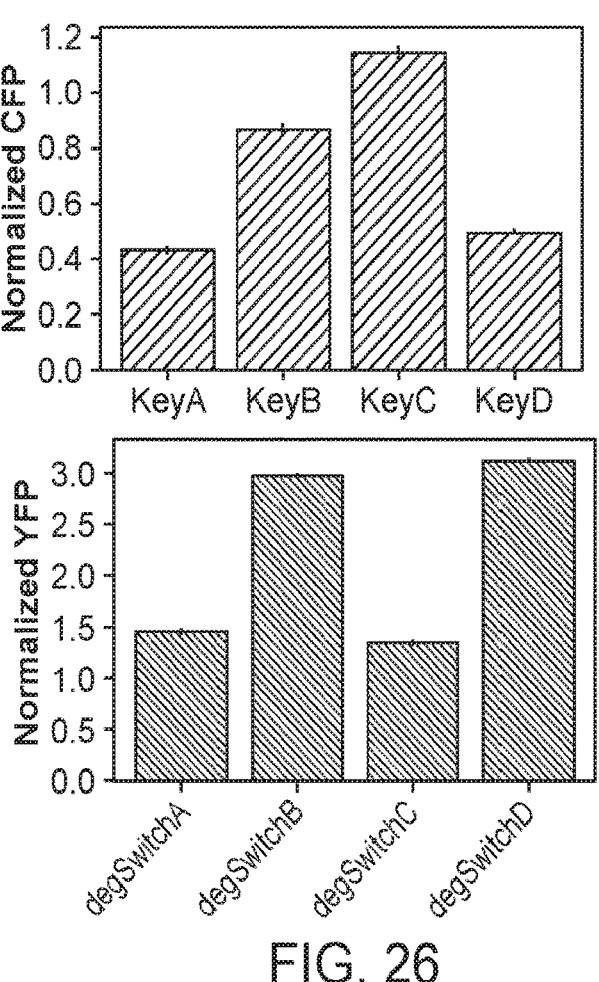
FIG. 26 provides expression data related to orthogonal YFP-degronSwitch and Key-CFP.
Figure 27:
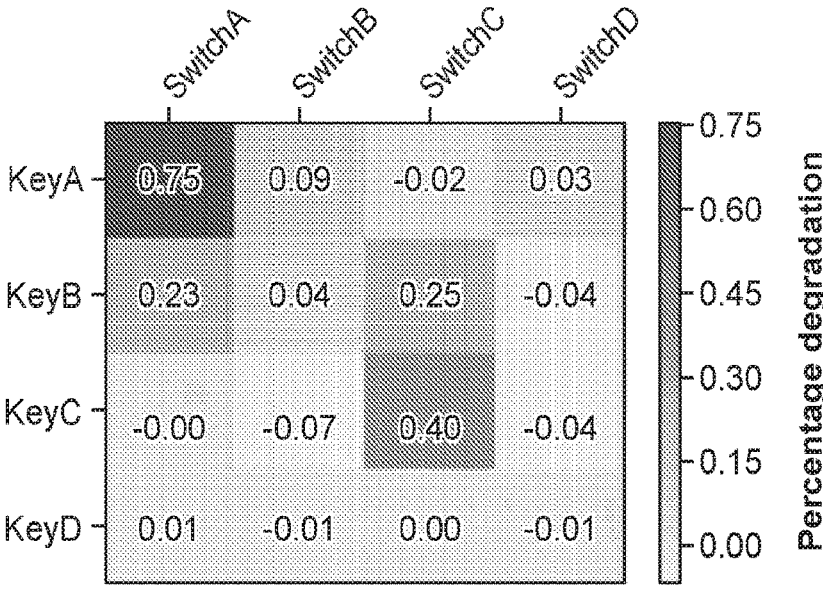
FIG. 27 demonstrates $degronLOCKR_{a-d}$ orthogonality.

FIG. 26: Expression of orthogonal YFP-degronSwitch and Key-CFP. Four different switches and keys (A, B, C, D) were expressed using the strong pTDH3 promoter. Fluorescence was measured at steady-state using a flow cytometer and error bars represent s.d. of biological replicates.

FIG. 27: degronLOCKR$_{a-d}$ orthogonality. All combinations of pTDH3-YFP-degronSwitch and pTDH3-Key-CFP were tested. Fluorescence was measured at steady-state using a flow cytometer. Percentage degradation was calculated by subtracting the YFP-degronSwitch fluorescence with the given Key-CFP coexpressed from the YFP-degron-Switch fluorescence without any Key expressed and normalizing by the YFP-degronSwitch fluorescence without any Key expressed. degronSwitch$_a$ is activated strongly by Key$_a$ and weakly by Key$_b$. degronSwitch$_c$ is activated strongly by Key$_c$ and weakly by Key$_b$. Because degronSwitch$_a$ and degronSwitch$_c$ are not activated by Key$_c$ and Key$_a$ respectively, these two are considered to be an orthogonal pair.

FIG. 40: Comparison of different degronSwitch variants in HEK293T cells. Fluorescence of RFP-degronSwitch variants in the presence and absence of Key-BFP were measured using flow cytometry. Original symmetric design ("Sym") was compared against an asymmetric design ("Asym"). Two toehold lengths (designated by a preceeding "t") were tested for each variant (i.e., "t12", "t9", t8" and "t5"). Data in bar graph represents geometric mean±s.d. of three biological replicates and untransduced control ("UnT") is provided for reference. Histograms are depicted for a representative sample. Asymmetric cage with a t8 toehold demonstrated the largest dynamic range.

Example 2: Modular and Tunable Biological Feedback Control Using a De Novo Protein Switch In this example, a de novo protein switch, degron-LOCKR, designed via host-agnostic parts with modular connectivity and predictable tunability is employed to implement feedback control on endogenous pathways and synthetic circuits in the yeast *S. cerevisiae*.

Figure 28:
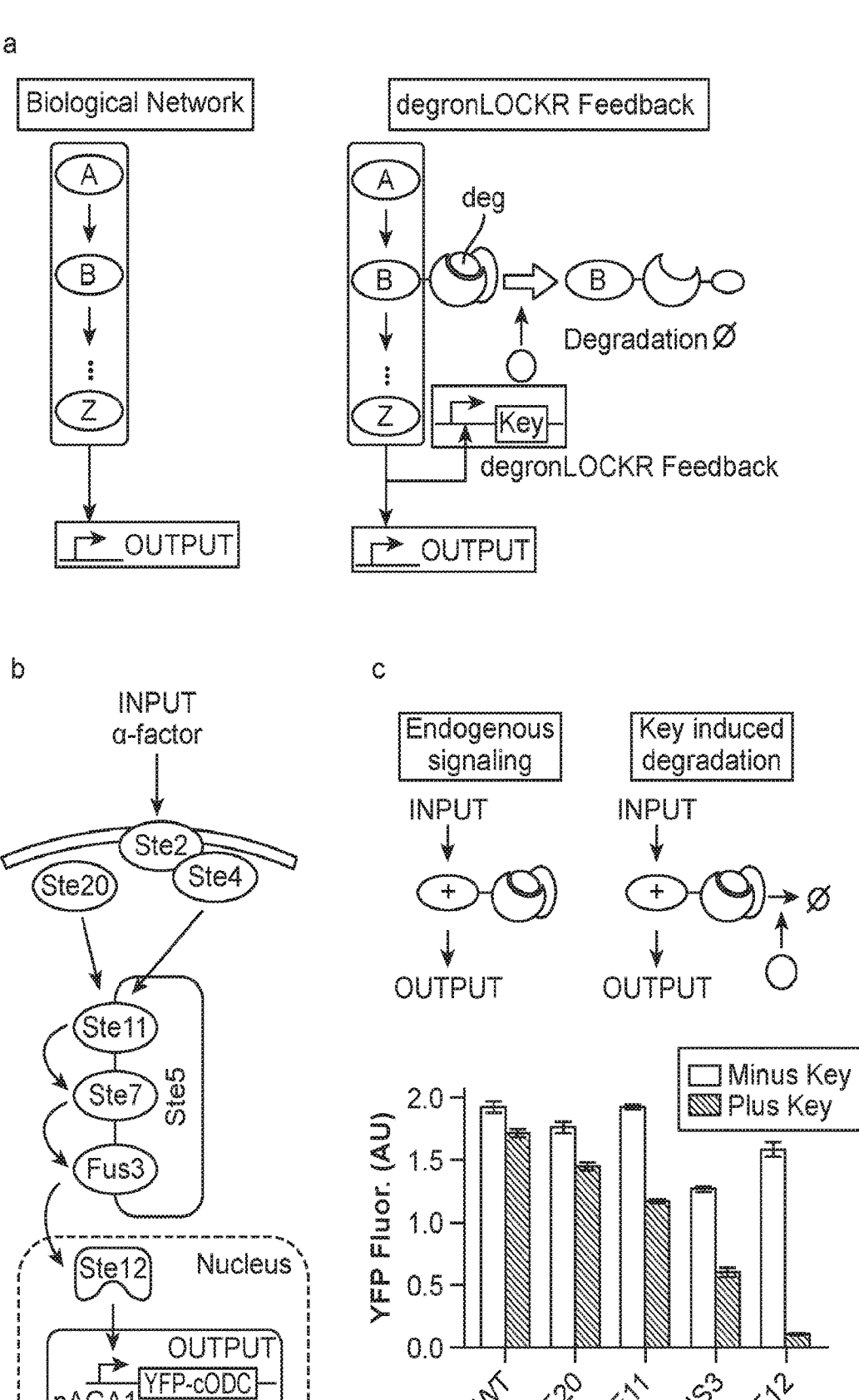
FIG. 28 provides degronLOCKR is a modular tool for controlling biological pathways. a) Schematic of degron-LOCKR as a modular tool to implement synthetic feedback control on an endogenous or synthetic biological network by fusing the degSwitch to an effector molecule and driving the expression of the key from the output of the network. b) Simplified schematic of the yeast mating pathway not showing complex endogenous feedback. Pathway is activated by addition of α-factor and signaling activity is measured using a pAGA1-YFP-cODC reporter. c) degronLOCKR induced degradation of positive signaling molecules to control mating pathway activity. The endogenous copy of indicated signaling molecule was fused to degSwitch and key was expressed using a progesterone inducible system. Cells were induced with a saturating dose of α-factor and pathway activity with and without key was compared. pAGA1-YFP-cODC was measured on a flow cytometer after four hours of growth. Data represent mean±s.d. of three biological replicates.

The degronLOCKR device is based on LOCKR (Latching Orthogonal Cage Key pRoteins) technology, and consists of the designer degSwitch and key proteins. The degSwitch is a six-helix bundle that has the cODC degron embedded in the destabilized sixth helix (latch), which is occluded via interaction with the five-helix scaffold (cage). The key, a genetically encoded peptide, can outcompete the latch for binding with the cage. This reveals the cODC degron, thus targeting the degSwitch and any fused cargo to the proteasome for degradation. degronLOCKR is a powerful device for synthetic biology because protein degradation is a universal method for post-translational regulation. It has been shown that degronLOCKR can control gene expression by regulating the stability of a transcription factor. Here, this functionality is capitalized on to implement modular feedback control on a biological network using degronLOCKR by expressing the key as a function of the output of the network (FIG. 28, panel a). The degronLOCKR feedback strategy offers several advantages over other approaches for implementing feedback control. First, the modular nature of the degronLOCKR allows the degSwitch to be directly fused to any protein of interest to generate on-target effects. Modifying endogenous genes with the degSwitch also preserves the native transcriptional and translational regulation of the signaling protein. Finally, degronLOCKR is a completely de novo designed protein thus allowing for predictable modifications to tune its characteristics.

degronLOCKR Synthetic Negative Feedback in Endogenous Yeast Pathway

As a qualitative proof of concept, degronLOCKR was used to implement synthetic negative feedback in the yeast MAPK mating pathway (FIG. 28, panel b), a complex signaling pathway with many endogenous feedback loops. The ability of degronLOCKR to modulate pathway output was tested by appending the degSwitch to the endogenous locus of several positive pathway molecules in a ΔFAR1 ΔBAR1 background strain and the key was expressed using an inducible system (Aranda-Diaz et al. ACS Synth. Biol. 6, 545-554 (2017)) (FIG. 28, panel c). The key was targeted to either the cytosol or nucleus using a nuclear localization sequence to trigger degradation of each molecule in a specific compartment of the cell (FIG. 29). This localized inducible degradation is a unique characteristic of degron-LOCKR that enables location specific action in the cell. The mating pathway was stimulated with a saturating dose of α-factor (100 nM) and monitored pathway activity using pAGA1-YFP-cODC (McCullagh et al. Nat. Cell Biol. 12, 954-962 (2010)) transcriptional reporter (cODC degron (Hoyt et al. J. Biol. Chem. 278, 12135-12143 (2003)) destabilizes the long lived fluorescent reporter, allowing dynamics to be observed). Degrading STE20 (MAPKKKK), STE11 (MAPKKK), and FUS3 (MAPK) had a moderate effect, while degrading STE12 (TF) completely eliminated the output of the mating pathway (FIG. 28, panel c, bottom). These data indicate that degronLOCKR is an effective tool for modulating endogenous pathways.

Figure 30:
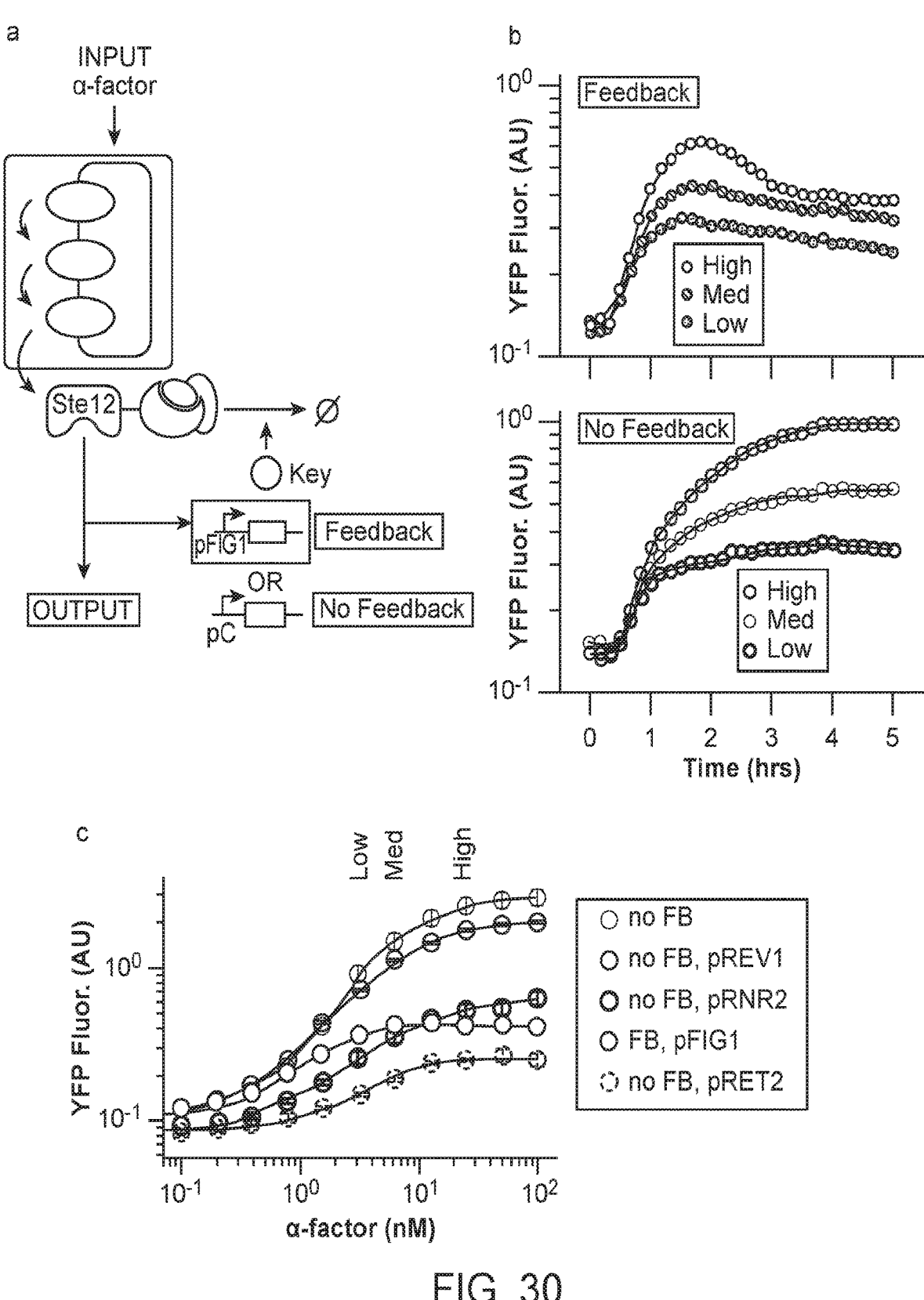
FIG. 30 demonstrates that degronLOCKR module successfully implements synthetic feedback control of the mating pathway. a) Schematic of synthetic negative feedback where the endogenous copy of STE12 is fused to the degSwitch and either the pathway reporter pFIG1 (synthetic feedback) or a constitutive promoter (no feedback) is used to express key-CFP-NLS. All output measurements are for pAGA1-YFP-cODC. b) Measurements of pAGA1-YFP-cODC dynamics. Synthetic feedback and no feedback (pREV1) strains were induced with a high (25 nM), medium (6.25 nM), or low (3.13 nM) dose of α-factor at time t=0 hr and flow cytometry measurements (points) were performed every 10 minutes. Lines represent a moving average taken over three data points. c) α-factor dose response of synthetic feedback (pFIG1) and four no feedback (no key, pREV1, pRNR2, pRET2) strains. pAGA1-YFP-cODC fluorescence was measured using flow cytometry four hours after α-factor induction. Points represent the mean±s.d. of three biological replicates. Solid lines are a hill function fit to the data. High, medium, and low doses of α-factor from the experiment in (b) are indicated on the graph.

Synthetic negative feedback control of the mating pathway was next implemented by expressing the key-CFP-NLS from a mating pathway responsive promoter (FIG. 1) in a strain where endogenous STE12 is fused to the degSwitch (FIG. 30, panel a). The effect of this feedback was compared to a strain with no feedback where STE12 is still fused to degSwitch but the key is driven by a constitutive promoter. pAGA1-YFP-cODC dynamics were followed after stimulation with high (25 nM), medium (6.25 nM), and low (3.13 nM) doses of α-factor (Fig FIG. 30, panel b) using automated flow cytometry. For comparison, a strain without feedback (pREV1-key-CFP-NLS) was simultaneously measured. Following stimulation with each dose of alpha-factor, the output of the synthetic feedback and no feedback strains initially followed each other closely. After around two hours, the synthetic feedback output started to decrease while the no feedback output increased to different steady-states corresponding to the different doses of α-factor. The strain with degronLOCKR synthetic feedback displayed larger transient overshoots for larger doses of α-factor, but eventually converged on the same steady-state output regardless of the input size. These data suggest that synthetic feedback desensitizes the steady-state output to α-factor of the mating pathway in this input regime. This effect is likely not due to saturation of signaling because of the different observed transients.

To obtain a more global comparison of the steady-state behaviors of the synthetic feedback and no feedback strains, the output dose response of each was measured as a function of α-factor. The feedback strain displayed attenuation of maximum output magnitude and decreased slope in the linear region of the dose response (FIG. 30, panel c). Comparing the synthetic feedback strain to no feedback strains with a range of constitutive promoter strengths (Lee et al. ACS Synth. Biol. 4, 975-986 (2015)) (pREV1, pRNR2, pRET2) indicates that the behavior generated by feedback cannot be achieved by expressing different constitutive amounts of the key. Taken together, the dynamic adaptation behavior and dose response clearly demonstrate the effect of synthetic negative feedback and utility of degronLOCKR as a tool for rapid rewiring of a complex endogenous signaling pathway.

degronLOCKR Feedback in a Synthetic Transcriptional Cascade

Figure 31:
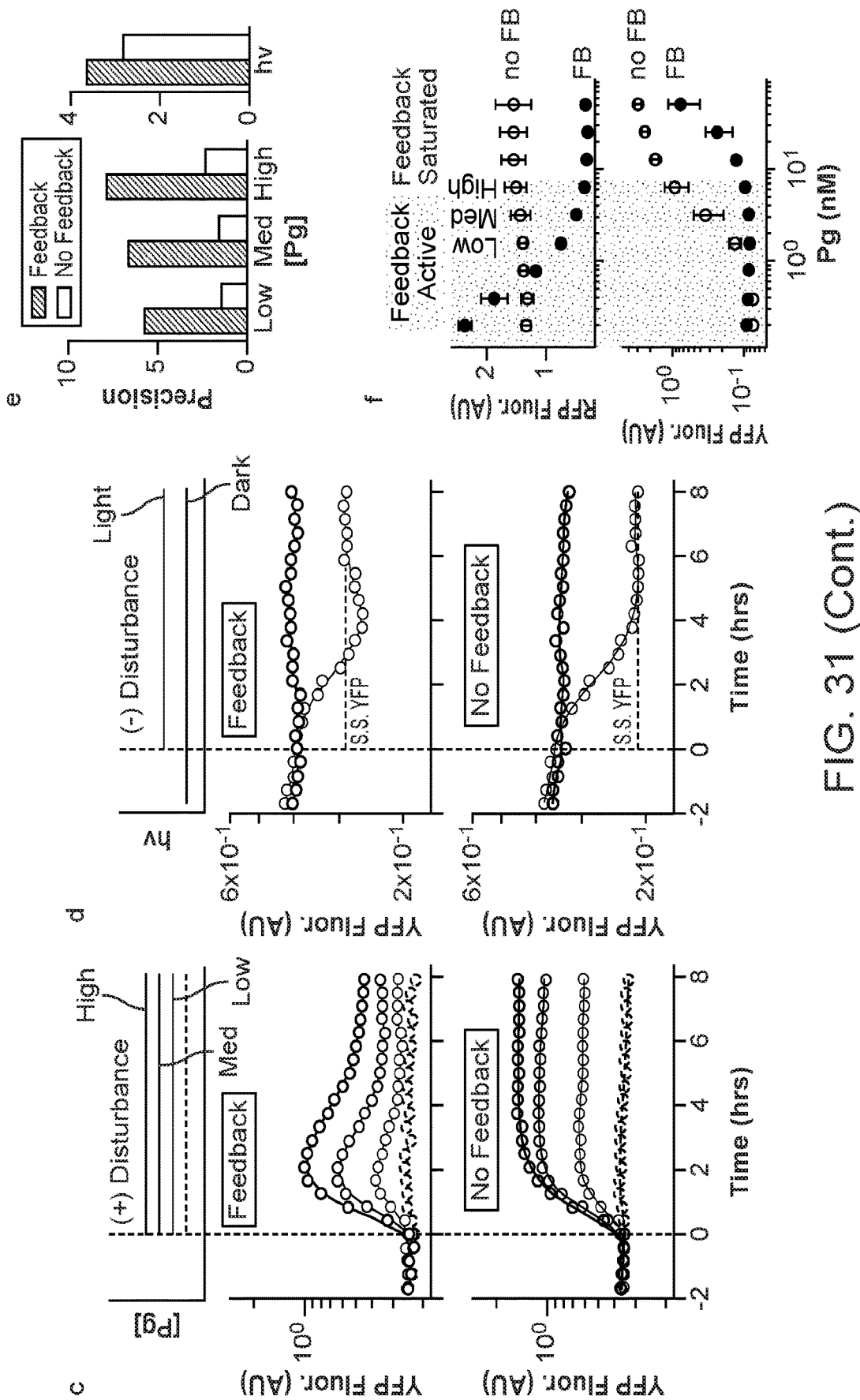
FIG. 31 provides operational properties of degronLOCKR feedback module quantified via control of a synthetic circuit. a) Schematic of synthetic feedback circuit. GEM-degSwitch is expressed constitutively and is activated by estradiol (E2) to drive expression of pGAL1-Z3PM-psd. Z3PM is activated by progesterone (Pg) to drive expression from pZ3. Blue light can be used to induce degradation of Z3PM-psd. pZ3-YFP-cODC is the measured output of the circuit, and pZ3-key-CFP-NLS drives feedback (synthetic feedback) in the circuit by activating degradation of GEM-degSwitch. In the circuit with no feedback a constitutive promoter is used to express key-CFP-NLS. b) Model simulation (see supplementary information) of the feedback and no feedback circuits. The simulated dynamics (left) and change of steady-state (right) of output following a Pg disturbance indicate that feedback buffers against increasing Pg concentration by degrading GEM and reducing Z3PM concentration. c) Dynamic measurements of pZ3-Venus-cODC using automated flow cytometry for the synthetic feedback and no feedback strains (pRNR2-key-CFP-NLS) following a positive disturbance. Cells were grown to steady-state expression in 0.78 nM Pg and 7.5 nM E2. At time 0 hrs cells were either kept at the same Pg concentration or induced to a new final concentration of 1.56 nM (low), 3.13 nM (med), or 6.25 nM (high) Pg. Dynamics were measured for another eight hours. Solid line represents a moving average taken over three data points. d) Dynamic measurements of pZ3-Venus-cODC using automated flow cytometry for the synthetic feedback and no feedback strains (pRPL18B-key-CFP-NLS driving key) following a negative disturbance. Cells were grown to steady-state expression in 1.57 nM Pg and 30 nM E2 then subjected to blue-light at time 0 hrs to activate the psd. Dynamics were measured for eight hours post-disturbance. Growth and sampling conditions are as in c). e) Precision of the synthetic feedback versus no feedback circuits to each of the disturbances. f) Comparison of steady-state circuit behavior (ten hours after stimulation) with and without feedback (pRNR2-key-CFP-NLS) as a function of Pg at a fixed concentration of 7.5 nM E2. RFP fluorescence is a proxy for Z3PM concentration and YFP fluorescence is the output of the circuit. Pg doses used for positive disturbance in c) are indicated. Points represent mean±s.d. of three biological replicates.

The quantitative capabilities and operational range of the degronLOCKR feedback module was next mapped using a simple synthetic transcriptional cascade consisting of two inducible synthetic transcription factors (Aranda-Diaz et al.) (FIG. 31, panel a). The first, GEM (Gal4 DNA binding domain-Estradiol hormone binding domain-Msn2 activation domain), is induced by estradiol (E2) and activates pGAL1 to produce Z3PM (Z3 zinc finger-Progesterone hormone binding domain-Msn2 activation domain). Z3PM, in turn, is induced by progesterone (Pg) and activates transcription of pZ3-YFP-cODC. To implement feedback, the same modular strategy that was successful for controlling the mating pathway was used: fusing GEM to the degSwitch and using pZ3 to express key-CFP-NLS (synthetic feedback). With feedback, the concentration of GEM is dependent on the output of Z3PM because the amount of key produced, and hence degradation rate of GEM, is a function of Z3PM activity. The circuit can be perturbed by addition of Pg or induction of a blue-light inducible degron (psd) (Renicke et al. Chem. Biol. 20, 619-626 (2013)) fused to Z3PM to increase or decrease the output, respectively. Feedback buffers against these disturbances by modulating the concentration of Z3PM. This type of disturbance rejection experiment is an essential test of feedback in technological systems.

Figure 32:
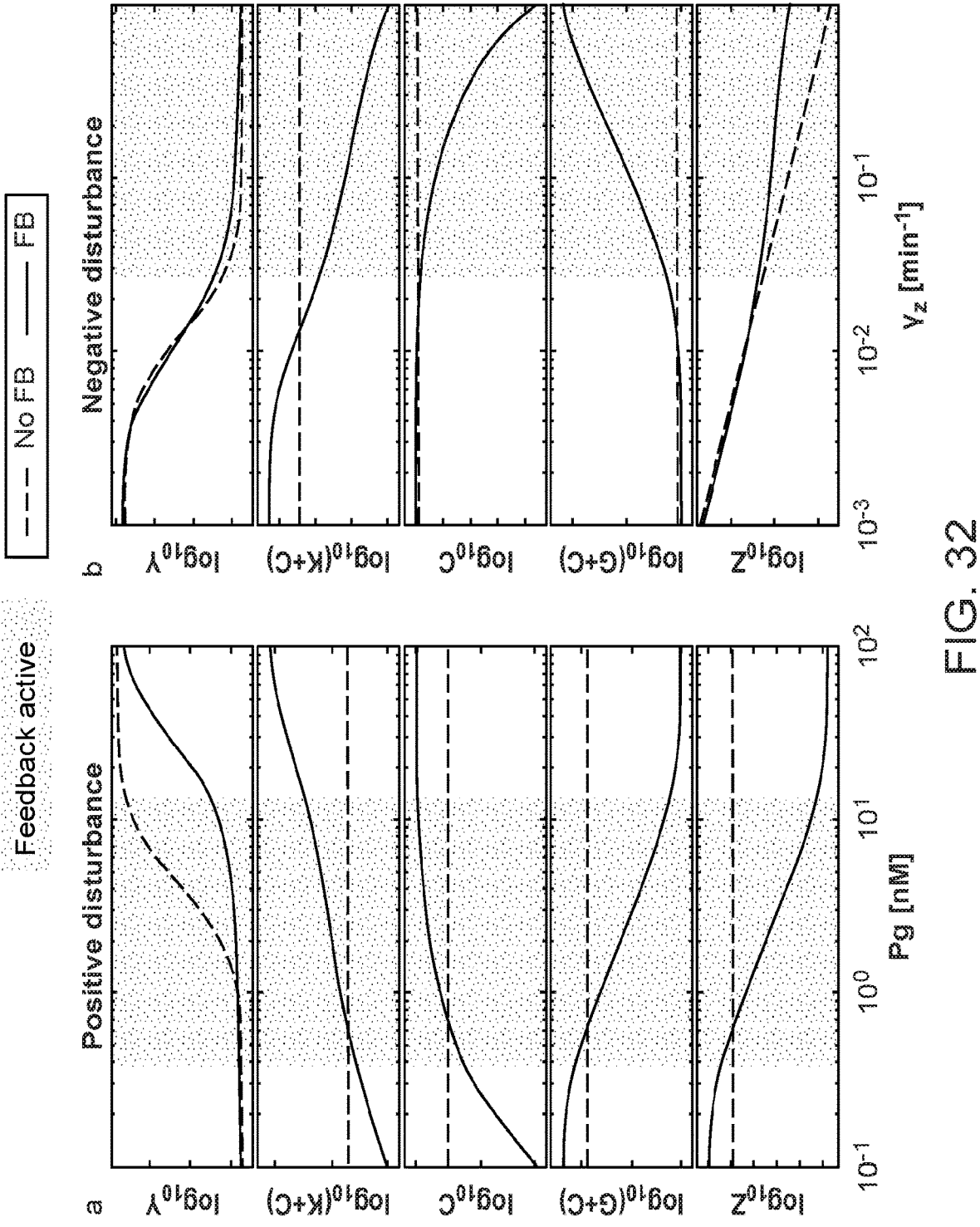
FIG. 32 provides steady state solutions in response to positive or negative disturbances. Steady values as a) progesterone (Pg) or b) ZPM degradation rate ($\gamma_Z$) change according to our Hill-like model. Continuous lines correspond to the feedback system (FB), while the dashed line shows an example where the feedback has been removed (i.e. $f_K = \mu_K^*$ instead of Eq.12; No FB). The gray box delimits the area where the feedback is considered "active", which is defined by the relative change in total GEM ($\Delta(G+C)/(G+C)$) over the relative change of the disturbance (either a) $\Delta P/P$ or b) $\Delta\gamma_Z/\gamma_Z$) is higher than 0.15. Noteworthy, in the absence of feedback, $\Delta(G+C)$ is equal zero for any disturbance except on the synthesis or degradation rate of the key or GEM directly.

A simple computational model of the circuit predicts that an increase in Pg results in a monotonic increase in output without feedback (key expressed constitutively), whereas feedback gives a transient increase in output followed by adaptation to a steady-state whose value is closer to the pre-disturbance value than the circuit with no feedback for the same increase in Pg (FIG. 31, panel b, left). Feedback attenuates the dependence of the output on the Pg disturbance by decreasing the production rate of Z3PM, therefore compensating for an increase in Z3PM activity after a Pg increase with a decrease in its concentration (FIG. 31, panel b, right; FIG. 32).

These predictions were experimentally verified by first inducing cells with 7.5 nM E2 and 0.78 nM Pg and which were grown until their output reached steady-state (FIG. 31, panel c). At that time, the cells were perturbed with a high (6.25 nM), medium (3.13 nM), or low (1.56 nM) step-input of Pg and the dynamics of pZ3-YFP-cODC were measured using an automated flow cytometry and optogenetically-enabled continuous culture platform. As a control, the same series of inductions were performed on an strain without feedback (pRNR2 expressing key) which had similar YFP steady-state output as the feedback strain at the pre-disturbance concentration of E2 and Pg. Without feedback, the step-input of Pg caused an increase in Z3PM activity and thus YFP expression until the output reached a new steady-state commensurate with the disturbance. In contrast, the synthetic feedback circuit increased key expression as Z3PM activity increased, resulting in GEM degradation and thus a decrease in Z3PM production. This buffering effect is visible starting two hours post-disturbance when the synthetic feedback circuit output begins to decrease while the no feedback circuit output continues to climb. This adaptation behavior is qualitatively similar to the synthetic negative feedback loop constructed for the mating pathway. Because of the well-defined inputs and disturbances, adaptation can be quantified using a precision metric calculated by taking the inverse of the absolute difference between post- and pre-disturbance output normalized by the pre-disturbance output (Ma et al. Cell 138, 760-773 (2009)) (FIG. 31, panel e). The feedback circuit generates much higher precision than the circuit without feedback for the Pg positive disturbance, showcasing a benefits of feedback control.

A similar experiment was performed where the cells were subjected to a negative disturbance. Cells were grown to steady-state at 30 nM E2 and 1.57 nM Pg, then induced with blue light to activate degradation of Z3PM (FIG. 31, panel d). As a control, a no feedback circuit was built as a control with the key expressed constitutively from pRPL18B to match the steady-state expression of the synthetic feedback circuit before disturbance. After an immediate decrease in YFP expression in both synthetic feedback and no feedback circuits as a result of Z3PM degradation, the no feedback circuit settled to a new lower steady-state. The feedback circuit, however, underwent a slight overshoot after which it recovered to a steady-state closer to the pre-disturbance value than the no feedback circuit. The amount of adaptation in the synthetic feedback circuit for the negative disturbance is not as dramatic as for the positive disturbance (FIG. 31, panel f). Model simulation shows that the negative disturbance pushes the circuit output to a lower expression level where the relative difference between a circuit with and without feedback will be smaller. Thus, even if feedback is still actively buffering against the negative disturbance the effect will be harder to observe. This underscores the fact that any feedback circuit, whether built with biological molecules or electronic components, has properties that need to be explored through thorough prototyping in order to enable productive modular use.

Figure 33:
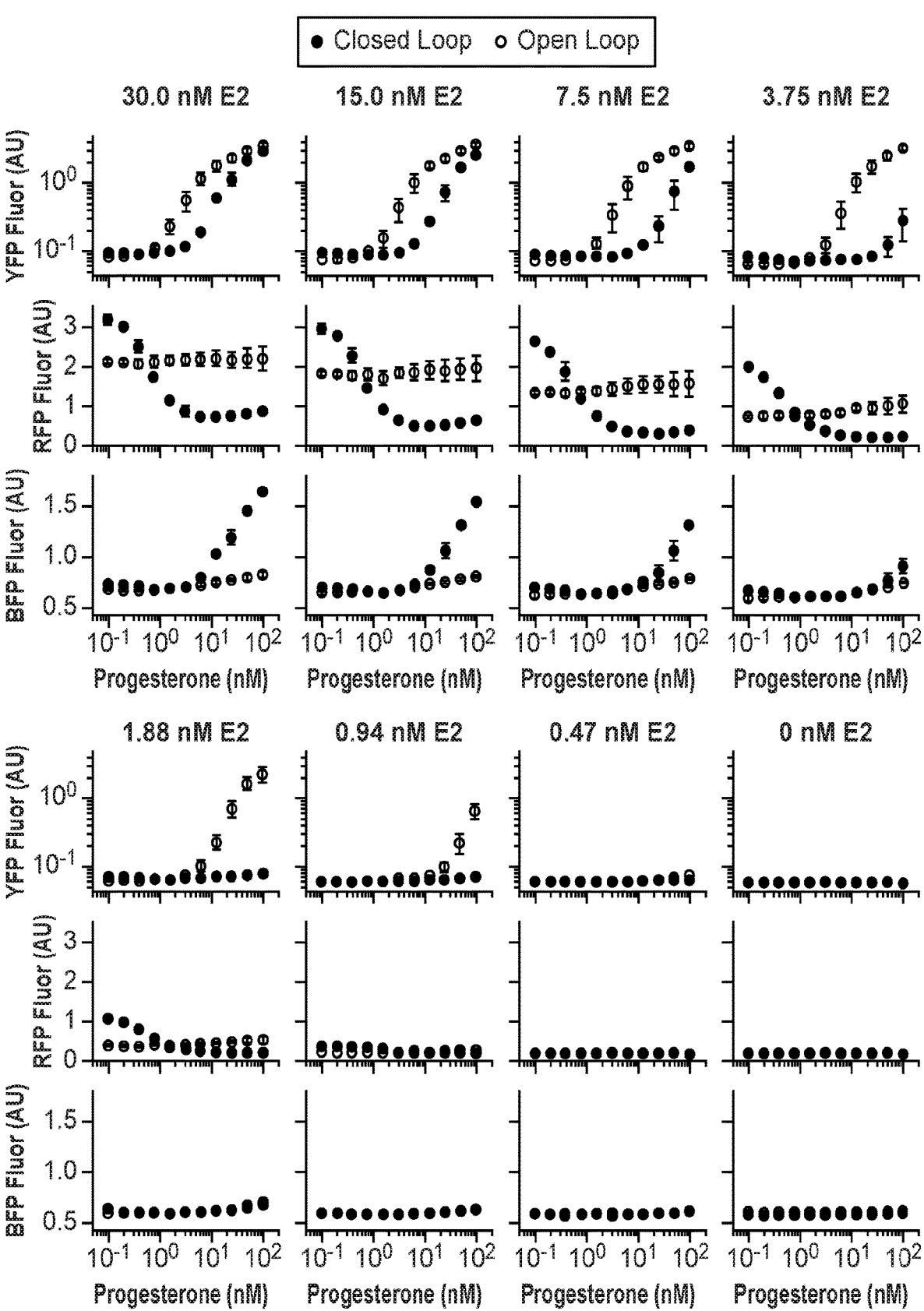
FIG. 33 depicts circuit behavior as a function of Pg for a fixed dose of E2.
Figure 34:
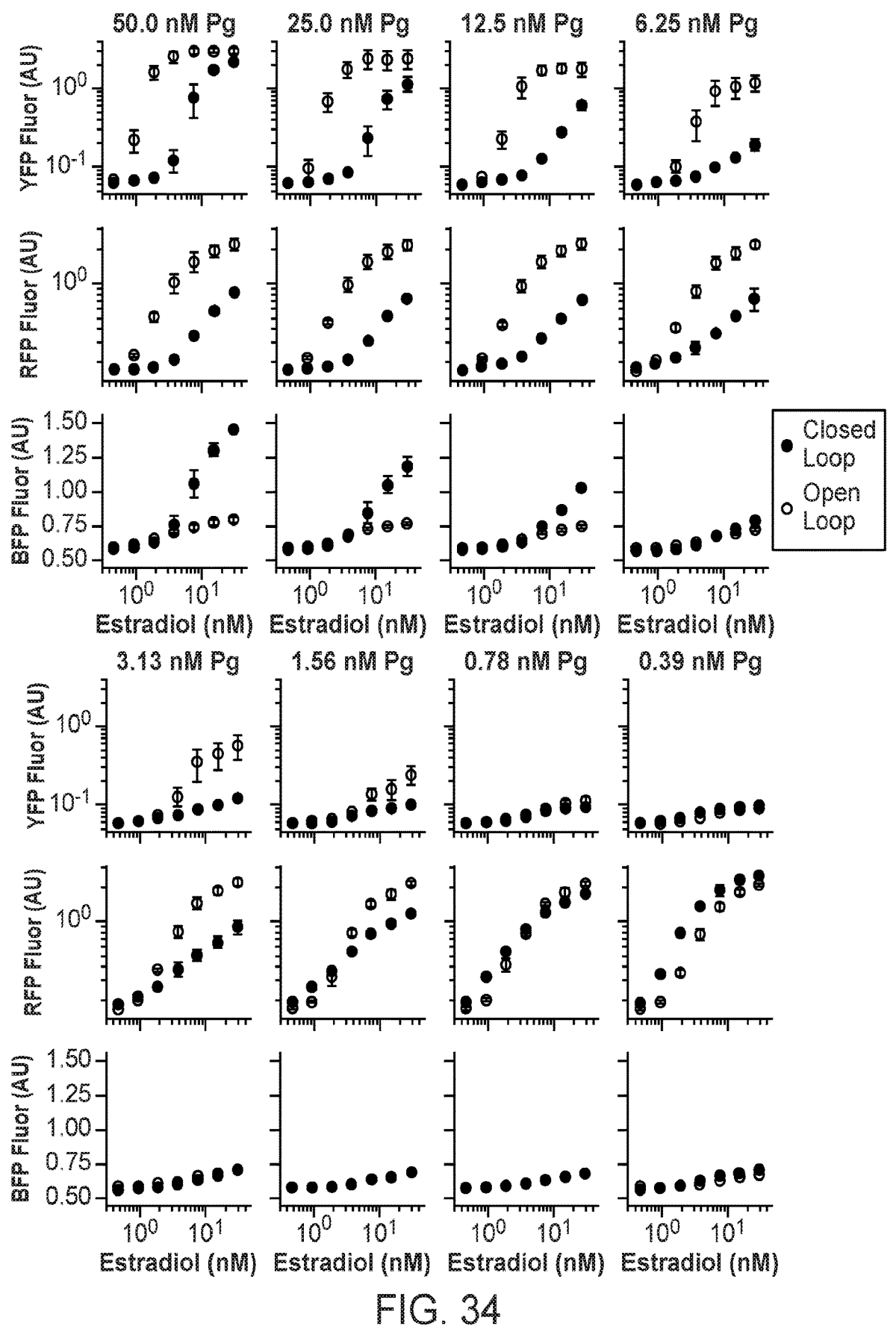
Figure 35:
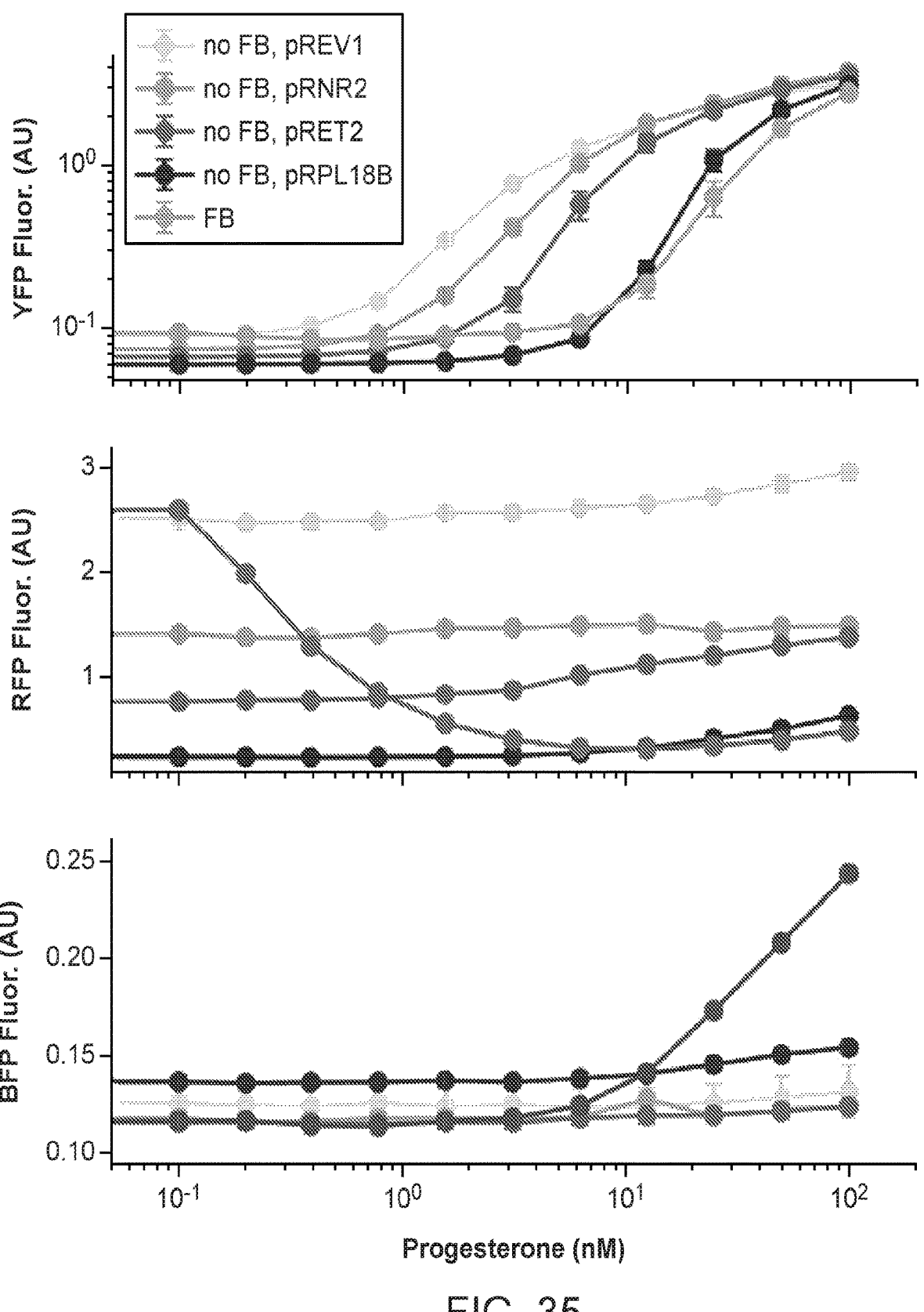
FIG. 35 depicts circuit behavior when expressing different amounts of key constitutively FIG. 36 demonstrates that the DegronLOCKR synthetic feedback strategy is predictably tunable. a) (Top) Exploring different methods to tune the feedback gain in the synthetic feedback circuit. (Bottom) Model simulation (see supplementary information) of circuit output and Z3PM as a function of Pg disturbance for decreasing key production rate or key/cage affinity. b & c) Experimental validation of tuning. b) (Top) Tuning feedback gain by varying the number of Z3 binding sites on pZ3 with the key at a fixed length. (Bottom) RFP and YFP fluorescence as a function of Pg for strong (pZ3-6x), medium (pZ3-4x), and weak (pZ3-3x) feedback strains versus no feedback (pREV1-key-CFP-NLS) strain. Points represent mean±s.d. of three biological replicates. c) (Top) Tuning feedback gain by varying the length of the key with the strength of the feedback promoter fixed at pZ3-6x. (Bottom) RFP and YFP fluorescence as a function of Pg for long (55 aa), medium (51 aa), and short (43 aa) key feedback strains versus no feedback (pREV1-NLS-key-CFP) strain. Points represent mean±s.d. of three biological replicates. d) Changing promoter strength and key length to tune feedback gain on the synthetic negative feedback loop in the mating pathway. pAGA1 is a stronger reporter of the mating pathway than pFIG1. e) (Top) Dynamic measurements of pAGA1-YFP-cODC for various feedback and no feedback strains following stimulation with 25 nM α-factor. Points represent flow cytometry measurements and lines represent a moving average taken over three data points. (Bottom) α-factor dose response of feedback strains versus a no feedback (pREV1-NLS-key-CFP) strain. YFP fluorescence was measured using flow cytometry four hours after α-factor induction. Points represent the mean of three biological replicates and error bars represent the standard error. Solid lines are a hill function fit to the data. The dose of α-factor used in the dynamic experiment (top) is indicated on the graph.

To further delineate the properties of the degronLOCK feedback module, the feedback and no feedback circuits were induced with the full range of E2 and Pg concentrations and measured pZ3-YFP-cODC output at steady-state using flow cytometry (FIG. 33 and FIG. 34). In these experiments, pGAL1-RFP was measured to gain more proximal information about the activity of GEM and thus the feedback action. At a fixed concentration of E2 (7.5 nM E2), increasing Pg leads to an increase in the YFP output of the no feedback circuit until saturation is reached (FIG. 35, FIG. 31, panel e). Because the key is expressed from a constitutive promoter in this strain, RFP fluorescence is insensitive to Pg. In contrast, RFP fluorescence decreases as a function of Pg in the synthetic feedback circuit, a result of degronLOCKR induced degradation of GEM. This effect eventually saturates above 6.25 nM Pg, as shown by the constant RFP expression beyond this concentration. The difference between these two regions of operation is clearly visible in the YFP output, which shows reduced sensitivity to Pg in the region of active feedback and a dramatic increase when feedback is saturated. These results are qualitatively recapitulated by the model, which shows the feedback saturating when the complex formation between the key and degSwitch saturates (FIG. 30 and FIG. 31).

Figure 36:
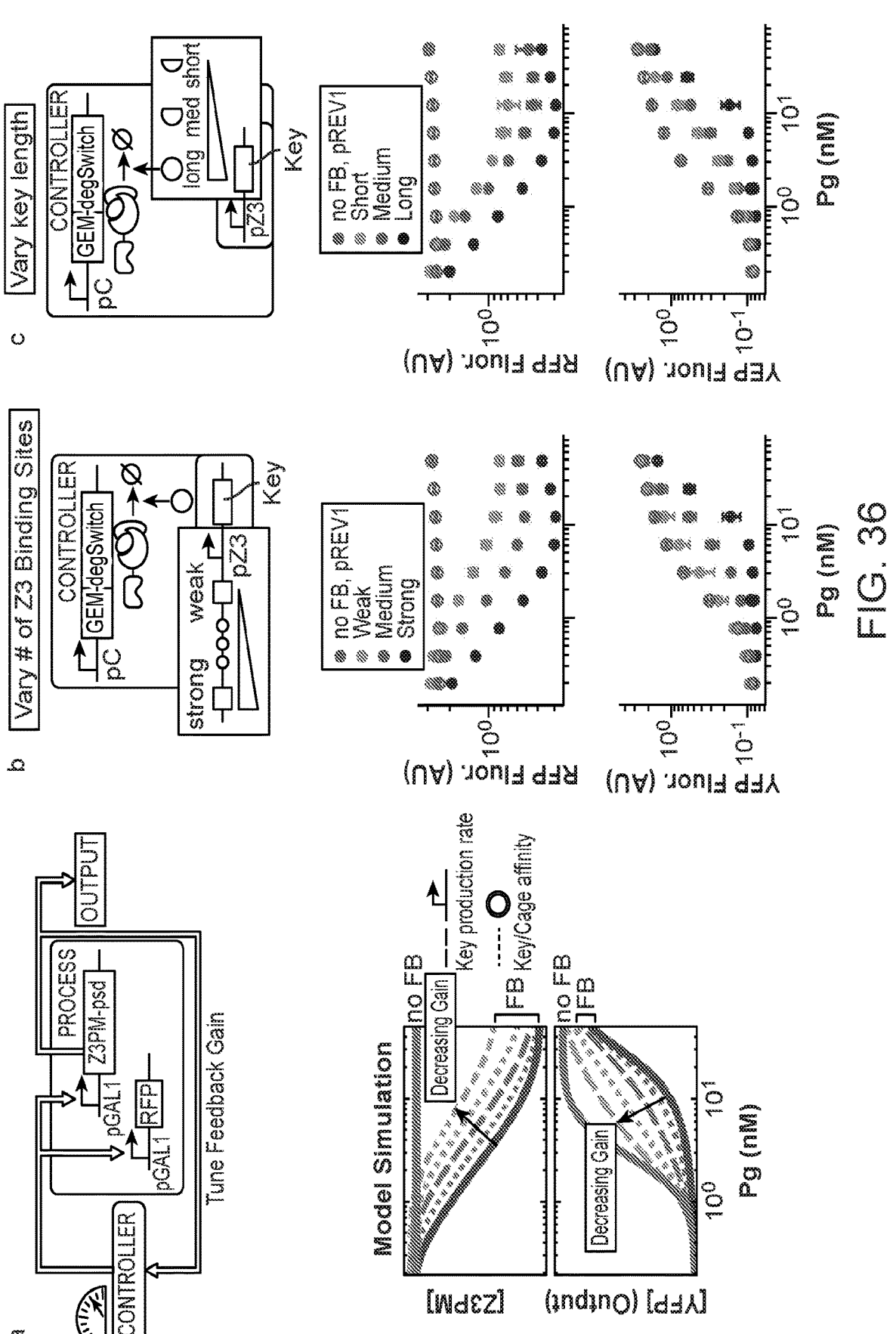
Figure 36:
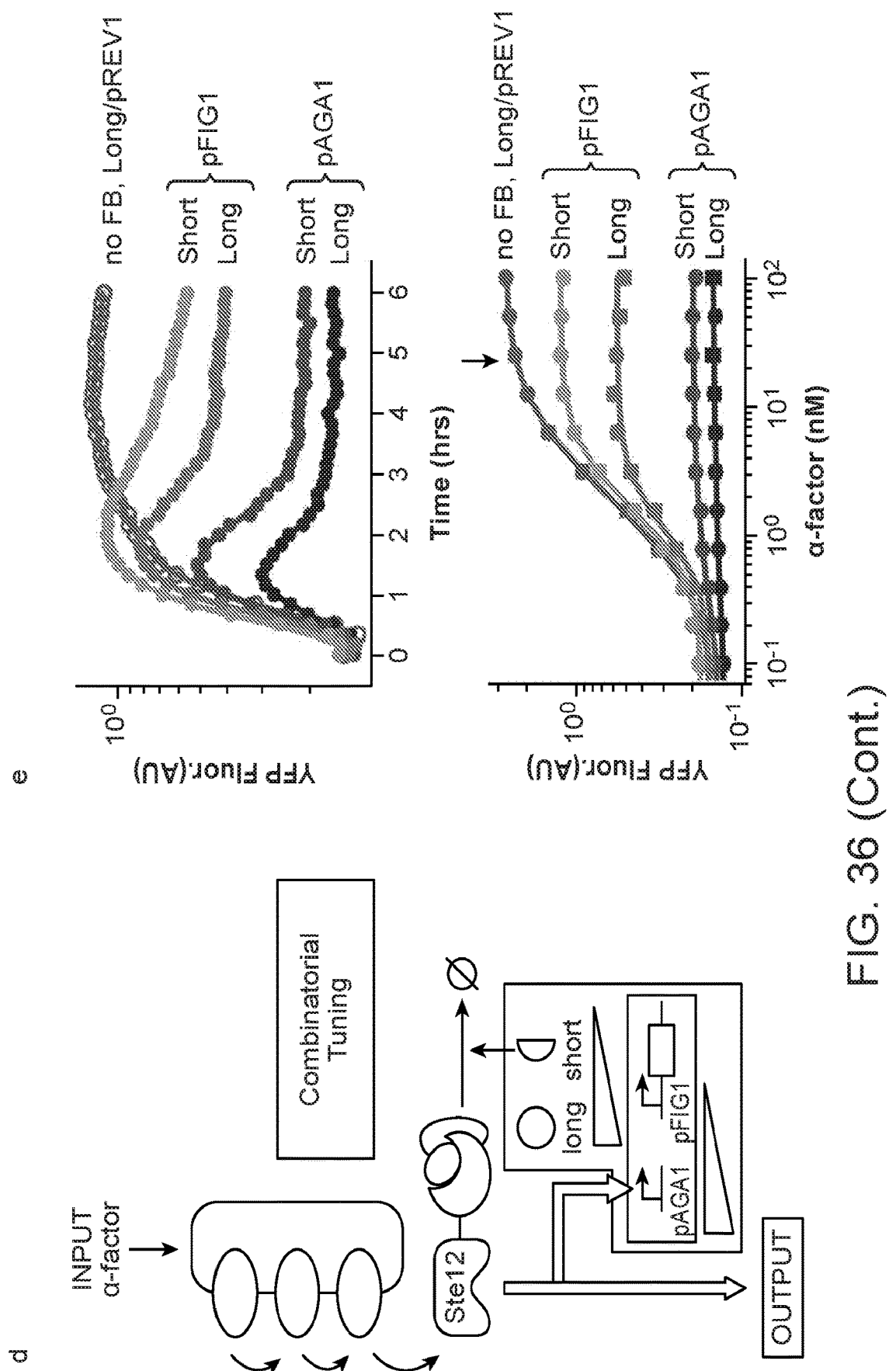
Figure 37:
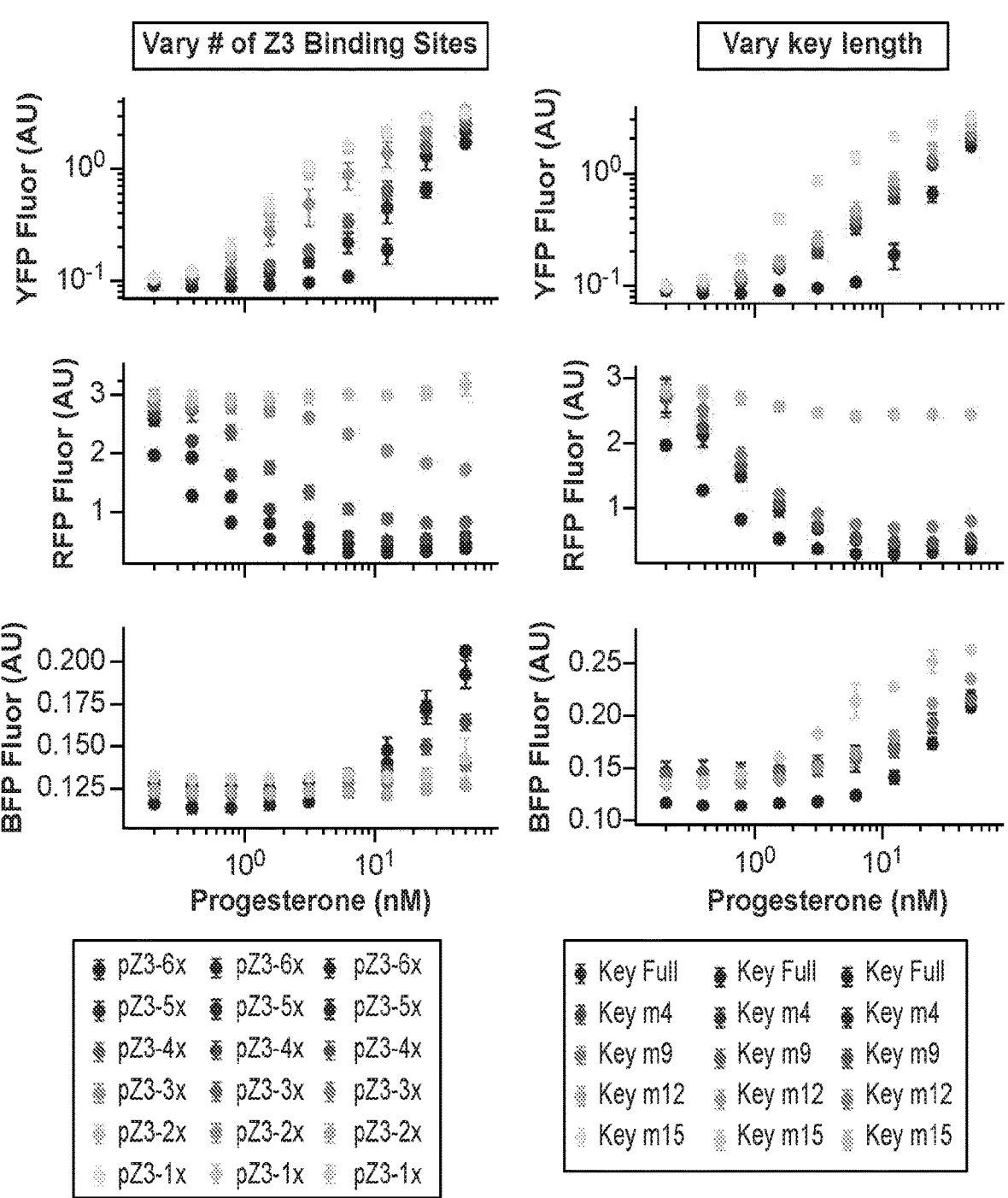
FIG. 37 demonstrates that changing promoter strength or key length modulates feedback gain.

Next the tunability degronLOCKR feedback control was investigated. An useful aspect of designed feedback controllers is the ability to tune the gain to suit the application. Two methods of tuning feedback gain were evaluated: changing the strength of the feedback promoter and changing the binding affinity of the key and cage (FIG. 36, panel a). The computational model predicts that both methods for tuning feedback gain are qualitatively similar and thus should be interchangeable (FIG. 36, panel b). To test this, medium and weak variants of the pZ3 promoter with four and three Z3 binding sites (BS), respectively, were created. To test the effect of weakening the feedback promoter strength, a Pg dose response at a fixed concentration of E2 of the different circuit variants was performed (FIG. 36, panel b). It was observed that weakening the promoter indeed changed the dependence of the steady-state output on Pg. As the number of binding sites was reduced, the output dose response for the feedback circuit converged to the circuit without feedback (FIG. 37). Next, the affinity of the key for the cage was decreased by decreasing the length of the key. The full-length key was truncated by four (medium) or 12 (short) residues and each key variant was tested in the feedback circuit using the full-strength pZ3 promoter (6×Z3 BS) (FIG. 36, panel c, FIG. 37). Similar to reducing the strength of the feedback promoter, a decrease in key length led to a change in the dependence of the steady-state output on Pg (FIG. 36, panel d). Reducing the strength of the feedback gain through either strategy also led to larger transients and reduced adaptation (FIG. 38). Tuning feedback gain through key length is an attractive alternative to promoter engineering, showcasing a unique strength of de novo proteins.

To show the generalizability of these tuning strategies, the mating pathway was revised and combinatorial tuning of the synthetic feedback loop was performed by changing both the strength of the feedback promoter and the length of the key (FIG. 36, panel d). Because pAGA1 is a much stronger promoter than FIG. 1, using pAGA1 to express the key generated a pulse of expression following induction with alpha-factor (FIG. 36, panel e). The size of the pulse, as well as the steady-state output following it were both increased by reducing the key length, which reduced the amount of feedback in the system. Similarly, reducing the key length while using the weaker promoter FIG. 1 to drive feedback yielded a larger transient and higher steady-state output. Measurement of steady-state output as a function of α-factor for different promoters and key lengths (FIG. 36, panel f, FIG. 39) clearly demonstrates that reducing promoter strength or key length increases the steady-state output of the pathway and the slope of the dose response, indicating reduced feedback gain. Taken together, these data demonstrate the facile tunability of the characteristics of the degronLOCKR feedback strategy.

The above represents a novel method for biological feedback control that can be used in a plug-and-play and tunable manner to control any biological network with a transcriptional output. This success highlights the value of degronLOCKR and de novo protein design for synthetic biology. These proteins, due to their de novo design, function across mammalian and plant species with minimal crosstalk for various applications, including therapeutics and biotechnology.

Methods

Construction of DNA Circuits

Hierarchical golden gate assembly was used to assemble plasmids for yeast strain construction according to Lee et al. (2015). Individual parts had their BsaI, BsmBI, and NotI cut sites removed to facilitate downstream assembly and linearization. Parts were either generated via PCR or purchased as gBlocks from IDT. These parts were then assembled into transcriptional units (promoter-gene-terminator) on cassette plasmids. These cassettes were then assembled together to form multi-gene plasmids for insertion into the yeast genome.

Yeast Strains and Growth Media

The base S. cerevisiae strain used in all experiments was BY4741 (MATa his3Δ1 leu2Δ0 met15Δ0 ura3Δ0). All yeast cultures were grown in YPD media (10 g/L Bacto Yeast Extract, 20 g/L Bacto peptone, 20 g/L dextrose). Selection of auxotrophic markers (URA3, LEU2, and/or HIS3) was performed on synthetic complete medium (6.7 g/L Bacto-yeast nitrogen base without amino acids, 2 g/L complete supplement amino acid mix, 20 g/L dextrose).

Knockouts of FAR1 and BAR1

A modified version of BY4741 (yAHN797) was created for the mating pathway experiments with FAR1 and BAR1 knocked out using the CRISPR/Cas9 method outlined in Lee et al. FAR1 was first targeted by two sgRNAs designed using the Benchling biology design tool to target the ORF of each gene. These sgRNAs were expressed on CEN6/ARS4 plasmids containing a Cas9 with two nuclear localization sequences and a URA3 auxotrophic marker. Repair DNA with homology to the 50 bp upstream and downstream of the ORF was generated by annealing oligos. A standard lithium acetate procedure was used to transform yeast with the plasmid containing sgRNA/Cas9 and repair DNA. The efficacy of sgRNA was assessed by comparing the number of colonies of transformants given repair DNA with respect to transformants that were not provided repair DNA. Colonies were screened by colony PCR to verify the knockout, and successful clones were grown in an overnight culture of YPD. 5 ul of overnight culture was then plated on synthetic complete medium containing 5-fluoroorotic acid (5-FOA) to counterselect the URA3 auxotrophic marker on the CEN6/ARS4 plasmid. The knockout process was then repeated to knock out BAR1.

Integration of degSwitch into Yeast Genome

Linear DNA consisting of degSwitch with a 5×GS linker and a URA3 auxotrophic marker was generated using overlap extension PCR. This linear DNA was then used as PCR template to add 80 bp of homology targeting the 3' end of the MAT pathway regulators GPA1, MSG5, SST2, STE5, STE7, STE11, and STE50. Individual lithium acetate yeast transformations were then performed using each of the linear DNA fragments to insert the degSwitch downstream of each of the seven genes into the parental strain yAHN797 and selectively plated on synthetic complete media lacking uracil. Insertions were confirmed using colony PCR.

Yeast Cell Culture and Induction

Yeast strains were streaked out from a glycerol stock on SDC plates with the appropriate auxotrophic marker, or YPD plates if no auxotrophic marker was present. Individual colonies from these plates were used to inoculate a culture in YPD to grow to saturation over 12-24 hours.

Alpha-Factor Induction

Saturated culture was diluted 1:500 in fresh YPD and 450 ul were aliquoted into individual wells of a 2 mL 96 well storage block (Corning) for a three hour outgrowth at 30 C and 900 RPM in a Multitron shaker (Infors HT). Alpha-factor mating pheromone was prepared at a 10× concentration by making the appropriate dilutions into YPD from a 50 uM stock solution (Zymo Research). After the 3 hour outgrowth, 50 ul of alpha-factor solution was added to the 96 well block and the block was returned to the shaker for a four hour growth.

Estradiol and Progesterone Induction

Saturated culture was diluted 1:500 in fresh YPD and 400 ul were aliquoted into individual wells of a 2 mL 96 well storage block (Corning) for a three hour outgrowth at 30 C and 900 RPM in a Multitron shaker (Infors HT). Estradiol (Sigma-Aldrich) and progesterone (Fisher Scientific) were prepared at a 10× concentration by making the appropriate dilutions into YPD from a 3.6 mM (estradiol) and 3.2 mM (progesterone) stock solution. After the three hour out-growth, 50 ul of estradiol and progesterone inducer were added to the 96 well block in the appropriate combinations and the block was returned to the shaker for a ten hour growth.

Yeast Culture

Saturated cultures were diluted 1:200, or 1:100 for mating pathway cultures, into 10 mL or 15 mL YPD. Cultures were grown for 2 hours in glass tubes at 30 C in a shaker. Cultures were then diluted to 0.01 OD600 and aliquoted into indi-vidual Falcon tubes at a total volume of 30 mL YPD. Another one hour outgrowth was performed in custom bioreactors at 30 C and stirred with magnetically-controlled stir bars. All cultures were grown in YPD at 0.5× Penicillin Streptomycin.

Hardware

In order to collect time-course measurements, a platform for automated flow cytometry and continuous culture was constructed. An existing automated experimental platform was adapted to perform small molecule induction at varying concentrations and long-term culturing. Yeast cultures were grown in 50 mL optically clear conical tubes (Falcon) that were held in eight temperature-controlled, magnetically stirred chambers. Liquid handling was accomplished using two syringe pumps (Cavro XCalibur Pump, TECAN) of a BD High-Throughput Sampler. This set-up allowed for sampling from individual cultures to a BD LSRII flow cytometer for measurement. To achieve continuously cul-turing, a specified volume of culture was first moved to waste and different ratios of hormone media and fresh media were added back. Commands to the HTS were controlled using LABVIEW 2013.

A sampling period consisted of three main steps: sample, extract dilution volume, and replenish dilution volume at respective hormone concentrations. During long time-course experiments, a sampling period was chosen to hold event rate near constant. A doubling time of 90 minutes was assumed, so 4 mL of culture was extracted and then replaced with fresh media and hormone every 25 minutes (dilution rate of $0.16\ mL min^{-1}$). Shorter experiments done on the mating pathway were not performed with continuous cul-turing, allowing for a higher sampling frequency of every 10 minutes.

Estradiol and Progesterone Induction (One Induction)

To study conditions where [E2] and [Pg] concentrations maintained the same throughout the experiment, only one induction was needed. Three stocks were created: (1) inducer, (2) refill stock at 1× [E2] and 1× [Pg] concentration, and (3) refill stock without hormone. During the induction timepoint, cultures were induced to respective concentra-tions by different ratios of (1) and (3). Cultures were held at their respective concentrations by adjusted ratios of (2) and (3).

Estradiol and Progesterone Induction (Two Induction)

To study disturbance rejection at same [E2] but different [Pg], cultures were induced twice. The first induction allowed all cultures to grow to steady state at the same pre-disturbance concentration. After cultures reached steady state (t=0 hrs), cultures were induced with more Pg or kept at the same concentration, and allowed to grow to steady-state again. Four stocks were created: (1) inducer to achieve pre-disturbance concentration, (2) inducer to achieve differ-ent disturbance [Pg], (3) refill stock at 1× [E2]/[Pg] to maintain desired concentrations, and (4) refill stock at 1× [E2] but without Pg. Cultures were induced at t=−10 hr with (1). All cultures were held at the same pre-disturbance concentration for 10 hours by replenishing with a 1:8 dilution between (3) and (4). At t=0, cultures were induced with different ratios of (2) and (4). Concentrations were maintained by adjusted ratios of (3) and (4), so that the highest disturbance [Pg] was achieved without dilution and the lowest [Pg] maintained with a 1:8 dilution.

Alpha Factor Induction

To study the dynamic response of degronLOCKR medi-ated feedback on the mating pathway, cultures were induced with input (alpha-factor) at t0. Different concentrations were achieved combining different volumes of a YPD 1×25 nM alpha-factor stock and YPD without alpha-factor.

Light Induction

Each bioreactor is equipped with an individual blue LED that is connected to a USB controllable LED driver (Migh-tex). Starting at light induction timepoint, cultures were exposed to a saturating light dose (45 seconds on/15 seconds off with an intensity amplitude of 25 mA). This light regime was maintained until expression reached steady-state.

Flow Cytometry

Analysis of fluorescent protein reporter expression was performed with a BD LSRII flow cytometer (BD Biosci-ences) equipped with a high-throughput sampler. Cultures were diluted in TE before running through the instrument to obtain an acceptable density of cells. YFP (Venus) fluores-cence was measured using the FITC channel, RFP (mKate2) was measured using the PE-Texas Red channel (for steady-state measurements) or mCherry channel (for dynamic mea-surements), and CFP was measured using the DAPI channel. For steady-state measurements, 5,000-10,000 events were collected per sample. For dynamic measurements, samples 2,000-10,000 events were collected per sampled. Fluores-cence values were calculated as the height (H) measurement for the appropriate channel and normalized to cell size by dividing by side scatter (SSC-H).

FIG. 28. degronLOCKR is a modular tool for controlling biological pathways. a) Schematic of degronLOCKR as a modular tool to implement synthetic feedback control on an endogenous or synthetic biological network by fusing the degSwitch to an effector molecule and driving the expres-sion of the key from the output of the network. b) Simplified schematic of the yeast mating pathway not showing complex endogenous feedback. Pathway is activated by addition of α-factor and signaling activity is measured using a pAGA1-YFP-cODC reporter. c) degronLOCKR induced degradation of positive signaling molecules to control mating pathway activity. The endogenous copy of indicated signaling mol-ecule was fused to degSwitch and key was expressed using a progesterone inducible system. Cells were induced with a saturating dose of α-factor and pathway activity with and without key was compared. pAGA1-YFP-cODC was mea-sured on a flow cytometer after four hours of growth. Data represent mean±s.d. of three biological replicates.

FIG. 30. degronLOCKR module successfully implements synthetic feedback control of the mating pathway a) Sche-matic of synthetic negative feedback where the endogenous copy of STE12 is fused to the degSwitch and either the pathway reporter FIG. 1 (synthetic feedback) or a constitu-tive promoter (no feedback) is used to express key-CFP-NLS. All output measurements are for pAGA1-YFP-cODC.

b) Measurements of pAGA1-YFP-cODC dynamics. Synthetic feedback and no feedback (pREV1) strains were induced with a high (25 nM), medium (6.25 nM), or low (3.13 nM) dose of α-factor at time t=0 hr and flow cytometry measurements (points) were performed every 10 minutes. Lines represent a moving average taken over three data points. c) α-factor dose response of synthetic feedback (FIG. 1) and four no feedback (no key, pREV1, pRNR2, pRET2) strains. pAGA1-YFP-cODC fluorescence was measured using flow cytometry four hours after α-factor induction. Points represent the mean±s.d. of three biological replicates. Solid lines are a hill function fit to the data. High, medium, and low doses of α-factor from the experiment in (b) are indicated on the graph.

FIG. 31. Operational properties of degronLOCKR feedback module quantified via control of a synthetic circuit a) Schematic of synthetic feedback circuit. GEM-degSwitch is expressed constitutively and is activated by estradiol (E2) to drive expression of pGAL1-Z3PM-psd. Z3PM is activated by progesterone (Pg) to drive expression from pZ3. Blue light can be used to induce degradation of Z3PM-psd. pZ3-YFP-cODC is the measured output of the circuit, and pZ3-key-CFP-NLS drives feedback (synthetic feedback) in the circuit by activating degradation of GEM-degSwitch. In the circuit with no feedback a constitutive promoter is used to express key-CFP-NLS. b) Model simulation (see supplementary information) of the feedback and no feedback circuits. The simulated dynamics (left) and change of steady-state (right) of output following a Pg disturbance indicate that feedback buffers against increasing Pg concentration by degrading GEM and reducing Z3PM concentration. c) Dynamic measurements of pZ3-Venus-cODC using automated flow cytometry for the synthetic feedback and no feedback strains (pRNR2-key-CFP-NLS) following a positive disturbance. Cells were grown to steady-state expression in 0.78 nM Pg and 7.5 nM E2. At time 0 hrs cells were either kept at the same Pg concentration or induced to a new final concentration of 1.56 nM (low), 3.13 nM (med), or 6.25 nM (high) Pg. Dynamics were measured for another eight hours. Solid line represents a moving average taken over three data points. d) Dynamic measurements of pZ3-Venus-cODC using automated flow cytometry for the synthetic feedback and no feedback strains (pRPL18B-key-CFP-NLS driving key) following a negative disturbance. Cells were grown to steady-state expression in 1.57 nM Pg and 30 nM E2 then subjected to blue-light at time 0 hrs to activate the psd. Dynamics were measured for eight hours post-disturbance. Growth and sampling conditions are as in c). e) Precision of the synthetic feedback versus no feedback circuits to each of the disturbances. f) Comparison of steady-state circuit behavior (ten hours after stimulation) with and without feedback (pRNR2-key-CFP-NLS) as a function of Pg at a fixed concentration of 7.5 nM E2. RFP fluorescence is a proxy for Z3PM concentration and YFP fluorescence is the output of the circuit. Pg doses used for positive disturbance in c) are indicated. Points represent mean±s.d. of three biological replicates.

FIG. 36. DegronLOCKR synthetic feedback strategy is predictably tunable a) (Top) Exploring different methods to tune the feedback gain in the synthetic feedback circuit. (Bottom) Model simulation (see supplementary information) of circuit output and Z3PM as a function of Pg disturbance for decreasing key production rate or key/cage affinity. b & c) Experimental validation of tuning. b) (Top) Tuning feedback gain by varying the number of Z3 binding sites on pZ3 with the key at a fixed length. (Bottom) RFP and YFP fluorescence as a function of Pg for strong (pZ3-6x), medium (pZ3-4x), and weak (pZ3-3x) feedback strains versus no feedback (pREV1-key-CFP-NLS) strain. Points represent mean±s.d. of three biological replicates. c) (Top) Tuning feedback gain by varying the length of the key with the strength of the feedback promoter fixed at pZ3-6x. (Bottom) RFP and YFP fluorescence as a function of Pg for long (55 aa), medium (51 aa), and short (43 aa) key feedback strains versus no feedback (pREV1-NLS-key-CFP) strain. Points represent mean±s.d. of three biological replicates. d) Changing promoter strength and key length to tune feedback gain on the synthetic negative feedback loop in the mating pathway. pAGA1 is a stronger reporter of the mating pathway than FIG. 1. e) (Top) Dynamic measurements of pAGA1-YFP-cODC for various feedback and no feedback strains following stimulation with 25 nM α-factor. Points represent flow cytometry measurements and lines represent a moving average taken over three data points. (Bottom) α-factor dose response of feedback strains versus a no feedback (pREV1-NLS-key-CFP) strain. YFP fluorescence was measured using flow cytometry four hours after α-factor induction. Points represent the mean of three biological replicates and error bars represent the standard error. Solid lines are a hill function fit to the data. The dose of α-factor used in the dynamic experiment (top) is indicated on the graph.

FIG. 29: Panel of mating pathway regulators tested with degronLOCKR. degSwitch was fused to the C-terminus of the endogenous copy of each regulator. Key with or without SV40 NLS was expressed using a Pg inducible system. STE20, STE11, and PTP3 were degraded using cytoplasmic key (Key-CFP), and STE12, DIG1 and DIG2 were degraded using nuclear key (Key-CFP-NLS). MSG5 and FUSS were degraded using either cytoplasmic (cyto) or nuclear (nuc) key. Cells were induced with 1 nM (low) or 100 nM (high) α-factor and 50 nM or 0 nM Pg and grown for four hours before YFP fluorescence was measured using a flow cytometer. Data represent mean±s.d. of three biological replicates.

FIG. 32: Steady state solutions in response to positive or negative disturbances. Steady values as a) progesterone (Pg) or b) ZPM degradation rate (yz) change according to our Hill-like model. Continuous lines correspond to the feedback system (FB), while the dashed line shows an example where the feedback has been removed (i.e. $f_K = \mu_{K^*}$ instead of Eq.12; No FB). The gray box delimits the area where the feedback is considered "active", which is defined by the relative change in total GEM ($\Delta(G+C)/(G+C)$) over the relative change of the disturbance (either a) $\Delta P/P$ or b) $\Delta \gamma_z/\gamma_z$) is higher than 0.15. Noteworthy, in the absence of feedback, $\Delta(G+C)$ is equal zero for any disturbance except on the synthesis or degradation rate of the key or GEM directly.

FIG. 33: Circuit behavior as a function of Pg for a fixed dose of E2. Comparison of steady-state circuit behavior (ten hours after stimulation) with and without feedback (pRNR2-key-CFP-NLS) as a function of Pg at all concentrations of E2. YFP fluorescence is the output of the circuit, RFP fluorescence is a proxy for Z3PM concentration, and BFP fluorescence is the amount of key produced. Points represent mean±s.d. of three biological replicates.

FIG. 34: Circuit behavior as a function of E2 for a fixed dose of Pg. Comparison of steady-state circuit behavior (ten hours after stimulation) with and without feedback (pRNR2-key-CFP-NLS) as a function of E2 at all concentrations of Pg. YFP fluorescence is the output of the circuit, RFP fluorescence is a proxy for Z3PM concentration, and BFP fluorescence is the amount of key produced. Points represent mean±s.d. of three biological replicates.

FIG. 35: Circuit behavior when expressing different amounts of key constitutively. Comparison of steady-state circuit behavior (ten hours after stimulation) with feedback and various levels of key expression without feedback (pREV1, pRNR2, pRET2, pRPL18B) as a function of Pg at a fixed concentration of 7.5 nM E2. YFP fluorescence is the output of the circuit, RFP fluorescence is a proxy for Z3PM concentration, and BFP fluorescence is the amount of key produced. Points represent mean±s.d. of three biological replicates.

FIG. 37: Changing promoter strength or key length modulates feedback gain. Comparison of steady-state circuit behavior (ten hours after stimulation) for various levels of feedback gain (left, tuning via changing feedback promoter strength; right, tuning via changing key length) as a function of Pg at a fixed concentration of 7.5 nM E2. Left, tuning via changing feedback promoter strength (x refers to number of Z3 operator sites); right, tuning via changing key length (m refers to number of residues removed from C-terminus of key). YFP fluorescence is the output of the circuit, RFP fluorescence is a proxy for Z3PM concentration, and BFP fluorescence is the amount of key produced. Points represent mean±s.d. of three biological replicates.

FIG. 38: Tuning feedback strength changes dynamic behavior of circuit output. Dynamic measurements of pZ3-Venus-cODC using automated flow cytometry for the synthetic feedback strain with various gains and no feedback strain (pREV1-key-CFP-NLS) following induction with 3.13 nM Pg and 7.5 nM E2 at time=0 hrs. Solid line represents a moving average taken over three data points.

FIG. 39: Combinatorial tuning of synthetic feedback in mating pathway. (Top) Dynamic measurements of pAGA1-YFP-cODC for various feedback and no feedback (pREV1, pRNR2, pRET2, pRPL18B) strains following stimulation with 25 nM α-factor. Points represent flow cytometry measurements and lines represent a moving average taken over three data points. (Bottom) α-factor dose response of feedback strains versus no feedback (pREV1, pRNR2, pRET2, pRPL18B) strains. YFP fluorescence was measured using flow cytometry four hours after α-factor induction. Points represent mean±s.d. of three biological replicates. Solid lines are a hill function fit to the data.

Example 3: degronLOCKR Functions in Human Primary T Cells

The ability of degronLOCKR to function in human primary T cells was demonstrated by inducibly degrading a mCherry fluorescent protein. Lentiviral transfer constructs were constructed containing mCherry fused to the asymmetric short scaffold degronSwitch with a t8 toehold and cODC degron embedded in the latch. The mCherry-degronSwitch fusion was expressed using pPGK constitutive promoter. In a second lentiviral construct a fusion of Key to tagBFP was expressed using four different constitutive promoters (pPGK, pSFFV, pCMV(G), pCMV(D)).

Experiments were performed in human primary CD4+ T cells. Cells were transduced with different combinations of the aforementioned lentiviruses. In one instance, cells were transduced with only mCherry-degronSwitch. In others, cells received both the mCherry-degronSwitch virus in addition to a virus expressing Key-tagBFP. After lentiviral transduction, fluorescence was measured using flow cytometry. Distributions are shown in FIG. 41. We observed that mCherry fluorescence was nearly completely abolished when cells were co-transduced with a virus containing any amount of Key production (Key production was quantified using tagBFP fluorescence). This data indicates that the Key is able to trigger the degronSwitch and activate degradation of mCherry.

Example 4: degronLOCKR-Mediated Feedback Functions in Jurkat T Cells

An inducible humanized synthetic transcription factor ZF3-p65-Ert2 (ZPE) was used as the model process to test whether feedback mediated by degronLOCKR would be functional in human T cells (inducible TF gift of Mo Khalil, Boston U). The output of the circuit is a mCherry fluorescent reporter produced by a pZF3 promoter, and ZPE fused to the degronSwitch is driven by a pSFFV constitutive promoter. Two versions of the circuit were constructed, one with no feedback, and one with feedback through the key. The circuit with feedback has the key driven by a separate pZF3 promoter and is fused to a mEGFP. Several variants of this feedback circuit were tested by mixing and matching different pZF3 promoter variants and key lengths. These experiments were performed by stably integrating the constructs into Jurkat T cells using lentivirus. Cells that received the circuit were gated out as mCherry positive (the pZF3 (4x)_mCMV promoter is leaky) and for the feedback version, BFP positive.

This experiment was performed by inducing cells with a range of tamoxifen (4OHT), which activates the ZPE transcription factor by translocating it into the nucleus. Cells were measured 5 days post-induction using flow cytometry. Sample distributions are shown in FIG. 42 for the circuit output and Key production for the circuit with Feedback.

Figure 43:
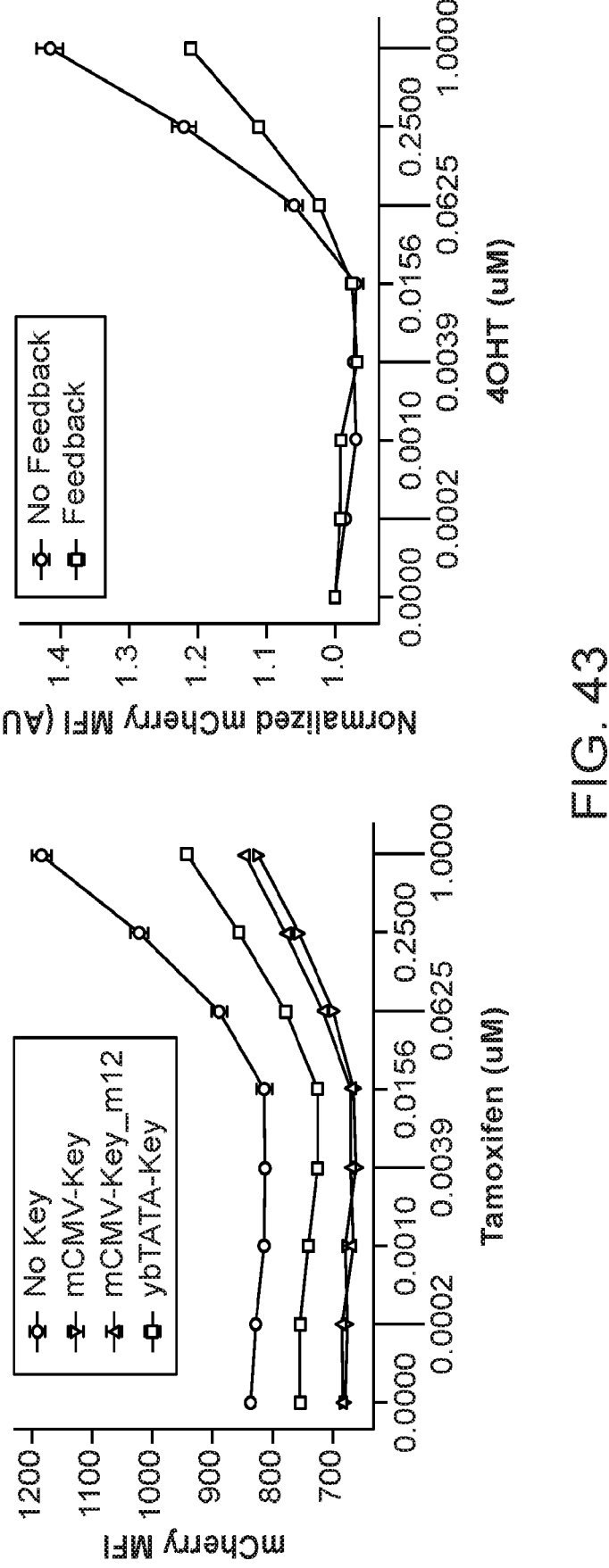
FIG. 43 shows a comparison of output for different feedback variants (left panel) and a normalized output for circuit with no feedback and feedback circuit with mCMV-Key (right panel).

The dose response of the no feedback and feedback circuits for a full range of 4OHT concentrations were compared. It appears that buffering from feedback can be tuned by changing the promoter or key length, similar to the effects previously observed in yeast. When observing the feedback off of the mCMV promoter driving full length key, we can see that the presence of feedback both reduces the maximal steady-state output and also reduces the slope of the dose-response (FIG. 43). These characteristics are classic hallmarks of feedback and suggest that our feedback circuit is having an effect on the circuit. In the future, mCherry could be replaced with a payload of interest. Our feedback circuits could perform both disturbance rejection and tune the dynamics of T cell activation (i.e., production of CAR) or delivery of a therapeutic payload.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy sequence listing. A copy of the sequence listing is available in electronic form from the USPTO web site (https://seqdata.uspto.gov/docdetail?docId=US12583896B2). An electronic copy of the sequence listing will also be available from the USPTO upon request and payment of the fee set forth in 37 CFR 1.19(b)(3).

What is claimed is:

1. A molecular feedback circuit, the circuit comprising:

a signaling protein that, when activated by an input of a signaling pathway, drives an output of the signaling pathway, wherein the signaling protein comprises a degradation-based switch polypeptide; and a regulatory nucleic acid sequence responsive to the output and operably linked to a nucleic acid sequence encoding a key polypeptide, wherein the output induces expression of the key polypeptide in a eukaryotic cell, wherein the degradation-based switch polypeptide comprises an amino acid sequence selected from a group consisting of the amino acid sequences of SEQ ID NOs: 1-25, wherein the amino acid sequence of the degradation-based switch polypeptide comprises:

a first domain comprising a degron;

a second domain comprising five alpha helices; and a third domain comprising an alpha helix, wherein, in the absence of the key polypeptide, the second and third domains form a three dimensional structure comprising a six helix bundle to sequester the degron and prevent the degron from triggering degradation of the signaling protein, and wherein the key polypeptide comprises an amino acid sequence selected from a group consisting of the amino acid sequences of SEQ ID NOs: 46-49, and wherein the amino acid sequence of the key polypeptide comprises an alpha helix that binds to the second domain with a binding affinity that is higher than the binding affinity of the third domain binding to the second domain, and, when expressed in a eukaryotic cell and bound to the second domain, modifies the three dimensional structure of the degradation-based switch polypeptide so that the degron is exposed and can target the signaling protein for degradation, thereby inducing degradation of the signaling protein in the eukaryotic cell.

2. The circuit according claim 1, wherein each helix of the second domain and the third domain are each 30 to 50 residues in length.

3. The circuit according claim 1, wherein the signaling protein is an intermediate member of the signaling pathway or a transcription factor.

4. The circuit according to claim 3, wherein the transcription factor is a synthetic transcription factor.

5. The circuit according to claim 3, wherein the regulatory sequence comprises a binding site for the transcription factor.

6. The circuit according to claim 5, wherein the regulatory sequence comprises a plurality of binding sites for the transcription factor.

7. The circuit according to claim 6, wherein the plurality of binding sites is 2 to 10 binding sites.

8. The circuit according to claim 3, wherein the output is expression of the transcription factor.

9. The circuit according to claim 3, wherein the signaling protein is a receptor and the input is a ligand for the receptor.

10. One or more nucleic acid molecules encoding the molecular feedback circuit according to claim 1.

11. A yeast or human cell genetically modified to comprise the one or more nucleic acid molecules according to claim 10.

*     *     *     *     *